(12) United States Patent
Berman et al.

(10) Patent No.: US 7,601,526 B2
(45) Date of Patent: Oct. 13, 2009

(54) **PURIFIED FABI POLYPEPTIDES FROM *FRANSICELLA TULARENSIS***

(75) Inventors: Judd M. Berman, Toronto (CA); Molly B. Schmid, Toronto (CA); Donald E. Awrey, Mississauga (CA); Teresa Clarke, Toronto (CA); Bryan Beattie, Oakville (CA); Mandy Dorsey, Brantford (CA)

(73) Assignee: Affinium Pharmaceuticals, Inc., Toronto (CA)

( * ) Notice: Subject to any disclaimer, the term of this patent is extended or adjusted under 35 U.S.C. 154(b) by 176 days.

(21) Appl. No.: 11/647,506

(22) Filed: Dec. 28, 2006

(65) Prior Publication Data

US 2008/0108793 A1     May 8, 2008

Related U.S. Application Data

(60) Provisional application No. 60/584,091, filed on Jun. 30, 2004.

(51) Int. Cl.
*C12N 9/00* (2006.01)
*C07K 14/00* (2006.01)

(52) U.S. Cl. ..................... 435/183; 530/350
(58) Field of Classification Search .............. None
See application file for complete search history.

(56) References Cited

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. TheRigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*

* cited by examiner

*Primary Examiner*—Suzanne M. Noakes
(74) *Attorney, Agent, or Firm*—Goodwin Procter LLP

(57) ABSTRACT

The present invention relates to novel drug targets for pathogenic bacteria. Accordingly, the invention provides purified protein derived from *Fransicella tularensis* comprising the amino acid sequence set forth in SEQ ID NO: 2. The invention also provides biochemical and biophysical characteristics of the polypeptides of the invention.

17 Claims, 60 Drawing Sheets

SEQ ID NO: 1

ATGGGTTTTCTAGCAGGAAAAAAAATATTAATCACTGGACTTTTAAGTAATAAGTCAATTG
CATATGGTATTGCTAAAGCTATGCATAGAGAGGGAGCCGAGCTTGCTTTTACTTATGTTGG
ACAGTTCAAAGATAGAGTGGAAAAATTATGTGCAGAATTTAATCCAGCTGCAGTTTTGCCT
TGCGATGTGATTTCTGATCAAGAGATTAAGGATTTATTTGTAGAGCTAGGTAAAGTTTGGG
ATGGTCTAGATGCCATAGTTCATTCTATAGCTTTTGCACCGCGTGATCAGTTAGAAGGTAA
CTTTATTGACTGTGTAACTCGCGAGGGTTTTAGTATCGCTCATGATATTAGTGCCTATTCT
TTTGCAGCATTAGCTAAAGAAGGTCGTAGTATGATGAAAAATCGTAATGCTTCTATGGTAG
CACTTACTTATATTGGAGCAGAAAAAGCTATGCCAAGTTACAATACTATGGGAGTTGCTAA
AGCATCTCTAGAAGCTACAGTTAGATATACAGCGTTAGCTTTAGGTGAGGATGGTATCAAG
GTAAATGCTGTATCAGCTGGTCCTATCAAAACTCTGGCAGCTTCTGGTATATCAAACTTCA
AGAAGATGCTTGATTATAATGCTATGGTTTCTCCACTTAAGAAAAATGTTGATATTATGGA
AGTTGGTAATACTGTAGCGTTTTTATGTTCAGATATGGCAACTGGTATCACTGGAGAAGTT
GTCCATGTTGATGCTGGATATCATTGTGTGTCTATGGGTAATGTTCTTTAA

FIGURE 1

SEQ ID NO: 2

MGFLAGKKILITGLLSNKSIAYGIAKAMHREGAELAFTYVGQFKDRVEKLCAEFNPAAVLP
CDVISDQEIKDLFVELGKVWDGLDAIVHSIAFAPRDQLEGNFIDCVTREGFSIAHDISAYS
FAALAKEGRSMMKNRNASMVALTYIGAEKAMPSYNTMGVAKASLEATVRYTALALGEDGIK
VNAVSAGPIKTLAASGISNFKKMLDYNAMVSPLKKNVDIMEVGNTVAFLCSDMATGITGEV
VHVDAGYHCVSMGNVL

FIGURE 2

SEQ ID NO: 3

ATGGGTACCATGGGTTTTCTAGCAGGAAAAAAATATTAATCACTGGACTTTTAAGTAATA
AGTCAATTGCATATGGTATTGCTAAAGCTATGCATAGAGAGGGAGCCGAGCTTGCTTTTAC
TTATGTTGGACAGTTCAAAGATAGAGTGGAAAAATTATGTGCAGAATTTAATCCAGCTGCA
GTTTTGCCTTGCGATGTGATTTCTGATCAAGAGATTAAGGATTTATTTGTAGAGCTAGGTA
AAGTTTGGCATGGTCTAGATGCCATAGTTCATTCTATAGCTTTTGCACCGCGTGATCAGTT
AGAAGGTAACTTTATTGACTGTGTAACTCGCGAGGGTTTTAGTATCGCTCATGATATTAGT
GCCTATTCTTTTGCAGCATTAGCTAAAGAAGGTCGTAGTATGATGAAAAATCGTAATGCTT
CTATGGTAGCACTTACTTATATTGGAGCAGAAAAGCTATGCCAAGTTACAATACTATGGG
AGTTGCTAAAGCATCTCTAGAAGCTACAGTTAGATATACAGCGTTAGCTTTAGGTGAGGAT
GGTATCAAGGTAAATGCTGTATCAGCTGGTCCTATCAAAACTCTGGCAGCTTCTGGTATAT
CAAACTTCAAGAAGATGCTTGATTATAATGCTATGGTTTCTCCACTTAAGAAAAATGTTGA
TATTATGGAAGTTGGTAATACTGTAGCGTTTTATGTTCAGATATGGCAACTGGTATCACT
GGAGAAGTTGTCCATGTTGATGCTGGATATCATTGTGTGTCTATGGGTAATGTTCTTTAA

FIGURE 3

SEQ ID NO: 4

MGTMGFLAGKKILITGLLSNKSIAYGIAKAMHREGAELAFTYVGQFKDRVEKLCAEFNPAA
VLPCDVISDQEIKDLFVELGKVWDGLDAIVHSIAFAPRDQLEGNFIDCVTREGFSIAHDIS
AYSFAALAKEGRSMMKNRNASMVALTYIGAEKAMPSYNTMGVAKASLEATVRYTALALGED
GIKVNAVSAGPIKTLAASGISNFKKMLDYNAMVSPLKKNVDIMEVGNTVAFLCSDMATGIT
GEVVHVDAGYHCVSMGNVL

FIGURE 4

SEQ ID NO: 5

ATGGGTACCATGGGTTTTCTAGCAGGAAAAAAAATATTAATCACTGGACTTTTAAGTAATA
AGTCAATTGCATATGGTATTGCTAAAGCTATGCATAGAGAGGGAGCCGAGCTTGCTTTTAC
TTATGTTGGACAGTTCAAAGATAGAGTGGAAAAATTATGTGCAGAATTTAATCCAGCTGCA
GTTTTGCCTTGCGATGTGATTTCTGATCAAGAGATTAAGGATTTATTTGTAGAGCTAGGTA
AAGTTTGGGATGGTCTAGATGCCATAGTTCATTCTATAGCTTTTGCACCGCGTGATCAGTT
AGAAGGTAACTTTATTGACTGTGTAACTCGCGAGGGTTTTAGTATCGCTCATGATATTAGT
GCCTATTCTTTTGCAGCATTAGCTAAAGAAGGTCGTAGTATGATGAAAAATCGTAATGCTT
CTATGGTAGCACTTACTTATATTGGAGCAGAAAAAGCTATGCCAAGTTACAATACTATGGG
AGTTGCTAAAGCATCTCTAGAAGCTACAGTTAGATATACAGCGTTAGCTTTAGGTGAGGAT
GGTATCAAGGTAAATGCTGTATCAGCTGGTCCTATCAAAACTCTGGCAGCTTCTGGTATAT
CAAACTTCAAGAAGATGCTTGATTATAATGCTATGGTTTCTCCACTTAAGAAAAATGTTGA
TATTATGGAAGTTGGTAATACTGTAGCGTTTTATGTTCAGATATGGCAACTGGTATCACT
GGAGAAGTTGTCCATGTTGATGCTGGATATCATTGTGTGTCTATGGGTAATGTTCTTTAA

FIGURE 5

SEQ ID NO: 6

MGSHHHHHHSSGLVPRGSHMGTMGFLAGKKILITGLLSNKSIAYGIAKAMHREGAELAFTY
VGQFKDRVEKLCAEFNPAAVLPCDVISDQEIKDLFVELGKVWDGLDAIVHSIAFAPRDQLE
GNFIDCVTREGFSIAHDISAYSFAALAKEGRSMMKNRNASMVALTYIGAEKAMPSYNTMGV
AKASLEATVRYTALALGEDGIKVNAVSAGPIKTLAASGISNFKKMLDYNAMVSPLKKNVDI
MEVGNTVAFLCSDMATGITGEVVHVDAGYHCVSMGNVL

FIGURE 6

SEQ ID NO: 7

ATGGGTACCATGGGTTTTCTAGCAGGAAAAAAAATATTAATCACTGGACTTTTAAGTAATA
AGTCAATTGCATATGGTATTGCTAAAGCTATGCATAGAGAGGGAGCCGAGCTTGCTTTTAC
TTATGTTGGACAGTTCAAAGATAGAGTGGAAAAATTATGTGCAGAATTTAATCCAGCTGCA
GTTTTGCCTTGCGATGTGATTTCTGATCAAGAGATTAAGGATTTATTTGTAGAGCTAGGTA
AAGTTTGGGATGGTCTAGATGCCATAGTTCATTCTATAGCTTTTGCACCGCGTGATCAGTT
AGAAGGTAACTTTATTGACTGTGTAACTCGCGAGGGTTTTAGTATCGCTCATGATATTAGT
GCCTATTCTTTTGCAGCATTAGCTAAAGAAGGTCGTAGTATGATGAAAAATCGTAATGCTT
CTATGGTAGCACTTACTTATATTGGAGCAGAAAAAGCTATGCCAAGTTACAATACTATGGG
AGTTGCTAAAGCATCTCTAGAAGCTACAGTTAGATATACAGCGTTAGCTTTAGGTGAGGAT
GGTATCAAGGTAAATGCTGTATCAGCTGGTCCTATCAAAACTCTGGCAGCTTCTGGTATAT
CAAACTTCAAGAAGATGCTTGATTATAATGCTATGGTTTCTCCACTTAAGAAAAATGTTGA
TATTATGGAAGTTGGTAATACTGTAGCGTTTTATGTTCAGATATGGCAACTGGTATCACT
GGAGAAGTTGTCCATGTTGATGCTGGATATCATTGTGTGTCTATGGGTAATGTTCTT**GGAT
CC**

FIGURE 7

SEQ ID NO: 8

MGTMGFLAGKKILITGLLSNKSIAYGIAKAMHREGAELAFTYVGQFKDRVEKLCAEFNPAA
VLPCDVISDQEIKDLFVELGKVWDGLDAIVHSIAFAPRDQLEGNFIDCVTREGFSIAHDIS
AYSFAALAKEGRSMMKNRNASMVALTYIGAEKAMPSYNTMGVAKASLEATVRYTALALGED
GIKVNAVSAGPIKTLAASGISNFKKMLDYNAMVSPLKKNVDIMEVGNTVAFLCSDMATGIT
GEVVHVDAGYHCVSMGNVLGS<u>ENLYFQHHHHHH</u>

FIGURE 8

```
FT FabI   MGFLAGKKILITGLSNKSIAYGIA...REGA.LAFTYVG-.F.DRVE..CA..N--PAA.LPCDVISD
SA FabI   .LN.ENKTY..MGHANK.SIAEG.A....D..GA..VFTYRKE.S.KE..K.LE.LNQPEAH..G.DVQSD
EC FabI   MGFLSGKR..V.G.ASKLSIAYGIA..MH.EGA.LAFTY.N...R.GRVEE.FAA..G--SDIVL.CDVAED
HP FabI   MGFLKGKK.L.VG.ANN.SIAYGIA.S.CFN.GATLAFTY.NE.SL..RV.RP.AQ.LN--SPYVY.LDVSK.
Consen    M--L--K-----G-----SIA-G-A------GA-L-FTY------------------DV---

FT FabI   .E.KDLF.E.CK.VWDGF.DA.VHSIAFAPRD.QLEG.N.IDCVT.REGF.S.A.DIS.YS.PAA.AKEGR.SM.KNR
SA FabI   .E.INGFE...GKDVGN.D.G.YHSIAFANM.D..RG.R.S.TS-REGF.L.A.QDIS.SYSLTI.A.HEA.KK.L.-PE
EC FabI   AS.DTK.FA.E.GK.VWPK.DGFVHS.IG.FAPG.D.QL.E.GDY.VNAVT.REGFK.T.A.DIS.SYS.FVAM.AKAC.RS.M.I-NP
HP FabI   .EHPKS.L.NS..KDLGSE.D.F.EVHS.VAFAPK.EA.LE.CSL.ETS-.KSA.NTA.M..EIS.V.YSLIELTNTL.KP.LL-NN
Consen    -----------K-----D---HS--FA----L-G----------F---A--IS-YS--------------

FT FabI   NA.SMVAL.T.Y.GAEKA.MP.SYNTMG.VAKASLEA.VRYTAL.A.LGE.D.GIKVNA..SAGPIE.TLAASGIS.N.EK.KM.L
SA FabI   GC.S.VATT.YLGGEFA.VQN.YNVMG.VAKASLEA.N.VK.Y.LA.D.LGP.D.NIRVNA..SAGPIRTL.SA.K.GV.GG.ENT.I.L
EC FabI   GS.AI.T.LSYLGAE.RA.PN.YNVMG.TAKASLEA.NV.MANA.N.GP.E.G.VRVNA.SAGPIRTLAASGIKD.F.RKML
HP FabI   GA.SV.I.T.LSYLGS.TKYMA.HYNVMG.LAKA.ALES.AVRYLAVDLGK.HH.IRVNA.SAGPIRTLASS.GIA.D.RMI.L
Consen    --------Y-G--------YN-MG-AKA-LE--VRY-A---G------VNA-SAGPI-TL---G---F---L FT FabI   DYNAMV.S.PL.KKNVD.IMEVGNTV.A.F.L.CSDMATG.IT.GEV.VHVDA.GYHC.V.SM.GN.V.L---------------- (SEQ ID NO: 1)
SA FabI   KEI.KER.A.PL.KKNVDQV.EVGKT.A.A.Y.L.LSDLS.SG.V.T.GENT.IHVDS.G.F.HA.L.K------------------ (SEQ ID NO: 9)
EC FabI   AHC.EAVT.PL.RRT.VT.EEDVGN.EA.A.F.L.CSDLS.AG.IS.GEV.VHVDG.G.F.SIAAM.NE.U.ELK------------ (SEQ ID NO: 10)
HP FabI   KWN.EINA.PL.KKNV.SL.EEVGNAG.MY.LL.SSL.SS.GV.SGEVHFVDA.G.T.HVMG.V.GA.V.EEKDNKATLLWDLHKEQ (SEQ ID NO: 11)
Consen    -------P----V----VG-----L-S----G--GE----VD-G--------------------------- (SEQ ID NO: 12)
```

| Sequence | FT FabI | SA FabI | EC FabI | HP FabI |
|----------|---------|---------|---------|---------|
| FT FabI  | 1.000   | 0.448   | 0.577   | 0.436   |
| SA FabI  | ---     | 1.000   | 0.416   | 0.407   |
| EC FabI  | ---     | ---     | 1.000   | 0.434   |
| HP FabI  | ---     | ---     | ---     | 1.000   |

| | | | | | | | | |
|---|---|---|---|---|---|---|---|---|
| FT | Xaa$_{91}$ - | Ala Phe Ala | Xaa | Arg | Xaa$_2$ | Leu | - Xaa$_{46}$ - |
| SA | Xaa$_{94}$ - | Ala Phe Ala | Xaa | Met | Xaa$_2$ | Leu | - Xaa$_{44}$ - |
| EC | Xaa$_{92}$ - | Gly Phe Ala | Xaa | Gly | Xaa$_2$ | Leu | - Xaa$_{45}$ - |
| HP | Xaa$_{92}$ - | Ala Phe Ala | Xaa | Lys | Xaa$_2$ | Leu | - Xaa$_{44}$ - |
| C  | Xaa$_{91-94}$ - | G/A Phe Ala | Xaa | Xaa | Xaa$_2$ | Leu | - Xaa$_{44-46}$ - |

B

| | | | | | | | | |
|---|---|---|---|---|---|---|---|---|
| FT | Tyr | Xaa$_6$ | Met Pro Ser Tyr | Xaa$_2$ | Met | Xaa$_3$ | Lys | - Xaa$_{27}$ - |
| SA | Tyr | Xaa$_6$ | Val Gln Asn Tyr | Xaa$_2$ | Met | Xaa$_3$ | Lys | - Xaa$_{27}$ - |
| EC | Tyr | Xaa$_6$ | Ile Pro Asn Tyr | Xaa$_2$ | Met | Xaa$_3$ | Lys | - Xaa$_{27}$ - |
| HP | Tyr | Xaa$_6$ | Met Ala His Tyr | Xaa$_2$ | Met | Xaa$_3$ | Lys | - Xaa$_{27}$ - |
| C  | Tyr | Xaa$_6$ | Xaa Xaa Xaa Tyr | Xaa$_2$ | Met | Xaa$_3$ | Lys | - Xaa$_{27}$ - |

C

| | | | | | | | | | | | |
|---|---|---|---|---|---|---|---|---|---|---|---|
| FT | Pro | Xaa$_3$ | Leu Ala | Xaa | Ser | Xaa | Ile Ser | Xaa | Phe | Xaa$_2$ | Met | - |
| SA | Pro | Xaa$_3$ | Leu Ser | Xaa | Lys | Xaa | Val Gly | Xaa | Phe | Xaa$_2$ | Ile | - |
| EC | Pro | Xaa$_3$ | Leu Ala | Xaa | Ser | Xaa | Ile Lys | Xaa | Phe | Xaa$_2$ | Met | - |
| HP | Pro | Xaa$_3$ | Leu Ala | Xaa | Ser | Xaa | Ile Ala | Xaa | Phe | Xaa$_2$ | Ile | - |
| C  | Pro | Xaa$_3$ | Leu A/S | Xaa | S/K | Xaa | I/V Xaa | Xaa | Phe | Xaa$_2$ | M/I | - |

| | | |
|---|---|---|
| FT | Xaa$_{54}$ | (SEQ ID No. 13) |
| SA | Xaa$_{49}$ | (SEQ ID No. 14) |
| EC | Xaa$_{56}$ | (SEQ ID No. 15) |
| HP | Xaa$_{70}$ | (SEQ ID No. 16) |
| C  | Xaa$_{54-70}$ | (SEQ ID No. 17) |

FIGURE 10

SEQ ID NO: 18
Ala Phe Ala Xaa Arg $Xaa_2$ Leu

SEQ ID NO: 19
Tyr $Xaa_6$ Met Pro Ser Tyr $Xaa_2$ Met $Xaa_3$ Lys

SEQ ID NO: 20
Pro $Xaa_3$ Leu Ala Xaa Ser Xaa Ile Ser Xaa Phe $Xaa_2$ Met

SEQ ID NO: 21
Tyr $Xaa_6$ Met Pro Ser Tyr $Xaa_2$ Met $Xaa_3$ Lys $Xaa_{27}$ Pro $Xaa_3$ Leu Ala Xaa Ser Xaa Ile Ser Xaa Phe $Xaa_2$ Met

SEQ ID NO: 22
Ala Phe Ala Xaa Arg $Xaa_2$ Leu $Xaa_{44-46}$ Tyr $Xaa_6$ Met Pro Ser Tyr $Xaa_2$ Met $Xaa_3$ Lys $Xaa_{27}$ Pro $Xaa_3$ Leu Ala Xaa Ser Xaa Ile Ser Xaa Phe $Xaa_2$ Met

Wherein: Xaa = any amino acid residue, $Xaa_n$ = n number of Xaa residues, $Xaa_{n-n}$ = variable number of Xaa residues

SEQ ID NO: 23
$Xaa^1$ Phe Ala $Xaa_4$ Leu $Xaa_{44-46}$ Tyr $Xaa_9$ Tyr $Xaa_2$ Met $Xaa_3$ Lys $Xaa_{27}$ Pro $Xaa_3$ Leu $Xaa^2$ Xaa $Xaa^3$ Xaa $Xaa^4$ Xaa Xaa Phe $Xaa_2$ $Xaa^5$

Wherein: $Xaa^1$ = Gly or Arg, $Xaa^2$ = Ala or Ser, $Xaa^3$ = Ser or Lys, $Xaa^4$ = Ile or Val, $Xaa^5$ = Met or Ile, Xaa = any amino acid residue, $Xaa_n$ = n number of Xaa residues, $Xaa_{n-n}$ = variable number of Xaa residues

SEQ ID NO: 24
Ile Lys Thr Leu Ala Ala Ser Gly Ile Ser Asn

SEQ ID NO: 25
Ile Arg Thr Leu Ser Ala Lys Gly Val Gly Gly

SEQ ID NO: 26
Ile Arg Thr Leu Ala Ala Ser Gly Ile Lys Asp

SEQ ID NO: 27
Ile Arg Thr Leu Ala Ser Ser Gly Ile Ala Asp

FIGURE 11

A = SEQ ID NO: 18
B = SEQ ID NO: 19
C = SEQ ID NO: 20
D = A + $X_{44-46}$ + B + $X_{27}$ + C (SEQ ID NO: 22)
Xaa = any amino acid residue
$Xaa_n$ = n number of Xaa residues
$Xaa_{n-n}$ = variable number of Xaa residues

| Residues in the catalytic domains of FabI ||||||
| --- | --- | --- | --- | --- | --- |
| Location | FT Average conservation | FT | SA | EC | HP |
| Binding site[1] | 0.935 | A92 | A95 | G93 | A93 |
| Binding site | 0.560 | R96 | M99 | G97 | K97 |
| Binding site | 0.906 | P154 | Q155 | P154 | A153 |
| Binding site | 0.877 | S155 | N156 | N155 | H154 |
| Binding site | 1.000 | P191 | P192 | P191 | P190 |
| Binding site | 0.872 | S198 | K199 | S198 | S197 |
| Binding site | 1.000 | L195 | L196 | L195 | L194 |
| Binding site | 1.000 | A94 | A97 | A95 | A95 |
| Binding site | 1.000 | F203 | F204 | F203 | F202 |
| Binding site | 1.000 | Y146 | Y147 | Y146 | Y145 |
| Binding site | 1.000 | Y156 | Y157 | Y156 | Y155 |
| Binding site | 0.960 | I200 | V201 | I200 | I199 |
| Binding site | 0.681 | S201 | G202 | K201 | A200 |
| Binding site | 0.986 | M206 | I207 | M206 | I205 |
| Binding site | 0.967 | A196 | S197 | A196 | A195 |
| Binding site | 0.950 | M153 | V154 | I153 | M152 |
| Binding site | 1.000 | M159 | M160 | M159 | M158 |
| Binding site | 1.000 | L99 | L102 | L100 | L100 |
| Binding site | 1.000 | F93 | F96 | F94 | F94 |
| Binding site | 1.000 | K163 | K164 | K163 | K162 |
| Flipping loop | | 192 IKTLAASGI SN 202 | 193 IRTLSAKGV GG 203 | 192 IRTLAASGI KD 202 | 191 IRTLASSGI AD 201 |
| [1]Binding site of the inhibitor and not residues involved in binding NADH ||||||

FIGURE 13

SEQ ID NO: 28

Met Xaa¹ Xaa² Leu Xaa Xaa³ Lys Xaa₂ Xaa⁴ Xaa⁵ Xaa Gly Xaa Xaa⁶ Xaa₃
Ser Ile Ala Xaa⁷ Gly Xaa⁸ Ala Xaa₆ Gly Ala Xaa Leu Xaa⁹ Phe Thr Tyr
Xaa₆₋₇ Xaa¹⁰ Xaa¹¹ Xaa¹² Xaa₅ Xaa¹³ Xaa¹⁴ Xaa₃₋₅ Xaa¹⁵ Xaa₃ Asp Val Xaa₂
Xaa¹⁶ Xaa₆ Xaa¹⁷ Xaa₃ Xaa¹⁸ Lys Xaa₅ Asp Xaa₂ Xaa¹⁹ His Ser Xaa²⁰ ▇▇▇  Box A
▇▇▇▇▇▇▇▇▇▇▇ Xaa Gly Xaa₆₋₇ Xaa²³ Xaa²⁴ Xaa²⁵ Phe Xaa₂ Ala
Xaa Xaa²⁶ Ile Ser Xaa Tyr Ser Xaa₄ Xaa²⁷ Xaa₇₋₈ Xaa²⁸ Xaa Xaa²⁹ Xaa
Xaa³⁰ Xaa₃ Xaa³¹ Xaa ▇▇▇▇▇▇▇▇▇▇▇▇▇▇▇▇▇▇▇▇▇▇▇  Box B
▇▇▇▇▇▇▇▇▇▇▇ Ala Xaa³⁶ Leu Glu Xaa³⁷ Xaa Val Arg Tyr
Xaa Ala Xaa₂ Xaa³⁸ Gly Xaa₃ Xaa³⁹ Xaa⁴⁰ Val Asn Ala Xaa Ser Ala Gly
▇▇▇▇▇▇▇▇▇▇▇▇▇▇▇▇▇▇▇▇▇▇▇▇▇▇▇▇▇ Leu  Box C
Xaa₇ Pro Xaa⁴⁶ Xaa₂ Xaa⁴⁷ Val Xaa₃ Xaa⁴⁸ Val Gly Xaa⁴⁹ Xaa₂ Xaa⁵⁰ Xaa
Leu Xaa Ser Xaa⁵¹ Xaa⁵² Xaa⁵³ Xaa Gly Xaa₂ Gly Glu Xaa⁵⁴ Xaa Xaa⁵⁵ Val
Asp Xaa Gly Xaa Xaa⁵⁶ Xaa₃ Xaa⁵⁷ Xaa₀₋₂₀ wherein: $Xaa^1$ = Gly or Leu, $Xaa^2$ = Phe or Asn, $Xaa^3$ = Gly or Asn, $Xaa^4$ = Leu or Val, $Xaa^5$ = Ile or Val, $Xaa^6$ = Ala or Leu, $Xaa^7$ = Tyr or Phe, $Xaa^8$ = Ile or Val, $Xaa^9$ = Ala or Val, $Xaa^{10}$ = Arg or Glu, $Xaa^{11}$ = Val or Leu, $Xaa^{12}$ = Glu or Arg, $Xaa^{13}$ = Phe or Leu, $Xaa^{14}$ = Asn or Gly, $Xaa^{15}$ = Val or Leu, $Xaa^{16}$ = Asp or Glu, $Xaa^{17}$ = Phe or Tyr, $Xaa^{18}$ = Gly or Lys, $Xaa^{19}$ = Val or Tyr, $Xaa^{20}$ = Ile or Val, $Xaa^{21}$ = Ala or Gly, $Xaa^{22}$ = Pro or Asn, $Xaa^{23}$ = Arg or Lys, $Xaa^{24}$ = Glu or Ser, $Xaa^{25}$ = Gly or Ala, $Xaa^{26}$ = Asp or Gly, $Xaa^{27}$ = Ala or Thr, $Xaa^{28}$ = Asn or Pro, $Xaa^{29}$ = Gly or Asn, $Xaa^{30}$ = Ser or Ala, $Xaa^{31}$ = Leu or Thr, $Xaa^{32}$ = Ile or Leu, $Xaa^{33}$ = Glu or Thr, $Xaa^{34}$ = Ala or Tyr, $Xaa^{35}$ = Thr or Val, $Xaa^{36}$ = Ser or Ala, $Xaa^{37}$ = Ala or Ser, $Xaa^{38}$ = Arg or Lys, $Xaa^{39}$ = Leu or Met, $Xaa^{40}$ = Ile or Val, $Xaa^{41}$ = Arg or Lys, $Xaa^{42}$ = Lys or Arg, $Xaa^{43}$ = Ala or Ser, $Xaa^{44}$ = Ser or Lys, $Xaa^{45}$ = Ile or Val, $Xaa^{46}$ = Leu or Ile, $Xaa^{47}$ = Asn or Thr, $Xaa^{48}$ = Glu or Asp, $Xaa^{49}$ = Asn or Lys, $Xaa^{50}$ = Ala or Met, $Xaa^{51}$ = Asp or Ser, $Xaa^{52}$ = Leu or Met, $Xaa^{53}$ = Ser or Ala, $Xaa^{54}$ = Val or Asn, $Xaa^{55}$ = His or Phe, $Xaa^{56}$ = His or Ser, $Xaa^{57}$ = Met or none

FIGURE 14A

SEQ ID NO: 29 Consensus overall + Ft core
Met Xaa$_2$ Leu Xaa$_2$ Lys Xaa$_5$ Gly Xaa$_5$ Ser Ile Ala Xaa Gly Xaa Ala
Xaa$_6$ Gly Ala Xaa Leu Xaa Phe Thr Try Xaa$_{23-26}$ Asp Val Xaa$_{14}$ Lys
Xaa$_5$ Asp Xaa$_3$ His Ser Xaa ▮▮▮▮▮▮▮▮▮▮▮▮ Xaa Gly    Box A
Xaa$_{9-10}$ Phe Xaa$_2$ Ala Xaa$_2$ Ile Ser Xaa Tyr Ser Xaa$_{22-23}$ ▮▮▮▮▮    Box B
▮▮▮▮▮▮▮▮▮▮▮▮▮▮▮▮▮▮▮▮▮▮▮▮▮▮▮▮ Ala Xaa Leu Glu
Xaa$_2$ Val Arg Tyr Xaa Ala Xaa$_3$ Gly Xaa$_5$ Val Asn Ala Xaa Ser Ala
Gly ▮▮▮▮▮▮▮▮▮▮▮▮▮▮▮▮▮▮▮▮▮▮▮▮▮▮▮▮▮▮    Box C
Leu Xaa$_7$ Pro Xaa$_4$ Val Xaa$_4$ Val Gly Xaa$_5$ Leu Xaa Ser Xaa$_4$ Gly Xaa$_2$
Gly Glu Xaa$_3$ Val Asp Xaa Gly Xaa$_{5-26}$

SEQ ID NO: 30 Consensus Core + Consensus overall
Met Xaa$_2$ Leu Xaa$_2$ Lys Xaa$_5$ Gly Xaa$_5$ Ser Ile Ala Xaa Gly Xaa Ala Xaa$_6$
Gly Ala Xaa Leu Xaa Phe Thr Try Xaa$_{23-26}$ Asp Val Xaa$_{14}$ Lys
Xaa$_5$ Asp Xaa$_3$ His Ser Xaa ▮▮▮▮▮▮▮▮▮ Xaa Gly Xaa$_{9-10}$ Phe    Box A
Xaa$_2$ Ala Xaa$_2$ Ile Ser Xaa Tyr Ser Xaa$_{22-23}$ ▮▮▮▮▮▮▮▮▮▮▮▮    Box B
▮▮▮▮▮▮▮▮▮▮▮▮ Ala Xaa Leu Glu Xaa$_2$ Val Arg Tyr Xaa Ala
Xaa$_3$ Gly Xaa$_5$ Val Asn Ala Xaa Ser Ala Gly ▮▮▮▮▮▮▮▮▮▮▮▮    Box C
▮▮▮▮▮▮▮▮▮▮▮▮▮▮▮▮▮▮▮▮▮ Leu Xaa$_7$ Pro Xaa$_4$ Val
Xaa$_4$ Val Gly Xaa$_5$ Leu Xaa Ser Xaa$_4$ Gly Xaa$_2$ Gly Glu Xaa$_3$ Val Asp Xaa
Gly Xaa$_{5-26}$ Xaa$^1$ = Gly or Ala, Xaa$^2$ = Ala or Ser, Xaa$^3$ = Ser or Lys, Xaa$^4$ = Ile or Val, Xaa$^5$ = Met or Ile

FIGURE 14B

SEQ ID NO: 31
CGCGGGGTACCATGGGTTTTCTAGCAGGAAAAAAATATTAATC (Forward)

SEQ ID NO: 32
GCGCGGATCCAAGAACATTACCCATAGACAC (Reverse)

FIGURE 15

| Ft FabI Construct | Protein Concentration (mg/ml) | Protein Yield (mg) | Purity (%) |
|---|---|---|---|
| N-tagged | 38.4 | 31 | 95 |
| C-tagged | 20.7 | 22 | 95 |
| Untagged Monomer | 24.0 | 10 | 80 |
| Untagged Multimer | 31.5 | 35 | 50 |

FIGURE 19

TABLE 1: Crystallographic Data

| Resolution (Å) | 50-2.4 |
|---|---|
| Total Data | 17859 |
| Completeness (last shell)* | 99.9 (99.9) |
| $R_{sym}$ (last shell) | 14.1 (31.3) |
| $<I/\sigma(I)>$ | 4.56 (1.47) |
| *last shell includes all reflections between 2.52 and 2.4 Å. | |

TABLE 2: Refinement & Model Parameters

| Final Model parameters | Number of amino acid chains | 1 |
|---|---|---|
| | Number of protein atoms | 1935 |
| | Number of solvent atoms / NADH / API-1059 | 244 / 43 / 27 |
| | Resolution range (Å) | 30-2.4 |
| | R-factor[a] | 17.3 |
| | $R_{free}$[b] | 22.2 |
| | Average main chain / side chain B-factor (Å$^2$) | 12.3 |
| | Average solvent / NADH / API-1059 B-factor (Å$^2$) | 24.8 / 7.8 / 11.3 |
| RMS deviation from ideal geometry | Covalent bond lengths (Å) | 0.012 |
| | Bond angles (°) | 1.623 |
| [a]R-factor – $\Sigma_{hkl}||F_{obs}| - |F_{calc}||/\Sigma_{hkl}|F_{obs}|$ [b]$R_{free}$ is a cross-validation residual calculated using 5% of the native data which were chosen randomly and excluded from the refinement. | | |

FIGURE 20

| | ATOM | 1 | N | GLY | A | 2 | 131.429 | 116.665 | -52.575 | 1.00 | 14.13 | N |
|---|---|---|---|---|---|---|---|---|---|---|---|---|
| | ATOM | 3 | CA | GLY | A | 2 | 131.014 | 116.773 | -54.004 | 1.00 | 14.27 | C |
| | ATOM | 6 | C | GLY | A | 2 | 132.198 | 116.772 | -54.955 | 1.00 | 13.96 | C |
| 5 | ATOM | 7 | O | GLY | A | 2 | 133.306 | 117.163 | -54.586 | 1.00 | 13.70 | O |
| | ATOM | 10 | N | PHE | A | 3 | 131.975 | 116.344 | -56.191 | 1.00 | 13.99 | N |
| | ATOM | 12 | CA | PHE | A | 3 | 133.087 | 116.233 | -57.127 | 1.00 | 14.26 | C |
| | ATOM | 14 | CB | PHE | A | 3 | 132.818 | 115.175 | -58.214 | 1.00 | 14.40 | C |
| | ATOM | 17 | CG | PHE | A | 3 | 131.646 | 115.463 | -59.114 | 1.00 | 15.00 | C |
| 10 | ATOM | 18 | CD1 | PHE | A | 3 | 131.742 | 116.393 | -60.135 | 1.00 | 16.62 | C |
| | ATOM | 20 | CE1 | PHE | A | 3 | 130.659 | 116.622 | -61.000 | 1.00 | 16.10 | C |
| | ATOM | 22 | CZ | PHE | A | 3 | 129.488 | 115.910 | -60.841 | 1.00 | 15.31 | C |
| | ATOM | 24 | CE2 | PHE | A | 3 | 129.389 | 114.969 | -59.847 | 1.00 | 15.15 | C |
| | ATOM | 26 | CD2 | PHE | A | 3 | 130.472 | 114.735 | -58.996 | 1.00 | 15.65 | C |
| 15 | ATOM | 28 | C | PHE | A | 3 | 133.598 | 117.565 | -57.707 | 1.00 | 14.04 | C |
| | ATOM | 29 | O | PHE | A | 3 | 134.567 | 117.567 | -58.451 | 1.00 | 14.67 | O |
| | ATOM | 30 | N | LEU | A | 4 | 132.974 | 118.686 | -57.365 | 1.00 | 13.87 | N |
| | ATOM | 32 | CA | LEU | A | 4 | 133.515 | 120.003 | -57.723 | 1.00 | 13.97 | C |
| | ATOM | 34 | CB | LEU | A | 4 | 132.501 | 120.791 | -58.565 | 1.00 | 13.99 | C |
| 20 | ATOM | 37 | CG | LEU | A | 4 | 132.093 | 120.207 | -59.926 | 1.00 | 13.91 | C |
| | ATOM | 39 | CD1 | LEU | A | 4 | 130.926 | 121.017 | -60.513 | 1.00 | 13.73 | C |
| | ATOM | 43 | CD2 | LEU | A | 4 | 133.279 | 120.159 | -60.899 | 1.00 | 12.55 | C |
| | ATOM | 47 | C | LEU | A | 4 | 133.920 | 120.833 | -56.497 | 1.00 | 13.86 | C |
| | ATOM | 48 | O | LEU | A | 4 | 134.005 | 122.068 | -56.586 | 1.00 | 13.28 | O |
| 25 | ATOM | 49 | N | ALA | A | 5 | 134.171 | 120.159 | -55.366 | 1.00 | 14.02 | N |
| | ATOM | 51 | CA | ALA | A | 5 | 134.482 | 120.838 | -54.089 | 1.00 | 14.27 | C |
| | ATOM | 53 | CB | ALA | A | 5 | 134.618 | 119.840 | -52.938 | 1.00 | 14.36 | C |
| | ATOM | 57 | C | ALA | A | 5 | 135.745 | 121.678 | -54.217 | 1.00 | 14.56 | C |
| | ATOM | 58 | O | ALA | A | 5 | 136.788 | 121.196 | -54.675 | 1.00 | 14.52 | O |
| 30 | ATOM | 59 | N | GLY | A | 6 | 135.620 | 122.956 | -53.865 | 1.00 | 14.94 | N |
| | ATOM | 61 | CA | GLY | A | 6 | 136.719 | 123.895 | -53.977 | 1.00 | 15.02 | C |
| | ATOM | 64 | C | GLY | A | 6 | 136.925 | 124.522 | -55.346 | 1.00 | 15.25 | C |
| | ATOM | 65 | O | GLY | A | 6 | 137.762 | 125.416 | -55.462 | 1.00 | 15.95 | O |
| | ATOM | 66 | N | LYS | A | 7 | 136.194 | 124.083 | -56.377 | 1.00 | 14.62 | N |
| 35 | ATOM | 68 | CA | LYS | A | 7 | 136.385 | 124.631 | -57.734 | 1.00 | 14.11 | C |
| | ATOM | 70 | CB | LYS | A | 7 | 135.940 | 123.636 | -58.822 | 1.00 | 14.26 | C |
| | ATOM | 73 | CG | LYS | A | 7 | 136.696 | 122.282 | -58.791 | 1.00 | 14.27 | C |
| | ATOM | 76 | CD | LYS | A | 7 | 137.204 | 121.848 | -60.159 | 1.00 | 13.97 | C |
| | ATOM | 79 | CE | LYS | A | 7 | 138.029 | 120.559 | -60.088 | 1.00 | 13.11 | C |
| 40 | ATOM | 82 | NZ | LYS | A | 7 | 139.483 | 120.745 | -60.381 | 1.00 | 9.91 | N |
| | ATOM | 86 | C | LYS | A | 7 | 135.669 | 125.974 | -57.919 | 1.00 | 13.52 | C |
| | ATOM | 87 | O | LYS | A | 7 | 134.556 | 126.169 | -57.463 | 1.00 | 13.44 | O |
| | ATOM | 88 | N | LYS | A | 8 | 136.326 | 126.887 | -58.617 | 1.00 | 12.83 | N |
| | ATOM | 90 | CA | LYS | A | 8 | 135.830 | 128.240 | -58.813 | 1.00 | 12.58 | C |
| 45 | ATOM | 92 | CB | BLYS | A | 8 | 136.920 | 129.256 | -58.458 | 0.35 | 12.51 | C |
| | ATOM | 93 | CB | ALYS | A | 8 | 136.933 | 129.264 | -58.501 | 0.65 | 12.64 | C |
| | ATOM | 98 | CG | BLYS | A | 8 | 137.158 | 129.342 | -56.951 | 0.35 | 12.65 | C |
| | ATOM | 99 | CG | ALYS | A | 8 | 137.307 | 129.327 | -57.022 | 0.65 | 13.20 | C |
| | ATOM | 104 | CD | BLYS | A | 8 | 138.501 | 129.961 | -56.599 | 0.35 | 13.15 | C |
| 50 | ATOM | 105 | CD | ALYS | A | 8 | 138.667 | 129.978 | -56.799 | 0.65 | 14.79 | C |
| | ATOM | 110 | CE | BLYS | A | 8 | 138.789 | 129.874 | -55.100 | 0.35 | 13.15 | C |
| | ATOM | 111 | CE | ALYS | A | 8 | 139.813 | 129.004 | -57.064 | 0.65 | 15.70 | C |
| | ATOM | 116 | NZ | BLYS | A | 8 | 137.616 | 130.239 | -54.243 | 0.35 | 13.30 | N |
| | ATOM | 117 | NZ | ALYS | A | 8 | 141.136 | 129.479 | -56.525 | 0.65 | 16.27 | N |
| 55 | ATOM | 124 | C | LYS | A | 8 | 135.360 | 128.379 | -60.263 | 1.00 | 11.72 | C |
| | ATOM | 125 | O | LYS | A | 8 | 136.145 | 128.274 | -61.191 | 1.00 | 11.00 | O |
| | ATOM | 126 | N | ILE | A | 9 | 134.059 | 128.556 | -60.441 | 1.00 | 10.59 | N |
| | ATOM | 128 | CA | ILE | A | 9 | 133.462 | 128.428 | -61.747 | 1.00 | 10.19 | C |
| | ATOM | 130 | CB | ILE | A | 9 | 132.680 | 127.091 | -61.852 | 1.00 | 9.81 | C |
| 60 | ATOM | 132 | CG1 | ILE | A | 9 | 133.643 | 125.922 | -61.565 | 1.00 | 10.29 | C |
| | ATOM | 135 | CD1 | ILE | A | 9 | 133.131 | 124.537 | -61.838 | 1.00 | 10.34 | C |
| | ATOM | 139 | CG2 | ILE | A | 9 | 131.996 | 127.005 | -63.215 | 1.00 | 9.29 | C |
| | ATOM | 143 | C | ILE | A | 9 | 132.562 | 129.608 | -62.041 | 1.00 | 10.02 | C |
| | ATOM | 144 | O | ILE | A | 9 | 131.760 | 130.009 | -61.199 | 1.00 | 10.36 | O |
| 65 | ATOM | 145 | N | LEU | A | 10 | 132.695 | 130.117 | -63.266 | 1.00 | 9.60 | N |
| | ATOM | 147 | CA | LEU | A | 10 | 131.973 | 131.283 | -63.771 | 1.00 | 8.93 | C |

(SEQ ID NO. 34)

FIGURE 20-1

| ATOM | 149 | CB  | BLEU  | A | 10 | 132.919 | 132.163 | -64.596 | 0.35 | 8.88  | C |
| ATOM | 150 | CB  | ALEU  | A | 10 | 132.912 | 132.163 | -64.596 | 0.65 | 8.56  | C |
| ATOM | 155 | CG  | BLEU  | A | 10 | 132.430 | 133.503 | -65.166 | 0.35 | 8.91  | C |
| ATOM | 156 | CG  | ALEU  | A | 10 | 132.371 | 133.477 | -65.162 | 0.65 | 7.92  | C |
| ATOM | 159 | CD1 | BLEU  | A | 10 | 131.874 | 133.352 | -66.583 | 0.35 | 8.74  | C |
| ATOM | 160 | CD1 | ALEU  | A | 10 | 131.959 | 134.455 | -64.036 | 0.65 | 7.02  | C |
| ATOM | 167 | CD2 | BLEU  | A | 10 | 131.408 | 134.178 | -64.245 | 0.35 | 8.99  | C |
| ATOM | 168 | CD2 | ALEU  | A | 10 | 133.414 | 134.112 | -66.081 | 0.65 | 6.92  | C |
| ATOM | 175 | C   | LEU   | A | 10 | 130.836 | 130.786 | -64.641 | 1.00 | 8.64  | C |
| ATOM | 176 | O   | LEU   | A | 10 | 131.075 | 130.071 | -65.601 | 1.00 | 8.32  | O |
| ATOM | 177 | N   | ILE   | A | 11 | 129.605 | 131.169 | -64.301 | 1.00 | 8.34  | N |
| ATOM | 179 | CA  | ILE   | A | 11 | 128.418 | 130.776 | -65.065 | 1.00 | 7.73  | C |
| ATOM | 181 | CB  | ILE   | A | 11 | 127.367 | 130.121 | -64.156 | 1.00 | 7.44  | C |
| ATOM | 183 | CG1 | ILE   | A | 11 | 127.936 | 128.853 | -63.519 | 1.00 | 6.94  | C |
| ATOM | 186 | CD1 | ILE   | A | 11 | 126.997 | 128.112 | -62.623 | 1.00 | 8.00  | C |
| ATOM | 190 | CG2 | ILE   | A | 11 | 126.117 | 129.821 | -64.949 | 1.00 | 7.77  | C |
| ATOM | 194 | C   | ILE   | A | 11 | 127.805 | 131.985 | -65.750 | 1.00 | 7.75  | C |
| ATOM | 195 | O   | ILE   | A | 11 | 127.365 | 132.897 | -65.080 | 1.00 | 7.46  | O |
| ATOM | 196 | N   | THR   | A | 12 | 127.792 | 131.978 | -67.085 | 1.00 | 7.74  | N |
| ATOM | 198 | CA  | THR   | A | 12 | 127.050 | 132.956 | -67.865 | 1.00 | 7.56  | C |
| ATOM | 200 | CB  | THR   | A | 12 | 127.746 | 133.252 | -69.220 | 1.00 | 7.40  | C |
| ATOM | 202 | OG1 | THR   | A | 12 | 127.845 | 132.052 | -69.990 | 1.00 | 7.22  | O |
| ATOM | 204 | CG2 | THR   | A | 12 | 129.189 | 133.698 | -69.046 | 1.00 | 7.03  | C |
| ATOM | 208 | C   | THR   | A | 12 | 125.663 | 132.411 | -68.145 | 1.00 | 7.60  | C |
| ATOM | 209 | O   | THR   | A | 12 | 125.399 | 131.237 | -67.927 | 1.00 | 7.61  | O |
| ATOM | 210 | N   | GLY   | A | 13 | 124.768 | 133.274 | -68.608 | 1.00 | 7.74  | N |
| ATOM | 212 | CA  | GLY   | A | 13 | 123.529 | 132.827 | -69.228 | 1.00 | 7.55  | C |
| ATOM | 215 | C   | GLY   | A | 13 | 122.331 | 132.574 | -68.339 | 1.00 | 7.82  | C |
| ATOM | 216 | O   | GLY   | A | 13 | 121.319 | 132.035 | -68.798 | 1.00 | 7.49  | O |
| ATOM | 217 | N   | LEU   | A | 14 | 122.422 | 132.958 | -67.076 | 1.00 | 8.23  | N |
| ATOM | 219 | CA  | LEU   | A | 14 | 121.277 | 132.877 | -66.182 | 1.00 | 8.79  | C |
| ATOM | 221 | CB  | LEU   | A | 14 | 121.765 | 132.968 | -64.734 | 1.00 | 8.84  | C |
| ATOM | 224 | CG  | LEU   | A | 14 | 120.824 | 132.659 | -63.564 | 1.00 | 9.99  | C |
| ATOM | 226 | CD1 | LEU   | A | 14 | 120.066 | 131.364 | -63.731 | 1.00 | 11.05 | C |
| ATOM | 230 | CD2 | LEU   | A | 14 | 121.615 | 132.615 | -62.252 | 1.00 | 10.33 | C |
| ATOM | 234 | C   | LEU   | A | 14 | 120.323 | 134.028 | -66.534 | 1.00 | 9.19  | C |
| ATOM | 235 | O   | LEU   | A | 14 | 120.744 | 135.178 | -66.604 | 1.00 | 8.89  | O |
| ATOM | 236 | N   | LEU   | A | 15 | 119.054 | 133.711 | -66.791 | 1.00 | 9.96  | N |
| ATOM | 238 | CA  | LEU   | A | 15 | 118.038 | 134.719 | -67.100 | 1.00 | 10.48 | C |
| ATOM | 240 | CB  | LEU   | A | 15 | 117.706 | 134.721 | -68.596 | 1.00 | 10.79 | C |
| ATOM | 243 | CG  | LEU   | A | 15 | 117.664 | 136.029 | -69.400 | 1.00 | 10.69 | C |
| ATOM | 245 | CD1 | LEU   | A | 15 | 116.570 | 135.983 | -70.451 | 1.00 | 9.32  | C |
| ATOM | 249 | CD2 | LEU   | A | 15 | 117.545 | 137.291 | -68.530 | 1.00 | 10.39 | C |
| ATOM | 253 | C   | LEU   | A | 15 | 116.758 | 134.473 | -66.342 | 1.00 | 11.24 | C |
| ATOM | 254 | O   | LEU   | A | 15 | 116.152 | 135.395 | -65.829 | 1.00 | 12.18 | O |
| ATOM | 255 | N   | SER   | A | 16 | 116.307 | 133.233 | -66.319 | 1.00 | 12.02 | N |
| ATOM | 257 | CA  | SER   | A | 16 | 115.137 | 132.861 | -65.541 | 1.00 | 12.37 | C |
| ATOM | 259 | CB  | SER   | A | 16 | 113.888 | 132.788 | -66.433 | 1.00 | 12.57 | C |
| ATOM | 262 | OG  | SER   | A | 16 | 113.700 | 131.504 | -67.036 | 1.00 | 12.24 | O |
| ATOM | 264 | C   | SER   | A | 16 | 115.408 | 131.531 | -64.862 | 1.00 | 12.97 | C |
| ATOM | 265 | O   | SER   | A | 16 | 116.470 | 130.924 | -65.050 | 1.00 | 12.72 | O |
| ATOM | 266 | N   | ASN   | A | 17 | 114.428 | 131.072 | -64.089 | 1.00 | 13.28 | N |
| ATOM | 268 | CA  | ASN   | A | 17 | 114.549 | 129.805 | -63.390 | 1.00 | 13.20 | C |
| ATOM | 270 | CB  | ASN   | A | 17 | 113.642 | 129.773 | -62.164 | 1.00 | 13.49 | C |
| ATOM | 273 | CG  | ASN   | A | 17 | 112.179 | 129.677 | -62.506 | 1.00 | 13.52 | C |
| ATOM | 274 | OD1 | ASN   | A | 17 | 111.345 | 129.647 | -61.611 | 1.00 | 16.65 | O |
| ATOM | 275 | ND2 | ASN   | A | 17 | 111.855 | 129.613 | -63.775 | 1.00 | 13.84 | N |
| ATOM | 278 | C   | ASN   | A | 17 | 114.306 | 128.594 | -64.277 | 1.00 | 12.94 | C |
| ATOM | 279 | O   | ASN   | A | 17 | 114.317 | 127.468 | -63.785 | 1.00 | 13.30 | O |
| ATOM | 280 | N   | LYS   | A | 18 | 114.075 | 128.833 | -65.569 | 1.00 | 12.50 | N |
| ATOM | 282 | CA  | LYS   | A | 18 | 113.956 | 127.784 | -66.582 | 1.00 | 12.02 | C |
| ATOM | 284 | CB  | LYS   | A | 18 | 112.783 | 128.094 | -67.506 | 1.00 | 12.82 | C |
| ATOM | 287 | CG  | LYS   | A | 18 | 111.424 | 128.221 | -66.805 | 1.00 | 14.89 | C |
| ATOM | 290 | CD  | LYS   | A | 18 | 111.224 | 127.097 | -65.788 | 1.00 | 19.16 | C |
| ATOM | 293 | CE  | LYS   | A | 18 | 109.765 | 126.941 | -65.306 | 1.00 | 21.59 | C |
| ATOM | 296 | NZ  | LYS   | A | 18 | 108.762 | 127.453 | -66.296 | 1.00 | 24.06 | N |
| ATOM | 300 | C   | LYS   | A | 18 | 115.221 | 127.661 | -67.432 | 1.00 | 10.90 | C |
| ATOM | 301 | O   | LYS   | A | 18 | 115.340 | 126.734 | -68.229 | 1.00 | 10.50 | O |

(SEQ ID NO. 34)

FIGURE 20-2

| | | | | | | | | | |
|---|---|---|---|---|---|---|---|---|---|
| ATOM | 302 | N | SER A | 19 | 116.136 | 128.614 | -67.258 | 1.00 9.84 | N |
| ATOM | 304 | CA | SER A | 19 | 117.416 | 128.646 | -67.944 | 1.00 9.33 | C |
| ATOM | 306 | CB | SER A | 19 | 118.241 | 129.878 | -67.501 | 1.00 9.21 | C |
| ATOM | 309 | OG | SER A | 19 | 117.792 | 131.088 | -68.075 | 1.00 6.68 | O |
| ATOM | 311 | C | SER A | 19 | 118.251 | 127.402 | -67.650 | 1.00 9.36 | C |
| ATOM | 312 | O | SER A | 19 | 118.323 | 126.928 | -66.526 | 1.00 8.77 | O |
| ATOM | 313 | N | ILE A | 20 | 118.904 | 126.896 | -68.683 | 1.00 9.92 | N |
| ATOM | 315 | CA | ILE A | 20 | 119.878 | 125.821 | -68.529 | 1.00 9.56 | C |
| ATOM | 317 | CB | ILE A | 20 | 120.476 | 125.446 | -69.884 | 1.00 9.07 | C |
| ATOM | 319 | CG1 | ILE A | 20 | 119.386 | 124.792 | -70.748 | 1.00 9.49 | C |
| ATOM | 322 | CD1 | ILE A | 20 | 119.704 | 124.695 | -72.227 | 1.00 10.27 | C |
| ATOM | 326 | CG2 | ILE A | 20 | 121.648 | 124.499 | -69.690 | 1.00 9.07 | C |
| ATOM | 330 | C | ILE A | 20 | 120.950 | 126.203 | -67.515 | 1.00 9.69 | C |
| ATOM | 331 | O | ILE A | 20 | 121.329 | 125.381 | -66.698 | 1.00 10.10 | O |
| ATOM | 332 | N | ALA A | 21 | 121.396 | 127.459 | -67.543 | 1.00 9.91 | N |
| ATOM | 334 | CA | ALA A | 21 | 122.378 | 127.979 | -66.583 | 1.00 9.99 | C |
| ATOM | 336 | CB | ALA A | 21 | 122.622 | 129.467 | -66.843 | 1.00 9.86 | C |
| ATOM | 340 | C | ALA A | 21 | 121.947 | 127.758 | -65.124 | 1.00 10.24 | C |
| ATOM | 341 | O | ALA A | 21 | 122.768 | 127.557 | -64.230 | 1.00 10.12 | O |
| ATOM | 342 | N | TYR A | 22 | 120.645 | 127.813 | -64.898 | 1.00 10.76 | N |
| ATOM | 344 | CA | TYR A | 22 | 120.093 | 127.615 | -63.580 | 1.00 11.39 | C |
| ATOM | 346 | CB | TYR A | 22 | 118.621 | 128.049 | -63.564 | 1.00 11.97 | C |
| ATOM | 349 | CG | TYR A | 22 | 118.005 | 128.109 | -62.190 | 1.00 13.75 | C |
| ATOM | 350 | CD1 | TYR A | 22 | 118.560 | 128.895 | -61.189 | 1.00 16.08 | C |
| ATOM | 352 | CE1 | TYR A | 22 | 117.978 | 128.965 | -59.932 | 1.00 17.55 | C |
| ATOM | 354 | CZ | TYR A | 22 | 116.837 | 128.223 | -59.671 | 1.00 18.14 | C |
| ATOM | 355 | OH | TYR A | 22 | 116.260 | 128.272 | -58.444 | 1.00 19.20 | O |
| ATOM | 357 | CE2 | TYR A | 22 | 116.272 | 127.432 | -60.644 | 1.00 18.00 | C |
| ATOM | 359 | CD2 | TYR A | 22 | 116.855 | 127.385 | -61.899 | 1.00 17.15 | C |
| ATOM | 361 | C | TYR A | 22 | 120.242 | 126.168 | -63.137 | 1.00 10.89 | C |
| ATOM | 362 | O | TYR A | 22 | 120.551 | 125.912 | -61.980 | 1.00 11.11 | O |
| ATOM | 363 | N | GLY A | 23 | 120.004 | 125.228 | -64.042 | 1.00 10.60 | N |
| ATOM | 365 | CA | GLY A | 23 | 120.252 | 123.821 | -63.769 | 1.00 10.89 | C |
| ATOM | 368 | C | GLY A | 23 | 121.740 | 123.521 | -63.578 | 1.00 11.08 | C |
| ATOM | 369 | O | GLY A | 23 | 122.128 | 122.714 | -62.722 | 1.00 11.09 | O |
| ATOM | 370 | N | ILE A | 24 | 122.587 | 124.195 | -64.356 | 1.00 10.88 | N |
| ATOM | 372 | CA | ILE A | 24 | 124.022 | 124.065 | -64.185 | 1.00 10.59 | C |
| ATOM | 374 | CB | ILE A | 24 | 124.784 | 124.829 | -65.304 | 1.00 10.49 | C |
| ATOM | 376 | CG1 | ILE A | 24 | 124.539 | 124.147 | -66.654 | 1.00 10.90 | C |
| ATOM | 379 | CD1 | ILE A | 24 | 124.796 | 125.011 | -67.849 | 1.00 11.60 | C |
| ATOM | 383 | CG2 | ILE A | 24 | 126.281 | 124.870 | -65.032 | 1.00 9.69 | C |
| ATOM | 387 | C | ILE A | 24 | 124.407 | 124.532 | -62.780 | 1.00 10.80 | C |
| ATOM | 388 | O | ILE A | 24 | 125.144 | 123.842 | -62.096 | 1.00 10.41 | O |
| ATOM | 389 | N | ALA A | 25 | 123.879 | 125.675 | -62.341 | 1.00 11.43 | N |
| ATOM | 391 | CA | ALA A | 25 | 124.264 | 126.272 | -61.044 | 1.00 12.01 | C |
| ATOM | 393 | CB | ALA A | 25 | 123.706 | 127.696 | -60.900 | 1.00 11.88 | C |
| ATOM | 397 | C | ALA A | 25 | 123.832 | 125.418 | -59.857 | 1.00 12.17 | C |
| ATOM | 398 | O | ALA A | 25 | 124.591 | 125.259 | -58.896 | 1.00 12.51 | O |
| ATOM | 399 | N | LYS A | 26 | 122.619 | 124.878 | -59.936 | 1.00 12.45 | N |
| ATOM | 401 | CA | LYS A | 26 | 122.103 | 123.926 | -58.951 | 1.00 13.02 | C |
| ATOM | 403 | CB | LYS A | 26 | 120.726 | 123.420 | -59.366 | 1.00 13.31 | C |
| ATOM | 406 | CG | LYS A | 26 | 119.585 | 124.257 | -58.828 | 1.00 15.63 | C |
| ATOM | 409 | CD | LYS A | 26 | 118.264 | 123.573 | -59.072 | 1.00 18.34 | C |
| ATOM | 412 | CE | LYS A | 26 | 117.197 | 124.064 | -58.127 | 1.00 22.07 | C |
| ATOM | 415 | NZ | LYS A | 26 | 116.433 | 125.206 | -58.701 | 1.00 25.21 | N |
| ATOM | 419 | C | LYS A | 26 | 122.996 | 122.708 | -58.800 | 1.00 12.88 | C |
| ATOM | 420 | O | LYS A | 26 | 123.263 | 122.260 | -57.679 | 1.00 12.49 | O |
| ATOM | 421 | N | ALA A | 27 | 123.404 | 122.160 | -59.944 | 1.00 12.81 | N |
| ATOM | 423 | CA | ALA A | 27 | 124.215 | 120.955 | -60.003 | 1.00 12.92 | C |
| ATOM | 425 | CB | ALA A | 27 | 124.310 | 120.432 | -61.436 | 1.00 13.15 | C |
| ATOM | 429 | C | ALA A | 27 | 125.595 | 121.234 | -59.466 | 1.00 13.05 | C |
| ATOM | 430 | O | ALA A | 27 | 126.152 | 120.419 | -58.740 | 1.00 13.54 | O |
| ATOM | 431 | N | MET A | 28 | 126.147 | 122.391 | -59.805 | 1.00 12.76 | N |
| ATOM | 433 | CA | MET A | 28 | 127.513 | 122.690 | -59.434 | 1.00 12.86 | C |
| ATOM | 435 | CB | MET A | 28 | 128.076 | 123.803 | -60.315 | 1.00 12.63 | C |
| ATOM | 438 | CG | MET A | 28 | 128.349 | 123.365 | -61.756 | 1.00 12.07 | C |
| ATOM | 441 | SD | MET A | 28 | 129.107 | 124.656 | -62.742 | 1.00 11.52 | S |
| ATOM | 442 | CE | MET A | 28 | 129.706 | 123.667 | -64.100 | 1.00 12.96 | C |

(SEQ ID NO. 34)

FIGURE 20-3

| ATOM | 446 | C | MET | A | 28 | 127.571 | 123.074 | -57.960 | 1.00 | 13.47 | C |
| ATOM | 447 | O | MET | A | 28 | 128.549 | 122.780 | -57.275 | 1.00 | 14.12 | O |
| ATOM | 448 | N | HIS | A | 29 | 126.520 | 123.722 | -57.475 | 1.00 | 13.42 | N |
| ATOM | 450 | CA | HIS | A | 29 | 126.445 | 124.105 | -56.075 | 1.00 | 13.58 | C |
| ATOM | 452 | CB | HIS | A | 29 | 125.254 | 125.020 | -55.823 | 1.00 | 13.21 | C |
| ATOM | 455 | CG | HIS | A | 29 | 125.182 | 125.517 | -54.424 | 1.00 | 12.72 | C |
| ATOM | 456 | ND1 | HIS | A | 29 | 125.998 | 126.523 | -53.954 | 1.00 | 13.40 | N |
| ATOM | 458 | CE1 | HIS | A | 29 | 125.717 | 126.751 | -52.681 | 1.00 | 13.68 | C |
| ATOM | 460 | NE2 | HIS | A | 29 | 124.758 | 125.920 | -52.308 | 1.00 | 12.45 | N |
| ATOM | 462 | CD2 | HIS | A | 29 | 124.406 | 125.138 | -53.380 | 1.00 | 12.46 | C |
| ATOM | 464 | C | HIS | A | 29 | 126.327 | 122.868 | -55.192 | 1.00 | 13.57 | C |
| ATOM | 465 | O | HIS | A | 29 | 126.989 | 122.783 | -54.162 | 1.00 | 13.92 | O |
| ATOM | 466 | N | ARG | A | 30 | 125.486 | 121.923 | -55.615 | 1.00 | 13.62 | N |
| ATOM | 468 | CA | ARG | A | 30 | 125.329 | 120.636 | -54.942 | 1.00 | 13.76 | C |
| ATOM | 470 | CB | ARG | A | 30 | 124.288 | 119.775 | -55.665 | 1.00 | 13.53 | C |
| ATOM | 473 | CG | ARG | A | 30 | 123.998 | 118.418 | -54.989 | 1.00 | 14.63 | C |
| ATOM | 476 | CD | ARG | A | 30 | 123.335 | 117.390 | -55.917 | 1.00 | 15.21 | C |
| ATOM | 479 | NE | ARG | A | 30 | 124.222 | 116.960 | -57.010 | 1.00 | 16.84 | N |
| ATOM | 481 | CZ | ARG | A | 30 | 123.981 | 117.111 | -58.333 | 1.00 | 16.69 | C |
| ATOM | 482 | NH1 | ARG | A | 30 | 122.885 | 117.694 | -58.793 | 1.00 | 15.80 | N |
| ATOM | 485 | NH2 | ARG | A | 30 | 124.856 | 116.653 | -59.208 | 1.00 | 17.91 | N |
| ATOM | 488 | C | ARG | A | 30 | 126.671 | 119.899 | -54.845 | 1.00 | 13.62 | C |
| ATOM | 489 | O | ARG | A | 30 | 126.975 | 119.283 | -53.820 | 1.00 | 13.94 | O |
| ATOM | 490 | N | GLU | A | 31 | 127.482 | 120.006 | -55.895 | 1.00 | 13.12 | N |
| ATOM | 492 | CA | GLU | A | 31 | 128.780 | 119.330 | -55.950 | 1.00 | 13.23 | C |
| ATOM | 494 | CB | GLU | A | 31 | 129.097 | 118.901 | -57.397 | 1.00 | 12.92 | C |
| ATOM | 497 | CG | GLU | A | 31 | 128.147 | 117.871 | -57.971 | 1.00 | 12.59 | C |
| ATOM | 500 | CD | GLU | A | 31 | 128.157 | 116.548 | -57.215 | 1.00 | 13.50 | C |
| ATOM | 501 | OE1 | GLU | A | 31 | 129.032 | 116.320 | -56.351 | 1.00 | 12.64 | O |
| ATOM | 502 | OE2 | GLU | A | 31 | 127.269 | 115.716 | -57.490 | 1.00 | 16.58 | O |
| ATOM | 503 | C | GLU | A | 31 | 129.945 | 120.147 | -55.355 | 1.00 | 12.95 | C |
| ATOM | 504 | O | GLU | A | 31 | 131.098 | 119.782 | -55.502 | 1.00 | 12.49 | O |
| ATOM | 505 | N | GLY | A | 32 | 129.633 | 121.260 | -54.702 | 1.00 | 13.52 | N |
| ATOM | 507 | CA | GLY | A | 32 | 130.586 | 121.967 | -53.855 | 1.00 | 13.41 | C |
| ATOM | 510 | C | GLY | A | 32 | 131.368 | 123.067 | -54.536 | 1.00 | 13.56 | C |
| ATOM | 511 | O | GLY | A | 32 | 132.342 | 123.569 | -53.977 | 1.00 | 14.10 | O |
| ATOM | 512 | N | ALA | A | 33 | 130.967 | 123.435 | -55.744 | 1.00 | 13.70 | N |
| ATOM | 514 | CA | ALA | A | 33 | 131.631 | 124.510 | -56.468 | 1.00 | 14.04 | C |
| ATOM | 516 | CB | ALA | A | 33 | 131.173 | 124.556 | -57.933 | 1.00 | 13.90 | C |
| ATOM | 520 | C | ALA | A | 33 | 131.356 | 125.844 | -55.796 | 1.00 | 14.37 | C |
| ATOM | 521 | O | ALA | A | 33 | 130.254 | 126.075 | -55.262 | 1.00 | 14.24 | O |
| ATOM | 522 | N | GLU | A | 34 | 132.373 | 126.704 | -55.805 | 1.00 | 14.41 | N |
| ATOM | 524 | CA | GLU | A | 34 | 132.191 | 128.122 | -55.541 | 1.00 | 14.76 | C |
| ATOM | 526 | CB | GLU | A | 34 | 133.456 | 128.729 | -54.939 | 1.00 | 15.10 | C |
| ATOM | 529 | CG | GLU | A | 34 | 133.168 | 129.946 | -54.063 | 1.00 | 18.86 | C |
| ATOM | 532 | CD | GLU | A | 34 | 134.403 | 130.466 | -53.348 | 1.00 | 22.47 | C |
| ATOM | 533 | OE1 | GLU | A | 34 | 134.604 | 131.706 | -53.301 | 1.00 | 22.05 | O |
| ATOM | 534 | OE2 | GLU | A | 34 | 135.174 | 129.616 | -52.832 | 1.00 | 28.20 | O |
| ATOM | 535 | C | GLU | A | 34 | 131.822 | 128.808 | -56.861 | 1.00 | 14.05 | C |
| ATOM | 536 | O | GLU | A | 34 | 132.573 | 128.735 | -57.831 | 1.00 | 14.27 | O |
| ATOM | 537 | N | LEU | A | 35 | 130.671 | 129.478 | -56.891 | 1.00 | 13.05 | N |
| ATOM | 539 | CA | LEU | A | 35 | 130.108 | 130.004 | -58.133 | 1.00 | 12.38 | C |
| ATOM | 541 | CB | LEU | A | 35 | 128.681 | 129.475 | -58.323 | 1.00 | 12.29 | C |
| ATOM | 544 | CG | LEU | A | 35 | 128.530 | 127.946 | -58.391 | 1.00 | 11.58 | C |
| ATOM | 546 | CD1 | LEU | A | 35 | 127.087 | 127.574 | -58.619 | 1.00 | 11.58 | C |
| ATOM | 550 | CD2 | LEU | A | 35 | 129.415 | 127.349 | -59.476 | 1.00 | 11.91 | C |
| ATOM | 554 | C | LEU | A | 35 | 130.076 | 131.521 | -58.208 | 1.00 | 12.42 | C |
| ATOM | 555 | O | LEU | A | 35 | 129.779 | 132.211 | -57.220 | 1.00 | 12.00 | O |
| ATOM | 556 | N | ALA | A | 36 | 130.373 | 132.030 | -59.401 | 1.00 | 11.97 | N |
| ATOM | 558 | CA | ALA | A | 36 | 130.152 | 133.424 | -59.751 | 1.00 | 11.63 | C |
| ATOM | 560 | CB | ALA | A | 36 | 131.480 | 134.135 | -59.935 | 1.00 | 11.56 | C |
| ATOM | 564 | C | ALA | A | 36 | 129.330 | 133.454 | -61.041 | 1.00 | 11.65 | C |
| ATOM | 565 | O | ALA | A | 36 | 129.352 | 132.485 | -61.815 | 1.00 | 12.06 | O |
| ATOM | 566 | N | PHE | A | 37 | 128.603 | 134.554 | -61.254 | 1.00 | 10.95 | N |
| ATOM | 568 | CA | PHE | A | 37 | 127.653 | 134.687 | -62.354 | 1.00 | 10.75 | C |
| ATOM | 570 | CB | PHE | A | 37 | 126.213 | 134.570 | -61.848 | 1.00 | 10.84 | C |
| ATOM | 573 | CG | PHE | A | 37 | 125.930 | 133.287 | -61.104 | 1.00 | 12.15 | C |
| ATOM | 574 | CD1 | PHE | A | 37 | 126.298 | 133.143 | -59.764 | 1.00 | 12.68 | C |

(SEQ ID NO. 34)

FIGURE 20-4

```
ATOM    576  CE1 PHE A   37     126.042 131.959 -59.084  1.00 13.21           C
ATOM    578  CZ  PHE A   37     125.411 130.914 -59.731  1.00 13.00           C
ATOM    580  CE2 PHE A   37     125.046 131.042 -61.055  1.00 12.77           C
ATOM    582  CD2 PHE A   37     125.301 132.228 -61.736  1.00 12.94           C
ATOM    584  C   PHE A   37     127.801 136.027 -63.059  1.00 10.27           C
ATOM    585  O   PHE A   37     128.180 137.022 -62.443  1.00 10.15           O
ATOM    586  N   THR A   38     127.481 136.051 -64.345  1.00  9.56           N
ATOM    588  CA  THR A   38     127.434 137.299 -65.083  1.00  9.58           C
ATOM    590  CB  THR A   38     128.232 137.178 -66.369  1.00  9.70           C
ATOM    592  OG1 THR A   38     127.696 136.117 -67.170  1.00  8.95           O
ATOM    594  CG2 THR A   38     129.662 136.756 -66.076  1.00  9.57           C
ATOM    598  C   THR A   38     126.003 137.733 -65.400  1.00  9.75           C
ATOM    599  O   THR A   38     125.077 136.917 -65.377  1.00  9.18           O
ATOM    600  N   TYR A   39     125.837 139.026 -65.699  1.00 10.09           N
ATOM    602  CA  TYR A   39     124.558 139.572 -66.155  1.00 10.06           C
ATOM    604  CB  TYR A   39     123.844 140.280 -65.000  1.00 10.84           C
ATOM    607  CG  TYR A   39     124.634 141.453 -64.446  1.00 11.33           C
ATOM    608  CD1 TYR A   39     125.575 141.266 -63.445  1.00 11.23           C
ATOM    610  CE1 TYR A   39     126.316 142.331 -62.948  1.00 12.62           C
ATOM    612  CZ  TYR A   39     126.109 143.601 -63.445  1.00 14.19           C
ATOM    613  OH  TYR A   39     126.847 144.661 -62.948  1.00 16.20           O
ATOM    615  CE2 TYR A   39     125.170 143.813 -64.452  1.00 12.97           C
ATOM    617  CD2 TYR A   39     124.451 142.740 -64.949  1.00 12.15           C
ATOM    619  C   TYR A   39     124.772 140.564 -67.287  1.00 10.19           C
ATOM    620  O   TYR A   39     125.864 141.092 -67.476  1.00 10.10           O
ATOM    621  N   VAL A   40     123.712 140.833 -68.032  1.00 10.34           N
ATOM    623  CA  VAL A   40     123.749 141.832 -69.083  1.00 10.68           C
ATOM    625  CB  VAL A   40     123.037 141.334 -70.352  1.00 10.62           C
ATOM    627  CG1 VAL A   40     123.171 142.360 -71.470  1.00 10.62           C
ATOM    631  CG2 VAL A   40     123.614 140.002 -70.780  1.00 10.60           C
ATOM    635  C   VAL A   40     123.089 143.123 -68.614  1.00 11.22           C
ATOM    636  O   VAL A   40     121.880 143.165 -68.381  1.00 11.33           O
ATOM    637  N   GLY A   41     123.909 144.161 -68.456  1.00 11.76           N
ATOM    639  CA  GLY A   41     123.462 145.522 -68.211  1.00 11.58           C
ATOM    642  C   GLY A   41     122.350 145.662 -67.202  1.00 11.42           C
ATOM    643  O   GLY A   41     122.506 145.284 -66.039  1.00 11.35           O
ATOM    644  N   GLN A   42     121.219 146.184 -67.672  1.00 11.47           N
ATOM    646  CA  GLN A   42     120.085 146.555 -66.813  1.00 11.68           C
ATOM    648  CB  GLN A   42     119.102 147.433 -67.603  1.00 11.68           C
ATOM    651  CG  GLN A   42     118.282 146.700 -68.678  1.00 11.12           C
ATOM    654  CD  GLN A   42     117.737 147.637 -69.731  1.00 10.07           C
ATOM    655  OE1 GLN A   42     116.551 147.625 -70.034  1.00 12.81           O
ATOM    656  NE2 GLN A   42     118.592 148.444 -70.286  1.00 10.33           N
ATOM    659  C   GLN A   42     119.350 145.369 -66.169  1.00 11.88           C
ATOM    660  O   GLN A   42     118.603 145.542 -65.211  1.00 12.09           O
ATOM    661  N   PHE A   43     119.611 144.165 -66.673  1.00 12.08           N
ATOM    663  CA  PHE A   43     119.004 142.930 -66.169  1.00 12.04           C
ATOM    665  CB  PHE A   43     118.841 141.944 -67.331  1.00 11.35           C
ATOM    668  CG  PHE A   43     118.006 142.496 -68.451  1.00 12.27           C
ATOM    669  CD1 PHE A   43     118.599 143.076 -69.574  1.00 12.71           C
ATOM    671  CE1 PHE A   43     117.818 143.610 -70.608  1.00 13.02           C
ATOM    673  CZ  PHE A   43     116.434 143.591 -70.514  1.00 12.70           C
ATOM    675  CE2 PHE A   43     115.832 143.028 -69.409  1.00 12.82           C
ATOM    677  CD2 PHE A   43     116.620 142.485 -68.371  1.00 13.50           C
ATOM    679  C   PHE A   43     119.793 142.316 -65.000  1.00 12.21           C
ATOM    680  O   PHE A   43     119.592 141.157 -64.636  1.00 12.39           O
ATOM    681  N   LYS A   44     120.653 143.119 -64.390  1.00 12.35           N
ATOM    683  CA  LYS A   44     121.478 142.697 -63.268  1.00 12.91           C
ATOM    685  CB  LYS A   44     122.251 143.908 -62.741  1.00 12.83           C
ATOM    688  CG  LYS A   44     123.192 143.636 -61.577  1.00 14.01           C
ATOM    691  CD  LYS A   44     123.870 144.923 -61.084  1.00 13.54           C
ATOM    694  CE  LYS A   44     124.681 144.663 -59.810  1.00 14.83           C
ATOM    697  NZ  LYS A   44     125.715 145.731 -59.566  1.00 15.20           N
ATOM    701  C   LYS A   44     120.702 142.033 -62.127  1.00 13.17           C
ATOM    702  O   LYS A   44     121.112 140.997 -61.627  1.00 13.46           O
ATOM    703  N   ASP A   45     119.596 142.622 -61.706  1.00 13.74           N
ATOM    705  CA  ASP A   45     118.899 142.173 -60.485  1.00 14.14           C
ATOM    707  CB  ASP A   45     118.002 143.286 -59.975  1.00 13.86           C
```

(SEQ ID NO. 34)

FIGURE 20-5

```
ATOM    710  CG   ASP A  45     118.793 144.421 -59.443  1.00 14.22           C
ATOM    711  OD1  ASP A  45     120.049 144.283 -59.443  1.00 11.97           O
ATOM    712  OD2  ASP A  45     118.264 145.471 -58.998  1.00 15.48           O
ATOM    713  C    ASP A  45     118.099 140.903 -60.658  1.00 14.59           C
ATOM    714  O    ASP A  45     117.813 140.201 -59.697  1.00 14.67           O
ATOM    715  N    ARG A  46     117.731 140.639 -61.900  1.00 15.17           N
ATOM    717  CA   ARG A  46     117.158 139.370 -62.314  1.00 15.74           C
ATOM    719  CB   ARG A  46     117.037 139.393 -63.844  1.00 16.25           C
ATOM    722  CG   ARG A  46     115.789 138.823 -64.369  1.00 17.82           C
ATOM    725  CD   ARG A  46     115.886 138.491 -65.802  1.00 19.59           C
ATOM    728  NE   ARG A  46     114.720 139.002 -66.498  1.00 23.12           N
ATOM    730  CZ   ARG A  46     113.722 138.279 -66.958  1.00 23.29           C
ATOM    731  NH1  ARG A  46     113.698 136.957 -66.841  1.00 23.54           N
ATOM    734  NH2  ARG A  46     112.731 138.903 -67.566  1.00 26.15           N
ATOM    737  C    ARG A  46     118.079 138.213 -61.929  1.00 15.54           C
ATOM    738  O    ARG A  46     117.651 137.181 -61.409  1.00 15.63           O
ATOM    739  N    VAL A  47     119.351 138.408 -62.242  1.00 15.23           N
ATOM    741  CA   VAL A  47     120.391 137.422 -62.019  1.00 15.09           C
ATOM    743  CB   VAL A  47     121.653 137.776 -62.830  1.00 15.00           C
ATOM    745  CG1  VAL A  47     122.812 136.851 -62.494  1.00 14.57           C
ATOM    749  CG2  VAL A  47     121.331 137.776 -64.334  1.00 14.72           C
ATOM    753  C    VAL A  47     120.721 137.358 -60.541  1.00 14.96           C
ATOM    754  O    VAL A  47     120.897 136.274 -60.022  1.00 15.06           O
ATOM    755  N    GLU A  48     120.781 138.510 -59.868  1.00 15.14           N
ATOM    757  CA   GLU A  48     121.083 138.559 -58.430  1.00 15.30           C
ATOM    759  CB   GLU A  48     121.049 139.992 -57.896  1.00 15.26           C
ATOM    762  CG   GLU A  48     122.136 140.918 -58.439  1.00 15.75           C
ATOM    765  CD   GLU A  48     123.465 140.808 -57.713  1.00 16.48           C
ATOM    766  OE1  GLU A  48     123.715 139.815 -56.984  1.00 17.57           O
ATOM    767  OE2  GLU A  48     124.276 141.732 -57.877  1.00 18.00           O
ATOM    768  C    GLU A  48     120.100 137.709 -57.632  1.00 15.71           C
ATOM    769  O    GLU A  48     120.499 136.965 -56.733  1.00 15.74           O
ATOM    770  N    LYS A  49     118.818 137.813 -57.962  1.00 15.99           N
ATOM    772  CA   LYS A  49     117.789 137.083 -57.228  1.00 16.69           C
ATOM    774  CB   LYS A  49     116.393 137.662 -57.486  1.00 17.02           C
ATOM    777  CG   LYS A  49     116.150 139.016 -56.783  1.00 20.17           C
ATOM    780  CD   LYS A  49     114.931 138.956 -55.816  1.00 24.01           C
ATOM    783  CE   LYS A  49     115.071 139.938 -54.625  1.00 25.80           C
ATOM    786  NZ   LYS A  49     114.973 141.380 -55.028  1.00 25.74           N
ATOM    790  C    LYS A  49     117.807 135.601 -57.549  1.00 15.96           C
ATOM    791  O    LYS A  49     117.534 134.793 -56.673  1.00 16.45           O
ATOM    792  N    LEU A  50     118.117 135.246 -58.796  1.00 15.17           N
ATOM    794  CA   LEU A  50     118.149 133.836 -59.216  1.00 14.45           C
ATOM    796  CB   LEU A  50     118.190 133.720 -60.745  1.00 14.43           C
ATOM    799  CG   LEU A  50     116.852 133.839 -61.469  1.00 14.26           C
ATOM    801  CD1  LEU A  50     117.042 133.997 -62.985  1.00 14.15           C
ATOM    805  CD2  LEU A  50     115.955 132.639 -61.162  1.00 15.50           C
ATOM    809  C    LEU A  50     119.346 133.085 -58.634  1.00 13.80           C
ATOM    810  O    LEU A  50     119.270 131.888 -58.373  1.00 13.77           O
ATOM    811  N    CYS A  51     120.443 133.792 -58.414  1.00 12.96           N
ATOM    813  CA   CYS A  51     121.665 133.148 -58.013  1.00 12.71           C
ATOM    815  CB   CYS A  51     122.825 133.649 -58.897  1.00 12.59           C
ATOM    818  SG   CYS A  51     123.565 135.230 -58.487  1.00 11.55           S
ATOM    819  C    CYS A  51     121.971 133.281 -56.512  1.00 12.76           C
ATOM    820  O    CYS A  51     122.922 132.677 -56.019  1.00 12.03           O
ATOM    821  N    ALA A  52     121.158 134.045 -55.785  1.00 13.13           N
ATOM    823  CA   ALA A  52     121.407 134.305 -54.350  1.00 13.34           C
ATOM    825  CB   ALA A  52     120.309 135.226 -53.751  1.00 13.09           C
ATOM    829  C    ALA A  52     121.520 133.026 -53.525  1.00 13.59           C
ATOM    830  O    ALA A  52     122.324 132.964 -52.631  1.00 13.11           O
ATOM    831  N    GLU A  53     120.707 132.019 -53.849  1.00 14.50           N
ATOM    833  CA   GLU A  53     120.681 130.723 -53.145  1.00 15.41           C
ATOM    835  CB   GLU A  53     119.495 129.872 -53.647  1.00 15.78           C
ATOM    838  CG   GLU A  53     119.597 129.486 -55.136  1.00 18.47           C
ATOM    841  CD   GLU A  53     118.429 128.656 -55.655  1.00 20.24           C
ATOM    842  OE1  GLU A  53     118.356 127.466 -55.321  1.00 24.39           O
ATOM    843  OE2  GLU A  53     117.606 129.172 -56.424  1.00 20.97           O
ATOM    844  C    GLU A  53     121.989 129.899 -53.269  1.00 15.41           C
```

(SEQ ID NO. 34)

FIGURE 20-6

| ATOM | 845 | O | GLU | A | 53 | 122.193 | 128.936 | -52.527 | 1.00 | 15.43 | O |
| ATOM | 846 | N | PHE | A | 54 | 122.857 | 130.265 | -54.208 | 1.00 | 15.39 | N |
| ATOM | 848 | CA | PHE | A | 54 | 124.118 | 129.546 | -54.432 | 1.00 | 15.45 | C |
| ATOM | 850 | CB | PHE | A | 54 | 124.428 | 129.457 | -55.932 | 1.00 | 15.30 | C |
| ATOM | 853 | CG | PHE | A | 54 | 123.284 | 128.948 | -56.753 | 1.00 | 14.02 | C |
| ATOM | 854 | CD1 | PHE | A | 54 | 122.774 | 129.703 | -57.789 | 1.00 | 11.87 | C |
| ATOM | 856 | CE1 | PHE | A | 54 | 121.704 | 129.245 | -58.533 | 1.00 | 13.27 | C |
| ATOM | 858 | CZ | PHE | A | 54 | 121.124 | 128.004 | -58.255 | 1.00 | 13.54 | C |
| ATOM | 860 | CE2 | PHE | A | 54 | 121.620 | 127.237 | -57.214 | 1.00 | 14.32 | C |
| ATOM | 862 | CD2 | PHE | A | 54 | 122.702 | 127.712 | -56.466 | 1.00 | 13.92 | C |
| ATOM | 864 | C | PHE | A | 54 | 125.279 | 130.201 | -53.709 | 1.00 | 15.79 | C |
| ATOM | 865 | O | PHE | A | 54 | 126.418 | 129.749 | -53.818 | 1.00 | 15.22 | O |
| ATOM | 866 | N | ASN | A | 55 | 124.984 | 131.267 | -52.970 | 1.00 | 16.69 | N |
| ATOM | 868 | CA | ASN | A | 55 | 125.998 | 132.006 | -52.231 | 1.00 | 17.58 | C |
| ATOM | 870 | CB | ASN | A | 55 | 126.483 | 131.177 | -51.030 | 1.00 | 17.99 | C |
| ATOM | 873 | CG | ASN | A | 55 | 125.354 | 130.872 | -50.030 | 1.00 | 20.57 | C |
| ATOM | 874 | OD1 | ASN | A | 55 | 124.371 | 131.633 | -49.895 | 1.00 | 23.79 | O |
| ATOM | 875 | ND2 | ASN | A | 55 | 125.477 | 129.740 | -49.342 | 1.00 | 24.37 | N |
| ATOM | 878 | C | ASN | A | 55 | 127.155 | 132.413 | -53.155 | 1.00 | 17.44 | C |
| ATOM | 879 | O | ASN | A | 55 | 128.303 | 131.985 | -52.981 | 1.00 | 18.12 | O |
| ATOM | 880 | N | PRO | A | 56 | 126.846 | 133.247 | -54.136 | 1.00 | 16.71 | N |
| ATOM | 881 | CA | PRO | A | 56 | 127.800 | 133.566 | -55.192 | 1.00 | 16.32 | C |
| ATOM | 883 | CB | PRO | A | 56 | 126.960 | 134.373 | -56.189 | 1.00 | 16.19 | C |
| ATOM | 886 | CG | PRO | A | 56 | 125.887 | 134.985 | -55.367 | 1.00 | 16.87 | C |
| ATOM | 889 | CD | PRO | A | 56 | 125.574 | 133.971 | -54.297 | 1.00 | 16.97 | C |
| ATOM | 892 | C | PRO | A | 56 | 128.988 | 134.379 | -54.704 | 1.00 | 16.12 | C |
| ATOM | 893 | O | PRO | A | 56 | 128.833 | 135.288 | -53.890 | 1.00 | 15.67 | O |
| ATOM | 894 | N | ALA | A | 57 | 130.168 | 134.039 | -55.212 | 1.00 | 16.13 | N |
| ATOM | 896 | CA | ALA | A | 57 | 131.394 | 134.780 | -54.941 | 1.00 | 15.77 | C |
| ATOM | 898 | CB | ALA | A | 57 | 132.589 | 133.997 | -55.442 | 1.00 | 15.65 | C |
| ATOM | 902 | C | ALA | A | 57 | 131.376 | 136.175 | -55.571 | 1.00 | 15.54 | C |
| ATOM | 903 | O | ALA | A | 57 | 131.954 | 137.102 | -55.012 | 1.00 | 15.76 | O |
| ATOM | 904 | N | ALA | A | 58 | 130.732 | 136.310 | -56.732 | 1.00 | 14.90 | N |
| ATOM | 906 | CA | ALA | A | 58 | 130.575 | 137.608 | -57.409 | 1.00 | 14.27 | C |
| ATOM | 908 | CB | ALA | A | 58 | 131.856 | 138.011 | -58.074 | 1.00 | 14.38 | C |
| ATOM | 912 | C | ALA | A | 58 | 129.475 | 137.570 | -58.454 | 1.00 | 13.73 | C |
| ATOM | 913 | O | ALA | A | 58 | 129.244 | 136.534 | -59.070 | 1.00 | 13.51 | O |
| ATOM | 914 | N | VAL | A | 59 | 128.810 | 138.706 | -58.660 | 1.00 | 13.25 | N |
| ATOM | 916 | CA | VAL | A | 59 | 127.816 | 138.862 | -59.735 | 1.00 | 12.77 | C |
| ATOM | 918 | CB | VAL | A | 59 | 126.400 | 139.054 | -59.171 | 1.00 | 12.48 | C |
| ATOM | 920 | CG1 | VAL | A | 59 | 125.352 | 139.085 | -60.269 | 1.00 | 12.14 | C |
| ATOM | 924 | CG2 | VAL | A | 59 | 126.088 | 137.953 | -58.188 | 1.00 | 12.51 | C |
| ATOM | 928 | C | VAL | A | 59 | 128.264 | 140.063 | -60.560 | 1.00 | 12.47 | C |
| ATOM | 929 | O | VAL | A | 59 | 128.262 | 141.179 | -60.068 | 1.00 | 12.50 | O |
| ATOM | 930 | N | LEU | A | 60 | 128.665 | 139.810 | -61.809 | 1.00 | 12.13 | N |
| ATOM | 932 | CA | LEU | A | 60 | 129.471 | 140.739 | -62.572 | 1.00 | 11.72 | C |
| ATOM | 934 | CB | LEU | A | 60 | 130.897 | 140.214 | -62.619 | 1.00 | 11.73 | C |
| ATOM | 937 | CG | LEU | A | 60 | 131.619 | 140.126 | -61.267 | 1.00 | 11.70 | C |
| ATOM | 939 | CD1 | LEU | A | 60 | 132.934 | 139.430 | -61.440 | 1.00 | 11.63 | C |
| ATOM | 943 | CD2 | LEU | A | 60 | 131.834 | 141.513 | -60.647 | 1.00 | 10.77 | C |
| ATOM | 947 | C | LEU | A | 60 | 128.944 | 140.960 | -63.997 | 1.00 | 11.80 | C |
| ATOM | 948 | O | LEU | A | 60 | 128.356 | 140.060 | -64.592 | 1.00 | 11.67 | O |
| ATOM | 949 | N | PRO | A | 61 | 129.136 | 142.164 | -64.543 | 1.00 | 11.44 | N |
| ATOM | 950 | CA | PRO | A | 61 | 128.650 | 142.460 | -65.891 | 1.00 | 11.11 | C |
| ATOM | 952 | CB | PRO | A | 61 | 128.799 | 143.987 | -66.000 | 1.00 | 11.25 | C |
| ATOM | 955 | CG | PRO | A | 61 | 129.852 | 144.352 | -65.018 | 1.00 | 11.33 | C |
| ATOM | 958 | CD | PRO | A | 61 | 129.812 | 143.322 | -63.927 | 1.00 | 11.12 | C |
| ATOM | 961 | C | PRO | A | 61 | 129.453 | 141.761 | -66.984 | 1.00 | 10.99 | C |
| ATOM | 962 | O | PRO | A | 61 | 130.685 | 141.725 | -66.949 | 1.00 | 11.36 | O |
| ATOM | 963 | N | CYS | A | 62 | 128.745 | 141.229 | -67.970 | 1.00 | 10.94 | N |
| ATOM | 965 | CA | CYS | A | 62 | 129.372 | 140.711 | -69.177 | 1.00 | 10.89 | C |
| ATOM | 967 | CB | CYS | A | 62 | 130.048 | 139.357 | -68.944 | 1.00 | 10.92 | C |
| ATOM | 970 | SG | CYS | A | 62 | 131.030 | 138.890 | -70.375 | 1.00 | 11.79 | S |
| ATOM | 971 | C | CYS | A | 62 | 128.364 | 140.597 | -70.302 | 1.00 | 10.29 | C |
| ATOM | 972 | O | CYS | A | 62 | 127.718 | 139.577 | -70.474 | 1.00 | 10.42 | O |
| ATOM | 973 | N | ASP | A | 63 | 128.247 | 141.680 | -71.046 | 1.00 | 10.27 | N |
| ATOM | 975 | CA | ASP | A | 63 | 127.495 | 141.743 | -72.286 | 1.00 | 10.30 | C |
| ATOM | 977 | CB | ASP | A | 63 | 126.927 | 143.149 | -72.484 | 1.00 | 10.45 | C |

(SEQ ID NO. 34)

FIGURE 20-7

| ATOM | 980 | CG | ASP A | 63 | 126.032 | 143.256 | -73.697 | 1.00 | 11.67 | C |
| ATOM | 981 | OD1 | ASP A | 63 | 126.101 | 142.389 | -74.606 | 1.00 | 12.08 | O |
| ATOM | 982 | OD2 | ASP A | 63 | 125.206 | 144.188 | -73.816 | 1.00 | 14.89 | O |
| ATOM | 983 | C | ASP A | 63 | 128.486 | 141.426 | -73.393 | 1.00 | 9.79 | C |
| ATOM | 984 | O | ASP A | 63 | 129.389 | 142.230 | -73.678 | 1.00 | 8.73 | O |
| ATOM | 985 | N | VAL A | 64 | 128.312 | 140.255 | -74.007 | 1.00 | 9.52 | N |
| ATOM | 987 | CA | VAL A | 64 | 129.336 | 139.709 | -74.907 | 1.00 | 9.63 | C |
| ATOM | 989 | CB | VAL A | 64 | 129.270 | 138.142 | -75.058 | 1.00 | 9.18 | C |
| ATOM | 991 | CG1 | VAL A | 64 | 129.496 | 137.485 | -73.731 | 1.00 | 8.94 | C |
| ATOM | 995 | CG2 | VAL A | 64 | 127.964 | 137.684 | -75.673 | 1.00 | 8.88 | C |
| ATOM | 999 | C | VAL A | 64 | 129.447 | 140.388 | -76.282 | 1.00 | 9.60 | C |
| ATOM | 1000 | O | VAL A | 64 | 130.309 | 139.999 | -77.054 | 1.00 | 9.30 | O |
| ATOM | 1001 | N | ILE A | 65 | 128.641 | 141.416 | -76.577 | 1.00 | 10.45 | N |
| ATOM | 1003 | CA | ILE A | 65 | 128.936 | 142.275 | -77.757 | 1.00 | 10.95 | C |
| ATOM | 1005 | CB | ILE A | 65 | 127.713 | 143.094 | -78.242 | 1.00 | 11.13 | C |
| ATOM | 1007 | CG1 | ILE A | 65 | 127.287 | 144.133 | -77.202 | 1.00 | 11.69 | C |
| ATOM | 1010 | CD1 | ILE A | 65 | 126.349 | 145.182 | -77.792 | 1.00 | 12.15 | C |
| ATOM | 1014 | CG2 | ILE A | 65 | 126.578 | 142.173 | -78.594 | 1.00 | 12.06 | C |
| ATOM | 1018 | C | ILE A | 65 | 130.105 | 143.230 | -77.517 | 1.00 | 10.58 | C |
| ATOM | 1019 | O | ILE A | 65 | 130.596 | 143.848 | -78.454 | 1.00 | 10.30 | O |
| ATOM | 1020 | N | SER A | 66 | 130.533 | 143.330 | -76.258 | 1.00 | 10.70 | N |
| ATOM | 1022 | CA | SER A | 66 | 131.501 | 144.328 | -75.804 | 1.00 | 10.53 | C |
| ATOM | 1024 | CB | SER A | 66 | 130.958 | 145.053 | -74.568 | 1.00 | 10.27 | C |
| ATOM | 1027 | OG | SER A | 66 | 131.958 | 145.878 | -73.998 | 1.00 | 10.42 | O |
| ATOM | 1029 | C | SER A | 66 | 132.823 | 143.661 | -75.449 | 1.00 | 10.33 | C |
| ATOM | 1030 | O | SER A | 66 | 132.880 | 142.828 | -74.549 | 1.00 | 9.73 | O |
| ATOM | 1031 | N | ASP A | 67 | 133.877 | 144.019 | -76.173 | 1.00 | 10.52 | N |
| ATOM | 1033 | CA | ASP A | 67 | 135.217 | 143.529 | -75.868 | 1.00 | 10.78 | C |
| ATOM | 1035 | CB | ASP A | 67 | 136.238 | 144.018 | -76.897 | 1.00 | 10.86 | C |
| ATOM | 1038 | CG | ASP A | 67 | 136.122 | 143.309 | -78.236 | 1.00 | 11.84 | C |
| ATOM | 1039 | OD1 | ASP A | 67 | 136.683 | 143.844 | -79.213 | 1.00 | 14.08 | O |
| ATOM | 1040 | OD2 | ASP A | 67 | 135.524 | 142.218 | -78.413 | 1.00 | 11.94 | O |
| ATOM | 1041 | C | ASP A | 67 | 135.629 | 144.012 | -74.504 | 1.00 | 10.46 | C |
| ATOM | 1042 | O | ASP A | 67 | 136.157 | 143.256 | -73.731 | 1.00 | 11.10 | O |
| ATOM | 1043 | N | GLN A | 68 | 135.376 | 145.282 | -74.217 | 1.00 | 10.92 | N |
| ATOM | 1045 | CA | GLN A | 68 | 135.802 | 145.904 | -72.962 | 1.00 | 11.08 | C |
| ATOM | 1047 | CB | GLN A | 68 | 135.448 | 147.406 | -72.932 | 1.00 | 11.47 | C |
| ATOM | 1050 | CG | GLN A | 68 | 136.191 | 148.214 | -71.854 | 1.00 | 14.09 | C |
| ATOM | 1053 | CD | GLN A | 68 | 137.709 | 147.978 | -71.877 | 1.00 | 16.34 | C |
| ATOM | 1054 | OE1 | GLN A | 68 | 138.382 | 148.407 | -72.810 | 1.00 | 18.14 | O |
| ATOM | 1055 | NE2 | GLN A | 68 | 138.232 | 147.260 | -70.870 | 1.00 | 15.78 | N |
| ATOM | 1058 | C | GLN A | 68 | 135.200 | 145.204 | -71.762 | 1.00 | 10.44 | C |
| ATOM | 1059 | O | GLN A | 68 | 135.907 | 144.951 | -70.804 | 1.00 | 10.42 | O |
| ATOM | 1060 | N | GLU A | 69 | 133.916 | 144.869 | -71.821 | 1.00 | 10.08 | N |
| ATOM | 1062 | CA | GLU A | 69 | 133.269 | 144.149 | -70.718 | 1.00 | 10.69 | C |
| ATOM | 1064 | CB | GLU A | 69 | 131.743 | 144.099 | -70.884 | 1.00 | 10.70 | C |
| ATOM | 1067 | CG | GLU A | 69 | 131.050 | 145.431 | -70.670 | 1.00 | 10.97 | C |
| ATOM | 1070 | CD | GLU A | 69 | 129.546 | 145.297 | -70.464 | 1.00 | 12.22 | C |
| ATOM | 1071 | OE1 | GLU A | 69 | 128.808 | 146.207 | -70.896 | 1.00 | 14.95 | O |
| ATOM | 1072 | OE2 | GLU A | 69 | 129.091 | 144.302 | -69.861 | 1.00 | 11.79 | O |
| ATOM | 1073 | C | GLU A | 69 | 133.802 | 142.726 | -70.546 | 1.00 | 10.83 | C |
| ATOM | 1074 | O | GLU A | 69 | 133.863 | 142.215 | -69.436 | 1.00 | 9.33 | O |
| ATOM | 1075 | N | ILE A | 70 | 134.173 | 142.077 | -71.643 | 1.00 | 11.39 | N |
| ATOM | 1077 | CA | ILE A | 70 | 134.706 | 140.733 | -71.534 | 1.00 | 12.28 | C |
| ATOM | 1079 | CB | ILE A | 70 | 134.771 | 140.040 | -72.901 | 1.00 | 12.32 | C |
| ATOM | 1081 | CG1 | ILE A | 70 | 133.350 | 139.792 | -73.418 | 1.00 | 12.11 | C |
| ATOM | 1084 | CD1 | ILE A | 70 | 133.291 | 139.349 | -74.862 | 1.00 | 12.92 | C |
| ATOM | 1088 | CG2 | ILE A | 70 | 135.492 | 138.691 | -72.773 | 1.00 | 13.25 | C |
| ATOM | 1092 | C | ILE A | 70 | 136.068 | 140.769 | -70.835 | 1.00 | 12.85 | C |
| ATOM | 1093 | O | ILE A | 70 | 136.355 | 139.908 | -70.017 | 1.00 | 12.97 | O |
| ATOM | 1094 | N | LYS A | 71 | 136.874 | 141.788 | -71.122 | 1.00 | 13.52 | N |
| ATOM | 1096 | CA | LYS A | 71 | 138.171 | 141.964 | -70.462 | 1.00 | 14.12 | C |
| ATOM | 1098 | CB | LYS A | 71 | 138.964 | 143.100 | -71.114 | 1.00 | 14.55 | C |
| ATOM | 1101 | CG | LYS A | 71 | 139.318 | 142.865 | -72.584 | 1.00 | 17.86 | C |
| ATOM | 1104 | CD | LYS A | 71 | 140.221 | 143.975 | -73.141 | 1.00 | 20.13 | C |
| ATOM | 1107 | CE | LYS A | 71 | 140.070 | 144.091 | -74.655 | 1.00 | 21.53 | C |
| ATOM | 1110 | NZ | LYS A | 71 | 140.914 | 145.193 | -75.186 | 1.00 | 23.55 | N |
| ATOM | 1114 | C | LYS A | 71 | 138.006 | 142.290 | -68.983 | 1.00 | 13.36 | C |

(SEQ ID NO. 34)

FIGURE 20-8

```
ATOM  1115  O    LYS A  71    138.652 141.675 -68.128  1.00 12.86           O
ATOM  1116  N    ASP A  72    137.141 143.262 -68.703  1.00 12.98           N
ATOM  1118  CA   ASP A  72    136.943 143.773 -67.353  1.00 13.23           C
ATOM  1120  CB   ASP A  72    136.062 145.025 -67.370  1.00 13.64           C
ATOM  1123  CG   ASP A  72    136.753 146.226 -67.983  1.00 14.57           C
ATOM  1124  OD1  ASP A  72    137.978 146.178 -68.215  1.00 15.60           O
ATOM  1125  OD2  ASP A  72    136.137 147.269 -68.293  1.00 16.77           O
ATOM  1126  C    ASP A  72    136.329 142.725 -66.428  1.00 13.11           C
ATOM  1127  O    ASP A  72    136.572 142.735 -65.213  1.00 12.85           O
ATOM  1128  N    LEU A  73    135.550 141.813 -67.006  1.00 12.94           N
ATOM  1130  CA   LEU A  73    135.012 140.689 -66.257  1.00 12.89           C
ATOM  1132  CB   LEU A  73    134.307 139.696 -67.177  1.00 12.92           C
ATOM  1135  CG   LEU A  73    133.896 138.352 -66.548  1.00 12.64           C
ATOM  1137  CD1  LEU A  73    132.825 138.567 -65.509  1.00 12.07           C
ATOM  1141  CD2  LEU A  73    133.423 137.381 -67.628  1.00 13.02           C
ATOM  1145  C    LEU A  73    136.128 139.978 -65.501  1.00 13.12           C
ATOM  1146  O    LEU A  73    135.984 139.703 -64.317  1.00 12.81           O
ATOM  1147  N    PHE A  74    137.215 139.655 -66.194  1.00 12.86           N
ATOM  1149  CA   PHE A  74    138.281 138.875 -65.580  1.00 13.62           C
ATOM  1151  CB   PHE A  74    139.056 138.093 -66.660  1.00 13.33           C
ATOM  1154  CG   PHE A  74    138.204 137.066 -67.352  1.00 12.45           C
ATOM  1155  CD1  PHE A  74    137.613 137.342 -68.570  1.00 12.34           C
ATOM  1157  CE1  PHE A  74    136.795 136.418 -69.173  1.00 11.73           C
ATOM  1159  CZ   PHE A  74    136.548 135.205 -68.555  1.00 11.29           C
ATOM  1161  CE2  PHE A  74    137.110 134.932 -67.342  1.00 10.66           C
ATOM  1163  CD2  PHE A  74    137.929 135.857 -66.743  1.00 10.68           C
ATOM  1165  C    PHE A  74    139.198 139.702 -64.653  1.00 14.31           C
ATOM  1166  O    PHE A  74    139.808 139.155 -63.746  1.00 13.83           O
ATOM  1167  N    VAL A  75    139.264 141.016 -64.867  1.00 15.61           N
ATOM  1169  CA   VAL A  75    139.969 141.903 -63.936  1.00 16.32           C
ATOM  1171  CB   VAL A  75    140.062 143.363 -64.461  1.00 16.66           C
ATOM  1173  CG1  VAL A  75    140.799 144.259 -63.443  1.00 16.07           C
ATOM  1177  CG2  VAL A  75    140.749 143.414 -65.832  1.00 15.71           C
ATOM  1181  C    VAL A  75    139.247 141.904 -62.600  1.00 17.04           C
ATOM  1182  O    VAL A  75    139.877 141.758 -61.545  1.00 17.30           O
ATOM  1183  N    GLU A  76    137.925 142.076 -62.658  1.00 17.73           N
ATOM  1185  CA   GLU A  76    137.087 142.121 -61.466  1.00 18.69           C
ATOM  1187  CB   GLU A  76    135.640 142.483 -61.812  1.00 19.03           C
ATOM  1190  CG   GLU A  76    135.434 143.860 -62.434  1.00 21.44           C
ATOM  1193  CD   GLU A  76    135.757 145.015 -61.511  1.00 24.11           C
ATOM  1194  OE1  GLU A  76    136.178 146.067 -62.039  1.00 27.10           O
ATOM  1195  OE2  GLU A  76    135.586 144.885 -60.277  1.00 26.07           O
ATOM  1196  C    GLU A  76    137.077 140.781 -60.746  1.00 18.91           C
ATOM  1197  O    GLU A  76    137.112 140.725 -59.518  1.00 18.58           O
ATOM  1198  N    LEU A  77    137.027 139.705 -61.523  1.00 19.43           N
ATOM  1200  CA   LEU A  77    136.949 138.364 -60.969  1.00 19.79           C
ATOM  1202  CB   LEU A  77    136.685 137.337 -62.064  1.00 19.84           C
ATOM  1205  CG   LEU A  77    136.165 135.987 -61.591  1.00 19.73           C
ATOM  1207  CD1  LEU A  77    134.905 136.132 -60.711  1.00 19.43           C
ATOM  1211  CD2  LEU A  77    135.896 135.139 -62.821  1.00 20.53           C
ATOM  1215  C    LEU A  77    138.244 138.038 -60.276  1.00 20.15           C
ATOM  1216  O    LEU A  77    138.237 137.410 -59.222  1.00 19.73           O
ATOM  1217  N    GLY A  78    139.350 138.494 -60.861  1.00 20.76           N
ATOM  1219  CA   GLY A  78    140.676 138.299 -60.294  1.00 21.47           C
ATOM  1222  C    GLY A  78    140.982 138.911 -58.920  1.00 22.09           C
ATOM  1223  O    GLY A  78    142.042 138.635 -58.372  1.00 21.99           O
ATOM  1224  N    LYS A  79    140.090 139.734 -58.365  1.00 22.88           N
ATOM  1226  CA   LYS A  79    140.292 140.282 -57.014  1.00 23.59           C
ATOM  1228  CB   LYS A  79    140.003 141.799 -56.897  1.00 24.35           C
ATOM  1231  CG   LYS A  79    139.438 142.553 -58.121  1.00 26.58           C
ATOM  1234  CD   LYS A  79    138.032 143.130 -57.843  1.00 29.28           C
ATOM  1237  CE   LYS A  79    138.063 144.603 -57.425  1.00 30.93           C
ATOM  1240  NZ   LYS A  79    136.835 145.321 -57.881  1.00 31.32           N
ATOM  1244  C    LYS A  79    139.480 139.548 -55.965  1.00 23.07           C
ATOM  1245  O    LYS A  79    139.664 139.776 -54.772  1.00 23.70           O
ATOM  1246  N    VAL A  80    138.561 138.694 -56.392  1.00 22.21           N
ATOM  1248  CA   VAL A  80    137.934 137.773 -55.462  1.00 21.83           C
ATOM  1250  CB   VAL A  80    136.396 137.740 -55.617  1.00 22.49           C
```

(SEQ ID NO. 34)

FIGURE 20-9

| ATOM | 1252 | CG1 | VAL A | 80 | 135.820 | 139.130 | -55.300 | 1.00 | 24.11 | C |
| ATOM | 1256 | CG2 | VAL A | 80 | 135.970 | 137.303 | -57.002 | 1.00 | 22.79 | C |
| ATOM | 1260 | C | VAL A | 80 | 138.550 | 136.384 | -55.549 | 1.00 | 20.41 | C |
| ATOM | 1261 | O | VAL A | 80 | 138.597 | 135.691 | -54.555 | 1.00 | 19.88 | O |
| ATOM | 1262 | N | TRP A | 81 | 139.044 | 135.998 | -56.725 | 1.00 | 19.27 | N |
| ATOM | 1264 | CA | TRP A | 81 | 139.638 | 134.675 | -56.933 | 1.00 | 18.26 | C |
| ATOM | 1266 | CB | TRP A | 81 | 138.798 | 133.863 | -57.915 | 1.00 | 17.85 | C |
| ATOM | 1269 | CG | TRP A | 81 | 137.489 | 133.365 | -57.398 | 1.00 | 15.91 | C |
| ATOM | 1270 | CD1 | TRP A | 81 | 137.093 | 133.256 | -56.097 | 1.00 | 14.51 | C |
| ATOM | 1272 | NE1 | TRP A | 81 | 135.826 | 132.730 | -56.027 | 1.00 | 13.50 | N |
| ATOM | 1274 | CE2 | TRP A | 81 | 135.379 | 132.495 | -57.300 | 1.00 | 13.90 | C |
| ATOM | 1275 | CD2 | TRP A | 81 | 136.408 | 132.882 | -58.185 | 1.00 | 13.13 | C |
| ATOM | 1276 | CE3 | TRP A | 81 | 136.200 | 132.727 | -59.562 | 1.00 | 12.89 | C |
| ATOM | 1278 | CZ3 | TRP A | 81 | 134.991 | 132.197 | -60.004 | 1.00 | 12.92 | C |
| ATOM | 1280 | CH2 | TRP A | 81 | 133.984 | 131.830 | -59.096 | 1.00 | 12.96 | C |
| ATOM | 1282 | CZ2 | TRP A | 81 | 134.155 | 131.972 | -57.746 | 1.00 | 13.66 | C |
| ATOM | 1284 | C | TRP A | 81 | 141.040 | 134.805 | -57.507 | 1.00 | 18.07 | C |
| ATOM | 1285 | O | TRP A | 81 | 141.286 | 135.657 | -58.356 | 1.00 | 18.17 | O |
| ATOM | 1286 | N | ASP A | 82 | 141.949 | 133.938 | -57.079 | 1.00 | 17.98 | N |
| ATOM | 1288 | CA | ASP A | 82 | 143.312 | 133.956 | -57.606 | 1.00 | 18.29 | C |
| ATOM | 1290 | CB | BASP A | 82 | 144.280 | 133.223 | -56.661 | 0.35 | 18.39 | C |
| ATOM | 1291 | CB | AASP A | 82 | 144.256 | 133.181 | -56.693 | 0.65 | 18.49 | C |
| ATOM | 1296 | CG | BASP A | 82 | 145.524 | 134.045 | -56.334 | 0.35 | 18.80 | C |
| ATOM | 1297 | CG | AASP A | 82 | 144.484 | 133.865 | -55.370 | 0.65 | 18.69 | C |
| ATOM | 1298 | OD1 | BASP A | 82 | 146.636 | 133.470 | -56.349 | 0.35 | 18.66 | O |
| ATOM | 1299 | OD1 | AASP A | 82 | 145.102 | 133.230 | -54.490 | 0.65 | 20.37 | O |
| ATOM | 1300 | OD2 | BASP A | 82 | 145.485 | 135.264 | -56.044 | 0.35 | 18.69 | O |
| ATOM | 1301 | OD2 | AASP A | 82 | 144.099 | 135.027 | -55.124 | 0.65 | 18.42 | O |
| ATOM | 1302 | C | ASP A | 82 | 143.343 | 133.342 | -59.010 | 1.00 | 18.32 | C |
| ATOM | 1303 | O | ASP A | 82 | 143.838 | 133.976 | -59.983 | 1.00 | 19.68 | O |
| ATOM | 1304 | N | GLY A | 83 | 142.817 | 132.124 | -59.116 | 1.00 | 16.63 | N |
| ATOM | 1306 | CA | GLY A | 83 | 142.642 | 131.475 | -60.401 | 1.00 | 15.73 | C |
| ATOM | 1309 | C | GLY A | 83 | 141.210 | 131.036 | -60.634 | 1.00 | 14.55 | C |
| ATOM | 1310 | O | GLY A | 83 | 140.394 | 131.058 | -59.726 | 1.00 | 14.81 | O |
| ATOM | 1311 | N | LEU A | 84 | 140.928 | 130.616 | -61.863 | 1.00 | 13.24 | N |
| ATOM | 1313 | CA | LEU A | 84 | 139.597 | 130.211 | -62.299 | 1.00 | 12.04 | C |
| ATOM | 1315 | CB | LEU A | 84 | 139.132 | 131.133 | -63.430 | 1.00 | 11.90 | C |
| ATOM | 1318 | CG | LEU A | 84 | 137.768 | 130.897 | -64.071 | 1.00 | 10.84 | C |
| ATOM | 1320 | CD1 | LEU A | 84 | 136.636 | 131.011 | -63.079 | 1.00 | 9.05 | C |
| ATOM | 1324 | CD2 | LEU A | 84 | 137.567 | 131.861 | -65.251 | 1.00 | 10.82 | C |
| ATOM | 1328 | C | LEU A | 84 | 139.632 | 128.773 | -62.790 | 1.00 | 11.28 | C |
| ATOM | 1329 | O | LEU A | 84 | 140.463 | 128.414 | -63.612 | 1.00 | 11.35 | O |
| ATOM | 1330 | N | ASP A | 85 | 138.737 | 127.945 | -62.285 | 1.00 | 10.35 | N |
| ATOM | 1332 | CA | ASP A | 85 | 138.672 | 126.560 | -62.728 | 1.00 | 10.04 | C |
| ATOM | 1334 | CB | ASP A | 85 | 138.162 | 125.682 | -61.599 | 1.00 | 9.95 | C |
| ATOM | 1337 | CG | ASP A | 85 | 139.203 | 125.479 | -60.549 | 1.00 | 10.72 | C |
| ATOM | 1338 | OD1 | ASP A | 85 | 140.278 | 124.917 | -60.908 | 1.00 | 11.44 | O |
| ATOM | 1339 | OD2 | ASP A | 85 | 139.065 | 125.886 | -59.373 | 1.00 | 9.23 | O |
| ATOM | 1340 | C | ASP A | 85 | 137.853 | 126.330 | -64.002 | 1.00 | 9.75 | C |
| ATOM | 1341 | O | ASP A | 85 | 138.192 | 125.461 | -64.806 | 1.00 | 8.91 | O |
| ATOM | 1342 | N | ALA A | 86 | 136.783 | 127.093 | -64.200 | 1.00 | 9.29 | N |
| ATOM | 1344 | CA | ALA A | 86 | 135.931 | 126.825 | -65.348 | 1.00 | 8.76 | C |
| ATOM | 1346 | CB | ALA A | 86 | 135.064 | 125.614 | -65.072 | 1.00 | 8.99 | C |
| ATOM | 1350 | C | ALA A | 86 | 135.076 | 127.999 | -65.763 | 1.00 | 8.12 | C |
| ATOM | 1351 | O | ALA A | 86 | 134.756 | 128.857 | -64.937 | 1.00 | 7.55 | O |
| ATOM | 1352 | N | ILE A | 87 | 134.767 | 128.031 | -67.067 | 1.00 | 7.69 | N |
| ATOM | 1354 | CA | ILE A | 87 | 133.806 | 128.955 | -67.663 | 1.00 | 7.05 | C |
| ATOM | 1356 | CB | ILE A | 87 | 134.477 | 129.886 | -68.701 | 1.00 | 6.99 | C |
| ATOM | 1358 | CG1 | ILE A | 87 | 135.446 | 130.830 | -67.994 | 1.00 | 6.63 | C |
| ATOM | 1361 | CD1 | ILE A | 87 | 136.458 | 131.473 | -68.867 | 1.00 | 6.63 | C |
| ATOM | 1365 | CG2 | ILE A | 87 | 133.425 | 130.679 | -69.482 | 1.00 | 5.55 | C |
| ATOM | 1369 | C | ILE A | 87 | 132.708 | 128.150 | -68.337 | 1.00 | 7.13 | C |
| ATOM | 1370 | O | ILE A | 87 | 132.983 | 127.267 | -69.131 | 1.00 | 7.04 | O |
| ATOM | 1371 | N | VAL A | 88 | 131.463 | 128.455 | -67.971 | 1.00 | 6.74 | N |
| ATOM | 1373 | CA | VAL A | 88 | 130.269 | 127.907 | -68.593 | 1.00 | 6.15 | C |
| ATOM | 1375 | CB | VAL A | 88 | 129.230 | 127.485 | -67.538 | 1.00 | 5.77 | C |
| ATOM | 1377 | CG1 | VAL A | 88 | 127.906 | 127.146 | -68.189 | 1.00 | 6.21 | C |
| ATOM | 1381 | CG2 | VAL A | 88 | 129.706 | 126.278 | -66.753 | 1.00 | 6.32 | C |

(SEQ ID NO. 34)

FIGURE 20-10

| ATOM | 1385 | C | VAL A | 88 | 129.689 | 129.008 | -69.488 | 1.00 | 5.99 | C |
| ATOM | 1386 | O | VAL A | 88 | 129.308 | 130.078 | -69.024 | 1.00 | 5.81 | O |
| ATOM | 1387 | N | HIS A | 89 | 129.672 | 128.732 | -70.778 | 1.00 | 5.60 | N |
| ATOM | 1389 | CA | HIS A | 89 | 129.019 | 129.546 | -71.786 | 1.00 | 5.72 | C |
| ATOM | 1391 | CB | HIS A | 89 | 129.854 | 129.462 | -73.056 | 1.00 | 5.30 | C |
| ATOM | 1394 | CG | HIS A | 89 | 129.458 | 130.408 | -74.146 | 1.00 | 5.56 | C |
| ATOM | 1395 | ND1 | HIS A | 89 | 128.594 | 130.051 | -75.160 | 1.00 | 3.58 | N |
| ATOM | 1397 | CE1 | HIS A | 89 | 128.498 | 131.050 | -76.020 | 1.00 | 5.12 | C |
| ATOM | 1399 | NE2 | HIS A | 89 | 129.291 | 132.024 | -75.622 | 1.00 | 4.51 | N |
| ATOM | 1401 | CD2 | HIS A | 89 | 129.912 | 131.643 | -74.459 | 1.00 | 5.09 | C |
| ATOM | 1403 | C | HIS A | 89 | 127.632 | 128.983 | -72.044 | 1.00 | 5.43 | C |
| ATOM | 1404 | O | HIS A | 89 | 127.496 | 127.886 | -72.586 | 1.00 | 5.33 | O |
| ATOM | 1405 | N | SER A | 90 | 126.603 | 129.731 | -71.648 | 1.00 | 5.53 | N |
| ATOM | 1407 | CA | SER A | 90 | 125.215 | 129.323 | -71.878 | 1.00 | 5.52 | C |
| ATOM | 1409 | CB | SER A | 90 | 124.575 | 128.839 | -70.569 | 1.00 | 5.51 | C |
| ATOM | 1412 | OG | SER A | 90 | 123.384 | 128.124 | -70.830 | 1.00 | 4.99 | O |
| ATOM | 1414 | C | SER A | 90 | 124.482 | 130.523 | -72.478 | 1.00 | 5.33 | C |
| ATOM | 1415 | O | SER A | 90 | 123.500 | 131.052 | -71.915 | 1.00 | 4.98 | O |
| ATOM | 1416 | N | ILE A | 91 | 125.002 | 130.941 | -73.629 | 1.00 | 5.27 | N |
| ATOM | 1418 | CA | ILE A | 91 | 124.637 | 132.189 | -74.278 | 1.00 | 5.25 | C |
| ATOM | 1420 | CB | ILE A | 91 | 125.827 | 133.176 | -74.215 | 1.00 | 5.40 | C |
| ATOM | 1422 | CG1 | ILE A | 91 | 126.068 | 133.642 | -72.780 | 1.00 | 5.42 | C |
| ATOM | 1425 | CD1 | ILE A | 91 | 127.434 | 134.377 | -72.613 | 1.00 | 5.40 | C |
| ATOM | 1429 | CG2 | ILE A | 91 | 125.590 | 134.423 | -75.138 | 1.00 | 5.09 | C |
| ATOM | 1433 | C | ILE A | 91 | 124.250 | 131.949 | -75.733 | 1.00 | 5.50 | C |
| ATOM | 1434 | O | ILE A | 91 | 124.940 | 131.211 | -76.456 | 1.00 | 5.83 | O |
| ATOM | 1435 | N | ALA A | 92 | 123.167 | 132.597 | -76.162 | 1.00 | 5.70 | N |
| ATOM | 1437 | CA | ALA A | 92 | 122.757 | 132.566 | -77.553 | 1.00 | 5.67 | C |
| ATOM | 1439 | CB | ALA A | 92 | 122.034 | 131.256 | -77.863 | 1.00 | 5.98 | C |
| ATOM | 1443 | C | ALA A | 92 | 121.875 | 133.757 | -77.945 | 1.00 | 6.36 | C |
| ATOM | 1444 | O | ALA A | 92 | 121.127 | 134.277 | -77.123 | 1.00 | 6.50 | O |
| ATOM | 1445 | N | PHE A | 93 | 121.989 | 134.156 | -79.214 | 1.00 | 6.48 | N |
| ATOM | 1447 | CA | PHE A | 93 | 121.133 | 135.155 | -79.836 | 1.00 | 6.96 | C |
| ATOM | 1449 | CB | PHE A | 93 | 121.380 | 136.560 | -79.270 | 1.00 | 6.77 | C |
| ATOM | 1452 | CG | PHE A | 93 | 120.460 | 137.609 | -79.849 | 1.00 | 7.75 | C |
| ATOM | 1453 | CD1 | PHE A | 93 | 119.141 | 137.707 | -79.424 | 1.00 | 10.42 | C |
| ATOM | 1455 | CE1 | PHE A | 93 | 118.283 | 138.666 | -79.951 | 1.00 | 9.84 | C |
| ATOM | 1457 | CZ | PHE A | 93 | 118.742 | 139.528 | -80.931 | 1.00 | 9.97 | C |
| ATOM | 1459 | CE2 | PHE A | 93 | 120.052 | 139.441 | -81.364 | 1.00 | 9.86 | C |
| ATOM | 1461 | CD2 | PHE A | 93 | 120.905 | 138.485 | -80.828 | 1.00 | 9.21 | C |
| ATOM | 1463 | C | PHE A | 93 | 121.298 | 135.207 | -81.370 | 1.00 | 6.72 | C |
| ATOM | 1464 | O | PHE A | 93 | 122.412 | 135.217 | -81.892 | 1.00 | 6.16 | O |
| ATOM | 1465 | N | ALA A | 94 | 120.163 | 135.218 | -82.062 | 1.00 | 7.04 | N |
| ATOM | 1467 | CA | ALA A | 94 | 120.076 | 135.681 | -83.454 | 1.00 | 7.89 | C |
| ATOM | 1469 | CB | ALA A | 94 | 119.853 | 134.521 | -84.444 | 1.00 | 7.47 | C |
| ATOM | 1473 | C | ALA A | 94 | 118.903 | 136.637 | -83.510 | 1.00 | 8.34 | C |
| ATOM | 1474 | O | ALA A | 94 | 117.901 | 136.440 | -82.818 | 1.00 | 7.63 | O |
| ATOM | 1475 | N | PRO A | 95 | 119.003 | 137.679 | -84.318 | 1.00 | 9.48 | N |
| ATOM | 1476 | CA | PRO A | 95 | 117.845 | 138.540 | -84.526 | 1.00 | 10.52 | C |
| ATOM | 1478 | CB | PRO A | 95 | 118.254 | 139.377 | -85.729 | 1.00 | 10.18 | C |
| ATOM | 1481 | CG | PRO A | 95 | 119.729 | 139.517 | -85.542 | 1.00 | 9.60 | C |
| ATOM | 1484 | CD | PRO A | 95 | 120.184 | 138.160 | -85.056 | 1.00 | 9.55 | C |
| ATOM | 1487 | C | PRO A | 95 | 116.610 | 137.693 | -84.795 | 1.00 | 11.73 | C |
| ATOM | 1488 | O | PRO A | 95 | 116.677 | 136.651 | -85.470 | 1.00 | 12.76 | O |
| ATOM | 1489 | N | ARG A | 96 | 115.492 | 138.114 | -84.234 | 1.00 | 13.03 | N |
| ATOM | 1491 | CA | ARG A | 96 | 114.252 | 137.355 | -84.350 | 1.00 | 14.48 | C |
| ATOM | 1493 | CB | ARG A | 96 | 113.143 | 138.058 | -83.541 | 1.00 | 14.53 | C |
| ATOM | 1496 | CG | ARG A | 96 | 112.056 | 138.716 | -84.333 | 1.00 | 18.34 | C |
| ATOM | 1499 | CD | ARG A | 96 | 111.737 | 140.152 | -83.957 | 1.00 | 22.44 | C |
| ATOM | 1502 | NE | ARG A | 96 | 110.491 | 140.243 | -83.206 | 1.00 | 25.86 | N |
| ATOM | 1504 | CZ | ARG A | 96 | 109.601 | 141.224 | -83.296 | 1.00 | 27.68 | C |
| ATOM | 1505 | NH1 | ARG A | 96 | 109.772 | 142.256 | -84.117 | 1.00 | 28.56 | N |
| ATOM | 1508 | NH2 | ARG A | 96 | 108.518 | 141.168 | -82.538 | 1.00 | 29.31 | N |
| ATOM | 1511 | C | ARG A | 96 | 113.872 | 137.068 | -85.831 | 1.00 | 14.59 | C |
| ATOM | 1512 | O | ARG A | 96 | 113.349 | 136.011 | -86.141 | 1.00 | 14.33 | O |
| ATOM | 1513 | N | ASP A | 97 | 114.187 | 137.994 | -86.734 | 1.00 | 15.57 | N |
| ATOM | 1515 | CA | ASP A | 97 | 113.871 | 137.846 | -88.170 | 1.00 | 16.60 | C |
| ATOM | 1517 | CB | ASP A | 97 | 114.067 | 139.182 | -88.905 | 1.00 | 16.60 | C |

(SEQ ID NO. 34)

FIGURE 20-11

| ATOM | 1520 | CG | ASP | A | 97 | 115.520 | 139.605 | -88.984 | 1.00 | 17.79 | C |
| ATOM | 1521 | OD1 | ASP | A | 97 | 116.080 | 139.665 | -90.089 | 1.00 | 20.17 | O |
| ATOM | 1522 | OD2 | ASP | A | 97 | 116.194 | 139.928 | -87.997 | 1.00 | 22.81 | O |
| ATOM | 1523 | C | ASP | A | 97 | 114.643 | 136.720 | -88.896 | 1.00 | 16.99 | C |
| ATOM | 1524 | O | ASP | A | 97 | 114.267 | 136.303 | -89.995 | 1.00 | 16.58 | O |
| ATOM | 1525 | N | GLN | A | 98 | 115.733 | 136.253 | -88.295 | 1.00 | 17.47 | N |
| ATOM | 1527 | CA | GLN | A | 98 | 116.487 | 135.132 | -88.855 | 1.00 | 17.94 | C |
| ATOM | 1529 | CB | GLN | A | 98 | 117.878 | 135.057 | -88.226 | 1.00 | 17.37 | C |
| ATOM | 1532 | CG | GLN | A | 98 | 118.762 | 136.243 | -88.538 | 1.00 | 15.95 | C |
| ATOM | 1535 | CD | GLN | A | 98 | 118.901 | 136.497 | -90.026 | 1.00 | 14.31 | C |
| ATOM | 1536 | OE1 | GLN | A | 98 | 119.629 | 135.780 | -90.717 | 1.00 | 13.19 | O |
| ATOM | 1537 | NE2 | GLN | A | 98 | 118.201 | 137.506 | -90.526 | 1.00 | 12.32 | N |
| ATOM | 1540 | C | GLN | A | 98 | 115.748 | 133.801 | -88.670 | 1.00 | 18.68 | C |
| ATOM | 1541 | O | GLN | A | 98 | 115.850 | 132.903 | -89.518 | 1.00 | 19.28 | O |
| ATOM | 1542 | N | LEU | A | 99 | 115.000 | 133.704 | -87.573 | 1.00 | 19.13 | N |
| ATOM | 1544 | CA | LEU | A | 99 | 114.291 | 132.494 | -87.181 | 1.00 | 19.56 | C |
| ATOM | 1546 | CB | LEU | A | 99 | 114.193 | 132.384 | -85.648 | 1.00 | 19.68 | C |
| ATOM | 1549 | CG | LEU | A | 99 | 115.431 | 131.992 | -84.808 | 1.00 | 20.76 | C |
| ATOM | 1551 | CD1 | LEU | A | 99 | 116.748 | 132.083 | -85.568 | 1.00 | 21.55 | C |
| ATOM | 1555 | CD2 | LEU | A | 99 | 115.508 | 132.827 | -83.536 | 1.00 | 20.41 | C |
| ATOM | 1559 | C | LEU | A | 99 | 112.898 | 132.498 | -87.781 | 1.00 | 19.60 | C |
| ATOM | 1560 | O | LEU | A | 99 | 112.306 | 133.559 | -87.992 | 1.00 | 20.66 | O |
| ATOM | 1561 | N | GLU | A | 100 | 112.373 | 131.303 | -88.022 | 1.00 | 19.27 | N |
| ATOM | 1563 | CA | GLU | A | 100 | 111.079 | 131.097 | -88.665 | 1.00 | 19.24 | C |
| ATOM | 1565 | CB | GLU | A | 100 | 109.960 | 131.857 | -87.948 | 1.00 | 19.81 | C |
| ATOM | 1568 | CG | GLU | A | 100 | 110.070 | 131.862 | -86.426 | 1.00 | 21.85 | C |
| ATOM | 1571 | CD | GLU | A | 100 | 109.091 | 130.922 | -85.773 | 1.00 | 24.60 | C |
| ATOM | 1572 | OE1 | GLU | A | 100 | 108.004 | 131.381 | -85.372 | 1.00 | 27.08 | O |
| ATOM | 1573 | OE2 | GLU | A | 100 | 109.414 | 129.723 | -85.666 | 1.00 | 27.94 | O |
| ATOM | 1574 | C | GLU | A | 100 | 111.106 | 131.447 | -90.158 | 1.00 | 18.14 | C |
| ATOM | 1575 | O | GLU | A | 100 | 111.837 | 132.314 | -90.614 | 1.00 | 18.55 | O |
| ATOM | 1576 | N | GLY | A | 101 | 110.297 | 130.746 | -90.923 | 1.00 | 16.73 | N |
| ATOM | 1578 | CA | GLY | A | 101 | 110.274 | 130.942 | -92.343 | 1.00 | 15.61 | C |
| ATOM | 1581 | C | GLY | A | 101 | 111.437 | 130.214 | -92.995 | 1.00 | 14.57 | C |
| ATOM | 1582 | O | GLY | A | 101 | 112.171 | 129.446 | -92.357 | 1.00 | 13.74 | O |
| ATOM | 1583 | N | ASN | A | 102 | 111.565 | 130.478 | -94.289 | 1.00 | 12.97 | N |
| ATOM | 1585 | CA | ASN | A | 102 | 112.536 | 129.856 | -95.148 | 1.00 | 12.01 | C |
| ATOM | 1587 | CB | ASN | A | 102 | 112.054 | 130.034 | -96.597 | 1.00 | 11.67 | C |
| ATOM | 1590 | CG | ASN | A | 102 | 113.023 | 129.506 | -97.611 | 1.00 | 11.01 | C |
| ATOM | 1591 | OD1 | ASN | A | 102 | 112.783 | 128.485 | -98.271 | 1.00 | 8.93 | O |
| ATOM | 1592 | ND2 | ASN | A | 102 | 114.111 | 130.209 | -97.771 | 1.00 | 7.71 | N |
| ATOM | 1595 | C | ASN | A | 102 | 113.890 | 130.524 | -94.870 | 1.00 | 11.22 | C |
| ATOM | 1596 | O | ASN | A | 102 | 113.978 | 131.746 | -94.798 | 1.00 | 10.56 | O |
| ATOM | 1597 | N | PHE | A | 103 | 114.929 | 129.712 | -94.686 | 1.00 | 10.53 | N |
| ATOM | 1599 | CA | PHE | A | 103 | 116.264 | 130.205 | -94.333 | 1.00 | 9.90 | C |
| ATOM | 1601 | CB | PHE | A | 103 | 117.290 | 129.058 | -94.276 | 1.00 | 9.26 | C |
| ATOM | 1604 | CG | PHE | A | 103 | 118.718 | 129.532 | -94.212 | 1.00 | 8.43 | C |
| ATOM | 1605 | CD1 | PHE | A | 103 | 119.175 | 130.239 | -93.098 | 1.00 | 8.48 | C |
| ATOM | 1607 | CE1 | PHE | A | 103 | 120.488 | 130.696 | -93.020 | 1.00 | 7.44 | C |
| ATOM | 1609 | CZ | PHE | A | 103 | 121.364 | 130.457 | -94.072 | 1.00 | 8.19 | C |
| ATOM | 1611 | CE2 | PHE | A | 103 | 120.912 | 129.758 | -95.213 | 1.00 | 8.37 | C |
| ATOM | 1613 | CD2 | PHE | A | 103 | 119.596 | 129.308 | -95.275 | 1.00 | 7.53 | C |
| ATOM | 1615 | C | PHE | A | 103 | 116.744 | 131.272 | -95.315 | 1.00 | 9.53 | C |
| ATOM | 1616 | O | PHE | A | 103 | 117.241 | 132.307 | -94.898 | 1.00 | 9.14 | O |
| ATOM | 1617 | N | ILE | A | 104 | 116.569 | 131.007 | -96.607 | 1.00 | 9.43 | N |
| ATOM | 1619 | CA | ILE | A | 104 | 117.020 | 131.903 | -97.665 | 1.00 | 10.10 | C |
| ATOM | 1621 | CB | ILE | A | 104 | 117.194 | 131.113 | -98.965 | 1.00 | 9.87 | C |
| ATOM | 1623 | CG1 | ILE | A | 104 | 118.391 | 130.158 | -98.821 | 1.00 | 9.69 | C |
| ATOM | 1626 | CD1 | ILE | A | 104 | 119.766 | 130.819 | -98.640 | 1.00 | 8.74 | C |
| ATOM | 1630 | CG2 | ILE | A | 104 | 117.369 | 132.035 | -100.180 | 1.00 | 11.21 | C |
| ATOM | 1634 | C | ILE | A | 104 | 116.186 | 133.196 | -97.836 | 1.00 | 10.81 | C |
| ATOM | 1635 | O | ILE | A | 104 | 116.759 | 134.249 | -98.081 | 1.00 | 10.39 | O |
| ATOM | 1636 | N | ASP | A | 105 | 114.865 | 133.121 | -97.669 | 1.00 | 11.82 | N |
| ATOM | 1638 | CA | ASP | A | 105 | 114.016 | 134.308 | -97.524 | 1.00 | 12.77 | C |
| ATOM | 1640 | CB | ASP | A | 105 | 112.549 | 133.912 | -97.234 | 1.00 | 13.40 | C |
| ATOM | 1643 | CG | ASP | A | 105 | 111.823 | 133.386 | -98.446 | 1.00 | 16.23 | C |
| ATOM | 1644 | OD1 | ASP | A | 105 | 110.701 | 132.856 | -98.290 | 1.00 | 20.14 | O |
| ATOM | 1645 | OD2 | ASP | A | 105 | 112.279 | 133.458 | -99.603 | 1.00 | 22.12 | O |

(SEQ ID NO. 34)

FIGURE 20-12

| | | | | | | | | | |
|---|---|---|---|---|---|---|---|---|---|
| | ATOM | 1646 | C | ASP A 105 | 114.486 | 135.207 | -96.361 | 1.00 12.87 | C |
| | ATOM | 1647 | O | ASP A 105 | 114.488 | 136.425 | -96.489 | 1.00 11.61 | O |
| | ATOM | 1648 | N | CYS A 106 | 114.870 | 134.603 | -95.238 | 1.00 13.20 | N |
| | ATOM | 1650 | CA | CYS A 106 | 115.145 | 135.353 | -94.004 | 1.00 14.36 | C |
| 5 | ATOM | 1652 | CB | CYS A 106 | 114.796 | 134.485 | -92.802 | 1.00 14.79 | C |
| | ATOM | 1655 | SG | CYS A 106 | 113.047 | 134.128 | -92.738 | 1.00 23.38 | S |
| | ATOM | 1656 | C | CYS A 106 | 116.578 | 135.829 | -93.787 | 1.00 12.92 | C |
| | ATOM | 1657 | O | CYS A 106 | 116.805 | 136.834 | -93.116 | 1.00 13.09 | O |
| | ATOM | 1658 | N | VAL A 107 | 117.547 | 135.071 | -94.280 | 1.00 11.78 | N |
| 10 | ATOM | 1660 | CA | VAL A 107 | 118.942 | 135.359 | -93.988 | 1.00 10.79 | C |
| | ATOM | 1662 | CB | VAL A 107 | 119.890 | 134.284 | -94.594 | 1.00 10.69 | C |
| | ATOM | 1664 | CG1 | VAL A 107 | 120.053 | 134.461 | -96.111 | 1.00 9.58 | C |
| | ATOM | 1668 | CG2 | VAL A 107 | 121.242 | 134.300 | -93.884 | 1.00 10.14 | C |
| | ATOM | 1672 | C | VAL A 107 | 119.344 | 136.757 | -94.474 | 1.00 10.39 | C |
| 15 | ATOM | 1673 | O | VAL A 107 | 118.958 | 137.189 | -95.560 | 1.00 9.39 | O |
| | ATOM | 1674 | N | THR A 108 | 120.091 | 137.475 | -93.639 | 1.00 10.24 | N |
| | ATOM | 1676 | CA | THR A 108 | 120.680 | 138.750 | -94.048 | 1.00 10.02 | C |
| | ATOM | 1678 | CB | THR A 108 | 119.891 | 139.931 | -93.444 | 1.00 9.97 | C |
| | ATOM | 1680 | OG1 | THR A 108 | 119.882 | 139.840 | -92.008 | 1.00 9.94 | O |
| 20 | ATOM | 1682 | CG2 | THR A 108 | 118.410 | 139.873 | -93.845 | 1.00 9.08 | C |
| | ATOM | 1686 | C | THR A 108 | 122.142 | 138.806 | -93.629 | 1.00 9.80 | C |
| | ATOM | 1687 | O | THR A 108 | 122.569 | 138.085 | -92.725 | 1.00 10.13 | O |
| | ATOM | 1688 | N | ARG A 109 | 122.917 | 139.641 | -94.300 | 1.00 9.48 | N |
| | ATOM | 1690 | CA | ARG A 109 | 124.320 | 139.807 | -93.946 | 1.00 9.69 | C |
| 25 | ATOM | 1692 | CB | ARG A 109 | 124.961 | 140.925 | -94.765 | 1.00 9.66 | C |
| | ATOM | 1695 | CG | ARG A 109 | 126.432 | 141.107 | -94.473 | 1.00 9.45 | C |
| | ATOM | 1698 | CD | ARG A 109 | 127.139 | 142.055 | -95.396 | 1.00 9.29 | C |
| | ATOM | 1701 | NE | ARG A 109 | 126.883 | 141.768 | -96.814 | 1.00 10.03 | N |
| | ATOM | 1703 | CZ | ARG A 109 | 127.682 | 141.052 | -97.603 | 1.00 10.85 | C |
| 30 | ATOM | 1704 | NH1 | ARG A 109 | 128.806 | 140.539 | -97.150 | 1.00 11.08 | N |
| | ATOM | 1707 | NH2 | ARG A 109 | 127.367 | 140.871 | -98.876 | 1.00 13.12 | N |
| | ATOM | 1710 | C | ARG A 109 | 124.494 | 140.093 | -92.455 | 1.00 9.46 | C |
| | ATOM | 1711 | O | ARG A 109 | 125.264 | 139.429 | -91.789 | 1.00 9.41 | O |
| | ATOM | 1712 | N | GLU A 110 | 123.758 | 141.069 | -91.941 | 1.00 9.29 | N |
| 35 | ATOM | 1714 | CA | GLU A 110 | 123.904 | 141.496 | -90.550 | 1.00 9.41 | C |
| | ATOM | 1716 | CB | GLU A 110 | 123.312 | 142.902 | -90.392 | 1.00 9.72 | C |
| | ATOM | 1719 | CG | GLU A 110 | 123.451 | 143.487 | -88.997 | 1.00 11.98 | C |
| | ATOM | 1722 | CD | GLU A 110 | 123.091 | 144.953 | -88.966 | 1.00 14.80 | C |
| | ATOM | 1723 | OE1 | GLU A 110 | 124.029 | 145.774 | -89.031 | 1.00 17.20 | O |
| 40 | ATOM | 1724 | OE2 | GLU A 110 | 121.880 | 145.279 | -88.904 | 1.00 14.26 | O |
| | ATOM | 1725 | C | GLU A 110 | 123.281 | 140.533 | -89.524 | 1.00 8.76 | C |
| | ATOM | 1726 | O | GLU A 110 | 123.787 | 140.377 | -88.425 | 1.00 8.20 | O |
| | ATOM | 1727 | N | GLY A 111 | 122.162 | 139.909 | -89.855 | 1.00 8.59 | N |
| | ATOM | 1729 | CA | GLY A 111 | 121.597 | 138.892 | -88.975 | 1.00 8.55 | C |
| 45 | ATOM | 1732 | C | GLY A 111 | 122.521 | 137.692 | -88.823 | 1.00 8.13 | C |
| | ATOM | 1733 | O | GLY A 111 | 122.626 | 137.117 | -87.750 | 1.00 7.35 | O |
| | ATOM | 1734 | N | PHE A 112 | 123.180 | 137.324 | -89.919 | 1.00 8.10 | N |
| | ATOM | 1736 | CA | PHE A 112 | 124.255 | 136.328 | -89.919 | 1.00 8.53 | C |
| | ATOM | 1738 | CB | PHE A 112 | 124.796 | 136.150 | -91.337 | 1.00 8.53 | C |
| 50 | ATOM | 1741 | CG | PHE A 112 | 125.604 | 134.892 | -91.564 | 1.00 7.64 | C |
| | ATOM | 1742 | CD1 | PHE A 112 | 126.958 | 134.865 | -91.291 | 1.00 6.67 | C |
| | ATOM | 1744 | CE1 | PHE A 112 | 127.720 | 133.737 | -91.556 | 1.00 5.59 | C |
| | ATOM | 1746 | CZ | PHE A 112 | 127.128 | 132.621 | -92.119 | 1.00 6.52 | C |
| | ATOM | 1748 | CE2 | PHE A 112 | 125.771 | 132.635 | -92.426 | 1.00 7.85 | C |
| 55 | ATOM | 1750 | CD2 | PHE A 112 | 125.019 | 133.766 | -92.162 | 1.00 8.07 | C |
| | ATOM | 1752 | C | PHE A 112 | 125.369 | 136.795 | -88.999 | 1.00 8.69 | C |
| | ATOM | 1753 | O | PHE A 112 | 125.784 | 136.062 | -88.098 | 1.00 8.72 | O |
| | ATOM | 1754 | N | SER A 113 | 125.821 | 138.030 | -89.202 | 1.00 8.49 | N |
| | ATOM | 1756 | CA | SER A 113 | 126.938 | 138.538 | -88.432 | 1.00 8.75 | C |
| 60 | ATOM | 1758 | CB | SER A 113 | 127.310 | 139.922 | -88.891 | 1.00 8.80 | C |
| | ATOM | 1761 | OG | SER A 113 | 128.630 | 140.173 | -88.466 | 1.00 10.57 | O |
| | ATOM | 1763 | C | SER A 113 | 126.690 | 138.571 | -86.918 | 1.00 8.54 | C |
| | ATOM | 1764 | O | SER A 113 | 127.547 | 138.146 | -86.149 | 1.00 8.31 | O |
| | ATOM | 1765 | N | ILE A 114 | 125.514 | 139.063 | -86.522 | 1.00 8.07 | N |
| 65 | ATOM | 1767 | CA | ILE A 114 | 125.134 | 139.228 | -85.125 | 1.00 8.01 | C |
| | ATOM | 1769 | CB | ILE A 114 | 123.817 | 140.016 | -85.028 | 1.00 8.07 | C |
| | ATOM | 1771 | CG1 | ILE A 114 | 124.050 | 141.475 | -85.416 | 1.00 8.58 | C |
| | ATOM | 1774 | CD1 | ILE A 114 | 122.809 | 142.317 | -85.383 | 1.00 9.17 | C |

(SEQ ID NO. 34)

FIGURE 20-13

| ATOM | 1778 | CG2 | ILE A 114 | 123.283 | 139.990 | -83.602 | 1.00 | 9.10 | C |
| --- | --- | --- | --- | --- | --- | --- | --- | --- | --- |
| ATOM | 1782 | C | ILE A 114 | 124.972 | 137.893 | -84.426 | 1.00 | 7.93 | C |
| ATOM | 1783 | O | ILE A 114 | 125.417 | 137.714 | -83.310 | 1.00 | 7.28 | O |
| ATOM | 1784 | N | ALA A 115 | 124.297 | 136.973 | -85.100 | 1.00 | 8.09 | N |
| ATOM | 1786 | CA | ALA A 115 | 124.091 | 135.627 | -84.604 | 1.00 | 8.24 | C |
| ATOM | 1788 | CB | ALA A 115 | 123.248 | 134.802 | -85.621 | 1.00 | 8.15 | C |
| ATOM | 1792 | C | ALA A 115 | 125.426 | 134.931 | -84.311 | 1.00 | 8.01 | C |
| ATOM | 1793 | O | ALA A 115 | 125.578 | 134.288 | -83.284 | 1.00 | 7.77 | O |
| ATOM | 1794 | N | HIS A 116 | 126.389 | 135.086 | -85.204 | 1.00 | 8.03 | N |
| ATOM | 1796 | CA | HIS A 116 | 127.707 | 134.487 | -85.014 | 1.00 | 8.51 | C |
| ATOM | 1798 | CB | HIS A 116 | 128.481 | 134.503 | -86.320 | 1.00 | 8.13 | C |
| ATOM | 1801 | CG | HIS A 116 | 128.004 | 133.494 | -87.318 | 1.00 | 9.75 | C |
| ATOM | 1802 | ND1 | HIS A 116 | 128.801 | 132.460 | -87.764 | 1.00 | 10.89 | N |
| ATOM | 1804 | CE1 | HIS A 116 | 128.120 | 131.720 | -88.624 | 1.00 | 10.24 | C |
| ATOM | 1806 | NE2 | HIS A 116 | 126.912 | 132.239 | -88.758 | 1.00 | 10.36 | N |
| ATOM | 1808 | CD2 | HIS A 116 | 126.811 | 133.347 | -87.949 | 1.00 | 9.86 | C |
| ATOM | 1810 | C | HIS A 116 | 128.516 | 135.198 | -83.910 | 1.00 | 8.46 | C |
| ATOM | 1811 | O | HIS A 116 | 129.299 | 134.572 | -83.202 | 1.00 | 7.79 | O |
| ATOM | 1812 | N | ASP A 117 | 128.306 | 136.503 | -83.765 | 1.00 | 8.12 | N |
| ATOM | 1814 | CA | ASP A 117 | 129.096 | 137.317 | -82.862 | 1.00 | 7.92 | C |
| ATOM | 1816 | CB | ASP A 117 | 128.731 | 138.786 | -83.080 | 1.00 | 8.23 | C |
| ATOM | 1819 | CG | ASP A 117 | 129.550 | 139.739 | -82.227 | 1.00 | 8.28 | C |
| ATOM | 1820 | OD1 | ASP A 117 | 128.957 | 140.688 | -81.676 | 1.00 | 6.73 | O |
| ATOM | 1821 | OD2 | ASP A 117 | 130.788 | 139.636 | -82.080 | 1.00 | 8.35 | O |
| ATOM | 1822 | C | ASP A 117 | 128.820 | 136.892 | -81.425 | 1.00 | 8.00 | C |
| ATOM | 1823 | O | ASP A 117 | 129.747 | 136.609 | -80.652 | 1.00 | 8.26 | O |
| ATOM | 1824 | N | ILE A 118 | 127.534 | 136.811 | -81.098 | 1.00 | 7.56 | N |
| ATOM | 1826 | CA | ILE A 118 | 127.068 | 136.489 | -79.757 | 1.00 | 7.43 | C |
| ATOM | 1828 | CB | ILE A 118 | 125.701 | 137.137 | -79.548 | 1.00 | 7.57 | C |
| ATOM | 1830 | CG1 | ILE A 118 | 125.852 | 138.657 | -79.601 | 1.00 | 8.79 | C |
| ATOM | 1833 | CD1 | ILE A 118 | 124.594 | 139.357 | -79.918 | 1.00 | 12.14 | C |
| ATOM | 1837 | CG2 | ILE A 118 | 125.088 | 136.727 | -78.196 | 1.00 | 7.47 | C |
| ATOM | 1841 | C | ILE A 118 | 126.998 | 134.990 | -79.452 | 1.00 | 7.24 | C |
| ATOM | 1842 | O | ILE A 118 | 127.288 | 134.570 | -78.339 | 1.00 | 7.24 | O |
| ATOM | 1843 | N | SER A 119 | 126.614 | 134.182 | -80.424 | 1.00 | 6.88 | N |
| ATOM | 1845 | CA | SER A 119 | 126.404 | 132.763 | -80.169 | 1.00 | 7.12 | C |
| ATOM | 1847 | CB | SER A 119 | 125.300 | 132.219 | -81.069 | 1.00 | 7.01 | C |
| ATOM | 1850 | OG | SER A 119 | 124.142 | 133.045 | -80.996 | 1.00 | 7.64 | O |
| ATOM | 1852 | C | SER A 119 | 127.696 | 131.927 | -80.298 | 1.00 | 7.03 | C |
| ATOM | 1853 | O | SER A 119 | 127.835 | 130.901 | -79.606 | 1.00 | 6.99 | O |
| ATOM | 1854 | N | ALA A 120 | 128.633 | 132.387 | -81.134 | 1.00 | 6.46 | N |
| ATOM | 1856 | CA | ALA A 120 | 129.865 | 131.655 | -81.429 | 1.00 | 6.53 | C |
| ATOM | 1858 | CB | ALA A 120 | 129.952 | 131.313 | -82.927 | 1.00 | 6.18 | C |
| ATOM | 1862 | C | ALA A 120 | 131.130 | 132.385 | -81.011 | 1.00 | 6.39 | C |
| ATOM | 1863 | O | ALA A 120 | 131.928 | 131.839 | -80.248 | 1.00 | 7.13 | O |
| ATOM | 1864 | N | TYR A 121 | 131.367 | 133.586 | -81.535 | 1.00 | 6.34 | N |
| ATOM | 1866 | CA | TYR A 121 | 132.629 | 134.279 | -81.236 | 1.00 | 6.35 | C |
| ATOM | 1868 | CB | TYR A 121 | 132.802 | 135.596 | -81.997 | 1.00 | 6.56 | C |
| ATOM | 1871 | CG | TYR A 121 | 133.963 | 136.371 | -81.433 | 1.00 | 7.84 | C |
| ATOM | 1872 | CD1 | TYR A 121 | 135.273 | 135.964 | -81.673 | 1.00 | 8.37 | C |
| ATOM | 1874 | CE1 | TYR A 121 | 136.344 | 136.641 | -81.111 | 1.00 | 8.79 | C |
| ATOM | 1876 | CZ | TYR A 121 | 136.119 | 137.724 | -80.287 | 1.00 | 9.35 | C |
| ATOM | 1877 | OH | TYR A 121 | 137.188 | 138.384 | -79.728 | 1.00 | 9.51 | O |
| ATOM | 1879 | CE2 | TYR A 121 | 134.826 | 138.138 | -80.006 | 1.00 | 9.35 | C |
| ATOM | 1881 | CD2 | TYR A 121 | 133.755 | 137.455 | -80.574 | 1.00 | 9.92 | C |
| ATOM | 1883 | C | TYR A 121 | 132.799 | 134.526 | -79.726 | 1.00 | 6.10 | C |
| ATOM | 1884 | O | TYR A 121 | 133.894 | 134.429 | -79.218 | 1.00 | 5.34 | O |
| ATOM | 1885 | N | SER A 122 | 131.710 | 134.817 | -79.030 | 1.00 | 6.16 | N |
| ATOM | 1887 | CA | SER A 122 | 131.764 | 135.106 | -77.607 | 1.00 | 6.52 | C |
| ATOM | 1889 | CB | SER A 122 | 130.355 | 135.353 | -77.040 | 1.00 | 6.31 | C |
| ATOM | 1892 | OG | SER A 122 | 129.554 | 134.202 | -77.139 | 1.00 | 6.69 | O |
| ATOM | 1894 | C | SER A 122 | 132.455 | 133.992 | -76.817 | 1.00 | 6.52 | C |
| ATOM | 1895 | O | SER A 122 | 133.075 | 134.266 | -75.790 | 1.00 | 6.44 | O |
| ATOM | 1896 | N | PHE A 123 | 132.355 | 132.749 | -77.295 | 1.00 | 5.92 | N |
| ATOM | 1898 | CA | PHE A 123 | 133.057 | 131.636 | -76.652 | 1.00 | 5.46 | C |
| ATOM | 1900 | CB | PHE A 123 | 132.676 | 130.291 | -77.278 | 1.00 | 5.48 | C |
| ATOM | 1903 | CG | PHE A 123 | 133.224 | 129.110 | -76.525 | 1.00 | 5.90 | C |
| ATOM | 1904 | CD1 | PHE A 123 | 134.358 | 128.460 | -76.962 | 1.00 | 5.91 | C |

(SEQ ID NO. 34)

FIGURE 20-14

```
ATOM   1906  CE1  PHE A 123    134.876 127.393 -76.256  1.00  7.30    C
ATOM   1908  CZ   PHE A 123    134.254 126.970 -75.088  1.00  6.28    C
ATOM   1910  CE2  PHE A 123    133.123 127.618 -74.649  1.00  6.00    C
ATOM   1912  CD2  PHE A 123    132.621 128.684 -75.354  1.00  5.94    C
ATOM   1914  C    PHE A 123    134.573 131.821 -76.690  1.00  5.26    C
ATOM   1915  O    PHE A 123    135.262 131.659 -75.670  1.00  4.25    O
ATOM   1916  N    ALA A 124    135.080 132.118 -77.880  1.00  5.63    N
ATOM   1918  CA   ALA A 124    136.500 132.369 -78.068  1.00  6.28    C
ATOM   1920  CB   ALA A 124    136.824 132.582 -79.542  1.00  6.36    C
ATOM   1924  C    ALA A 124    136.964 133.562 -77.238  1.00  6.87    C
ATOM   1925  O    ALA A 124    138.029 133.522 -76.636  1.00  7.16    O
ATOM   1926  N    ALA A 125    136.136 134.604 -77.183  1.00  7.56    N
ATOM   1928  CA   ALA A 125    136.456 135.812 -76.461  1.00  7.25    C
ATOM   1930  CB   ALA A 125    135.390 136.840 -76.705  1.00  7.34    C
ATOM   1934  C    ALA A 125    136.627 135.539 -74.952  1.00  7.81    C
ATOM   1935  O    ALA A 125    137.536 136.057 -74.331  1.00  7.46    O
ATOM   1936  N    LEU A 126    135.744 134.725 -74.378  1.00  8.57    N
ATOM   1938  CA   LEU A 126    135.843 134.322 -72.979  1.00  9.32    C
ATOM   1940  CB   LEU A 126    134.605 133.530 -72.558  1.00  9.26    C
ATOM   1943  CG   LEU A 126    133.376 134.431 -72.429  1.00 10.74    C
ATOM   1945  CD1  LEU A 126    132.113 133.611 -72.344  1.00 12.09    C
ATOM   1949  CD2  LEU A 126    133.485 135.357 -71.203  1.00 11.15    C
ATOM   1953  C    LEU A 126    137.093 133.485 -72.743  1.00  9.81    C
ATOM   1954  O    LEU A 126    137.754 133.629 -71.724  1.00 10.55    O
ATOM   1955  N    ALA A 127    137.404 132.618 -73.695  1.00 10.06    N
ATOM   1957  CA   ALA A 127    138.616 131.820 -73.667  1.00 10.69    C
ATOM   1959  CB   ALA A 127    138.633 130.868 -74.862  1.00 10.51    C
ATOM   1963  C    ALA A 127    139.853 132.716 -73.707  1.00 11.25    C
ATOM   1964  O    ALA A 127    140.820 132.497 -72.986  1.00 10.41    O
ATOM   1965  N    LYS A 128    139.801 133.731 -74.561  1.00 12.17    N
ATOM   1967  CA   LYS A 128    140.931 134.628 -74.775  1.00 13.14    C
ATOM   1969  CB   LYS A 128    140.584 135.654 -75.869  1.00 13.80    C
ATOM   1972  CG   LYS A 128    141.702 135.989 -76.838  1.00 14.97    C
ATOM   1975  CD   LYS A 128    141.798 137.470 -77.048  1.00 16.78    C
ATOM   1978  CE   LYS A 128    142.104 137.838 -78.487  1.00 17.79    C
ATOM   1981  NZ   LYS A 128    143.150 137.023 -79.115  1.00 16.34    N
ATOM   1985  C    LYS A 128    141.261 135.350 -73.477  1.00 12.92    C
ATOM   1986  O    LYS A 128    142.415 135.372 -73.016  1.00 12.69    O
ATOM   1987  N    GLU A 129    140.229 135.921 -72.877  1.00 12.69    N
ATOM   1989  CA   GLU A 129    140.410 136.820 -71.748  1.00 13.00    C
ATOM   1991  CB   GLU A 129    139.286 137.860 -71.731  1.00 12.95    C
ATOM   1994  CG   GLU A 129    139.254 138.728 -72.977  1.00 14.32    C
ATOM   1997  CD   GLU A 129    140.558 139.475 -73.234  1.00 15.56    C
ATOM   1998  OE1  GLU A 129    140.899 139.701 -74.418  1.00 17.84    O
ATOM   1999  OE2  GLU A 129    141.243 139.839 -72.259  1.00 16.15    O
ATOM   2000  C    GLU A 129    140.496 136.100 -70.401  1.00 12.77    C
ATOM   2001  O    GLU A 129    141.048 136.644 -69.460  1.00 12.52    O
ATOM   2002  N    GLY A 130    139.980 134.877 -70.322  1.00 12.90    N
ATOM   2004  CA   GLY A 130    139.998 134.110 -69.089  1.00 13.15    C
ATOM   2007  C    GLY A 130    141.125 133.088 -69.018  1.00 13.26    C
ATOM   2008  O    GLY A 130    141.274 132.405 -68.020  1.00 12.62    O
ATOM   2009  N    ARG A 131    141.924 132.978 -70.066  1.00 13.95    N
ATOM   2011  CA   ARG A 131    142.914 131.902 -70.132  1.00 15.33    C
ATOM   2013  CB   ARG A 131    143.532 131.791 -71.539  1.00 15.60    C
ATOM   2016  CG   ARG A 131    145.039 131.722 -71.568  1.00 18.48    C
ATOM   2019  CD   ARG A 131    145.618 130.743 -72.539  1.00 21.28    C
ATOM   2022  NE   ARG A 131    145.670 131.319 -73.866  1.00 25.28    N
ATOM   2024  CZ   ARG A 131    146.326 130.787 -74.899  1.00 29.84    C
ATOM   2025  NH1  ARG A 131    147.005 129.640 -74.772  1.00 31.31    N
ATOM   2028  NH2  ARG A 131    146.298 131.408 -76.075  1.00 29.98    N
ATOM   2031  C    ARG A 131    143.996 132.073 -69.067  1.00 15.45    C
ATOM   2032  O    ARG A 131    144.452 131.105 -68.475  1.00 15.52    O
ATOM   2033  N    SER A 132    144.411 133.306 -68.836  1.00 15.91    N
ATOM   2035  CA   SER A 132    145.420 133.590 -67.831  1.00 16.56    C
ATOM   2037  CB   SER A 132    145.726 135.093 -67.800  1.00 16.80    C
ATOM   2040  OG   SER A 132    146.491 135.422 -66.654  1.00 19.05    O
ATOM   2042  C    SER A 132    145.003 133.092 -66.444  1.00 16.45    C
ATOM   2043  O    SER A 132    145.812 132.525 -65.726  1.00 16.29    O
```

(SEQ ID NO. 34)

FIGURE 20-15

| | | | | | | | | | |
|---|---|---|---|---|---|---|---|---|---|
| ATOM | 2044 | N | MET | A | 133 | 143.740 133.274 -66.078 | 1.00 | 16.62 | N |
| ATOM | 2046 | CA | MET | A | 133 | 143.251 132.771 -64.798 | 1.00 | 17.01 | C |
| ATOM | 2048 | CB | MET | A | 133 | 141.909 133.415 -64.450 | 1.00 | 17.43 | C |
| ATOM | 2051 | CG | MET | A | 133 | 142.036 134.826 -63.923 | 1.00 | 17.45 | C |
| ATOM | 2054 | SD | MET | A | 133 | 140.456 135.457 -63.389 | 1.00 | 19.27 | S |
| ATOM | 2055 | CE | MET | A | 133 | 140.379 134.858 -61.678 | 1.00 | 19.23 | C |
| ATOM | 2059 | C | MET | A | 133 | 143.099 131.250 -64.753 | 1.00 | 17.24 | C |
| ATOM | 2060 | O | MET | A | 133 | 143.225 130.645 -63.682 | 1.00 | 17.27 | O |
| ATOM | 2061 | N | MET | A | 134 | 142.815 130.643 -65.905 | 1.00 | 17.15 | N |
| ATOM | 2063 | CA | MET | A | 134 | 142.506 129.213 -65.992 | 1.00 | 17.11 | C |
| ATOM | 2065 | CB | MET | A | 134 | 141.536 128.951 -67.162 | 1.00 | 16.85 | C |
| ATOM | 2068 | CG | MET | A | 134 | 140.109 129.397 -66.955 | 1.00 | 16.52 | C |
| ATOM | 2071 | SD | MET | A | 134 | 139.004 128.796 -68.257 | 1.00 | 13.13 | S |
| ATOM | 2072 | CE | MET | A | 134 | 139.509 129.822 -69.647 | 1.00 | 15.38 | C |
| ATOM | 2076 | C | MET | A | 134 | 143.742 128.335 -66.211 | 1.00 | 17.43 | C |
| ATOM | 2077 | O | MET | A | 134 | 143.636 127.108 -66.191 | 1.00 | 16.72 | O |
| ATOM | 2078 | N | LYS | A | 135 | 144.900 128.936 -66.466 | 1.00 | 17.97 | N |
| ATOM | 2080 | CA | LYS | A | 135 | 146.047 128.130 -66.858 | 1.00 | 18.91 | C |
| ATOM | 2082 | CB | LYS | A | 135 | 147.169 128.973 -67.501 | 1.00 | 19.56 | C |
| ATOM | 2085 | CG | LYS | A | 135 | 147.907 129.962 -66.612 | 1.00 | 22.36 | C |
| ATOM | 2088 | CD | LYS | A | 135 | 149.049 130.680 -67.391 | 1.00 | 25.66 | C |
| ATOM | 2091 | CE | LYS | A | 135 | 149.296 132.154 -66.912 | 1.00 | 27.94 | C |
| ATOM | 2094 | NZ | LYS | A | 135 | 149.686 133.134 -68.054 | 1.00 | 28.37 | N |
| ATOM | 2098 | C | LYS | A | 135 | 146.554 127.245 -65.713 | 1.00 | 18.68 | C |
| ATOM | 2099 | O | LYS | A | 135 | 146.424 127.577 -64.535 | 1.00 | 18.58 | O |
| ATOM | 2100 | N | ASN | A | 136 | 147.045 126.072 -66.097 | 1.00 | 18.68 | N |
| ATOM | 2102 | CA | ASN | A | 136 | 147.757 125.152 -65.214 | 1.00 | 18.78 | C |
| ATOM | 2104 | CB | ASN | A | 136 | 149.154 125.717 -64.953 | 1.00 | 18.93 | C |
| ATOM | 2107 | CG | ASN | A | 136 | 149.900 125.995 -66.248 | 1.00 | 20.73 | C |
| ATOM | 2108 | OD1 | ASN | A | 136 | 149.834 125.199 -67.204 | 1.00 | 21.33 | O |
| ATOM | 2109 | ND2 | ASN | A | 136 | 150.586 127.135 -66.308 | 1.00 | 23.50 | N |
| ATOM | 2112 | C | ASN | A | 136 | 147.034 124.753 -63.926 | 1.00 | 18.27 | C |
| ATOM | 2113 | O | ASN | A | 136 | 147.622 124.731 -62.843 | 1.00 | 18.47 | O |
| ATOM | 2114 | N | ARG | A | 137 | 145.752 124.420 -64.069 | 1.00 | 17.54 | N |
| ATOM | 2116 | CA | ARG | A | 137 | 144.956 123.925 -62.964 | 1.00 | 16.74 | C |
| ATOM | 2118 | CB | ARG | A | 137 | 144.422 125.118 -62.155 | 1.00 | 17.16 | C |
| ATOM | 2121 | CG | ARG | A | 137 | 143.610 126.134 -62.936 | 1.00 | 17.35 | C |
| ATOM | 2124 | CD | ARG | A | 137 | 143.266 127.402 -62.126 | 1.00 | 18.22 | C |
| ATOM | 2127 | NE | ARG | A | 137 | 142.394 127.124 -60.980 | 1.00 | 18.74 | N |
| ATOM | 2129 | CZ | ARG | A | 137 | 142.627 127.499 -59.708 | 1.00 | 21.04 | C |
| ATOM | 2130 | NH1 | ARG | A | 137 | 143.698 128.214 -59.367 | 1.00 | 21.86 | N |
| ATOM | 2133 | NH2 | ARG | A | 137 | 141.758 127.179 -58.761 | 1.00 | 20.08 | N |
| ATOM | 2136 | C | ARG | A | 137 | 143.812 122.985 -63.387 | 1.00 | 15.77 | C |
| ATOM | 2137 | O | ARG | A | 137 | 142.783 122.921 -62.721 | 1.00 | 15.59 | O |
| ATOM | 2138 | N | ASN | A | 138 | 143.991 122.238 -64.476 | 1.00 | 14.73 | N |
| ATOM | 2140 | CA | ASN | A | 138 | 142.952 121.318 -64.952 | 1.00 | 14.13 | C |
| ATOM | 2142 | CB | ASN | A | 138 | 142.807 120.105 -64.011 | 1.00 | 14.26 | C |
| ATOM | 2145 | CG | ASN | A | 138 | 144.041 119.218 -64.009 | 1.00 | 16.51 | C |
| ATOM | 2146 | OD1 | ASN | A | 138 | 144.581 118.882 -65.077 | 1.00 | 17.39 | O |
| ATOM | 2147 | ND2 | ASN | A | 138 | 144.495 118.825 -62.811 | 1.00 | 16.14 | N |
| ATOM | 2150 | C | ASN | A | 138 | 141.614 122.043 -65.095 | 1.00 | 12.80 | C |
| ATOM | 2151 | O | ASN | A | 138 | 140.566 121.579 -64.638 | 1.00 | 12.23 | O |
| ATOM | 2152 | N | ALA | A | 139 | 141.683 123.201 -65.730 | 1.00 | 11.77 | N |
| ATOM | 2154 | CA | ALA | A | 139 | 140.534 124.058 -65.906 | 1.00 | 11.33 | C |
| ATOM | 2156 | CB | ALA | A | 139 | 140.995 125.506 -66.167 | 1.00 | 11.39 | C |
| ATOM | 2160 | C | ALA | A | 139 | 139.667 123.544 -67.058 | 1.00 | 10.67 | C |
| ATOM | 2161 | O | ALA | A | 139 | 140.114 122.718 -67.847 | 1.00 | 10.35 | O |
| ATOM | 2162 | N | SER | A | 140 | 138.447 124.071 -67.158 | 1.00 | 9.85 | N |
| ATOM | 2164 | CA | SER | A | 140 | 137.437 123.576 -68.078 | 1.00 | 9.12 | C |
| ATOM | 2166 | CB | SER | A | 140 | 136.490 122.653 -67.334 | 1.00 | 9.18 | C |
| ATOM | 2169 | OG | SER | A | 140 | 137.192 121.743 -66.492 | 1.00 | 9.48 | O |
| ATOM | 2171 | C | SER | A | 140 | 136.623 124.703 -68.725 | 1.00 | 8.95 | C |
| ATOM | 2172 | O | SER | A | 140 | 136.394 125.750 -68.125 | 1.00 | 8.77 | O |
| ATOM | 2173 | N | MET | A | 141 | 136.206 124.485 -69.967 | 1.00 | 8.23 | N |
| ATOM | 2175 | CA | MET | A | 141 | 135.194 125.311 -70.584 | 1.00 | 8.20 | C |
| ATOM | 2177 | CB | BMET | A | 141 | 135.787 126.115 -71.738 | 0.35 | 8.02 | C |
| ATOM | 2178 | CB | AMET | A | 141 | 135.793 126.138 -71.712 | 0.65 | 8.41 | C |
| ATOM | 2183 | CG | BMET | A | 141 | 136.876 127.090 -71.326 | 0.35 | 7.11 | C |

(SEQ ID NO. 34)

FIGURE 20-16

```
ATOM   2184  CG  AMET A 141     136.634 127.301 -71.217  0.65  8.96           C
ATOM   2189  SD  BMET A 141     137.219 128.291 -72.617  0.35  6.48           S
ATOM   2190  SD  AMET A 141     136.818 128.549 -72.483  0.65 10.74           S
ATOM   2191  CE  BMET A 141     135.692 129.383 -72.548  0.35  4.75           C
ATOM   2192  CE  AMET A 141     138.153 127.906 -73.188  0.65 11.36           C
ATOM   2199  C   MET A 141     134.130 124.395 -71.106  1.00  8.45           C
ATOM   2200  O   MET A 141     134.446 123.307 -71.569  1.00  8.32           O
ATOM   2201  N   VAL A 142     132.868 124.789 -70.988  1.00  9.19           N
ATOM   2203  CA  VAL A 142     131.837 124.115 -71.753  1.00 10.13           C
ATOM   2205  CB  VAL A 142     131.210 122.864 -71.018  1.00 10.70           C
ATOM   2207  CG1 VAL A 142     131.553 122.826 -69.540  1.00 10.91           C
ATOM   2211  CG2 VAL A 142     129.705 122.737 -71.261  1.00 11.34           C
ATOM   2215  C   VAL A 142     130.800 125.087 -72.314  1.00 10.39           C
ATOM   2216  O   VAL A 142     130.362 126.010 -71.634  1.00 10.61           O
ATOM   2217  N   ALA A 143     130.436 124.851 -73.577  1.00  9.76           N
ATOM   2219  CA  ALA A 143     129.466 125.648 -74.285  1.00  9.22           C
ATOM   2221  CB  ALA A 143     130.015 126.033 -75.667  1.00  9.42           C
ATOM   2225  C   ALA A 143     128.224 124.822 -74.460  1.00  9.01           C
ATOM   2226  O   ALA A 143     128.285 123.595 -74.530  1.00  8.64           O
ATOM   2227  N   LEU A 144     127.096 125.506 -74.576  1.00  8.53           N
ATOM   2229  CA  LEU A 144     125.858 124.856 -74.923  1.00  8.51           C
ATOM   2231  CB  LEU A 144     124.723 125.335 -74.005  1.00  8.95           C
ATOM   2234  CG  LEU A 144     124.733 124.357 -72.819  1.00  9.75           C
ATOM   2236  CD1 LEU A 144     125.340 124.971 -71.583  1.00 11.19           C
ATOM   2240  CD2 LEU A 144     123.384 123.822 -72.582  1.00 11.03           C
ATOM   2244  C   LEU A 144     125.524 125.048 -76.384  1.00  8.18           C
ATOM   2245  O   LEU A 144     125.505 126.170 -76.890  1.00  8.11           O
ATOM   2246  N   THR A 145     125.286 123.922 -77.051  1.00  8.16           N
ATOM   2248  CA  THR A 145     124.918 123.876 -78.455  1.00  8.17           C
ATOM   2250  CB  THR A 145     126.132 123.410 -79.290  1.00  8.51           C
ATOM   2252  OG1 THR A 145     125.859 123.524 -80.702  1.00  8.93           O
ATOM   2254  CG2 THR A 145     126.458 121.911 -79.053  1.00  9.14           C
ATOM   2258  C   THR A 145     123.684 122.985 -78.675  1.00  7.62           C
ATOM   2259  O   THR A 145     123.079 122.510 -77.728  1.00  7.11           O
ATOM   2260  N   TYR A 146     123.328 122.782 -79.940  1.00  7.44           N
ATOM   2262  CA  TYR A 146     122.084 122.137 -80.329  1.00  7.20           C
ATOM   2264  CB  TYR A 146     120.968 123.189 -80.392  1.00  7.64           C
ATOM   2267  CG  TYR A 146     119.605 122.667 -80.816  1.00  6.55           C
ATOM   2268  CD1 TYR A 146     118.941 121.721 -80.057  1.00  5.90           C
ATOM   2270  CE1 TYR A 146     117.690 121.237 -80.433  1.00  5.11           C
ATOM   2272  CZ  TYR A 146     117.094 121.716 -81.576  1.00  7.29           C
ATOM   2273  OH  TYR A 146     115.859 121.232 -81.966  1.00  7.36           O
ATOM   2275  CE2 TYR A 146     117.744 122.672 -82.357  1.00  6.79           C
ATOM   2277  CD2 TYR A 146     118.986 123.140 -81.965  1.00  6.81           C
ATOM   2279  C   TYR A 146     122.260 121.505 -81.704  1.00  7.10           C
ATOM   2280  O   TYR A 146     123.022 122.009 -82.541  1.00  6.41           O
ATOM   2281  N   ILE A 147     121.514 120.427 -81.941  1.00  6.30           N
ATOM   2283  CA  ILE A 147     121.717 119.561 -83.107  1.00  5.58           C
ATOM   2285  CB  ILE A 147     120.876 118.266 -82.955  1.00  4.98           C
ATOM   2287  CG1 ILE A 147     121.366 117.198 -83.936  1.00  2.00           C
ATOM   2290  CD1 ILE A 147     120.686 115.857 -83.783  1.00  2.00           C
ATOM   2294  CG2 ILE A 147     119.375 118.549 -83.119  1.00  5.17           C
ATOM   2298  C   ILE A 147     121.451 120.264 -84.447  1.00  5.53           C
ATOM   2299  O   ILE A 147     121.834 119.766 -85.499  1.00  5.40           O
ATOM   2300  N   GLY A 148     120.835 121.441 -84.401  1.00  6.31           N
ATOM   2302  CA  GLY A 148     120.728 122.316 -85.568  1.00  6.66           C
ATOM   2305  C   GLY A 148     122.061 122.746 -86.166  1.00  7.02           C
ATOM   2306  O   GLY A 148     122.125 123.179 -87.325  1.00  6.91           O
ATOM   2307  N   ALA A 149     123.126 122.636 -85.373  1.00  7.53           N
ATOM   2309  CA  ALA A 149     124.499 122.777 -85.875  1.00  8.19           C
ATOM   2311  CB  ALA A 149     125.477 122.676 -84.731  1.00  7.85           C
ATOM   2315  C   ALA A 149     124.844 121.712 -86.926  1.00  8.70           C
ATOM   2316  O   ALA A 149     125.524 121.999 -87.893  1.00  9.09           O
ATOM   2317  N   GLU A 150     124.374 120.488 -86.713  1.00  9.24           N
ATOM   2319  CA  GLU A 150     124.821 119.320 -87.475  1.00  9.91           C
ATOM   2321  CB  GLU A 150     124.848 118.081 -86.582  1.00  9.48           C
ATOM   2324  CG  GLU A 150     125.515 118.278 -85.230  1.00 11.48           C
ATOM   2327  CD  GLU A 150     125.319 117.084 -84.296  1.00 11.66           C
```

(SEQ ID NO. 34)

FIGURE 20-17

```
ATOM  2328  OE1  GLU A 150    125.226 117.318 -83.078  1.00 10.06      O
ATOM  2329  OE2  GLU A 150    125.262 115.922 -84.783  1.00 12.90      O
ATOM  2330  C    GLU A 150    123.910 119.035 -88.669  1.00 10.23      C
ATOM  2331  O    GLU A 150    124.370 118.528 -89.681  1.00  9.90      O
ATOM  2332  N    LYS A 151    122.618 119.337 -88.505  1.00 10.85      N
ATOM  2334  CA   LYS A 151    121.594 119.109 -89.517  1.00 11.44      C
ATOM  2336  CB   LYS A 151    120.663 117.972 -89.078  1.00 11.91      C
ATOM  2339  CG   LYS A 151    121.358 116.676 -88.681  1.00 12.40      C
ATOM  2342  CD   LYS A 151    121.770 115.892 -89.901  1.00 14.10      C
ATOM  2345  CE   LYS A 151    122.694 114.756 -89.533  1.00 15.24      C
ATOM  2348  NZ   LYS A 151    123.266 114.141 -90.753  1.00 16.64      N
ATOM  2352  C    LYS A 151    120.736 120.348 -89.749  1.00 11.43      C
ATOM  2353  O    LYS A 151    120.396 121.068 -88.809  1.00 10.81      O
ATOM  2354  N    ALA A 152    120.388 120.578 -91.013  1.00 12.01      N
ATOM  2356  CA   ALA A 152    119.393 121.571 -91.388  1.00 12.64      C
ATOM  2358  CB   ALA A 152    119.303 121.724 -92.892  1.00 12.74      C
ATOM  2362  C    ALA A 152    118.032 121.184 -90.816  1.00 13.42      C
ATOM  2363  O    ALA A 152    117.678 120.027 -90.705  1.00 13.98      O
ATOM  2364  N    MET A 153    117.263 122.193 -90.481  1.00 14.29      N
ATOM  2366  CA   MET A 153    116.123 122.037 -89.623  1.00 14.52      C
ATOM  2368  CB   MET A 153    116.671 122.025 -88.214  1.00 14.94      C
ATOM  2371  CG  BMET A 153    115.768 121.693 -87.079  0.35 15.12      C
ATOM  2372  CG  AMET A 153    115.620 121.651 -87.203  0.65 16.48      C
ATOM  2377  SD  BMET A 153    116.871 121.683 -85.617  0.35 15.76      S
ATOM  2378  SD  AMET A 153    115.852 122.419 -85.602  0.65 20.17      S
ATOM  2379  CE  BMET A 153    117.092 119.939 -85.343  0.35 14.59      C
ATOM  2380  CE  AMET A 153    114.605 121.525 -84.711  0.65 19.64      C
ATOM  2387  C    MET A 153    115.242 123.259 -89.847  1.00 13.73      C
ATOM  2388  O    MET A 153    115.728 124.371 -89.727  1.00 13.59      O
ATOM  2389  N    PRO A 154    113.965 123.062 -90.162  1.00 13.06      N
ATOM  2390  CA   PRO A 154    113.021 124.169 -90.316  1.00 12.82      C
ATOM  2392  CB   PRO A 154    111.658 123.462 -90.292  1.00 12.97      C
ATOM  2395  CG   PRO A 154    111.923 122.127 -90.811  1.00 13.07      C
ATOM  2398  CD   PRO A 154    113.301 121.768 -90.364  1.00 13.32      C
ATOM  2401  C    PRO A 154    113.101 125.182 -89.178  1.00 12.34      C
ATOM  2402  O    PRO A 154    113.110 124.787 -88.009  1.00 12.12      O
ATOM  2403  N    SER A 155    113.221 126.457 -89.547  1.00 11.75      N
ATOM  2405  CA   SER A 155    113.063 127.620 -88.656  1.00 11.28      C
ATOM  2407  CB   SER A 155    111.879 127.459 -87.714  1.00 11.44      C
ATOM  2410  OG   SER A 155    110.701 127.300 -88.472  1.00 13.16      O
ATOM  2412  C    SER A 155    114.288 128.022 -87.858  1.00 10.37      C
ATOM  2413  O    SER A 155    114.499 129.203 -87.648  1.00 10.29      O
ATOM  2414  N    TYR A 156    115.094 127.056 -87.417  1.00  9.15      N
ATOM  2416  CA   TYR A 156    116.275 127.358 -86.618  1.00  7.84      C
ATOM  2418  CB   TYR A 156    116.959 126.071 -86.154  1.00  7.68      C
ATOM  2421  CG   TYR A 156    117.841 126.267 -84.940  1.00  6.70      C
ATOM  2422  CD1  TYR A 156    117.332 126.815 -83.773  1.00  5.85      C
ATOM  2424  CE1  TYR A 156    118.128 126.993 -82.655  1.00  6.02      C
ATOM  2426  CZ   TYR A 156    119.453 126.628 -82.697  1.00  5.39      C
ATOM  2427  OH   TYR A 156    120.246 126.823 -81.585  1.00  5.42      O
ATOM  2429  CE2  TYR A 156    119.989 126.097 -83.847  1.00  5.92      C
ATOM  2431  CD2  TYR A 156    119.179 125.905 -84.960  1.00  6.09      C
ATOM  2433  C    TYR A 156    117.243 128.223 -87.427  1.00  7.35      C
ATOM  2434  O    TYR A 156    117.936 129.054 -86.884  1.00  6.40      O
ATOM  2435  N    ASN A 157    117.294 127.976 -88.730  1.00  7.11      N
ATOM  2437  CA   ASN A 157    117.859 128.913 -89.689  1.00  7.36      C
ATOM  2439  CB   ASN A 157    116.870 130.089 -89.924  1.00  7.43      C
ATOM  2442  CG   ASN A 157    115.548 129.661 -90.586  1.00  6.88      C
ATOM  2443  OD1  ASN A 157    114.643 130.478 -90.754  1.00  7.21      O
ATOM  2444  ND2  ASN A 157    115.436 128.396 -90.946  1.00  5.14      N
ATOM  2447  C    ASN A 157    119.271 129.398 -89.298  1.00  6.88      C
ATOM  2448  O    ASN A 157    120.198 128.590 -89.168  1.00  7.42      O
ATOM  2449  N    THR A 158    119.437 130.695 -89.083  1.00  6.15      N
ATOM  2451  CA   THR A 158    120.760 131.259 -88.876  1.00  6.15      C
ATOM  2453  CB   THR A 158    120.661 132.778 -88.866  1.00  5.63      C
ATOM  2455  OG1  THR A 158    119.911 133.195 -90.006  1.00  6.03      O
ATOM  2457  CG2  THR A 158    122.041 133.437 -89.031  1.00  6.73      C
ATOM  2461  C    THR A 158    121.405 130.777 -87.595  1.00  5.75      C
```

(SEQ ID NO. 34)

FIGURE 20-18

| ATOM | 2462 | O | THR A 158 | 122.629 130.738 -87.502 | 1.00 | 5.41 | O |
|---|---|---|---|---|---|---|---|
| ATOM | 2463 | N | MET A 159 | 120.582 130.450 -86.598 | 1.00 | 5.74 | N |
| ATOM | 2465 | CA | MET A 159 | 121.096 129.921 -85.336 | 1.00 | 5.95 | C |
| ATOM | 2467 | CB | MET A 159 | 119.990 129.790 -84.268 | 1.00 | 5.82 | C |
| ATOM | 2470 | CG | MET A 159 | 119.777 131.041 -83.427 | 1.00 | 6.13 | C |
| ATOM | 2473 | SD | MET A 159 | 121.252 131.688 -82.592 | 1.00 | 6.61 | S |
| ATOM | 2474 | CE | MET A 159 | 121.802 130.209 -81.818 | 1.00 | 6.93 | C |
| ATOM | 2478 | C | MET A 159 | 121.763 128.571 -85.560 | 1.00 | 6.11 | C |
| ATOM | 2479 | O | MET A 159 | 122.738 128.253 -84.893 | 1.00 | 6.23 | O |
| ATOM | 2480 | N | GLY A 160 | 121.212 127.767 -86.463 | 1.00 | 6.05 | N |
| ATOM | 2482 | CA | GLY A 160 | 121.831 126.516 -86.835 | 1.00 | 6.26 | C |
| ATOM | 2485 | C | GLY A 160 | 123.256 126.727 -87.299 | 1.00 | 6.28 | C |
| ATOM | 2486 | O | GLY A 160 | 124.183 126.066 -86.815 | 1.00 | 6.41 | O |
| ATOM | 2487 | N | VAL A 161 | 123.412 127.668 -88.227 | 1.00 | 6.52 | N |
| ATOM | 2489 | CA | VAL A 161 | 124.708 128.023 -88.815 | 1.00 | 6.42 | C |
| ATOM | 2491 | CB | VAL A 161 | 124.546 129.061 -89.954 | 1.00 | 6.54 | C |
| ATOM | 2493 | CG1 | VAL A 161 | 125.868 129.421 -90.578 | 1.00 | 7.31 | C |
| ATOM | 2497 | CG2 | VAL A 161 | 123.625 128.503 -91.037 | 1.00 | 6.86 | C |
| ATOM | 2501 | C | VAL A 161 | 125.658 128.551 -87.752 | 1.00 | 6.43 | C |
| ATOM | 2502 | O | VAL A 161 | 126.824 128.148 -87.705 | 1.00 | 6.04 | O |
| ATOM | 2503 | N | ALA A 162 | 125.143 129.424 -86.890 | 1.00 | 6.51 | N |
| ATOM | 2505 | CA | ALA A 162 | 125.912 129.991 -85.782 | 1.00 | 6.56 | C |
| ATOM | 2507 | CB | ALA A 162 | 125.086 131.062 -85.053 | 1.00 | 6.47 | C |
| ATOM | 2511 | C | ALA A 162 | 126.368 128.923 -84.785 | 1.00 | 6.87 | C |
| ATOM | 2512 | O | ALA A 162 | 127.478 129.007 -84.241 | 1.00 | 6.65 | O |
| ATOM | 2513 | N | LYS A 163 | 125.509 127.937 -84.533 | 1.00 | 6.72 | N |
| ATOM | 2515 | CA | LYS A 163 | 125.862 126.845 -83.655 | 1.00 | 6.77 | C |
| ATOM | 2517 | CB | LYS A 163 | 124.625 126.026 -83.279 | 1.00 | 7.00 | C |
| ATOM | 2520 | CG | LYS A 163 | 123.700 126.725 -82.253 | 1.00 | 7.03 | C |
| ATOM | 2523 | CD | LYS A 163 | 124.368 126.897 -80.902 | 1.00 | 7.60 | C |
| ATOM | 2526 | CE | LYS A 163 | 123.342 127.165 -79.807 | 1.00 | 8.61 | C |
| ATOM | 2529 | NZ | LYS A 163 | 123.898 127.833 -78.614 | 1.00 | 5.80 | N |
| ATOM | 2533 | C | LYS A 163 | 126.946 125.945 -84.269 | 1.00 | 6.48 | C |
| ATOM | 2534 | O | LYS A 163 | 127.754 125.383 -83.542 | 1.00 | 6.71 | O |
| ATOM | 2535 | N | ALA A 164 | 126.961 125.798 -85.589 | 1.00 | 5.96 | N |
| ATOM | 2537 | CA | ALA A 164 | 128.010 125.034 -86.259 | 1.00 | 5.71 | C |
| ATOM | 2539 | CB | ALA A 164 | 127.686 124.831 -87.713 | 1.00 | 5.98 | C |
| ATOM | 2543 | C | ALA A 164 | 129.336 125.759 -86.112 | 1.00 | 5.74 | C |
| ATOM | 2544 | O | ALA A 164 | 130.362 125.150 -85.872 | 1.00 | 5.51 | O |
| ATOM | 2545 | N | SER A 165 | 129.285 127.072 -86.232 | 1.00 | 5.72 | N |
| ATOM | 2547 | CA | SER A 165 | 130.427 127.918 -85.983 | 1.00 | 5.66 | C |
| ATOM | 2549 | CB | SER A 165 | 130.055 129.364 -86.307 | 1.00 | 5.76 | C |
| ATOM | 2552 | OG | SER A 165 | 131.096 130.266 -85.993 | 1.00 | 6.17 | O |
| ATOM | 2554 | C | SER A 165 | 130.883 127.760 -84.527 | 1.00 | 5.53 | C |
| ATOM | 2555 | O | SER A 165 | 132.072 127.567 -84.264 | 1.00 | 5.44 | O |
| ATOM | 2556 | N | LEU A 166 | 129.941 127.826 -83.587 | 1.00 | 5.63 | N |
| ATOM | 2558 | CA | LEU A 166 | 130.257 127.638 -82.168 | 1.00 | 5.63 | C |
| ATOM | 2560 | CB | LEU A 166 | 128.986 127.671 -81.297 | 1.00 | 5.62 | C |
| ATOM | 2563 | CG | LEU A 166 | 129.169 127.291 -79.806 | 1.00 | 6.25 | C |
| ATOM | 2565 | CD1 | LEU A 166 | 130.179 128.194 -79.118 | 1.00 | 6.86 | C |
| ATOM | 2569 | CD2 | LEU A 166 | 127.856 127.307 -79.044 | 1.00 | 6.18 | C |
| ATOM | 2573 | C | LEU A 166 | 130.994 126.324 -81.948 | 1.00 | 5.46 | C |
| ATOM | 2574 | O | LEU A 166 | 132.011 126.299 -81.292 | 1.00 | 5.81 | O |
| ATOM | 2575 | N | GLU A 167 | 130.474 125.233 -82.498 | 1.00 | 5.20 | N |
| ATOM | 2577 | CA | GLU A 167 | 131.030 123.903 -82.259 | 1.00 | 5.00 | C |
| ATOM | 2579 | CB | GLU A 167 | 130.121 122.819 -82.829 | 1.00 | 4.29 | C |
| ATOM | 2582 | CG | GLU A 167 | 128.823 122.723 -82.049 | 1.00 | 5.51 | C |
| ATOM | 2585 | CD | GLU A 167 | 127.949 121.569 -82.473 | 1.00 | 6.43 | C |
| ATOM | 2586 | OE1 | GLU A 167 | 126.774 121.547 -82.026 | 1.00 | 7.15 | O |
| ATOM | 2587 | OE2 | GLU A 167 | 128.427 120.689 -83.227 | 1.00 | 5.63 | O |
| ATOM | 2588 | C | GLU A 167 | 132.428 123.742 -82.816 | 1.00 | 4.83 | C |
| ATOM | 2589 | O | GLU A 167 | 133.284 123.125 -82.164 | 1.00 | 5.09 | O |
| ATOM | 2590 | N | ALA A 168 | 132.663 124.273 -84.009 | 1.00 | 5.24 | N |
| ATOM | 2592 | CA | ALA A 168 | 134.017 124.346 -84.556 | 1.00 | 5.88 | C |
| ATOM | 2594 | CB | ALA A 168 | 133.991 124.869 -86.000 | 1.00 | 6.25 | C |
| ATOM | 2598 | C | ALA A 168 | 134.893 125.250 -83.677 | 1.00 | 6.17 | C |
| ATOM | 2599 | O | ALA A 168 | 136.070 124.973 -83.435 | 1.00 | 6.57 | O |
| ATOM | 2600 | N | THR A 169 | 134.313 126.324 -83.174 | 1.00 | 6.14 | N |

(SEQ ID NO. 34)

FIGURE 20-19

| ATOM | 2602 | CA  | THR A 169 | 135.043 127.193 -82.249 | 1.00 | 6.44  | C |
| ATOM | 2604 | CB  | THR A 169 | 134.204 128.422 -81.914 | 1.00 | 6.11  | C |
| ATOM | 2606 | OG1 | THR A 169 | 134.016 129.170 -83.125 | 1.00 | 6.34  | O |
| ATOM | 2608 | CG2 | THR A 169 | 134.944 129.348 -80.963 | 1.00 | 6.68  | C |
| ATOM | 2612 | C   | THR A 169 | 135.508 126.457 -80.982 | 1.00 | 5.97  | C |
| ATOM | 2613 | O   | THR A 169 | 136.645 126.630 -80.546 | 1.00 | 5.06  | O |
| ATOM | 2614 | N   | VAL A 170 | 134.648 125.616 -80.431 | 1.00 | 5.88  | N |
| ATOM | 2616 | CA  | VAL A 170 | 135.016 124.759 -79.297 | 1.00 | 6.34  | C |
| ATOM | 2618 | CB  | VAL A 170 | 133.824 123.917 -78.840 | 1.00 | 6.55  | C |
| ATOM | 2620 | CG1 | VAL A 170 | 134.247 122.736 -77.944 | 1.00 | 6.07  | C |
| ATOM | 2624 | CG2 | VAL A 170 | 132.794 124.819 -78.132 | 1.00 | 6.63  | C |
| ATOM | 2628 | C   | VAL A 170 | 136.215 123.866 -79.635 | 1.00 | 7.02  | C |
| ATOM | 2629 | O   | VAL A 170 | 137.127 123.742 -78.834 | 1.00 | 7.17  | O |
| ATOM | 2630 | N   | ARG A 171 | 136.228 123.273 -80.828 | 1.00 | 7.91  | N |
| ATOM | 2632 | CA  | ARG A 171 | 137.347 122.429 -81.278 | 1.00 | 8.10  | C |
| ATOM | 2634 | CB  | ARG A 171 | 137.011 121.766 -82.624 | 1.00 | 8.17  | C |
| ATOM | 2637 | CG  | ARG A 171 | 135.942 120.674 -82.518 | 1.00 | 8.85  | C |
| ATOM | 2640 | CD  | ARG A 171 | 135.851 119.807 -83.727 | 1.00 | 9.09  | C |
| ATOM | 2643 | NE  | ARG A 171 | 135.302 120.528 -84.870 | 1.00 | 11.83 | N |
| ATOM | 2645 | CZ  | ARG A 171 | 133.997 120.663 -85.145 | 1.00 | 12.61 | C |
| ATOM | 2646 | NH1 | ARG A 171 | 133.614 121.329 -86.232 | 1.00 | 11.76 | N |
| ATOM | 2649 | NH2 | ARG A 171 | 133.073 120.132 -84.358 | 1.00 | 12.57 | N |
| ATOM | 2652 | C   | ARG A 171 | 138.682 123.189 -81.408 | 1.00 | 8.22  | C |
| ATOM | 2653 | O   | ARG A 171 | 139.725 122.727 -80.941 | 1.00 | 8.25  | O |
| ATOM | 2654 | N   | TYR A 172 | 138.643 124.336 -82.075 | 1.00 | 8.04  | N |
| ATOM | 2656 | CA  | TYR A 172 | 139.833 125.143 -82.248 | 1.00 | 7.91  | C |
| ATOM | 2658 | CB  | TYR A 172 | 139.583 126.261 -83.270 | 1.00 | 7.57  | C |
| ATOM | 2661 | CG  | TYR A 172 | 139.751 125.754 -84.690 | 1.00 | 7.76  | C |
| ATOM | 2662 | CD1 | TYR A 172 | 138.662 125.302 -85.430 | 1.00 | 7.98  | C |
| ATOM | 2664 | CE1 | TYR A 172 | 138.823 124.812 -86.724 | 1.00 | 6.26  | C |
| ATOM | 2666 | CZ  | TYR A 172 | 140.082 124.756 -87.273 | 1.00 | 5.69  | C |
| ATOM | 2667 | OH  | TYR A 172 | 140.260 124.269 -88.544 | 1.00 | 4.06  | O |
| ATOM | 2669 | CE2 | TYR A 172 | 141.180 125.189 -86.557 | 1.00 | 6.80  | C |
| ATOM | 2671 | CD2 | TYR A 172 | 141.014 125.678 -85.277 | 1.00 | 6.99  | C |
| ATOM | 2673 | C   | TYR A 172 | 140.295 125.681 -80.895 | 1.00 | 7.86  | C |
| ATOM | 2674 | O   | TYR A 172 | 141.478 125.813 -80.659 | 1.00 | 7.42  | O |
| ATOM | 2675 | N   | THR A 173 | 139.355 125.971 -80.007 | 1.00 | 7.99  | N |
| ATOM | 2677 | CA  | THR A 173 | 139.687 126.420 -78.656 | 1.00 | 8.25  | C |
| ATOM | 2679 | CB  | THR A 173 | 138.427 126.988 -77.948 | 1.00 | 8.65  | C |
| ATOM | 2681 | OG1 | THR A 173 | 137.947 128.124 -78.676 | 1.00 | 7.87  | O |
| ATOM | 2683 | CG2 | THR A 173 | 138.755 127.573 -76.550 | 1.00 | 8.81  | C |
| ATOM | 2687 | C   | THR A 173 | 140.330 125.292 -77.842 | 1.00 | 8.03  | C |
| ATOM | 2688 | O   | THR A 173 | 141.289 125.530 -77.106 | 1.00 | 8.03  | O |
| ATOM | 2689 | N   | ALA A 174 | 139.827 124.070 -78.017 | 1.00 | 7.75  | N |
| ATOM | 2691 | CA  | ALA A 174 | 140.358 122.887 -77.339 | 1.00 | 7.59  | C |
| ATOM | 2693 | CB  | ALA A 174 | 139.532 121.648 -77.689 | 1.00 | 7.30  | C |
| ATOM | 2697 | C   | ALA A 174 | 141.826 122.673 -77.713 | 1.00 | 7.66  | C |
| ATOM | 2698 | O   | ALA A 174 | 142.666 122.387 -76.853 | 1.00 | 7.50  | O |
| ATOM | 2699 | N   | LEU A 175 | 142.125 122.846 -78.998 | 1.00 | 7.53  | N |
| ATOM | 2701 | CA  | LEU A 175 | 143.473 122.671 -79.503 | 1.00 | 7.54  | C |
| ATOM | 2703 | CB  | LEU A 175 | 143.449 122.536 -81.025 | 1.00 | 7.59  | C |
| ATOM | 2706 | CG  | LEU A 175 | 144.807 122.548 -81.749 | 1.00 | 8.95  | C |
| ATOM | 2708 | CD1 | LEU A 175 | 145.691 121.378 -81.363 | 1.00 | 7.31  | C |
| ATOM | 2712 | CD2 | LEU A 175 | 144.550 122.564 -83.251 | 1.00 | 10.85 | C |
| ATOM | 2716 | C   | LEU A 175 | 144.383 123.818 -79.056 | 1.00 | 7.40  | C |
| ATOM | 2717 | O   | LEU A 175 | 145.539 123.591 -78.695 | 1.00 | 7.52  | O |
| ATOM | 2718 | N   | ALA A 176 | 143.845 125.036 -79.043 | 1.00 | 7.20  | N |
| ATOM | 2720 | CA  | ALA A 176 | 144.600 126.228 -78.658 | 1.00 | 7.01  | C |
| ATOM | 2722 | CB  | ALA A 176 | 143.807 127.487 -78.986 | 1.00 | 6.88  | C |
| ATOM | 2726 | C   | ALA A 176 | 144.970 126.240 -77.180 | 1.00 | 6.88  | C |
| ATOM | 2727 | O   | ALA A 176 | 146.007 126.766 -76.823 | 1.00 | 6.96  | O |
| ATOM | 2728 | N   | LEU A 177 | 144.129 125.656 -76.328 | 1.00 | 6.83  | N |
| ATOM | 2730 | CA  | LEU A 177 | 144.298 125.780 -74.876 | 1.00 | 6.83  | C |
| ATOM | 2732 | CB  | LEU A 177 | 142.991 126.239 -74.224 | 1.00 | 5.81  | C |
| ATOM | 2735 | CG  | LEU A 177 | 142.398 127.556 -74.695 | 1.00 | 4.95  | C |
| ATOM | 2737 | CD1 | LEU A 177 | 141.133 127.848 -73.886 | 1.00 | 3.09  | C |
| ATOM | 2741 | CD2 | LEU A 177 | 143.411 128.666 -74.558 | 1.00 | 2.09  | C |
| ATOM | 2745 | C   | LEU A 177 | 144.736 124.489 -74.205 | 1.00 | 7.44  | C |

(SEQ ID NO. 34)

FIGURE 20-20

| | ATOM | 2746 | O | LEU | A | 177 | 144.971 | 124.473 | -72.996 | 1.00 | 7.53 | O |
|---|---|---|---|---|---|---|---|---|---|---|---|---|
| | ATOM | 2747 | N | GLY | A | 178 | 144.820 | 123.403 | -74.965 | 1.00 | 8.53 | N |
| | ATOM | 2749 | CA | GLY | A | 178 | 145.185 | 122.125 | -74.389 | 1.00 | 9.44 | C |
| | ATOM | 2752 | C | GLY | A | 178 | 146.547 | 122.187 | -73.734 | 1.00 | 10.63 | C |
| 5 | ATOM | 2753 | O | GLY | A | 178 | 146.767 | 121.565 | -72.696 | 1.00 | 11.50 | O |
| | ATOM | 2754 | N | GLU | A | 179 | 147.466 | 122.947 | -74.327 | 1.00 | 11.99 | N |
| | ATOM | 2756 | CA | GLU | A | 179 | 148.822 | 123.116 | -73.776 | 1.00 | 12.98 | C |
| | ATOM | 2758 | CB | GLU | A | 179 | 149.654 | 124.041 | -74.657 | 1.00 | 13.39 | C |
| | ATOM | 2761 | CG | GLU | A | 179 | 149.016 | 125.424 | -74.878 | 1.00 | 15.11 | C |
| 10 | ATOM | 2764 | CD | GLU | A | 179 | 149.681 | 126.212 | -76.009 | 1.00 | 17.86 | C |
| | ATOM | 2765 | OE1 | GLU | A | 179 | 150.200 | 127.318 | -75.701 | 1.00 | 18.08 | O |
| | ATOM | 2766 | OE2 | GLU | A | 179 | 149.672 | 125.741 | -77.198 | 1.00 | 17.79 | O |
| | ATOM | 2767 | C | GLU | A | 179 | 148.803 | 123.660 | -72.337 | 1.00 | 13.28 | C |
| | ATOM | 2768 | O | GLU | A | 179 | 149.730 | 123.426 | -71.560 | 1.00 | 13.88 | O |
| 15 | ATOM | 2769 | N | ASP | A | 180 | 147.751 | 124.389 | -71.984 | 1.00 | 13.11 | N |
| | ATOM | 2771 | CA | ASP | A | 180 | 147.624 | 124.945 | -70.640 | 1.00 | 12.66 | C |
| | ATOM | 2773 | CB | ASP | A | 180 | 147.060 | 126.368 | -70.739 | 1.00 | 13.07 | C |
| | ATOM | 2776 | CG | ASP | A | 180 | 148.061 | 127.367 | -71.310 | 1.00 | 13.81 | C |
| | ATOM | 2777 | OD1 | ASP | A | 180 | 147.598 | 128.391 | -71.848 | 1.00 | 15.85 | O |
| 20 | ATOM | 2778 | OD2 | ASP | A | 180 | 149.310 | 127.235 | -71.264 | 1.00 | 13.68 | O |
| | ATOM | 2779 | C | ASP | A | 180 | 146.760 | 124.076 | -69.709 | 1.00 | 11.88 | C |
| | ATOM | 2780 | O | ASP | A | 180 | 146.329 | 124.535 | -68.654 | 1.00 | 11.43 | O |
| | ATOM | 2781 | N | GLY | A | 181 | 146.522 | 122.818 | -70.095 | 1.00 | 11.18 | N |
| | ATOM | 2783 | CA | GLY | A | 181 | 145.700 | 121.901 | -69.316 | 1.00 | 10.57 | C |
| 25 | ATOM | 2786 | C | GLY | A | 181 | 144.205 | 122.199 | -69.309 | 1.00 | 10.46 | C |
| | ATOM | 2787 | O | GLY | A | 181 | 143.453 | 121.577 | -68.538 | 1.00 | 9.78 | O |
| | ATOM | 2788 | N | ILE | A | 182 | 143.761 | 123.109 | -70.181 | 1.00 | 10.08 | N |
| | ATOM | 2790 | CA | ILE | A | 182 | 142.362 | 123.512 | -70.216 | 1.00 | 10.32 | C |
| | ATOM | 2792 | CB | ILE | A | 182 | 142.180 | 125.009 | -70.631 | 1.00 | 10.34 | C |
| 30 | ATOM | 2794 | CG1 | ILE | A | 182 | 143.098 | 125.936 | -69.818 | 1.00 | 9.73 | C |
| | ATOM | 2797 | CD1 | ILE | A | 182 | 142.952 | 127.398 | -70.152 | 1.00 | 9.07 | C |
| | ATOM | 2801 | CG2 | ILE | A | 182 | 140.714 | 125.435 | -70.454 | 1.00 | 10.31 | C |
| | ATOM | 2805 | C | ILE | A | 182 | 141.601 | 122.602 | -71.176 | 1.00 | 10.25 | C |
| | ATOM | 2806 | O | ILE | A | 182 | 141.941 | 122.523 | -72.366 | 1.00 | 11.08 | O |
| 35 | ATOM | 2807 | N | LYS | A | 183 | 140.582 | 121.914 | -70.663 | 1.00 | 9.47 | N |
| | ATOM | 2809 | CA | LYS | A | 183 | 139.689 | 121.104 | -71.506 | 1.00 | 8.98 | C |
| | ATOM | 2811 | CB | LYS | A | 183 | 139.240 | 119.822 | -70.789 | 1.00 | 8.81 | C |
| | ATOM | 2814 | CG | LYS | A | 183 | 138.449 | 119.985 | -69.489 | 1.00 | 7.93 | C |
| | ATOM | 2817 | CD | LYS | A | 183 | 138.300 | 118.621 | -68.838 | 1.00 | 7.95 | C |
| 40 | ATOM | 2820 | CE | LYS | A | 183 | 137.820 | 118.649 | -67.399 | 1.00 | 6.88 | C |
| | ATOM | 2823 | NZ | LYS | A | 183 | 138.676 | 119.441 | -66.486 | 1.00 | 6.34 | N |
| | ATOM | 2827 | C | LYS | A | 183 | 138.495 | 121.941 | -71.952 | 1.00 | 8.61 | C |
| | ATOM | 2828 | O | LYS | A | 183 | 138.020 | 122.789 | -71.204 | 1.00 | 9.00 | O |
| | ATOM | 2829 | N | VAL | A | 184 | 138.018 | 121.698 | -73.169 | 1.00 | 8.01 | N |
| 45 | ATOM | 2831 | CA | VAL | A | 184 | 137.053 | 122.574 | -73.825 | 1.00 | 7.27 | C |
| | ATOM | 2833 | CB | VAL | A | 184 | 137.754 | 123.532 | -74.801 | 1.00 | 6.88 | C |
| | ATOM | 2835 | CG1 | VAL | A | 184 | 136.768 | 124.488 | -75.405 | 1.00 | 4.78 | C |
| | ATOM | 2839 | CG2 | VAL | A | 184 | 138.863 | 124.295 | -74.084 | 1.00 | 7.01 | C |
| | ATOM | 2843 | C | VAL | A | 184 | 136.035 | 121.745 | -74.580 | 1.00 | 7.40 | C |
| 50 | ATOM | 2844 | O | VAL | A | 184 | 136.328 | 121.193 | -75.650 | 1.00 | 7.12 | O |
| | ATOM | 2845 | N | ASN | A | 185 | 134.830 | 121.676 | -74.024 | 1.00 | 7.28 | N |
| | ATOM | 2847 | CA | ASN | A | 185 | 133.808 | 120.782 | -74.516 | 1.00 | 7.17 | C |
| | ATOM | 2849 | CB | ASN | A | 185 | 133.630 | 119.617 | -73.531 | 1.00 | 7.47 | C |
| | ATOM | 2852 | CG | ASN | A | 185 | 134.882 | 118.752 | -73.415 | 1.00 | 7.26 | C |
| 55 | ATOM | 2853 | OD1 | ASN | A | 185 | 135.513 | 118.673 | -72.348 | 1.00 | 10.08 | O |
| | ATOM | 2854 | ND2 | ASN | A | 185 | 135.265 | 118.142 | -74.507 | 1.00 | 4.66 | N |
| | ATOM | 2857 | C | ASN | A | 185 | 132.494 | 121.514 | -74.697 | 1.00 | 7.58 | C |
| | ATOM | 2858 | O | ASN | A | 185 | 132.370 | 122.684 | -74.334 | 1.00 | 7.51 | O |
| | ATOM | 2859 | N | ALA | A | 186 | 131.515 | 120.813 | -75.262 | 1.00 | 7.53 | N |
| 60 | ATOM | 2861 | CA | ALA | A | 186 | 130.171 | 121.342 | -75.438 | 1.00 | 7.67 | C |
| | ATOM | 2863 | CB | ALA | A | 186 | 129.976 | 121.815 | -76.872 | 1.00 | 8.10 | C |
| | ATOM | 2867 | C | ALA | A | 186 | 129.133 | 120.285 | -75.091 | 1.00 | 7.62 | C |
| | ATOM | 2868 | O | ALA | A | 186 | 129.387 | 119.083 | -75.218 | 1.00 | 7.99 | O |
| | ATOM | 2869 | N | VAL | A | 187 | 127.972 | 120.732 | -74.633 | 1.00 | 7.01 | N |
| 65 | ATOM | 2871 | CA | VAL | A | 187 | 126.845 | 119.852 | -74.398 | 1.00 | 6.51 | C |
| | ATOM | 2873 | CB | VAL | A | 187 | 126.322 | 119.964 | -72.952 | 1.00 | 6.51 | C |
| | ATOM | 2875 | CG1 | VAL | A | 187 | 124.936 | 119.271 | -72.788 | 1.00 | 6.41 | C |
| | ATOM | 2879 | CG2 | VAL | A | 187 | 127.321 | 119.381 | -71.990 | 1.00 | 6.71 | C |

(SEQ ID NO. 34)

FIGURE 20-21

| ATOM | 2883 | C | VAL | A | 187 | 125.770 | 120.268 | -75.383 | 1.00 | 6.47 | C |
| ATOM | 2884 | O | VAL | A | 187 | 125.362 | 121.428 | -75.400 | 1.00 | 5.81 | O |
| ATOM | 2885 | N | SER | A | 188 | 125.340 | 119.319 | -76.220 | 1.00 | 6.91 | N |
| ATOM | 2887 | CA | SER | A | 188 | 124.275 | 119.544 | -77.189 | 1.00 | 6.26 | C |
| ATOM | 2889 | CB | SER | A | 188 | 124.573 | 118.806 | -78.478 | 1.00 | 6.09 | C |
| ATOM | 2892 | OG | SER | A | 188 | 123.608 | 119.107 | -79.469 | 1.00 | 5.96 | O |
| ATOM | 2894 | C | SER | A | 188 | 122.951 | 119.085 | -76.584 | 1.00 | 6.31 | C |
| ATOM | 2895 | O | SER | A | 188 | 122.643 | 117.889 | -76.532 | 1.00 | 6.31 | O |
| ATOM | 2896 | N | ALA | A | 189 | 122.169 | 120.043 | -76.107 | 1.00 | 6.27 | N |
| ATOM | 2898 | CA | ALA | A | 189 | 120.937 | 119.725 | -75.393 | 1.00 | 6.24 | C |
| ATOM | 2900 | CB | ALA | A | 189 | 120.587 | 120.851 | -74.413 | 1.00 | 5.99 | C |
| ATOM | 2904 | C | ALA | A | 189 | 119.777 | 119.454 | -76.357 | 1.00 | 5.63 | C |
| ATOM | 2905 | O | ALA | A | 189 | 119.732 | 119.992 | -77.452 | 1.00 | 5.57 | O |
| ATOM | 2906 | N | GLY | A | 190 | 118.866 | 118.582 | -75.955 | 1.00 | 5.75 | N |
| ATOM | 2908 | CA | GLY | A | 190 | 117.572 | 118.486 | -76.600 | 1.00 | 6.21 | C |
| ATOM | 2911 | C | GLY | A | 190 | 116.791 | 119.751 | -76.270 | 1.00 | 6.64 | C |
| ATOM | 2912 | O | GLY | A | 190 | 117.170 | 120.488 | -75.350 | 1.00 | 6.95 | O |
| ATOM | 2913 | N | PRO | A | 191 | 115.712 | 120.017 | -76.994 | 1.00 | 6.86 | N |
| ATOM | 2914 | CA | PRO | A | 191 | 114.924 | 121.217 | -76.740 | 1.00 | 7.36 | C |
| ATOM | 2916 | CB | PRO | A | 191 | 113.841 | 121.193 | -77.830 | 1.00 | 7.47 | C |
| ATOM | 2919 | CG | PRO | A | 191 | 113.790 | 119.824 | -78.333 | 1.00 | 8.27 | C |
| ATOM | 2922 | CD | PRO | A | 191 | 115.159 | 119.205 | -78.090 | 1.00 | 7.35 | C |
| ATOM | 2925 | C | PRO | A | 191 | 114.310 | 121.265 | -75.339 | 1.00 | 8.11 | C |
| ATOM | 2926 | O | PRO | A | 191 | 113.916 | 120.258 | -74.742 | 1.00 | 8.02 | O |
| ATOM | 2927 | N | ILE | A | 192 | 114.241 | 122.487 | -74.827 | 1.00 | 8.89 | N |
| ATOM | 2929 | CA | ILE | A | 192 | 113.695 | 122.786 | -73.514 | 1.00 | 9.49 | C |
| ATOM | 2931 | CB | ILE | A | 192 | 114.821 | 122.926 | -72.437 | 1.00 | 9.02 | C |
| ATOM | 2933 | CG1 | ILE | A | 192 | 115.757 | 121.719 | -72.472 | 1.00 | 9.82 | C |
| ATOM | 2936 | CD1 | ILE | A | 192 | 116.886 | 121.719 | -71.436 | 1.00 | 9.88 | C |
| ATOM | 2940 | CG2 | ILE | A | 192 | 114.207 | 123.124 | -71.060 | 1.00 | 8.67 | C |
| ATOM | 2944 | C | ILE | A | 192 | 112.922 | 124.101 | -73.624 | 1.00 | 10.25 | C |
| ATOM | 2945 | O | ILE | A | 192 | 113.421 | 125.092 | -74.170 | 1.00 | 9.56 | O |
| ATOM | 2946 | N | LYS | A | 193 | 111.713 | 124.103 | -73.087 | 1.00 | 11.56 | N |
| ATOM | 2948 | CA | LYS | A | 193 | 110.901 | 125.310 | -72.999 | 1.00 | 13.09 | C |
| ATOM | 2950 | CB | LYS | A | 193 | 109.513 | 124.900 | -72.508 | 1.00 | 14.07 | C |
| ATOM | 2953 | CG | LYS | A | 193 | 108.399 | 125.960 | -72.510 | 1.00 | 17.45 | C |
| ATOM | 2956 | CD | LYS | A | 193 | 107.438 | 125.666 | -71.317 | 1.00 | 21.00 | C |
| ATOM | 2959 | CE | LYS | A | 193 | 105.984 | 126.002 | -71.643 | 1.00 | 24.10 | C |
| ATOM | 2962 | NZ | LYS | A | 193 | 105.787 | 127.491 | -71.831 | 1.00 | 26.60 | N |
| ATOM | 2966 | C | LYS | A | 193 | 111.569 | 126.326 | -72.053 | 1.00 | 12.67 | C |
| ATOM | 2967 | O | LYS | A | 193 | 111.403 | 126.262 | -70.839 | 1.00 | 13.60 | O |
| ATOM | 2968 | N | THR | A | 194 | 112.354 | 127.236 | -72.622 | 1.00 | 12.13 | N |
| ATOM | 2970 | CA | THR | A | 194 | 112.982 | 128.321 | -71.879 | 1.00 | 11.63 | C |
| ATOM | 2972 | CB | THR | A | 194 | 114.514 | 128.124 | -71.818 | 1.00 | 11.39 | C |
| ATOM | 2974 | OG1 | THR | A | 194 | 115.067 | 128.172 | -73.137 | 1.00 | 11.00 | O |
| ATOM | 2976 | CG2 | THR | A | 194 | 114.879 | 126.740 | -71.321 | 1.00 | 11.24 | C |
| ATOM | 2980 | C | THR | A | 194 | 112.644 | 129.631 | -72.583 | 1.00 | 11.71 | C |
| ATOM | 2981 | O | THR | A | 194 | 111.798 | 129.659 | -73.472 | 1.00 | 11.81 | O |
| ATOM | 2982 | N | LEU | A | 195 | 113.317 | 130.711 | -72.200 | 1.00 | 11.84 | N |
| ATOM | 2984 | CA | LEU | A | 195 | 113.200 | 131.984 | -72.911 | 1.00 | 11.64 | C |
| ATOM | 2986 | CB | LEU | A | 195 | 113.811 | 133.098 | -72.070 | 1.00 | 11.47 | C |
| ATOM | 2989 | CG | LEU | A | 195 | 112.991 | 133.461 | -70.830 | 1.00 | 11.71 | C |
| ATOM | 2991 | CD1 | LEU | A | 195 | 113.797 | 134.350 | -69.930 | 1.00 | 11.23 | C |
| ATOM | 2995 | CD2 | LEU | A | 195 | 111.687 | 134.155 | -71.208 | 1.00 | 11.98 | C |
| ATOM | 2999 | C | LEU | A | 195 | 113.857 | 131.935 | -74.308 | 1.00 | 11.59 | C |
| ATOM | 3000 | O | LEU | A | 195 | 113.651 | 132.836 | -75.135 | 1.00 | 11.15 | O |
| ATOM | 3001 | N | ALA | A | 196 | 114.660 | 130.894 | -74.558 | 1.00 | 10.96 | N |
| ATOM | 3003 | CA | ALA | A | 196 | 115.207 | 130.638 | -75.896 | 1.00 | 10.66 | C |
| ATOM | 3005 | CB | ALA | A | 196 | 116.357 | 129.614 | -75.831 | 1.00 | 10.59 | C |
| ATOM | 3009 | C | ALA | A | 196 | 114.121 | 130.166 | -76.869 | 1.00 | 10.48 | C |
| ATOM | 3010 | O | ALA | A | 196 | 114.372 | 130.067 | -78.060 | 1.00 | 9.66 | O |
| ATOM | 3011 | N | ALA | A | 197 | 112.926 | 129.862 | -76.353 | 1.00 | 10.62 | N |
| ATOM | 3013 | CA | ALA | A | 197 | 111.760 | 129.562 | -77.187 | 1.00 | 10.98 | C |
| ATOM | 3015 | CB | ALA | A | 197 | 110.992 | 128.382 | -76.606 | 1.00 | 10.93 | C |
| ATOM | 3019 | C | ALA | A | 197 | 110.808 | 130.767 | -77.409 | 1.00 | 11.29 | C |
| ATOM | 3020 | O | ALA | A | 197 | 109.799 | 130.615 | -78.096 | 1.00 | 11.43 | O |
| ATOM | 3021 | N | SER | A | 198 | 111.127 | 131.938 | -76.840 | 1.00 | 11.55 | N |
| ATOM | 3023 | CA | SER | A | 198 | 110.343 | 133.169 | -77.040 | 1.00 | 11.88 | C |

(SEQ ID NO. 34)

FIGURE 20-22

| | | | | | | | | | | |
|---|---|---|---|---|---|---|---|---|---|---|
| ATOM | 3025 | CB | SER | A | 198 | 111.033 | 134.394 | -76.424 | 1.00 11.38 | C |
| ATOM | 3028 | OG | SER | A | 198 | 111.491 | 134.147 | -75.120 | 1.00 11.07 | O |
| ATOM | 3030 | C | SER | A | 198 | 110.145 | 133.460 | -78.525 | 1.00 12.87 | C |
| ATOM | 3031 | O | SER | A | 198 | 111.125 | 133.609 | -79.265 | 1.00 13.00 | O |
| ATOM | 3032 | N | GLY | A | 199 | 108.887 | 133.533 | -78.954 | 1.00 13.65 | N |
| ATOM | 3034 | CA | GLY | A | 199 | 108.557 | 133.905 | -80.317 | 1.00 14.30 | C |
| ATOM | 3037 | C | GLY | A | 199 | 108.609 | 132.762 | -81.311 | 1.00 15.37 | C |
| ATOM | 3038 | O | GLY | A | 199 | 108.348 | 132.957 | -82.503 | 1.00 15.73 | O |
| ATOM | 3039 | N | ILE | A | 200 | 108.945 | 131.565 | -80.838 | 1.00 16.41 | N |
| ATOM | 3041 | CA | ILE | A | 200 | 109.079 | 130.405 | -81.708 | 1.00 16.79 | C |
| ATOM | 3043 | CB | ILE | A | 200 | 110.204 | 129.454 | -81.206 | 1.00 17.04 | C |
| ATOM | 3045 | CG1 | ILE | A | 200 | 111.557 | 130.185 | -81.096 | 1.00 18.19 | C |
| ATOM | 3048 | CD1 | ILE | A | 200 | 111.993 | 130.945 | -82.378 | 1.00 18.47 | C |
| ATOM | 3052 | CG2 | ILE | A | 200 | 110.317 | 128.233 | -82.120 | 1.00 16.92 | C |
| ATOM | 3056 | C | ILE | A | 200 | 107.748 | 129.687 | -81.679 | 1.00 17.27 | C |
| ATOM | 3057 | O | ILE | A | 200 | 107.331 | 129.223 | -80.628 | 1.00 16.62 | O |
| ATOM | 3058 | N | SER | A | 201 | 107.079 | 129.614 | -82.830 | 1.00 18.32 | N |
| ATOM | 3060 | CA | SER | A | 201 | 105.781 | 128.932 | -82.941 | 1.00 18.96 | C |
| ATOM | 3062 | CB | SER | A | 201 | 105.101 | 129.263 | -84.280 | 1.00 19.35 | C |
| ATOM | 3065 | OG | SER | A | 201 | 104.731 | 130.634 | -84.324 | 1.00 20.41 | O |
| ATOM | 3067 | C | SER | A | 201 | 105.916 | 127.421 | -82.824 | 1.00 19.04 | C |
| ATOM | 3068 | O | SER | A | 201 | 106.983 | 126.861 | -83.060 | 1.00 18.82 | O |
| ATOM | 3069 | N | ASN | A | 202 | 104.817 | 126.778 | -82.444 | 1.00 19.55 | N |
| ATOM | 3071 | CA | ASN | A | 202 | 104.740 | 125.325 | -82.354 | 1.00 20.09 | C |
| ATOM | 3073 | CB | ASN | A | 202 | 104.723 | 124.719 | -83.769 | 1.00 20.33 | C |
| ATOM | 3076 | CG | ASN | A | 202 | 103.707 | 125.382 | -84.680 | 1.00 22.03 | C |
| ATOM | 3077 | OD1 | ASN | A | 202 | 104.063 | 125.870 | -85.757 | 1.00 24.80 | O |
| ATOM | 3078 | ND2 | ASN | A | 202 | 102.437 | 125.420 | -84.248 | 1.00 21.26 | N |
| ATOM | 3081 | C | ASN | A | 202 | 105.883 | 124.695 | -81.548 | 1.00 19.84 | C |
| ATOM | 3082 | O | ASN | A | 202 | 106.359 | 123.615 | -81.892 | 1.00 19.78 | O |
| ATOM | 3083 | N | PHE | A | 203 | 106.341 | 125.364 | -80.499 | 1.00 19.64 | N |
| ATOM | 3085 | CA | PHE | A | 203 | 107.463 | 124.830 | -79.741 | 1.00 19.68 | C |
| ATOM | 3087 | CB | PHE | A | 203 | 108.044 | 125.873 | -78.780 | 1.00 19.16 | C |
| ATOM | 3090 | CG | PHE | A | 203 | 109.435 | 125.549 | -78.332 | 1.00 16.67 | C |
| ATOM | 3091 | CD1 | PHE | A | 203 | 110.526 | 125.967 | -79.073 | 1.00 15.61 | C |
| ATOM | 3093 | CE1 | PHE | A | 203 | 111.822 | 125.659 | -78.670 | 1.00 16.38 | C |
| ATOM | 3095 | CZ | PHE | A | 203 | 112.027 | 124.906 | -77.511 | 1.00 15.91 | C |
| ATOM | 3097 | CE2 | PHE | A | 203 | 110.926 | 124.465 | -76.780 | 1.00 14.78 | C |
| ATOM | 3099 | CD2 | PHE | A | 203 | 109.647 | 124.784 | -77.198 | 1.00 14.65 | C |
| ATOM | 3101 | C | PHE | A | 203 | 107.056 | 123.566 | -78.977 | 1.00 20.51 | C |
| ATOM | 3102 | O | PHE | A | 203 | 107.769 | 122.583 | -78.981 | 1.00 18.85 | O |
| ATOM | 3103 | N | LYS | A | 204 | 105.896 | 123.628 | -78.330 | 1.00 22.24 | N |
| ATOM | 3105 | CA | LYS | A | 204 | 105.324 | 122.509 | -77.586 | 1.00 23.82 | C |
| ATOM | 3107 | CB | LYS | A | 204 | 103.968 | 122.921 | -77.022 | 1.00 24.75 | C |
| ATOM | 3110 | CG | LYS | A | 204 | 103.516 | 122.155 | -75.793 | 1.00 27.85 | C |
| ATOM | 3113 | CD | LYS | A | 204 | 102.210 | 122.734 | -75.216 | 1.00 31.78 | C |
| ATOM | 3116 | CE | LYS | A | 204 | 102.359 | 124.220 | -74.790 | 1.00 34.01 | C |
| ATOM | 3119 | NZ | LYS | A | 204 | 103.727 | 124.548 | -74.260 | 1.00 34.50 | N |
| ATOM | 3123 | C | LYS | A | 204 | 105.129 | 121.286 | -78.457 | 1.00 24.19 | C |
| ATOM | 3124 | O | LYS | A | 204 | 105.401 | 120.176 | -78.022 | 1.00 23.88 | O |
| ATOM | 3125 | N | LYS | A | 205 | 104.646 | 121.498 | -79.678 | 1.00 24.92 | N |
| ATOM | 3127 | CA | LYS | A | 205 | 104.470 | 120.415 | -80.642 | 1.00 25.85 | C |
| ATOM | 3129 | CB | LYS | A | 205 | 103.810 | 120.915 | -81.931 | 1.00 26.52 | C |
| ATOM | 3132 | CG | LYS | A | 205 | 102.292 | 121.022 | -81.868 | 1.00 28.99 | C |
| ATOM | 3135 | CD | LYS | A | 205 | 101.665 | 120.793 | -83.248 | 1.00 32.13 | C |
| ATOM | 3138 | CE | LYS | A | 205 | 102.176 | 121.790 | -84.296 | 1.00 33.60 | C |
| ATOM | 3141 | NZ | LYS | A | 205 | 103.032 | 121.121 | -85.338 | 1.00 35.13 | N |
| ATOM | 3145 | C | LYS | A | 205 | 105.806 | 119.810 | -81.013 | 1.00 25.47 | C |
| ATOM | 3146 | O | LYS | A | 205 | 105.950 | 118.592 | -81.105 | 1.00 25.95 | O |
| ATOM | 3147 | N | MET | A | 206 | 106.776 | 120.674 | -81.248 | 1.00 24.76 | N |
| ATOM | 3149 | CA | MET | A | 206 | 108.125 | 120.246 | -81.552 | 1.00 24.40 | C |
| ATOM | 3151 | CB | BMET | A | 206 | 109.001 | 121.461 | -81.857 | 0.35 24.37 | C |
| ATOM | 3152 | CB | AMET | A | 206 | 109.007 | 121.470 | -81.805 | 0.65 24.65 | C |
| ATOM | 3157 | CG | BMET | A | 206 | 110.448 | 121.142 | -82.116 | 0.35 24.56 | C |
| ATOM | 3158 | CG | AMET | A | 206 | 110.414 | 121.178 | -82.273 | 0.65 25.65 | C |
| ATOM | 3163 | SD | BMET | A | 206 | 111.379 | 121.083 | -80.604 | 0.35 24.93 | S |
| ATOM | 3164 | SD | AMET | A | 206 | 111.331 | 122.703 | -82.635 | 0.65 28.96 | S |
| ATOM | 3165 | CE | BMET | A | 206 | 111.377 | 122.788 | -80.112 | 0.35 25.46 | C |

(SEQ ID NO. 34)

FIGURE 20-23

```
ATOM   3166 CE  AMET A 206     110.330 123.487 -83.991  0.65 28.03           C
ATOM   3173 C   MET  A 206     108.666 119.408 -80.382  1.00 23.78           C
ATOM   3174 O   MET  A 206     109.221 118.323 -80.599  1.00 23.92           O
ATOM   3175 N   LEU  A 207     108.456 119.883 -79.157  1.00 22.60           N
ATOM   3177 CA  LEU  A 207     108.767 119.127 -77.936  1.00 22.05           C
ATOM   3179 CB  LEU  A 207     108.276 119.879 -76.693  1.00 21.98           C
ATOM   3182 CG  LEU  A 207     109.238 120.610 -75.759  1.00 21.49           C
ATOM   3184 CD1 LEU  A 207     110.522 121.003 -76.418  1.00 21.84           C
ATOM   3188 CD2 LEU  A 207     108.549 121.825 -75.176  1.00 21.22           C
ATOM   3192 C   LEU  A 207     108.146 117.733 -77.926  1.00 21.91           C
ATOM   3193 O   LEU  A 207     108.811 116.761 -77.559  1.00 21.76           O
ATOM   3194 N   ASP  A 208     106.882 117.636 -78.326  1.00 22.07           N
ATOM   3196 CA  ASP  A 208     106.162 116.357 -78.308  1.00 22.58           C
ATOM   3198 CB  ASP  A 208     104.654 116.543 -78.516  1.00 22.82           C
ATOM   3201 CG  ASP  A 208     103.978 117.273 -77.366  1.00 24.26           C
ATOM   3202 OD1 ASP  A 208     104.555 117.366 -76.250  1.00 26.77           O
ATOM   3203 OD2 ASP  A 208     102.851 117.801 -77.500  1.00 27.12           O
ATOM   3204 C   ASP  A 208     106.697 115.413 -79.369  1.00 22.37           C
ATOM   3205 O   ASP  A 208     106.865 114.240 -79.110  1.00 22.27           O
ATOM   3206 N   TYR  A 209     106.970 115.937 -80.556  1.00 22.63           N
ATOM   3208 CA  TYR  A 209     107.533 115.144 -81.637  1.00 23.11           C
ATOM   3210 CB  TYR  A 209     107.740 116.000 -82.896  1.00 23.72           C
ATOM   3213 CG  TYR  A 209     108.657 115.347 -83.919  1.00 26.17           C
ATOM   3214 CD1 TYR  A 209     108.187 114.331 -84.748  1.00 28.19           C
ATOM   3216 CE1 TYR  A 209     109.017 113.712 -85.672  1.00 29.79           C
ATOM   3218 CZ  TYR  A 209     110.342 114.094 -85.770  1.00 31.12           C
ATOM   3219 OH  TYR  A 209     111.164 113.463 -86.693  1.00 34.84           O
ATOM   3221 CE2 TYR  A 209     110.847 115.093 -84.946  1.00 29.90           C
ATOM   3223 CD2 TYR  A 209     110.001 115.714 -84.023  1.00 28.26           C
ATOM   3225 C   TYR  A 209     108.868 114.553 -81.188  1.00 22.56           C
ATOM   3226 O   TYR  A 209     109.102 113.358 -81.298  1.00 22.55           O
ATOM   3227 N   ASN  A 210     109.734 115.421 -80.692  1.00 22.04           N
ATOM   3229 CA  ASN  A 210     111.032 115.038 -80.157  1.00 21.73           C
ATOM   3231 CB  ASN  A 210     111.699 116.246 -79.503  1.00 21.78           C
ATOM   3234 CG  ASN  A 210     113.172 116.234 -79.674  1.00 22.14           C
ATOM   3235 OD1 ASN  A 210     113.873 115.541 -78.949  1.00 22.49           O
ATOM   3236 ND2 ASN  A 210     113.665 116.989 -80.659  1.00 22.96           N
ATOM   3239 C   ASN  A 210     110.987 113.914 -79.130  1.00 21.13           C
ATOM   3240 O   ASN  A 210     111.824 113.022 -79.163  1.00 20.92           O
ATOM   3241 N   ALA  A 211     110.026 113.981 -78.212  1.00 20.49           N
ATOM   3243 CA  ALA  A 211     109.862 112.954 -77.189  1.00 20.14           C
ATOM   3245 CB  ALA  A 211     108.962 113.462 -76.073  1.00 20.08           C
ATOM   3249 C   ALA  A 211     109.320 111.635 -77.789  1.00 20.14           C
ATOM   3250 O   ALA  A 211     109.674 110.556 -77.324  1.00 19.56           O
ATOM   3251 N   MET  A 212     108.500 111.724 -78.833  1.00 19.95           N
ATOM   3253 CA  MET  A 212     108.038 110.528 -79.547  1.00 20.77           C
ATOM   3255 CB  MET  A 212     106.908 110.869 -80.532  1.00 21.54           C
ATOM   3258 CG  MET  A 212     105.516 110.986 -79.887  1.00 25.56           C
ATOM   3261 SD  MET  A 212     104.206 111.568 -81.079  1.00 34.55           S
ATOM   3262 CE  MET  A 212     104.847 110.856 -82.733  1.00 31.98           C
ATOM   3266 C   MET  A 212     109.146 109.777 -80.301  1.00 19.52           C
ATOM   3267 O   MET  A 212     109.177 108.563 -80.281  1.00 19.52           O
ATOM   3268 N   VAL  A 213     110.047 110.483 -80.973  1.00 18.61           N
ATOM   3270 CA  VAL  A 213     111.085 109.812 -81.757  1.00 17.83           C
ATOM   3272 CB  VAL  A 213     111.465 110.603 -83.027  1.00 18.05           C
ATOM   3274 CG1 VAL  A 213     110.207 111.006 -83.793  1.00 18.42           C
ATOM   3278 CG2 VAL  A 213     112.313 111.809 -82.699  1.00 18.58           C
ATOM   3282 C   VAL  A 213     112.340 109.459 -80.948  1.00 16.82           C
ATOM   3283 O   VAL  A 213     113.120 108.596 -81.351  1.00 16.68           O
ATOM   3284 N   SER  A 214     112.512 110.095 -79.797  1.00 15.78           N
ATOM   3286 CA  SER  A 214     113.654 109.812 -78.934  1.00 15.14           C
ATOM   3288 CB  SER  A 214     113.768 110.846 -77.809  1.00 15.00           C
ATOM   3291 OG  SER  A 214     114.277 112.063 -78.330  1.00 15.17           O
ATOM   3293 C   SER  A 214     113.571 108.400 -78.339  1.00 14.54           C
ATOM   3294 O   SER  A 214     112.512 107.961 -77.912  1.00 14.35           O
ATOM   3295 N   PRO  A 215     114.691 107.691 -78.333  1.00 13.96           N
ATOM   3296 CA  PRO  A 215     114.792 106.401 -77.653  1.00 13.75           C
ATOM   3298 CB  PRO  A 215     116.305 106.160 -77.605  1.00 13.88           C
```

(SEQ ID NO. 34)

FIGURE 20-24

```
ATOM   3301  CG   PRO A 215     116.824 106.842 -78.810  1.00 14.27           C
ATOM   3304  CD   PRO A 215     115.954 108.062 -79.002  1.00 13.91           C
ATOM   3307  C    PRO A 215     114.213 106.389 -76.229  1.00 13.41           C
ATOM   3308  O    PRO A 215     113.486 105.458 -75.906  1.00 12.51           O
ATOM   3309  N    LEU A 216     114.512 107.390 -75.402  1.00 13.34           N
ATOM   3311  CA   LEU A 216     114.011 107.381 -74.023  1.00 13.95           C
ATOM   3313  CB   LEU A 216     115.007 108.023 -73.043  1.00 13.83           C
ATOM   3316  CG   LEU A 216     116.255 107.154 -72.827  1.00 13.63           C
ATOM   3318  CD1  LEU A 216     117.426 107.969 -72.320  1.00 13.70           C
ATOM   3322  CD2  LEU A 216     115.963 105.996 -71.885  1.00 13.67           C
ATOM   3326  C    LEU A 216     112.607 107.976 -73.907  1.00 14.29           C
ATOM   3327  O    LEU A 216     112.020 107.982 -72.831  1.00 14.36           O
ATOM   3328  N    LYS A 217     112.071 108.434 -75.028  1.00 14.83           N
ATOM   3330  CA   LYS A 217     110.658 108.741 -75.156  1.00 15.88           C
ATOM   3332  CB   LYS A 217     109.789 107.479 -74.990  1.00 16.34           C
ATOM   3335  CG   LYS A 217     110.065 106.376 -76.031  1.00 18.00           C
ATOM   3338  CD   LYS A 217     109.605 106.757 -77.452  1.00 21.09           C
ATOM   3341  CE   LYS A 217     108.092 106.706 -77.591  1.00 23.17           C
ATOM   3344  NZ   LYS A 217     107.620 106.970 -78.983  1.00 24.55           N
ATOM   3348  C    LYS A 217     110.271 109.836 -74.169  1.00 16.01           C
ATOM   3349  O    LYS A 217     109.250 109.771 -73.492  1.00 16.51           O
ATOM   3350  N    LYS A 218     111.114 110.852 -74.096  1.00 16.15           N
ATOM   3352  CA   LYS A 218     110.897 111.942 -73.169  1.00 16.23           C
ATOM   3354  CB   LYS A 218     111.303 111.514 -71.758  1.00 16.70           C
ATOM   3357  CG   LYS A 218     112.748 111.850 -71.386  1.00 18.98           C
ATOM   3360  CD   LYS A 218     113.341 110.863 -70.372  1.00 21.67           C
ATOM   3363  CE   LYS A 218     114.593 111.450 -69.695  1.00 22.94           C
ATOM   3366  NZ   LYS A 218     115.651 110.444 -69.425  1.00 24.00           N
ATOM   3370  C    LYS A 218     111.673 113.181 -73.595  1.00 15.61           C
ATOM   3371  O    LYS A 218     112.502 113.132 -74.507  1.00 15.69           O
ATOM   3372  N    ASN A 219     111.374 114.286 -72.922  1.00 14.59           N
ATOM   3374  CA   ASN A 219     112.117 115.522 -73.046  1.00 13.62           C
ATOM   3376  CB   ASN A 219     111.161 116.725 -72.963  1.00 13.62           C
ATOM   3379  CG   ASN A 219     110.258 116.872 -74.207  1.00 13.99           C
ATOM   3380  OD1  ASN A 219     110.682 116.635 -75.348  1.00 17.10           O
ATOM   3381  ND2  ASN A 219     109.024 117.282 -73.987  1.00 13.34           N
ATOM   3384  C    ASN A 219     113.158 115.573 -71.921  1.00 12.82           C
ATOM   3385  O    ASN A 219     112.911 115.086 -70.806  1.00 12.33           O
ATOM   3386  N    VAL A 220     114.319 116.164 -72.204  1.00 11.48           N
ATOM   3388  CA   VAL A 220     115.313 116.389 -71.167  1.00 10.66           C
ATOM   3390  CB   VAL A 220     116.734 116.550 -71.742  1.00 10.12           C
ATOM   3392  CG1  VAL A 220     117.095 115.341 -72.588  1.00 10.74           C
ATOM   3396  CG2  VAL A 220     116.897 117.828 -72.535  1.00 10.08           C
ATOM   3400  C    VAL A 220     114.934 117.586 -70.283  1.00 10.85           C
ATOM   3401  O    VAL A 220     114.118 118.410 -70.657  1.00 10.41           O
ATOM   3402  N    ASP A 221     115.522 117.663 -69.097  1.00 11.32           N
ATOM   3404  CA   ASP A 221     115.384 118.839 -68.248  1.00 11.30           C
ATOM   3406  CB   ASP A 221     114.551 118.524 -66.995  1.00 11.61           C
ATOM   3409  CG   ASP A 221     115.207 117.514 -66.057  1.00 12.35           C
ATOM   3410  OD1  ASP A 221     116.451 117.382 -65.987  1.00 12.52           O
ATOM   3411  OD2  ASP A 221     114.518 116.813 -65.310  1.00 14.84           O
ATOM   3412  C    ASP A 221     116.754 119.428 -67.911  1.00 11.02           C
ATOM   3413  O    ASP A 221     117.787 118.890 -68.313  1.00 10.31           O
ATOM   3414  N    ILE A 222     116.745 120.532 -67.170  1.00 11.27           N
ATOM   3416  CA   ILE A 222     117.942 121.351 -66.996  1.00 11.64           C
ATOM   3418  CB   ILE A 222     117.595 122.819 -66.573  1.00 11.55           C
ATOM   3420  CG1  ILE A 222     116.733 122.858 -65.310  1.00 12.41           C
ATOM   3423  CD1  ILE A 222     116.556 124.268 -64.734  1.00 13.12           C
ATOM   3427  CG2  ILE A 222     116.911 123.554 -67.707  1.00 11.19           C
ATOM   3431  C    ILE A 222     118.918 120.749 -66.010  1.00 11.67           C
ATOM   3432  O    ILE A 222     120.082 121.142 -65.976  1.00 11.72           O
ATOM   3433  N    MET A 223     118.435 119.822 -65.186  1.00 12.28           N
ATOM   3435  CA   MET A 223     119.298 119.089 -64.267  1.00 12.64           C
ATOM   3437  CB   MET A 223     118.503 118.463 -63.111  1.00 13.07           C
ATOM   3440  CG   MET A 223     117.977 119.475 -62.084  1.00 14.62           C
ATOM   3443  SD   MET A 223     119.192 120.707 -61.543  1.00 16.41           S
ATOM   3444  CE   MET A 223     120.431 119.644 -60.826  1.00 17.71           C
ATOM   3448  C    MET A 223     120.083 118.021 -65.025  1.00 12.08           C
```

(SEQ ID NO. 34)

FIGURE 20-25

| | | | | | | | | | | |
|---|---|---|---|---|---|---|---|---|---|---|
| | ATOM | 3449 | O | MET | A | 223 | 121.261 | 117.823 | -64.743 | 1.00 | 12.46 | O |
| | ATOM | 3450 | N | GLU | A | 224 | 119.455 | 117.352 | -65.990 | 1.00 | 11.14 | N |
| | ATOM | 3452 | CA | GLU | A | 224 | 120.166 | 116.357 | -66.772 | 1.00 | 11.03 | C |
| | ATOM | 3454 | CB | GLU | A | 224 | 119.239 | 115.604 | -67.724 | 1.00 | 11.32 | C |
| 5 | ATOM | 3457 | CG | GLU | A | 224 | 118.204 | 114.749 | -67.015 | 1.00 | 12.37 | C |
| | ATOM | 3460 | CD | GLU | A | 224 | 117.205 | 114.110 | -67.961 | 1.00 | 13.38 | C |
| | ATOM | 3461 | OE1 | GLU | A | 224 | 116.759 | 112.984 | -67.667 | 1.00 | 14.36 | O |
| | ATOM | 3462 | OE2 | GLU | A | 224 | 116.848 | 114.727 | -68.988 | 1.00 | 12.15 | O |
| | ATOM | 3463 | C | GLU | A | 224 | 121.280 | 117.053 | -67.536 | 1.00 | 10.66 | C |
| 10 | ATOM | 3464 | O | GLU | A | 224 | 122.417 | 116.548 | -67.584 | 1.00 | 10.93 | O |
| | ATOM | 3465 | N | VAL | A | 225 | 120.969 | 118.225 | -68.101 | 1.00 | 10.08 | N |
| | ATOM | 3467 | CA | VAL | A | 225 | 121.966 | 119.018 | -68.835 | 1.00 | 9.33 | C |
| | ATOM | 3469 | CB | VAL | A | 225 | 121.319 | 120.174 | -69.625 | 1.00 | 9.38 | C |
| | ATOM | 3471 | CG1 | VAL | A | 225 | 122.390 | 121.047 | -70.326 | 1.00 | 9.64 | C |
| 15 | ATOM | 3475 | CG2 | VAL | A | 225 | 120.330 | 119.612 | -70.662 | 1.00 | 10.14 | C |
| | ATOM | 3479 | C | VAL | A | 225 | 123.025 | 119.550 | -67.875 | 1.00 | 8.75 | C |
| | ATOM | 3480 | O | VAL | A | 225 | 124.212 | 119.372 | -68.111 | 1.00 | 8.29 | O |
| | ATOM | 3481 | N | GLY | A | 226 | 122.587 | 120.164 | -66.776 | 1.00 | 8.41 | N |
| | ATOM | 3483 | CA | GLY | A | 226 | 123.492 | 120.729 | -65.776 | 1.00 | 8.02 | C |
| 20 | ATOM | 3486 | C | GLY | A | 226 | 124.404 | 119.721 | -65.085 | 1.00 | 7.51 | C |
| | ATOM | 3487 | O | GLY | A | 226 | 125.553 | 120.032 | -64.772 | 1.00 | 7.45 | O |
| | ATOM | 3488 | N | ASN | A | 227 | 123.905 | 118.513 | -64.844 | 1.00 | 7.33 | N |
| | ATOM | 3490 | CA | ASN | A | 227 | 124.729 | 117.451 | -64.277 | 1.00 | 7.39 | C |
| | ATOM | 3492 | CB | ASN | A | 227 | 123.876 | 116.226 | -63.947 | 1.00 | 7.82 | C |
| 25 | ATOM | 3495 | CG | ASN | A | 227 | 123.079 | 116.393 | -62.656 | 1.00 | 8.78 | C |
| | ATOM | 3496 | OD1 | ASN | A | 227 | 123.518 | 117.077 | -61.748 | 1.00 | 11.03 | O |
| | ATOM | 3497 | ND2 | ASN | A | 227 | 121.904 | 115.768 | -62.580 | 1.00 | 8.36 | N |
| | ATOM | 3500 | C | ASN | A | 227 | 125.871 | 117.067 | -65.233 | 1.00 | 7.12 | C |
| | ATOM | 3501 | O | ASN | A | 227 | 126.996 | 116.796 | -64.800 | 1.00 | 6.84 | O |
| 30 | ATOM | 3502 | N | THR | A | 228 | 125.584 | 117.082 | -66.535 | 1.00 | 6.75 | N |
| | ATOM | 3504 | CA | THR | A | 228 | 126.579 | 116.741 | -67.536 | 1.00 | 6.47 | C |
| | ATOM | 3506 | CB | THR | A | 228 | 125.914 | 116.445 | -68.863 | 1.00 | 5.98 | C |
| | ATOM | 3508 | OG1 | THR | A | 228 | 125.019 | 115.338 | -68.701 | 1.00 | 5.82 | O |
| | ATOM | 3510 | CG2 | THR | A | 228 | 126.933 | 115.966 | -69.886 | 1.00 | 5.79 | C |
| 35 | ATOM | 3514 | C | THR | A | 228 | 127.635 | 117.831 | -67.660 | 1.00 | 6.84 | C |
| | ATOM | 3515 | O | THR | A | 228 | 128.843 | 117.538 | -67.621 | 1.00 | 6.84 | O |
| | ATOM | 3516 | N | VAL | A | 229 | 127.192 | 119.085 | -67.758 | 1.00 | 7.16 | N |
| | ATOM | 3518 | CA | VAL | A | 229 | 128.109 | 120.232 | -67.747 | 1.00 | 7.16 | C |
| | ATOM | 3520 | CB | VAL | A | 229 | 127.317 | 121.556 | -67.813 | 1.00 | 7.35 | C |
| 40 | ATOM | 3522 | CG1 | VAL | A | 229 | 128.233 | 122.777 | -67.615 | 1.00 | 7.15 | C |
| | ATOM | 3526 | CG2 | VAL | A | 229 | 126.591 | 121.655 | -69.150 | 1.00 | 8.09 | C |
| | ATOM | 3530 | C | VAL | A | 229 | 129.041 | 120.222 | -66.510 | 1.00 | 7.16 | C |
| | ATOM | 3531 | O | VAL | A | 229 | 130.249 | 120.467 | -66.632 | 1.00 | 6.90 | O |
| | ATOM | 3532 | N | ALA | A | 230 | 128.463 | 119.942 | -65.340 | 1.00 | 7.40 | N |
| 45 | ATOM | 3534 | CA | ALA | A | 230 | 129.199 | 119.821 | -64.077 | 1.00 | 8.09 | C |
| | ATOM | 3536 | CB | ALA | A | 230 | 128.237 | 119.494 | -62.928 | 1.00 | 8.17 | C |
| | ATOM | 3540 | C | ALA | A | 230 | 130.269 | 118.749 | -64.131 | 1.00 | 8.54 | C |
| | ATOM | 3541 | O | ALA | A | 230 | 131.422 | 118.966 | -63.733 | 1.00 | 8.66 | O |
| | ATOM | 3542 | N | PHE | A | 231 | 129.874 | 117.573 | -64.594 | 1.00 | 9.07 | N |
| 50 | ATOM | 3544 | CA | PHE | A | 231 | 130.834 | 116.505 | -64.827 | 1.00 | 9.35 | C |
| | ATOM | 3546 | CB | PHE | A | 231 | 130.151 | 115.275 | -65.420 | 1.00 | 9.32 | C |
| | ATOM | 3549 | CG | PHE | A | 231 | 131.114 | 114.210 | -65.821 | 1.00 | 10.91 | C |
| | ATOM | 3550 | CD1 | PHE | A | 231 | 131.519 | 114.083 | -67.147 | 1.00 | 11.88 | C |
| | ATOM | 3552 | CE1 | PHE | A | 231 | 132.437 | 113.120 | -67.500 | 1.00 | 11.72 | C |
| 55 | ATOM | 3554 | CZ | PHE | A | 231 | 132.960 | 112.270 | -66.528 | 1.00 | 11.45 | C |
| | ATOM | 3556 | CE2 | PHE | A | 231 | 132.577 | 112.396 | -65.224 | 1.00 | 10.33 | C |
| | ATOM | 3558 | CD2 | PHE | A | 231 | 131.667 | 113.364 | -64.864 | 1.00 | 10.61 | C |
| | ATOM | 3560 | C | PHE | A | 231 | 131.996 | 116.966 | -65.735 | 1.00 | 9.12 | C |
| | ATOM | 3561 | O | PHE | A | 231 | 133.152 | 116.638 | -65.474 | 1.00 | 8.61 | O |
| 60 | ATOM | 3562 | N | LEU | A | 232 | 131.681 | 117.740 | -66.777 | 1.00 | 8.98 | N |
| | ATOM | 3564 | CA | LEU | A | 232 | 132.683 | 118.172 | -67.749 | 1.00 | 8.86 | C |
| | ATOM | 3566 | CB | LEU | A | 232 | 132.026 | 118.578 | -69.073 | 1.00 | 8.66 | C |
| | ATOM | 3569 | CG | LEU | A | 232 | 131.414 | 117.482 | -69.959 | 1.00 | 9.06 | C |
| | ATOM | 3571 | CD1 | LEU | A | 232 | 130.618 | 118.095 | -71.126 | 1.00 | 9.82 | C |
| 65 | ATOM | 3575 | CD2 | LEU | A | 232 | 132.452 | 116.523 | -70.518 | 1.00 | 9.06 | C |
| | ATOM | 3579 | C | LEU | A | 232 | 133.581 | 119.304 | -67.212 | 1.00 | 9.16 | C |
| | ATOM | 3580 | O | LEU | A | 232 | 134.532 | 119.719 | -67.875 | 1.00 | 9.22 | O |
| | ATOM | 3581 | N | CYS | A | 233 | 133.286 | 119.804 | -66.018 | 1.00 | 9.52 | N |

(SEQ ID NO: 34)

FIGURE 20-26

| | | | | | | | | | |
|---|---|---|---|---|---|---|---|---|---|
| ATOM | 3583 | CA | CYS | A | 233 | 134.190 | 120.726 | -65.322 | 1.00 | 9.84 | C |
| ATOM | 3585 | CB | CYS | A | 233 | 133.427 | 121.988 | -64.868 | 1.00 | 9.64 | C |
| ATOM | 3588 | SG | CYS | A | 233 | 132.629 | 122.866 | -66.232 | 1.00 | 7.94 | S |
| ATOM | 3589 | C | CYS | A | 233 | 134.896 | 120.054 | -64.119 | 1.00 | 9.94 | C |
| ATOM | 3590 | O | CYS | A | 233 | 135.513 | 120.738 | -63.288 | 1.00 | 10.19 | O |
| ATOM | 3591 | N | SER | A | 234 | 134.809 | 118.726 | -64.045 | 1.00 | 9.56 | N |
| ATOM | 3593 | CA | SER | A | 234 | 135.419 | 117.956 | -62.956 | 1.00 | 9.56 | C |
| ATOM | 3595 | CB | SER | A | 234 | 134.458 | 116.865 | -62.471 | 1.00 | 9.52 | C |
| ATOM | 3598 | OG | SER | A | 234 | 134.388 | 115.782 | -63.376 | 1.00 | 9.63 | O |
| ATOM | 3600 | C | SER | A | 234 | 136.771 | 117.334 | -63.363 | 1.00 | 9.63 | C |
| ATOM | 3601 | O | SER | A | 234 | 137.111 | 117.272 | -64.544 | 1.00 | 9.22 | O |
| ATOM | 3602 | N | ASP | A | 235 | 137.536 | 116.909 | -62.366 | 1.00 | 9.68 | N |
| ATOM | 3604 | CA | ASP | A | 235 | 138.782 | 116.175 | -62.576 | 1.00 | 10.57 | C |
| ATOM | 3606 | CB | ASP | A | 235 | 139.542 | 116.047 | -61.263 | 1.00 | 10.70 | C |
| ATOM | 3609 | CG | ASP | A | 235 | 140.111 | 117.362 | -60.791 | 1.00 | 11.44 | C |
| ATOM | 3610 | OD1 | ASP | A | 235 | 139.997 | 118.396 | -61.494 | 1.00 | 11.42 | O |
| ATOM | 3611 | OD2 | ASP | A | 235 | 140.698 | 117.452 | -59.712 | 1.00 | 14.14 | O |
| ATOM | 3612 | C | ASP | A | 235 | 138.579 | 114.784 | -63.174 | 1.00 | 10.53 | C |
| ATOM | 3613 | O | ASP | A | 235 | 139.491 | 114.235 | -63.774 | 1.00 | 11.56 | O |
| ATOM | 3614 | N | MET | A | 236 | 137.384 | 114.228 | -63.010 | 1.00 | 10.62 | N |
| ATOM | 3616 | CA | MET | A | 236 | 136.992 | 112.984 | -63.666 | 1.00 | 10.71 | C |
| ATOM | 3618 | CB | MET | A | 236 | 135.595 | 112.594 | -63.204 | 1.00 | 10.89 | C |
| ATOM | 3621 | CG | MET | A | 236 | 135.567 | 112.091 | -61.765 | 1.00 | 13.17 | C |
| ATOM | 3624 | SD | MET | A | 236 | 133.945 | 111.438 | -61.304 | 1.00 | 17.10 | S |
| ATOM | 3625 | CE | MET | A | 236 | 132.893 | 112.927 | -61.419 | 1.00 | 17.31 | C |
| ATOM | 3629 | C | MET | A | 236 | 137.007 | 113.058 | -65.204 | 1.00 | 10.24 | C |
| ATOM | 3630 | O | MET | A | 236 | 137.264 | 112.059 | -65.889 | 1.00 | 9.96 | O |
| ATOM | 3631 | N | ALA | A | 237 | 136.723 | 114.243 | -65.732 | 1.00 | 9.91 | N |
| ATOM | 3633 | CA | ALA | A | 237 | 136.572 | 114.445 | -67.165 | 1.00 | 9.38 | C |
| ATOM | 3635 | CB | ALA | A | 237 | 135.448 | 115.436 | -67.424 | 1.00 | 9.71 | C |
| ATOM | 3639 | C | ALA | A | 237 | 137.844 | 114.916 | -67.808 | 1.00 | 8.83 | C |
| ATOM | 3640 | O | ALA | A | 237 | 137.826 | 115.408 | -68.906 | 1.00 | 8.63 | O |
| ATOM | 3641 | N | THR | A | 238 | 138.971 | 114.718 | -67.153 | 1.00 | 8.92 | N |
| ATOM | 3643 | CA | THR | A | 238 | 140.213 | 115.333 | -67.626 | 1.00 | 8.76 | C |
| ATOM | 3645 | CB | BTHR | A | 238 | 141.316 | 115.300 | -66.519 | 0.35 | 8.66 | C |
| ATOM | 3646 | CB | ATHR | A | 238 | 141.238 | 115.380 | -66.467 | 0.65 | 9.00 | C |
| ATOM | 3649 | OG1 | BTHR | A | 238 | 141.300 | 114.042 | -65.830 | 0.35 | 8.52 | O |
| ATOM | 3650 | OG1 | ATHR | A | 238 | 142.287 | 116.291 | -66.791 | 0.65 | 11.23 | O |
| ATOM | 3653 | CG2 | BTHR | A | 238 | 141.044 | 116.341 | -65.429 | 0.35 | 8.50 | C |
| ATOM | 3654 | CG2 | ATHR | A | 238 | 141.926 | 114.069 | -66.273 | 0.65 | 8.91 | C |
| ATOM | 3661 | C | THR | A | 238 | 140.784 | 114.727 | -68.923 | 1.00 | 8.08 | C |
| ATOM | 3662 | O | THR | A | 238 | 141.722 | 115.260 | -69.492 | 1.00 | 7.50 | O |
| ATOM | 3663 | N | GLY | A | 239 | 140.214 | 113.625 | -69.395 | 1.00 | 7.68 | N |
| ATOM | 3665 | CA | GLY | A | 239 | 140.596 | 113.051 | -70.681 | 1.00 | 7.21 | C |
| ATOM | 3668 | C | GLY | A | 239 | 139.735 | 113.486 | -71.863 | 1.00 | 6.84 | C |
| ATOM | 3669 | O | GLY | A | 239 | 139.976 | 113.019 | -72.979 | 1.00 | 6.79 | O |
| ATOM | 3670 | N | ILE | A | 240 | 138.763 | 114.378 | -71.633 | 1.00 | 6.45 | N |
| ATOM | 3672 | CA | ILE | A | 240 | 137.795 | 114.787 | -72.644 | 1.00 | 6.59 | C |
| ATOM | 3674 | CB | ILE | A | 240 | 136.335 | 114.593 | -72.145 | 1.00 | 6.79 | C |
| ATOM | 3676 | CG1 | ILE | A | 240 | 136.113 | 113.171 | -71.618 | 1.00 | 7.38 | C |
| ATOM | 3679 | CD1 | ILE | A | 240 | 134.961 | 113.065 | -70.621 | 1.00 | 8.69 | C |
| ATOM | 3683 | CG2 | ILE | A | 240 | 135.335 | 114.878 | -73.272 | 1.00 | 6.38 | C |
| ATOM | 3687 | C | ILE | A | 240 | 137.988 | 116.241 | -73.044 | 1.00 | 6.42 | C |
| ATOM | 3688 | O | ILE | A | 240 | 137.975 | 117.124 | -72.200 | 1.00 | 6.31 | O |
| ATOM | 3689 | N | THR | A | 241 | 138.167 | 116.465 | -74.345 | 1.00 | 6.56 | N |
| ATOM | 3691 | CA | THR | A | 241 | 138.262 | 117.797 | -74.924 | 1.00 | 6.60 | C |
| ATOM | 3693 | CB | THR | A | 241 | 139.644 | 118.421 | -74.571 | 1.00 | 6.78 | C |
| ATOM | 3695 | OG1 | THR | A | 241 | 139.654 | 119.813 | -74.880 | 1.00 | 6.47 | O |
| ATOM | 3697 | CG2 | THR | A | 241 | 140.783 | 117.852 | -75.403 | 1.00 | 6.52 | C |
| ATOM | 3701 | C | THR | A | 241 | 137.948 | 117.786 | -76.445 | 1.00 | 7.17 | C |
| ATOM | 3702 | O | THR | A | 241 | 138.157 | 116.788 | -77.158 | 1.00 | 7.44 | O |
| ATOM | 3703 | N | GLY | A | 242 | 137.402 | 118.894 | -76.932 | 1.00 | 7.72 | N |
| ATOM | 3705 | CA | GLY | A | 242 | 136.908 | 118.989 | -78.301 | 1.00 | 7.53 | C |
| ATOM | 3708 | C | GLY | A | 242 | 135.634 | 118.188 | -78.543 | 1.00 | 7.72 | C |
| ATOM | 3709 | O | GLY | A | 242 | 135.218 | 118.032 | -79.702 | 1.00 | 7.74 | O |
| ATOM | 3710 | N | GLU | A | 243 | 134.985 | 117.728 | -77.468 | 1.00 | 7.23 | N |
| ATOM | 3712 | CA | GLU | A | 243 | 133.867 | 116.781 | -77.568 | 1.00 | 7.68 | C |
| ATOM | 3714 | CB | GLU | A | 243 | 133.968 | 115.743 | -76.438 | 1.00 | 7.73 | C |

(SEQ ID NO. 34)

FIGURE 20-27

```
ATOM  3717  CG   GLU A 243    132.957 114.603 -76.481  1.00  8.13    C
ATOM  3720  CD   GLU A 243    132.980 113.844 -77.788  1.00  9.06    C
ATOM  3721  OE1  GLU A 243    133.525 112.732 -77.839  1.00 10.63    O
ATOM  3722  OE2  GLU A 243    132.443 114.352 -78.780  1.00 11.06    O
ATOM  3723  C    GLU A 243    132.491 117.467 -77.494  1.00  7.89    C
ATOM  3724  O    GLU A 243    132.317 118.459 -76.779  1.00  7.90    O
ATOM  3725  N    VAL A 244    131.516 116.918 -78.220  1.00  7.85    N
ATOM  3727  CA   VAL A 244    130.125 117.339 -78.099  1.00  7.91    C
ATOM  3729  CB   VAL A 244    129.534 117.742 -79.488  1.00  7.83    C
ATOM  3731  CG1  VAL A 244    128.069 118.136 -79.390  1.00  8.74    C
ATOM  3735  CG2  VAL A 244    130.294 118.915 -80.057  1.00  8.36    C
ATOM  3739  C    VAL A 244    129.360 116.186 -77.458  1.00  7.72    C
ATOM  3740  O    VAL A 244    129.303 115.127 -78.016  1.00  8.23    O
ATOM  3741  N    VAL A 245    128.815 116.386 -76.260  1.00  7.67    N
ATOM  3743  CA   VAL A 245    128.004 115.375 -75.597  1.00  7.33    C
ATOM  3745  CB   VAL A 245    128.381 115.227 -74.117  1.00  7.24    C
ATOM  3747  CG1  VAL A 245    127.573 114.120 -73.461  1.00  7.11    C
ATOM  3751  CG2  VAL A 245    129.850 114.912 -73.982  1.00  8.28    C
ATOM  3755  C    VAL A 245    126.523 115.746 -75.725  1.00  7.31    C
ATOM  3756  O    VAL A 245    126.094 116.781 -75.233  1.00  6.67    O
ATOM  3757  N    HIS A 246    125.758 114.883 -76.389  1.00  7.32    N
ATOM  3759  CA   HIS A 246    124.326 115.072 -76.597  1.00  7.70    C
ATOM  3761  CB   HIS A 246    123.826 114.220 -77.786  1.00  7.67    C
ATOM  3764  CG   HIS A 246    124.411 114.638 -79.097  1.00  8.56    C
ATOM  3765  ND1  HIS A 246    125.717 114.369 -79.447  1.00 10.05    N
ATOM  3767  CE1  HIS A 246    125.960 114.868 -80.648  1.00  9.54    C
ATOM  3769  NE2  HIS A 246    124.864 115.464 -81.080  1.00  7.94    N
ATOM  3771  CD2  HIS A 246    123.886 115.348 -80.124  1.00  8.72    C
ATOM  3773  C    HIS A 246    123.606 114.663 -75.340  1.00  7.44    C
ATOM  3774  O    HIS A 246    123.794 113.551 -74.869  1.00  8.60    O
ATOM  3775  N    VAL A 247    122.830 115.574 -74.774  1.00  6.93    N
ATOM  3777  CA   VAL A 247    121.943 115.284 -73.655  1.00  6.38    C
ATOM  3779  CB   VAL A 247    122.323 116.109 -72.390  1.00  6.62    C
ATOM  3781  CG1  VAL A 247    121.420 115.755 -71.178  1.00  5.96    C
ATOM  3785  CG2  VAL A 247    123.810 115.907 -72.047  1.00  5.64    C
ATOM  3789  C    VAL A 247    120.552 115.628 -74.177  1.00  6.55    C
ATOM  3790  O    VAL A 247    120.052 116.734 -73.976  1.00  6.49    O
ATOM  3791  N    ASP A 248    119.966 114.671 -74.895  1.00  6.38    N
ATOM  3793  CA   ASP A 248    118.784 114.889 -75.728  1.00  6.38    C
ATOM  3795  CB   ASP A 248    119.235 115.269 -77.146  1.00  5.99    C
ATOM  3798  CG   ASP A 248    119.974 114.138 -77.858  1.00  7.33    C
ATOM  3799  OD1  ASP A 248    120.309 113.125 -77.186  1.00  7.92    O
ATOM  3800  OD2  ASP A 248    120.268 114.183 -79.089  1.00  5.22    O
ATOM  3801  C    ASP A 248    117.875 113.654 -75.789  1.00  6.44    C
ATOM  3802  O    ASP A 248    117.119 113.468 -76.742  1.00  6.24    O
ATOM  3803  N    ALA A 249    117.950 112.818 -74.755  1.00  6.79    N
ATOM  3805  CA   ALA A 249    117.210 111.560 -74.684  1.00  6.55    C
ATOM  3807  CB   ALA A 249    115.712 111.851 -74.585  1.00  6.51    C
ATOM  3811  C    ALA A 249    117.504 110.615 -75.870  1.00  6.38    C
ATOM  3812  O    ALA A 249    116.671 109.782 -76.200  1.00  6.06    O
ATOM  3813  N    GLY A 250    118.678 110.745 -76.490  1.00  5.79    N
ATOM  3815  CA   GLY A 250    119.054 109.908 -77.616  1.00  6.15    C
ATOM  3818  C    GLY A 250    118.595 110.352 -79.006  1.00  6.65    C
ATOM  3819  O    GLY A 250    118.858 109.655 -79.974  1.00  5.79    O
ATOM  3820  N    TYR A 251    117.908 111.491 -79.101  1.00  7.40    N
ATOM  3822  CA   TYR A 251    117.399 112.006 -80.378  1.00  9.01    C
ATOM  3824  CB   TYR A 251    116.868 113.451 -80.194  1.00  9.38    C
ATOM  3827  CG   TYR A 251    116.312 114.063 -81.465  1.00 10.95    C
ATOM  3828  CD1  TYR A 251    115.004 113.822 -81.865  1.00 14.83    C
ATOM  3830  CE1  TYR A 251    114.493 114.385 -83.035  1.00 15.16    C
ATOM  3832  CZ   TYR A 251    115.301 115.187 -83.803  1.00 14.96    C
ATOM  3833  OH   TYR A 251    114.816 115.750 -84.951  1.00 15.78    O
ATOM  3835  CE2  TYR A 251    116.604 115.431 -83.421  1.00 13.80    C
ATOM  3837  CD2  TYR A 251    117.096 114.873 -82.267  1.00 11.95    C
ATOM  3839  C    TYR A 251    118.432 111.979 -81.524  1.00  8.71    C
ATOM  3840  O    TYR A 251    118.109 111.577 -82.633  1.00  8.48    O
ATOM  3841  N    HIS A 252    119.657 112.403 -81.223  1.00  9.04    N
ATOM  3843  CA   HIS A 252    120.760 112.507 -82.201  1.00  9.57    C
```

(SEQ ID NO. 34)

FIGURE 20-28

```
ATOM   3845  CB   HIS A 252     122.018 112.992 -81.484  1.00  8.98           C
ATOM   3848  CG   HIS A 252     122.623 111.932 -80.635  1.00  8.18           C
ATOM   3849  ND1  HIS A 252     123.483 110.989 -81.142  1.00  7.27           N
ATOM   3851  CE1  HIS A 252     123.805 110.135 -80.192  1.00  7.36           C
ATOM   3853  NE2  HIS A 252     123.169 110.479 -79.090  1.00  8.16           N
ATOM   3855  CD2  HIS A 252     122.409 111.590 -79.345  1.00  8.64           C
ATOM   3857  C    HIS A 252     121.124 111.186 -82.914  1.00 10.31           C
ATOM   3858  O    HIS A 252     121.632 111.206 -84.036  1.00 10.25           O
ATOM   3859  N    CYS A 253     120.901 110.047 -82.256  1.00 11.55           N
ATOM   3861  CA   CYS A 253     121.317 108.746 -82.814  1.00 12.57           C
ATOM   3863  CB   CYS A 253     121.777 107.784 -81.716  1.00 12.10           C
ATOM   3866  SG   CYS A 253     120.467 107.007 -80.762  1.00 11.77           S
ATOM   3867  C    CYS A 253     120.256 108.068 -83.652  1.00 13.67           C
ATOM   3868  O    CYS A 253     120.508 107.008 -84.186  1.00 13.63           O
ATOM   3869  N    VAL A 254     119.092 108.686 -83.795  1.00 15.28           N
ATOM   3871  CA   VAL A 254     117.956 108.034 -84.459  1.00 17.00           C
ATOM   3873  CB   VAL A 254     116.721 108.018 -83.505  1.00 16.87           C
ATOM   3875  CG1  VAL A 254     115.469 107.723 -84.226  1.00 18.38           C
ATOM   3879  CG2  VAL A 254     116.907 106.980 -82.416  1.00 16.89           C
ATOM   3883  C    VAL A 254     117.615 108.682 -85.814  1.00 18.06           C
ATOM   3884  O    VAL A 254     117.869 109.847 -86.041  1.00 17.68           O
ATOM   3885  N    SER A 255     117.063 107.895 -86.716  1.00 20.07           N
ATOM   3887  CA   SER A 255     116.497 108.408 -87.955  1.00 22.22           C
ATOM   3889  CB   SER A 255     117.464 108.211 -89.108  1.00 21.81           C
ATOM   3892  OG   SER A 255     116.775 108.308 -90.329  1.00 21.90           O
ATOM   3894  C    SER A 255     115.197 107.668 -88.236  1.00 24.40           C
ATOM   3895  O    SER A 255     115.107 106.447 -88.059  1.00 25.06           O
ATOM   3896  N    MET A 256     114.184 108.393 -88.685  1.00 26.97           N
ATOM   3898  CA   MET A 256     112.845 107.819 -88.764  1.00 28.84           C
ATOM   3900  CB   MET A 256     111.845 108.760 -88.081  1.00 29.85           C
ATOM   3903  CG   MET A 256     111.881 108.623 -86.556  1.00 32.05           C
ATOM   3906  SD   MET A 256     112.508 106.977 -86.120  1.00 38.65           S
ATOM   3907  CE   MET A 256     112.327 106.870 -84.226  1.00 38.45           C
ATOM   3911  C    MET A 256     112.427 107.461 -90.184  1.00 29.62           C
ATOM   3912  O    MET A 256     112.408 106.269 -90.531  1.00 30.87           O
ATOM   3913  O7N  NAD A 301     115.829 124.304 -76.423  1.00  8.50           O
ATOM   3914  C7N  NAD A 301     116.647 124.869 -75.705  1.00  7.97           C
ATOM   3915  N7N  NAD A 301     116.265 125.677 -74.712  1.00  7.59           N
ATOM   3918  C3N  NAD A 301     118.113 124.656 -75.987  1.00  7.71           C
ATOM   3919  C2N  NAD A 301     119.039 125.670 -75.720  1.00  6.40           C
ATOM   3921  C4N  NAD A 301     118.542 123.454 -76.561  1.00  7.42           C
ATOM   3923  C5N  NAD A 301     119.897 123.307 -76.842  1.00  7.14           C
ATOM   3925  C6N  NAD A 301     120.774 124.340 -76.542  1.00  7.08           C
ATOM   3927  N1N  NAD A 301     120.339 125.498 -75.999  1.00  7.92           N
ATOM   3928  C1M  NAD A 301     121.351 126.542 -75.704  1.00  8.04           C
ATOM   3930  C2M  NAD A 301     121.092 127.934 -76.262  1.00  7.45           C
ATOM   3932  O2M  NAD A 301     121.365 128.079 -77.648  1.00  6.71           O
ATOM   3934  C3M  NAD A 301     122.055 128.750 -75.405  1.00  7.76           C
ATOM   3936  O3M  NAD A 301     123.374 128.744 -75.961  1.00  6.45           O
ATOM   3938  O4M  NAD A 301     121.491 126.763 -74.289  1.00  7.59           O
ATOM   3939  C4M  NAD A 301     122.050 128.052 -74.045  1.00  7.26           C
ATOM   3941  C5M  NAD A 301     121.214 128.750 -72.973  1.00  8.51           C
ATOM   3944  O5M  NAD A 301     119.881 128.939 -73.448  1.00  7.84           O
ATOM   3945  PN   NAD A 301     118.562 128.704 -72.573  1.00  8.77           P
ATOM   3946  O1N  NAD A 301     118.957 128.537 -71.130  1.00  9.46           O
ATOM   3947  O2N  NAD A 301     117.689 127.673 -73.218  1.00  8.97           O
ATOM   3948  O3P  NAD A 301     117.697 130.063 -72.788  1.00  9.68           O
ATOM   3949  PA   NAD A 301     117.969 131.443 -71.997  1.00  9.10           P
ATOM   3950  O1A  NAD A 301     117.725 131.213 -70.525  1.00  6.75           O
ATOM   3951  O2A  NAD A 301     117.249 132.553 -72.723  1.00  7.59           O
ATOM   3952  O5B  NAD A 301     119.558 131.619 -72.108  1.00  7.16           O
ATOM   3953  C5B  NAD A 301     120.133 132.376 -73.136  1.00  7.56           C
ATOM   3956  C4B  NAD A 301     121.060 133.363 -72.457  1.00  7.92           C
ATOM   3958  C3B  NAD A 301     120.329 134.424 -71.637  1.00  8.09           C
ATOM   3960  O3B  NAD A 301     120.730 134.424 -70.264  1.00  8.07           O
ATOM   3962  O4B  NAD A 301     121.832 134.031 -73.472  1.00  8.28           O
ATOM   3963  C1B  NAD A 301     122.058 135.327 -72.952  1.00  7.94           C
ATOM   3965  C2B  NAD A 301     120.738 135.719 -72.301  1.00  8.35           C
```

(SEQ ID NO. 34)

FIGURE 20-29

```
ATOM   3967  O2B  NAD A 301      120.932 136.788 -71.381  1.00  8.34           O
ATOM   3969  N9A  NAD A 301      122.436 136.385 -73.905  1.00  7.66           N
ATOM   3970  C4A  NAD A 301      123.481 137.166 -73.727  1.00  7.50           C
ATOM   3971  N3A  NAD A 301      124.440 137.113 -72.665  1.00  6.31           N
ATOM   3972  C2A  NAD A 301      125.441 137.990 -72.647  1.00  7.08           C
ATOM   3974  N1A  NAD A 301      125.579 138.909 -73.599  1.00  7.26           N
ATOM   3975  C5A  NAD A 301      123.569 138.120 -74.789  1.00  7.38           C
ATOM   3976  C6A  NAD A 301      124.727 139.033 -74.638  1.00  8.28           C
ATOM   3977  N6A  NAD A 301      124.954 139.988 -75.549  1.00 10.17           N
ATOM   3980  N7A  NAD A 301      122.511 137.866 -75.592  1.00  6.90           N
ATOM   3981  C8A  NAD A 301      121.828 136.813 -75.038  1.00  6.83           C
ATOM   3983  O42  059 A 302      114.814 137.352 -80.326  1.00 13.34           O
ATOM   3984  C34  059 A 302      115.076 136.169 -80.143  1.00 12.82           C
ATOM   3985  C35  059 A 302      113.984 135.232 -79.684  1.00 12.27           C
ATOM   3988  C36  059 A 302      114.314 133.750 -79.516  1.00 11.81           C
ATOM   3991  C30  059 A 302      115.755 133.422 -79.788  1.00 12.43           C
ATOM   3992  C31  059 A 302      116.242 132.130 -79.654  1.00 12.16           C
ATOM   3994  C29  059 A 302      116.699 134.461 -80.217  1.00 12.61           C
ATOM   3995  N33  059 A 302      116.305 135.730 -80.375  1.00 13.65           N
ATOM   3997  N28  059 A 302      117.978 134.122 -80.467  1.00 11.49           N
ATOM   3998  C32  059 A 302      118.422 132.867 -80.329  1.00 10.95           C
ATOM   4000  C22  059 A 302      117.585 131.845 -79.922  1.00  9.82           C
ATOM   4001  C21  059 A 302      118.171 130.500 -79.791  1.00  8.15           C
ATOM   4003  C20  059 A 302      117.462 129.450 -79.385  1.00  8.43           C
ATOM   4005  C19  059 A 302      118.085 128.110 -79.289  1.00  9.57           C
ATOM   4006  O23  059 A 302      119.291 128.026 -79.510  1.00  8.82           O
ATOM   4007  N16  059 A 302      117.313 127.027 -79.015  1.00  9.82           N
ATOM   4008  C24  059 A 302      117.913 125.701 -78.959  1.00  8.82           C
ATOM   4012  C15  059 A 302      115.852 127.023 -78.803  1.00 10.32           C
ATOM   4015  C8   059 A 302      115.214 126.796 -80.153  1.00 11.15           C
ATOM   4016  C9   059 A 302      114.842 127.833 -81.018  1.00 10.96           C
ATOM   4018  C3   059 A 302      114.350 127.184 -82.118  1.00 10.62           C
ATOM   4019  C4   059 A 302      113.828 127.763 -83.317  1.00 11.04           C
ATOM   4021  C2   059 A 302      114.432 125.749 -81.920  1.00 10.17           C
ATOM   4022  N7   059 A 302      114.965 125.570 -80.713  1.00 10.69           N
ATOM   4023  C28  059 A 302      115.220 124.256 -80.087  1.00 10.95           C
ATOM   4027  C1   059 A 302      113.938 124.936 -82.994  1.00 10.74           C
ATOM   4029  C6   059 A 302      113.439 125.521 -84.154  1.00 10.49           C
ATOM   4031  C5   059 A 302      113.378 126.906 -84.307  1.00 11.15           C
ATOM   4033  O    HOH X 400      115.544 142.609 -63.959  1.00  3.59           O
ATOM   4036  O    HOH X 401      122.377 111.438 -76.047  1.00  4.71           O
ATOM   4039  O    HOH X 402      138.215 111.782 -68.346  1.00  5.37           O
ATOM   4042  O    HOH X 403      120.929 118.895 -79.580  1.00  4.70           O
ATOM   4045  O    HOH X 404      134.860 120.582 -70.391  1.00  4.53           O
ATOM   4048  O    HOH X 405      130.110 112.628 -76.729  0.50 17.62           O
ATOM   4051  O    HOH X 406      142.861 128.144 -55.481  1.00 16.60           O
ATOM   4054  O    HOH X 407      130.498 122.413 -86.780  1.00  7.79           O
ATOM   4057  O    HOH X 408      109.822 127.165 -96.788  1.00 23.71           O
ATOM   4060  O    HOH X 409      125.352 129.993 -78.774  1.00  4.96           O
ATOM   4063  O    HOH X 410      141.931 121.187 -74.653  1.00  5.14           O
ATOM   4066  O    HOH X 411      116.252 137.509 -76.251  1.00 27.29           O
ATOM   4069  O    HOH X 412      118.784 138.605 -73.027  1.00 22.27           O
ATOM   4072  O    HOH X 413      126.649 144.258 -68.798  1.00 12.30           O
ATOM   4075  O    HOH X 414      144.322 124.589 -66.903  1.00 10.65           O
ATOM   4078  O    HOH X 415      106.479 143.410 -84.207  1.00  6.97           O
ATOM   4081  O    HOH X 416      125.523 111.054 -83.208  1.00 12.21           O
ATOM   4084  O    HOH X 417      121.037 129.621 -69.642  1.00  5.50           O
ATOM   4087  O    HOH X 418      113.301 139.109 -70.943  1.00 37.41           O
ATOM   4090  O    HOH X 419      132.824 143.314 -67.439  1.00  8.55           O
ATOM   4093  O    HOH X 420      146.700 134.780 -71.988  1.00 17.31           O
ATOM   4096  O    HOH X 421      130.320 143.152 -95.670  1.00  9.23           O
ATOM   4099  O    HOH X 422      114.434 126.902 -94.825  1.00 19.91           O
ATOM   4102  O    HOH X 423      133.153 145.340 -78.821  1.00 12.68           O
ATOM   4105  O    HOH X 424      119.632 116.354 -80.319  1.00  4.40           O
ATOM   4108  O    HOH X 425      124.847 145.820 -71.574  1.00 12.78           O
ATOM   4111  O    HOH X 426      146.656 121.815 -65.818  1.00 13.43           O
ATOM   4114  O    HOH X 427      123.539 122.325 -90.162  1.00 14.08           O
ATOM   4117  O    HOH X 428      129.247 129.813 -54.269  1.00  7.04           O
```

(SEQ ID NO. 34)

FIGURE 20-30

| ATOM | 4120 | O | HOH X 429 | 126.792 146.908 -64.179 | 1.00 27.49 | O |
| ATOM | 4123 | O | HOH X 430 | 144.725 135.413 -73.975 | 1.00 13.37 | O |
| ATOM | 4126 | O | HOH X 431 | 108.847 114.278 -71.131 | 1.00 19.67 | O |
| ATOM | 4129 | O | HOH X 432 | 120.308 117.932 -57.653 | 1.00 19.99 | O |
| ATOM | 4132 | O | HOH X 433 | 117.621 144.114 -63.218 | 1.00  9.37 | O |
| ATOM | 4135 | O | HOH X 434 | 114.296 117.588 -75.034 | 1.00 14.86 | O |
| ATOM | 4138 | O | HOH X 435 | 113.188 127.423 -58.494 | 1.00 23.65 | O |
| ATOM | 4141 | O | HOH X 436 | 127.167 144.557 -88.126 | 1.00 26.67 | O |
| ATOM | 4144 | O | HOH X 437 | 110.404 138.899 -87.407 | 1.00 25.22 | O |
| ATOM | 4147 | O | HOH X 438 | 111.274 124.632 -68.697 | 1.00  9.11 | O |
| ATOM | 4150 | O | HOH X 439 | 106.623 140.806 -80.060 | 1.00 10.80 | O |
| ATOM | 4153 | O | HOH X 440 | 136.625 139.854 -77.552 | 1.00 11.91 | O |
| ATOM | 4156 | O | HOH X 441 | 126.579 146.831 -67.052 | 1.00 21.92 | O |
| ATOM | 4159 | O | HOH X 442 | 126.641 117.190 -89.934 | 1.00 15.62 | O |
| ATOM | 4162 | O | HOH X 443 | 149.186 137.536 -75.012 | 1.00 35.79 | O |
| ATOM | 4165 | O | HOH X 444 | 117.338 134.230 -74.627 | 1.00 16.65 | O |
| ATOM | 4168 | O | HOH X 445 | 124.678 135.895 -70.030 | 1.00  6.93 | O |
| ATOM | 4171 | O | HOH X 446 | 115.629 139.548 -96.931 | 1.00 26.80 | O |
| ATOM | 4174 | O | HOH X 447 | 128.321 138.615 -54.619 | 1.00 27.06 | O |
| ATOM | 4177 | O | HOH X 448 | 102.702 123.943 -80.040 | 1.00 23.09 | O |
| ATOM | 4180 | O | HOH X 449 | 141.069 132.331 -54.287 | 1.00 33.77 | O |
| ATOM | 4183 | O | HOH X 450 | 109.115 131.126 -73.852 | 1.00 25.67 | O |
| ATOM | 4186 | O | HOH X 451 | 118.285 111.191 -90.480 | 1.00 35.10 | O |
| ATOM | 4189 | O | HOH X 452 | 132.270 148.642 -81.073 | 1.00 34.23 | O |
| ATOM | 4192 | O | HOH X 453 | 126.824 148.299 -56.697 | 1.00 42.20 | O |
| ATOM | 4195 | O | HOH X 454 | 108.582 135.590 -72.107 | 1.00 32.73 | O |
| ATOM | 4198 | O | HOH X 455 | 113.924 121.709 -67.474 | 1.00  3.78 | O |
| ATOM | 4201 | O | HOH X 456 | 137.198 122.580 -64.121 | 1.00  4.57 | O |
| ATOM | 4204 | O | HOH X 457 | 121.928 142.797 -93.567 | 1.00  4.10 | O |
| ATOM | 4207 | O | HOH X 458 | 124.767 134.010 -65.326 | 1.00  4.59 | O |
| ATOM | 4210 | O | HOH X 459 | 127.842 138.472 -92.499 | 1.00  4.13 | O |
| ATOM | 4213 | O | HOH X 460 | 112.541 119.612 -72.416 | 1.00  5.57 | O |
| ATOM | 4216 | O | HOH X 461 | 145.570 133.820 -61.891 | 1.00 21.52 | O |
| ATOM | 4219 | O | HOH X 462 | 105.801 141.484 -82.587 | 1.00 16.23 | O |
| ATOM | 4222 | O | HOH X 463 | 113.719 124.538 -67.558 | 1.00  9.09 | O |
| ATOM | 4225 | O | HOH X 464 | 138.151 141.740 -80.625 | 1.00 10.62 | O |
| ATOM | 4228 | O | HOH X 465 | 139.130 119.524 -63.759 | 1.00 15.15 | O |
| ATOM | 4231 | O | HOH X 466 | 121.323 139.323 -67.477 | 1.00 16.31 | O |
| ATOM | 4234 | O | HOH X 467 | 126.742 141.480 -82.650 | 1.00 18.73 | O |
| ATOM | 4237 | O | HOH X 468 | 126.564 147.594 -61.240 | 1.00 31.01 | O |
| ATOM | 4240 | O | HOH X 469 | 129.508 142.269 -91.292 | 1.00 32.53 | O |
| ATOM | 4243 | O | HOH X 470 | 120.314 114.092 -64.024 | 1.00 18.55 | O |
| ATOM | 4246 | O | HOH X 471 | 117.022 117.487 -80.096 | 1.00 11.98 | O |
| ATOM | 4249 | O | HOH X 472 | 114.888 136.956 -60.881 | 1.00 14.70 | O |
| ATOM | 4252 | O | HOH X 473 | 126.971 141.985 -57.208 | 1.00 39.02 | O |
| ATOM | 4255 | O | HOH X 474 | 111.654 134.998 -81.754 | 1.00 15.78 | O |
| ATOM | 4258 | O | HOH X 475 | 126.906 135.582 -51.492 | 1.00 30.11 | O |
| ATOM | 4261 | O | HOH X 476 | 129.884 141.023 -56.889 | 1.00 21.96 | O |
| ATOM | 4264 | O | HOH X 477 | 140.772 141.039 -79.388 | 1.00 29.65 | O |
| ATOM | 4267 | O | HOH X 478 | 130.143 114.305 -88.325 | 0.50 27.71 | O |
| ATOM | 4270 | O | HOH X 479 | 149.758 129.913 -63.373 | 1.00 27.58 | O |
| ATOM | 4273 | O | HOH X 480 | 128.960 124.708 -52.854 | 1.00 20.20 | O |
| ATOM | 4276 | O | HOH X 481 | 130.257 119.793 -85.116 | 1.00 16.66 | O |
| ATOM | 4279 | O | HOH X 482 | 107.132 129.684 -77.860 | 1.00 16.15 | O |
| ATOM | 4282 | O | HOH X 483 | 108.734 137.742 -81.874 | 1.00 26.51 | O |
| ATOM | 4285 | O | HOH X 484 | 149.188 130.383 -71.881 | 1.00 21.29 | O |
| ATOM | 4288 | O | HOH X 485 | 128.346 118.017 -82.769 | 1.00 27.15 | O |
| ATOM | 4291 | O | HOH X 486 | 144.675 138.106 -69.283 | 1.00 24.03 | O |
| ATOM | 4294 | O | HOH X 487 | 135.622 116.117 -53.058 | 1.00 29.47 | O |
| ATOM | 4297 | O | HOH X 488 | 131.180 136.833 -51.510 | 1.00 30.82 | O |
| ATOM | 4300 | O | HOH X 489 | 123.414 111.087 -90.474 | 1.00 21.31 | O |
| ATOM | 4303 | O | HOH X 490 | 129.347 142.645 -54.723 | 1.00 46.35 | O |
| ATOM | 4306 | O | HOH X 491 | 134.868 145.023 -80.865 | 1.00 26.65 | O |
| ATOM | 4309 | O | HOH X 492 | 110.918 118.373 -69.028 | 1.00 30.53 | O |
| ATOM | 4312 | O | HOH X 493 | 145.442 138.674 -73.496 | 1.00 36.70 | O |
| ATOM | 4315 | O | HOH X 494 | 112.375 138.029 -91.994 | 1.00 25.55 | O |
| ATOM | 4318 | O | HOH X 495 | 132.982 113.876 -47.480 | 1.00 38.50 | O |
| ATOM | 4321 | O | HOH X 496 | 127.427 147.115 -74.096 | 1.00 32.20 | O |

(SEQ ID NO. 34)

FIGURE 20-31

| | | | | | | | | |
|---|---|---|---|---|---|---|---|---|
| ATOM | 4324 | O | HOH X 497 | 136.706 | 117.393 | -59.612 | 1.00 | 24.32 | O |
| ATOM | 4327 | O | HOH X 498 | 110.850 | 136.773 | -68.809 | 1.00 | 30.92 | O |
| ATOM | 4330 | O | HOH X 499 | 151.818 | 122.470 | -77.032 | 1.00 | 28.36 | O |
| ATOM | 4333 | O | HOH X 500 | 115.459 | 123.240 | -61.394 | 1.00 | 20.82 | O |
| ATOM | 4336 | O | HOH X 501 | 123.024 | 137.667 | -55.300 | 1.00 | 19.58 | O |
| ATOM | 4339 | O | HOH X 502 | 114.439 | 111.358 | -86.470 | 1.00 | 33.74 | O |
| ATOM | 4342 | O | HOH X 503 | 121.548 | 136.729 | -68.632 | 1.00 | 19.61 | O |
| ATOM | 4345 | O | HOH X 504 | 123.193 | 125.827 | -49.121 | 1.00 | 31.62 | O |
| ATOM | 4348 | O | HOH X 505 | 109.580 | 106.606 | -85.351 | 1.00 | 30.79 | O |
| ATOM | 4351 | O | HOH X 506 | 104.989 | 130.753 | -70.918 | 1.00 | 38.08 | O |
| ATOM | 4354 | O | HOH X 507 | 122.851 | 143.780 | -74.503 | 1.00 | 36.52 | O |
| ATOM | 4357 | O | HOH X 508 | 120.107 | 115.692 | -60.178 | 1.00 | 25.81 | O |
| ATOM | 4360 | O | HOH X 509 | 115.632 | 126.150 | -92.046 | 1.00 | 13.67 | O |
| ATOM | 4363 | O | HOH X 510 | 104.958 | 131.175 | -79.981 | 1.00 | 24.14 | O |
| ATOM | 4366 | O | HOH X 511 | 110.257 | 140.318 | -68.243 | 1.00 | 31.92 | O |
| ATOM | 4369 | O | HOH X 512 | 116.491 | 117.386 | -55.158 | 1.00 | 35.75 | O |
| ATOM | 4372 | O | HOH X 513 | 114.039 | 115.545 | -58.153 | 1.00 | 38.47 | O |
| ATOM | 4375 | O | HOH X 514 | 145.945 | 129.848 | -63.407 | 1.00 | 21.61 | O |
| ATOM | 4378 | O | HOH X 515 | 142.036 | 143.290 | -81.683 | 1.00 | 30.83 | O |
| ATOM | 4381 | O | HOH X 516 | 134.977 | 135.489 | -48.905 | 1.00 | 36.31 | O |
| ATOM | 4384 | O | HOH X 517 | 105.483 | 114.730 | -68.686 | 1.00 | 36.76 | O |
| ATOM | 4387 | O | HOH X 518 | 123.919 | 137.408 | -52.826 | 1.00 | 29.28 | O |
| ATOM | 4390 | O | HOH X 519 | 105.063 | 113.360 | -77.278 | 1.00 | 32.70 | O |
| ATOM | 4393 | O | HOH X 520 | 129.354 | 146.654 | -78.204 | 1.00 | 35.97 | O |
| ATOM | 4396 | O | HOH X 521 | 108.027 | 128.252 | -61.407 | 1.00 | 37.04 | O |
| ATOM | 4399 | O | HOH X 522 | 132.201 | 152.876 | -80.231 | 1.00 | 39.83 | O |
| ATOM | 4402 | O | HOH X 523 | 133.779 | 147.452 | -68.961 | 1.00 | 25.26 | O |
| ATOM | 4405 | O | HOH X 524 | 115.677 | 112.916 | -64.756 | 1.00 | 31.75 | O |
| ATOM | 4408 | O | HOH X 525 | 111.567 | 124.124 | -94.268 | 1.00 | 28.03 | O |
| ATOM | 4411 | O | HOH X 526 | 132.342 | 145.608 | -62.289 | 1.00 | 38.94 | O |
| ATOM | 4414 | O | HOH X 527 | 133.666 | 147.664 | -60.120 | 0.50 | 36.65 | O |
| ATOM | 4417 | O | HOH X 528 | 118.818 | 113.763 | -56.472 | 1.00 | 37.72 | O |
| ATOM | 4420 | O | HOH X 529 | 130.846 | 112.594 | -92.884 | 0.50 | 30.15 | O |
| ATOM | 4423 | O | HOH X 530 | 125.171 | 113.546 | -83.707 | 1.00 | 40.24 | O |
| ATOM | 4426 | O | HOH X 531 | 113.021 | 124.091 | -64.615 | 1.00 | 26.34 | O |
| ATOM | 4429 | O | HOH X 532 | 108.744 | 139.750 | -93.994 | 1.00 | 38.65 | O |
| ATOM | 4432 | O | HOH X 533 | 110.470 | 108.868 | -68.327 | 1.00 | 28.08 | O |
| ATOM | 4435 | O | HOH X 534 | 136.501 | 114.775 | -59.576 | 1.00 | 23.94 | O |
| ATOM | 4438 | O | HOH X 535 | 128.596 | 120.463 | -51.229 | 1.00 | 44.50 | O |
| ATOM | 4441 | O | HOH X 536 | 139.883 | 122.915 | -62.487 | 1.00 | 10.69 | O |
| ATOM | 4444 | O | HOH X 537 | 124.831 | 119.488 | -81.656 | 1.00 | 4.30 | O |
| ATOM | 4447 | O | HOH X 538 | 125.899 | 128.344 | -75.275 | 1.00 | 8.12 | O |
| ATOM | 4450 | O | HOH X 539 | 133.622 | 118.314 | -81.814 | 1.00 | 15.52 | O |
| ATOM | 4453 | O | HOH X 540 | 110.230 | 129.929 | -70.231 | 1.00 | 21.23 | O |
| ATOM | 4456 | O | HOH X 541 | 130.267 | 138.063 | -86.453 | 1.00 | 20.00 | O |
| ATOM | 4459 | O | HOH X 542 | 132.378 | 113.339 | -81.191 | 1.00 | 17.91 | O |
| ATOM | 4462 | O | HOH X 543 | 133.405 | 136.954 | -52.698 | 1.00 | 25.34 | O |
| ATOM | 4465 | O | HOH X 544 | 106.566 | 116.450 | -74.773 | 1.00 | 15.22 | O |
| ATOM | 4468 | O | HOH X 545 | 110.810 | 121.455 | -71.656 | 1.00 | 15.45 | O |
| ATOM | 4471 | O | HOH X 546 | 108.666 | 127.379 | -85.338 | 1.00 | 32.31 | O |
| ATOM | 4474 | O | HOH X 547 | 113.594 | 125.373 | -62.452 | 1.00 | 22.49 | O |
| ATOM | 4477 | O | HOH X 548 | 112.197 | 103.747 | -77.647 | 1.00 | 19.53 | O |
| ATOM | 4480 | O | HOH X 549 | 100.006 | 114.464 | -76.115 | 1.00 | 40.90 | O |
| ATOM | 4483 | O | HOH X 550 | 142.207 | 125.977 | -55.267 | 1.00 | 24.99 | O |
| ATOM | 4486 | O | HOH X 551 | 134.863 | 141.888 | -58.330 | 1.00 | 37.62 | O |
| ATOM | 4489 | O | HOH X 552 | 143.100 | 141.787 | -72.702 | 1.00 | 28.42 | O |
| ATOM | 4492 | O | HOH X 553 | 109.448 | 107.840 | -64.971 | 1.00 | 39.50 | O |
| ATOM | 4495 | O | HOH X 554 | 114.144 | 111.570 | -89.340 | 1.00 | 31.89 | O |
| ATOM | 4498 | O | HOH X 555 | 109.140 | 103.233 | -65.013 | 1.00 | 43.72 | O |
| ATOM | 4501 | O | HOH X 556 | 116.411 | 139.445 | -72.241 | 1.00 | 37.23 | O |
| ATOM | 4504 | O | HOH X 557 | 105.783 | 105.354 | -67.940 | 1.00 | 38.89 | O |
| ATOM | 4507 | O | HOH X 558 | 102.378 | 128.536 | -81.779 | 1.00 | 29.77 | O |
| ATOM | 4510 | O | HOH X 559 | 131.045 | 133.713 | -51.732 | 1.00 | 33.76 | O |
| ATOM | 4513 | O | HOH X 560 | 104.097 | 129.832 | -75.835 | 1.00 | 30.53 | O |
| ATOM | 4516 | O | HOH X 561 | 126.522 | 122.422 | -51.085 | 1.00 | 42.04 | O |
| ATOM | 4519 | O | HOH X 562 | 142.156 | 138.672 | -65.251 | 1.00 | 43.69 | O |
| ATOM | 4522 | O | HOH X 563 | 126.443 | 145.054 | -56.765 | 1.00 | 39.34 | O |
| ATOM | 4525 | O | HOH X 564 | 129.413 | 148.132 | -64.558 | 1.00 | 29.40 | O |

(SEQ ID NO. 34)

FIGURE 20-32

```
ATOM 4528 O HOH X 565   136.894 113.771 -50.020 1.00 39.37      O
ATOM 4531 O HOH X 566   117.342 135.404 -76.792 1.00 23.78      O
ATOM 4534 O HOH X 567   107.280 121.315 -68.267 1.00 33.79      O
ATOM 4537 O HOH X 568   142.105 136.741 -53.424 1.00 31.60      O
ATOM 4540 O HOH X 569   103.284 124.719 -68.936 1.00 47.41      O
ATOM 4543 O HOH X 570   105.240 106.626 -71.025 1.00 48.09      O
ATOM 4546 O HOH X 571   102.796 110.330 -72.183 1.00 40.43      O
ATOM 4549 O HOH X 572   116.967 116.122 -60.706 1.00 32.25      O
ATOM 4552 O HOH X 573   107.994 121.477 -71.410 1.00 34.24      O
ATOM 4555 O HOH X 574   130.563 112.087 -55.911 0.50 25.95      O
ATOM 4558 O HOH X 575   118.453 141.064 -90.075 1.00 10.90      O
ATOM 4561 O HOH X 576   142.376 135.930 -67.183 1.00 13.61      O
ATOM 4564 O HOH X 577   112.235 141.438 -86.687 1.00 10.04      O
ATOM 4567 O HOH X 578   115.774 115.828 -77.434 1.00 11.87      O
ATOM 4570 O HOH X 579   111.276 131.485 -67.966 1.00 12.25      O
ATOM 4573 O HOH X 580   118.083 132.560 -54.953 1.00 20.76      O
ATOM 4576 O HOH X 581   114.973 138.879 -92.431 1.00  9.99      O
ATOM 4579 O HOH X 582   122.755 144.005 -76.969 1.00 29.63      O
ATOM 4582 O HOH X 583   114.757 141.168 -86.069 1.00 10.55      O
ATOM 4585 O HOH X 584   113.922 114.313 -68.390 1.00 25.29      O
ATOM 4588 O HOH X 585   114.510 139.930 -80.755 1.00 23.20      O
ATOM 4591 O HOH X 586   126.871 143.189 -91.829 1.00 35.27      O
ATOM 4594 O HOH X 587   121.554 147.338 -91.125 1.00 38.24      O
ATOM 4597 O HOH X 588   144.696 115.260 -64.844 1.00 36.35      O
ATOM 4600 O HOH X 589   112.000 105.603 -71.158 1.00 32.72      O
ATOM 4603 O HOH X 590   114.689 132.941 -56.812 1.00 29.23      O
ATOM 4606 O HOH X 591   112.629 126.884 -92.412 1.00 26.14      O
ATOM 4609 O HOH X 592   117.569 111.566 -63.076 1.00 27.65      O
ATOM 4612 O HOH X 593   110.616 135.876 -87.041 1.00 26.92      O
ATOM 4615 O HOH X 594   103.330 101.405 -68.733 1.00 33.78      O
ATOM 4618 O HOH X 595   132.413 140.494 -56.308 1.00 47.97      O
ATOM 4621 O HOH X 596   142.385 140.978 -61.612 1.00 30.59      O
ATOM 4624 O HOH X 597    97.191 128.528 -82.326 1.00 47.65      O
ATOM 4627 O HOH X 598   120.771 113.140 -60.445 1.00 31.37      O
ATOM 4630 O HOH X 599   115.660 142.061 -99.977 1.00 39.70      O
ATOM 4633 O HOH X 600   143.976 135.780 -70.730 1.00  9.35      O
ATOM 4636 O HOH X 601   132.664 122.608 -50.793 1.00 34.19      O
ATOM 4639 O HOH X 602   133.944 117.833 -49.702 1.00 37.18      O
ATOM 4642 O HOH X 603   131.472 120.693 -49.593 1.00 41.58      O
ATOM 4645 O HOH X 604   137.117 127.735 -53.487 1.00 30.57      O
ATOM 4648 O HOH X 605   140.027 125.271 -56.559 1.00 27.85      O
ATOM 4651 O HOH X 606   114.952 130.776 -69.880 1.00 12.35      O
ATOM 4654 O HOH X 607   115.516 119.897 -64.150 1.00 19.75      O
ATOM 4657 O HOH X 608   127.977 127.694 -55.040 1.00  6.05      O
ATOM 4660 O HOH X 609   122.187 123.199 -55.391 1.00 15.33      O
ATOM 4663 O HOH X 610   131.276 127.892 -52.024 1.00 34.83      O
ATOM 4666 O HOH X 611   126.093 139.458 -54.607 1.00 36.51      O
ATOM 4669 O HOH X 612   127.733 133.072 -49.198 1.00 38.10      O
ATOM 4672 O HOH X 613   119.352 140.160 -71.721 1.00 26.03      O
ATOM 4675 O HOH X 614   141.242 140.880 -68.244 1.00 14.66      O
ATOM 4678 O HOH X 615   133.707 143.300 -64.993 1.00 32.86      O
ATOM 4681 O HOH X 616   142.657 142.717 -58.842 0.50 32.87      O
ATOM 4684 O HOH X 617   143.619 129.968 -56.353 1.00 23.63      O
ATOM 4687 O HOH X 618   116.844 136.714 -74.218 1.00 22.50      O
ATOM 4690 O HOH X 619   108.694 128.702 -89.298 1.00 39.36      O
ATOM 4693 O HOH X 620   106.515 130.086 -87.759 1.00 42.63      O
ATOM 4696 O HOH X 621   109.791 132.798 -95.777 1.00 23.87      O
ATOM 4699 O HOH X 622   119.729 143.761 -93.174 1.00 29.66      O
ATOM 4702 O HOH X 623   144.405 119.392 -67.544 1.00 30.41      O
ATOM 4705 O HOH X 624   141.170 119.736 -67.369 1.00 18.82      O
ATOM 4708 O HOH X 625   131.336 117.003 -82.303 1.00 29.85      O
ATOM 4711 O HOH X 626   147.662 124.057 -77.351 1.00 12.02      O
ATOM 4714 O HOH X 627   150.951 127.664 -73.281 1.00 27.32      O
ATOM 4717 O HOH X 628   115.600 118.779 -81.820 1.00 11.14      O
ATOM 4720 O HOH X 629   106.100 132.746 -84.217 1.00 25.05      O
ATOM 4723 O HOH X 630   104.190 119.814 -74.111 1.00 31.98      O
ATOM 4726 O HOH X 631   107.549 112.543 -72.451 1.00 32.85      O
ATOM 4729 O HOH X 632   105.842 113.826 -74.501 1.00 37.13      O
```

(SEQ ID NO. 34)

FIGURE 20-33

```
     ATOM   4732  O   HOH X 633    106.238 109.825 -76.227  1.00 36.89           O
     ATOM   4735  O   HOH X 634    113.260 114.938 -76.245  1.00 23.31           O
     ATOM   4738  O   HOH X 635    106.123 133.467 -76.804  1.00 13.85           O
     ATOM   4741  O   HOH X 636    104.129 127.107 -78.130  1.00  5.08           O
 5   ATOM   4744  O   HOH X 637    135.404 113.055 -57.983  1.00 36.50           O
     ATOM   4747  O   HOH X 638    129.593 147.205 -67.068  1.00 27.27           O
     ATOM   4750  O   HOH X 639    132.238 146.233 -67.180  1.00 20.62           O
     ATOM   4753  O   HOH X 640    133.474 147.941 -76.571  1.00  9.40           O
     ATOM   4756  O   HOH X 641    136.759 147.665 -76.719  1.00 30.13           O
10   ATOM   4759  O   HOH X 642    137.495 146.577 -64.297  1.00 33.87           O
     ATOM   4762  O   HOH X 643    123.839 136.893 -68.238  1.00 20.71           O
     ATOM   4765  O   HOH X 644    128.577 121.107 -86.359  1.00 35.61           O
```

(SEQ ID NO. 34)

```
FT_FabI  MGFLAGKKILITELLNKSIAYGIAKAMHRGAELAFTYVG-FKDRVEKCAEFN--PAAVLPCDVISD
SA_FabI  MLNLENKTYIIMGIANKRSIAEGIAKVSDSLGAKLVFTYRKESRKEDKILEQLNQPEAHEYGIDVQSD
EC_FabI  MGFLSGKRILVTGMASKLSIAYGIAQAMHREGAELAFTYQNDKLKGRVEEFAAQLG--SDIVLQCDVAED
HP_FabI  MGFLKGKKGLIVGVANNKSIAYGIAQSCFNCGATLAFTYLNESLEKRVRPEAQELN--SPYVYELDVSKE

FT_FabI  EKDLFVELGKVWDGEDAVVHSIAFAPRIQLEGNRIDCVTREGFSAHDISAYSFAAAKEGRSMMKNR
SA_FabI  EVINGFECGKDVGNIDGIYHSIAFANMEDLRGRESETS-REGFLAQDISSYSLTIVAHEAKKIM-PE
EC_FabI  ASIDTMFAELGKVWPKFDGFVHSIGFAPGDQLDGDLVNAVTREGFKAHDISSYSFVAMAKACRSMIL-NP
HP_FabI  EHFKSLKNSMKKDLGSEDFIVHSVAFAPKEALEGSLIETS-KSAENTAMEISVYSLIELTNTLKPIL-NN

FT_FabI  NASMVALTYIGAEKAMPEYNIMGVAKASLEATVRYTAIALGEDGIKVNAVSAGPIKTLAASGISNEKKML
SA_FabI  GGSIVATLYLGGEFAVQNYNVMGVAKASLEANVKYIALDLGPDNIRVNAISAGPIRTLSAKGVGGENTIL
EC_FabI  GSAIGTLSYLGAERAIPNYNVMGLAKASLEANVRYMANAIGPEGVRVNAISAGPIRTLAASGIKDFRKML
HP_FabI  CASVITLSYLGSTKYMALYNVMGLAKAELESAVRYLAVDLGKHHIRVNALSAGPIRTLASSGIADFRMIL

FT_FabI  DYNAMVEPLKKNVDIMEVGNTVAELCSDMAIGLIGEVVHVDAGYHCVSMGNVL----------------
SA_FabI  KEIKERAPLKPNVDQVEVGKIAAYLLSDLSGVIGENIHVDSGHHALK------------------
EC_FabI  AHCEAVTPERRIVTTEDVGNSAAELCSDLSAGISGEVVHVDGGESIAAMNELELK------------
HP_FabI  KWNEINAPLRKNVSLEEVGNAGMYLLSSLSSGVSGEVHFVDAGYHVNGMGAVEEKDNKATLLWDLHKEQ
```

Abbreviations: EC - *Escherichia coli*, HP – *Helicobacter pylori*, SA - *Staphylococcus aureus*, and FT – *Francisella tularensis*.

FIGURE 22
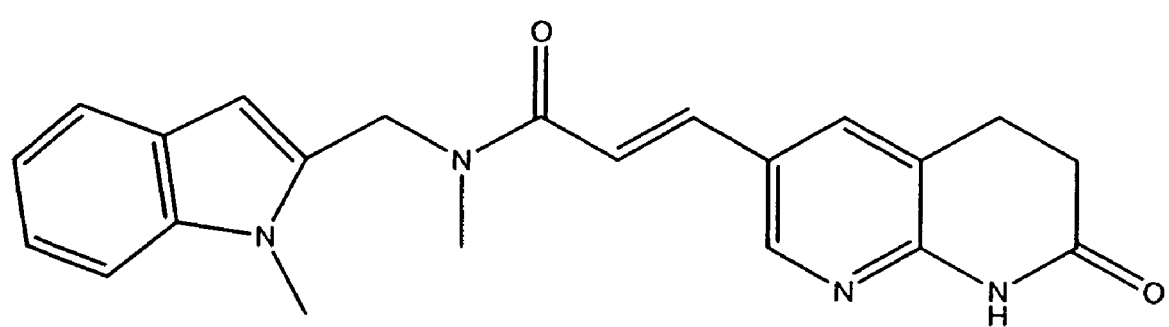

PURIFIED FABI POLYPEPTIDES FROM *FRANSICELLA TULARENSIS*

PRIORITY

This application is a continuation of PCT/US2005/023115 filed Jun. 30, 2005 which in turn claims the benefit of U.S. Ser. No. 60/584,091, filed Jun. 30, 2004, both of which are hereby incorporated by reference in its entirety.

GOVERNMENT SUPPORT

This invention was made with government support under NIH Grant 1U01A157291-01 awarded by the National Institutes of Health. The government has certain rights in the invention.

INTRODUCTION

The discovery of novel antimicrobial agents that work by innovative mechanisms is a problem researchers in all fields of drug development face today. The increasing prevalence of drug-resistant pathogens (bacteria, fungi, parasites, etc.) has led to significantly higher mortality rates from infectious diseases and currently presents a serious crisis worldwide. Despite the introduction of second and third generation antimicrobial drugs, certain pathogens have developed resistance to all currently available drugs.

One of the problems contributing to the development of multiple drug resistant pathogens is the limited number of protein targets for antimicrobial drugs. Many of the antibiotics currently in use are structurally related or act through common targets or pathways. Accordingly, adaptive mutation of a single gene may render a pathogenic species resistant to multiple classes of antimicrobial drugs. Therefore, the rapid discovery of drug targets is urgently needed in order to combat the constantly evolving threat by such infectious microorganisms.

Recent advances in bacterial and viral genomics research provides an opportunity for rapid progress in the identification of drug targets. The complete genomic sequences for a number of microorganisms are available. However, knowledge of the complete genomic sequence is only the first step in a long process toward discovery of a viable drug target. The genomic sequence must be annotated to identify open reading frames (ORFs), the essentiality of the protein encoded by the ORF must be determined and the mechanism of action of the gene product must be determined in order to develop a targeted approach to drug discovery.

There are a variety of computer programs available to annotate genomic sequences. Genome annotation involves both identification of genes as well assignment of function thereto based on sequence comparison to homologous proteins with known or predicted functions. However, genome annotation has turned out to be much more of an art than a science. Factors such as splice variants and sequencing errors coupled with the particular algorithms and databases used to annotate the genome can result in significantly different annotations for the same genome. For example, upon reanalysis of the genome of *Mycoplasma pneumoniae* using more rigorous sequence comparisons coupled with molecular biological techniques, such as gel electrophoresis and mass spectrometry, researchers were able to identify several previously unidentified coding sequences, to dismiss a previous identified coding sequence as a likely pseudogene, and to adjust the length of several previously defined ORFs (Dandkar et al. (2000) Nucl. Acids Res. 28(17): 3278-3288). Furthermore, while overall conservation between amino acid sequences generally indicates a conservation of structure and function, specific changes at key residues can lead to significant variation in the biochemical and biophysical properties of a protein. In a comparison of three different functional annotations of the *Mycoplasma genitalium* genome, it was discovered that some genes were assigned three different functions and it was estimated that the overall error rate in the annotations was at least 8% (Brenner (1999) Trends Genet. 15(4): 132-3). Accordingly, molecular biological techniques are required to ensure proper genome annotation and identify valid drug targets.

However, confirmation of genome annotation using molecular biological techniques is not an easy proposition due to the unpredictability in expression and purification of polypeptide sequences. Further, in order to carry out structural studies to validate proteins as potential drug targets, it is generally necessary to modify the native proteins in order to facilitate these analyses, e.g., by labeling the protein (e.g., with a heavy atom, isotopic label, polypeptide tag, etc.) or by creating fragments of the polypeptide corresponding to functional domains of a multi-domain protein. Moreover, it is well-known that even small changes in the amino acid sequence of a protein may lead to dramatic affects on protein solubility (Eberstadt et al. (1998) Nature 392: 941-945). Accordingly, genome-wide validation of protein targets will require considerable effort even in light of the sequence of the entire genome of an organism and/or purification conditions for homologs of a particular target.

We have developed reliable, high throughput methods to address some of the shortcomings identified above. In part, using these methods, we have now identified, expressed, and purified a novel antimicrobial target from *Fransicella tularensis*, or *F. tularensis*. Various biophysical, bioinformatic and biochemical studies have been used to characterize the structure and function of the polypeptides of the invention.

SUMMARY OF THE INVENTION

As part of an effort at genome-wide structural and functional characterization of microbial targets, polypeptides from *F. tularensis* are provided. In various aspects, nucleic acid and amino acid sequences of the polypeptides are provided. Further, purified, soluble forms of the polypeptides of the invention suitable for structural and functional characterization using a variety of techniques, including, for example, affinity chromatography, mass spectrometry, NMR and x-ray crystallography are provided. Modified versions of the polypeptides of the invention to facilitate characterization, including polypeptides labeled with isotopic or heavy atoms and fusion proteins are also provided.

A polypeptide of the invention has been crystallized and its structure solved as described in detail below, thereby providing information about the structure of the polypeptide, and druggable regions, domains and the like contained therein, all of which may be used in rational-based drug design efforts.

All of the information learned and described herein about the polypeptides of the invention may be used to design modulators of one or more of their biological activities. In particular, information critical to the design of therapeutic and diagnostic molecules, including, for example, the protein domain, druggable regions, structural information, and the like for the polypeptides of the invention is now available or attainable as a result of the ability to prepare, purify and characterize them, and domains, fragments, variants and derivatives thereof.

In other aspects, structural and functional information about the polypeptides of the invention has and will be obtained. Such information, for example, may be incorporated into databases containing information on the polypeptides of the invention, as well as other polypeptide targets from other microbial species. Such databases will provide investigators with a powerful tool to analyze the polypeptides of the invention and aid in the rapid discovery and design of therapeutic and diagnostic molecules.

In another aspect, modulators, inhibitors, agonists or antagonists against the polypeptides of the invention, or biological complexes containing them, or orthologues thereto, may be used to treat any disease or other treatable condition of a patient (including humans and animals), and particularly a disease caused by *F. tularensis*, such as, for example, one of the following: tularemia, or other diseases or disorders associated with an *F. tularensis* infection, such as, for example, infection of the lymph nodes, lungs and pleura, spleen, liver, and/or kidney, upper respiratory problems, bronchitis, and pleuropneumonitis.

Relationships between polypeptides from the same and multiple species may be compared by isolating and studying the various polypeptides of the invention and other proteins. By such comparison studies, which may involve multi-variable analysis as appropriate, it is possible to identify drugs that will affect multiple species or drugs that will affect one or a few species. In such a manner, so-called "wide spectrum" and narrow spectrum" anti-infectives may be identified. Alternatively, drugs that are selective for one or more bacterial or other non-mammalian species, and not for one or more mammalian species (especially human), may be identified (and vice-versa).

In other embodiments, kits including the subject nucleic acids, polypeptides, crystallized polypeptides, antibodies, and other subject materials, and optionally instructions for their use are provided. Uses for such kits include, for example, diagnostic and therapeutic applications.

Other embodiments and practices, and their features and characteristics, will be apparent from the description, figures and claims that follow, with all of the claims hereby being incorporated by this reference into this Summary.

BRIEF DESCRIPTION OF THE FIGURES

FIG. 1 shows the nucleic acid coding sequence for FabI from *F. tularensis* (SEQ ID NO: 1).

FIG. 2 shows the amino acid sequence for FabI from *F. tularensis* (SEQ ID NO: 2).

FIG. 3 shows the nucleic acid sequence for untagged *F. tularensis* FabI as described in the examples (SEQ ID NO: 3). The sequence in bold was added to facilitate cloning into an expression vector.

FIG. 4 shows the amino acid sequence for untagged *F. tularensis* FabI as described in the examples (SEQ ID NO: 4). The sequence in bold is encoded by nucleic acid seqeunces added to facilitate cloning into an expression vector.

FIG. 5 shows the nucleic acid sequence for *F. tularensis* FabI tagged at the N-terminus with a His-tag as described in the examples (SEQ ID NO: 5). The sequence in bold was added to facilitate cloning into an expression vector. The unerlined sequence represents the coding seqeunce for the His-tag.

FIG. 6 shows the amino acid sequence for *F. tularensis* FabI tagged at the N-terminus with a His-tag as described in the examples (SEQ ID NO: 6). The sequence in bold was added to facilitate cloning into an expression vector. The unerlined sequence represents the seqeunce for the His-tag.

FIG. 7 shows the nucleic acid sequence for *F. tularensis* FabI tagged at the C-terminus with a His-tag as described in the examples (SEQ ID NO: 7). The sequence in bold was added to facilitate cloning into an expression vector. The unerlined sequence represents the coding seqeunce for the His-tag.

FIG. 8 shows the amino acid sequence for *F. tularensis* FabI tagged at the C-terminus with a His-tag as described in the examples (SEQ ID NO: 8). The sequence in bold was added to facilitate cloning into an expression vector. The unerlined sequence represents the seqeunce for the His-tag.

FIG. 9 shows an alignment of FabI amino acid sequences from *F. tularensis* (FT FabI; SEQ ID NO: 1), *Staphylococcus aureus* (SA FabI; SEQ ID NO: 9), *Escherichia coli* (EC FabI; SEQ ID NO: 10), and *Helicobacter pylori* (HP FabI; SEQ ID NO: 11). Consen respresent the consensus FabI sequence showing the residues conserved among all four FabI sequences (SEQ ID NO: 12; -represents any amino acid). The table shows the percent identities of the amino acid sequences for FabI from *F. tularensis, S. aureus, E. coli* and *H. pylori*.

FIG. 10 shows schematic of the amino acid sequences for FabI from *F. tularensis* (SEQ ID NO: 13), *S. aureus* (SEQ ID NO: 14), *E. coli* (SEQ ID NO: 15) and *H. pylori* (SEQ ID NO: 16). The consensus binding site residues (C) are shown as SEQ ID NO: 17. The shaded residues represent amino acids in the binding site as identified from the crystal structures of FabI from *S. aureus* and *F. tularensis*. A diagramatic view of the FabI sequences is shown in FIG. 12. A summary of the binding site residues for FabI is shown in FIG. 13. Box A represents amino acid residues 92-99 of FabI from *F. tularensis*, residues 95-102 of FabI from *S. aureus*, residues 93-100 of FabI from *E. coli*, and residues 93-100 of FabI from *H. pylori*. Box B represents amino acids 146-163 of FabI from *F. tularensis*, residues 147-164 of FabI from *S. aureus*, residues 146-163 of FabI from *E. coli*, and residues 145-162 of FabI from *H. pylori*. Box C represents amino acids 191-206 of FabI from *F. tularensis*, residues 192-207 of FabI from *S. aureus*, residues 191-206 of FabI from *E. coli*, and residues 190-205 of FabI from *H. pylori*. FT=*F. tularensis*, SA=*S. aureus*, EC=*E. coli*, HP=*H. pylori*, C=consensus binding site residues, G/A=Gly or Ala, A/S=Ala or Ser, S/K=Ser or Lys, I/V=Ile or Val, M/I=Met or Ile, Xaa=any amino acid residue, $Xaa_n$=n number of Xaa residues, $Xaa_{n-a}$=variable number of Xaa residues.

FIG. 11 shows a variety of FabI sequences. SEQ ID NO: 18 shows the Box A amino acid sequence for *F. tularensis* FabI from FIG. 10, SEQ ID NO: 19 shows the Box B amino acid sequence for *F. tularensis* FabI from FIG. 10, SEQ ID NO: 20 shows the Box C amino acid sequence for *F. tularensis* FabI from FIG. 10, SEQ ID NO: 21 shows the amino acid sequence for residues 146-206 of *F. tularensis* FabI (e.g., Box B+$Xaa_{27}$+Box C), SEQ ID NO: 22 shows the amino acid sequences for residues 92-206 of *F. tularensis* FabI (e.g., Box A+$Xaa_{44-46}$+Box B+$Xaa_{27}$+Box C), SEQ ID NO: 23 shows the amino acid sequence for the conensus binding site residues of FabI (e.g., consensus of Box A+$Xaa_{44-46}$+Box B+$Xaa_{27}$+Box C), SEQ ID NO: 24 shows the amino acid sequence for the flipping loop of *F. tularensis* FabI (residues 192-202), SEQ ID NO: 25 shows the amino acid sequence for the flipping loop of *S. aureus* FabI (residues 193-203), SEQ ID NO: 26 shows the amino acid sequence for the flipping loop of *E. coli* FabI (residues 192-202), and SEQ ID NO: 27 shows the amino acid sequence for the flipping loop of *H. pylori* FabI (residues 191-201). Xaa=any amino acid residue, $Xaa_n$=n number of Xaa residues, and $Xaa_{a-n}$=variable number of Xaa residues.

FIG. 13 shows a table of the binding residues and flipping loops for FabI from *F. tularensis* (FT), *S. aureus* (SA), *E. coli*

(EC) and *H. pylori* (HP). The flipping loops are SEQ ID NOs: 23-26 for *F. tularensis, S. aureus, E. coli* and *H. pylori*, respectively.

pages to FIG. 20, labeled 1, 2, 3, etc. The information in such FIG. is presented in the following tabular format, with a generic entry provided as an example:

| Record Header | No. | Atom Type | Residue | Residue Number | X | Y | Z | OCC | B |
|---|---|---|---|---|---|---|---|---|---|
| ATOM 1 | 1 | CB | HIS | 1 | 4.497 | 15.607 | 34.172 | 1 | 70.54 |

FIG. 14 shows several consensus sequences for FabI based on the alignments of four FabI sequences shown in FIG. 9. SEQ ID NO: 28 represents an overall consensus sequence for FabI. The specified residues represent amino acids conserved among all four FabI sequences. The residues designated $Xaa_n$ represent amino acid residues conserved among three of the four Fabi sequences; the amino acid variation among the FabI sequences is specified at the bottom of the figure for each numbered residue. SEQ ID NO: 29 comprises residues conserved among the four FabI sequences shown in FIG. 9 as well as the binding site residues for *F. tularensis* (e.g., SEQ ID NO: 12 and SEQ ID NO: 22). SEQ ID NO: 30 comprises residues conserved among the four FabI sequences shown in FIG. 9 as well as the consensus binding site residues (e.g., SEQ ID NO: 12 and SEQ ID NO: 23). For SEQ ID NOs: 28-30, Xaa represents any amino acid (e.g., residues not conserved among the FabI sequences), $Xaa_n$ represents n number of Xaa residues, and $Xaa_{a-n}$ represents a variable number of Xaa residues. The Box A, B and C sequences are shaded and labeled.

FIG. 15 shows the sequences for the forward (SEQ ID NO: 31) and reverse (SEQ ID NO: 32) primers used to clone *F. tularensis* FabI into an expression vector as described in the examples.

Figure 12:
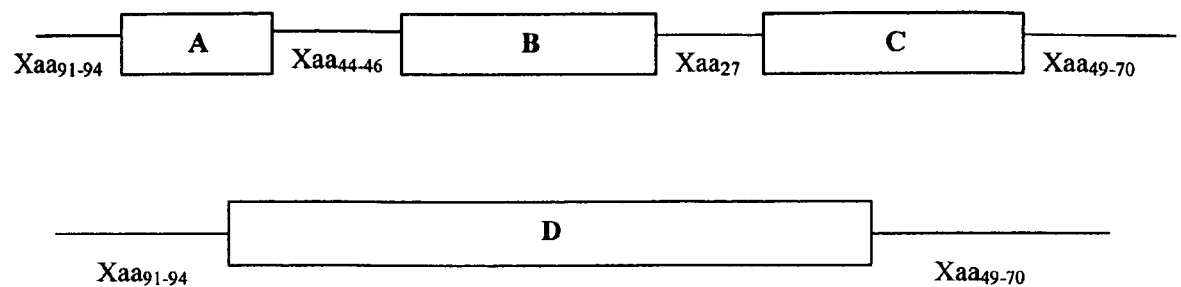
FIG. 12 shows a diagram of the FabI amino acid sequence including Boxes A, B, and C. Box D represents Box A+$Xaa_{44-46}$+Box B+$Xaa_{27}$+Box C.
Figure 16:
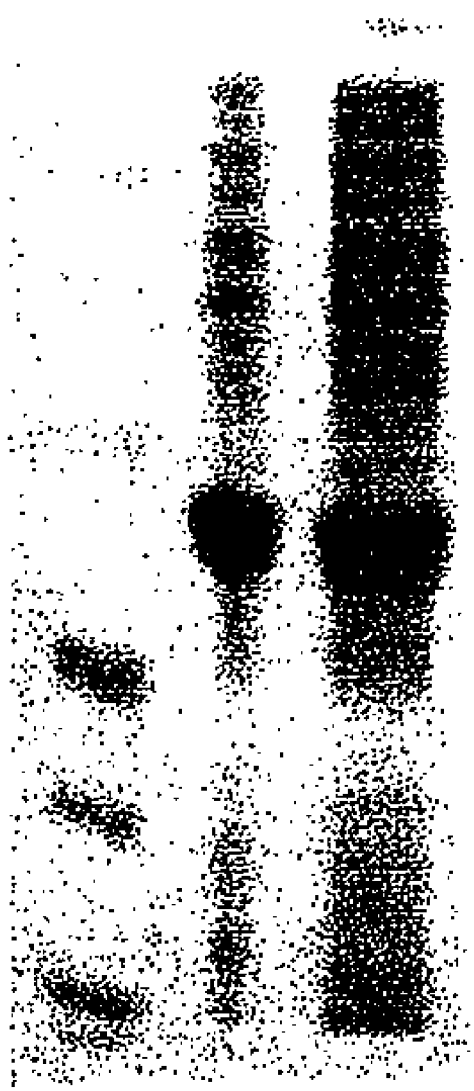

FIG. 16 shows an image of an SDS-PAGE gel used to analyze the expression og *F. tularensis* FabI (FT FabI) protein. Cells containing expressed FT FabI were lysed and resolved by SDS-PAGE. MW=molecular weight, Lane P=FT FabI whole cell lysate, Lane S=FT FabI soluble lysate.

Figure 17:
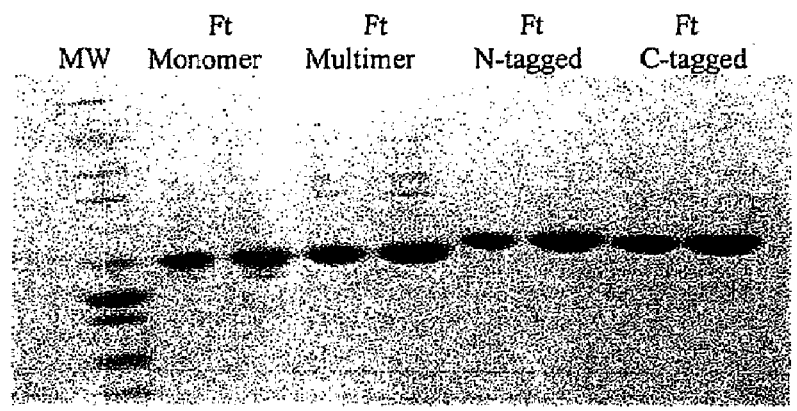

FIG. 17 shows an image of an SDS-PAGE gel used to resolve purified *F. tularensis* FabI protein. The concentrated proteins obtained following purification were resolved by SDS-PAGE and stained with Coomassie Blue. MW=molecular weight, FT monomer=untagged *F. tularensis* FabI monomer at 5 μg and 10 μg, FT multimer=untagged *F. tularensis* FabI multimer at 5 μg and 10 μg, FT N-tagged =*F. tularensis* FabI polypeptide with N-terminal His-tag at 5 μg and 10 μg, and FT C-tagged =*F. tularensis* FabI polypeptide with C-terminal His-tag at 5 μg and 10 μg. The table shows the quantity (mg), concentration (mg/mL), and purity (w/w %) of untagged, N-terminal His-tagged, and C-terminal His-tagged FabI from *F. tularensis* obtained as described in the examples.

Figure 18:
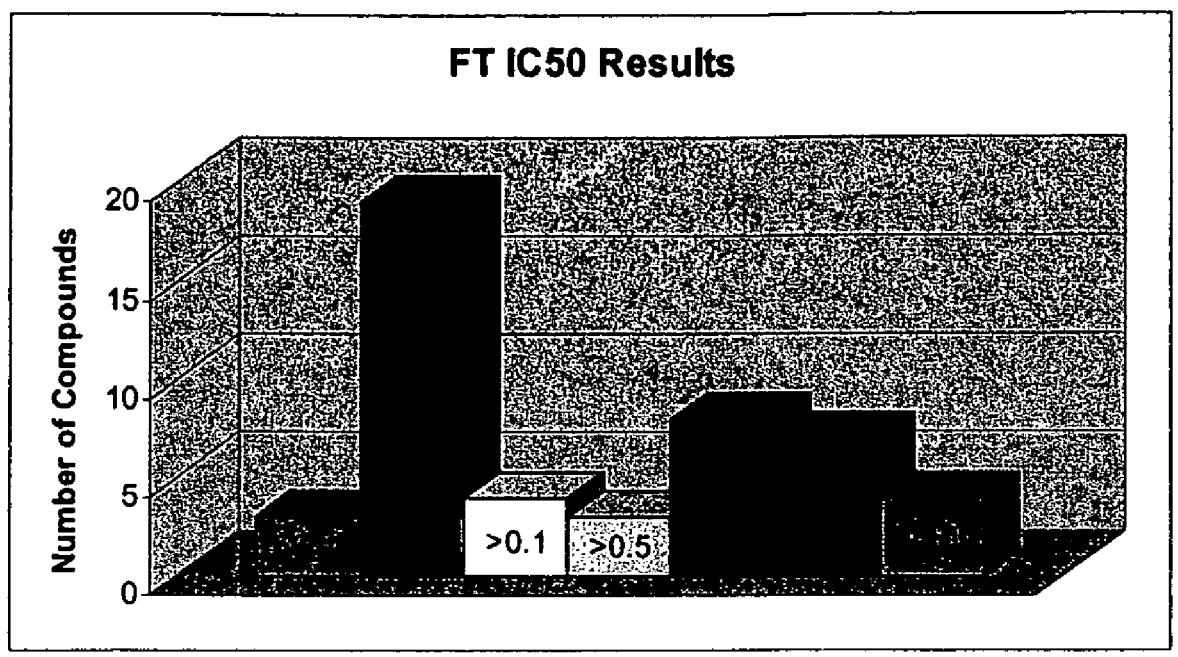

FIG. 18 is a graph showing the inhibitory concentration 50% ($IC_{50}$) for 48 test compounds evaluated against FT FabI. The results were binned according to potency with the majority of compounds having $IC_{50}$ values falling in the fange of 0.01-0.1 μM.

FIG. 19 contains Tables 1 and 2, which show information related to the x-ray structure for a polypeptide of the invention as described more fully in EXAMPLE 16.

FIG. 20 lists the atomic structure coordinates for a polypeptide (SEQ ID NO: 34) of the invention derived from x-ray diffraction from a crystal of such polypeptide, as described in more detail in EXAMPLE 16. There are multiple pages to FIG. 20, labeled 1, 2, 3, etc. The information in such FIG. is presented in the following tabular format, with a generic entry provided as an example:

In the table, "Record Header" describes the row type, such as "ATOM". "No." refers to the row number. The first "Atom Type" column refers to the atom whose coordinates are measured, with the first letter in the column identifying the atom by its elemental symbol and the subsequent letter defining the location of the atom in the amino acid residue or other molecule. "Residue" and "residue number" identifies the residue of the subject polypeptide. "X, Y, Z" crystallographically define the atomic position of the atom measured. "Occ" is an occupancy factor that refers to the fraction of the molecules in which each atom occupies the position specified by the coordinates. A value of "1" indicates that each atom has the same conformation, i.e., the same position, in all molecules of the crystal. "B" is a thermal factor that is related to the root mean square deviation in the position of the atom around the given atomic coordinate.

FIG. 21 depicts the sequence alignment of several pathogenic bacterial orthologs of FabI.

FIG. 22 depicts images of the crystals of the *F. tularensis* FabI NADH API-1059 complex. FIG. 22A depicts the crystals, which are very small diamonds (50 μm) that diffract to 2.4 Å. The chemical structure of API-1059 is shown in FIG. 22B.

Figure 23:

FIG. 23 depicts a ribbon diagram generated in PYMOL of the monomer of *F. tularensis* FabI. NADH and API-1059 are shown in the binding pocket.

Figure 24A:
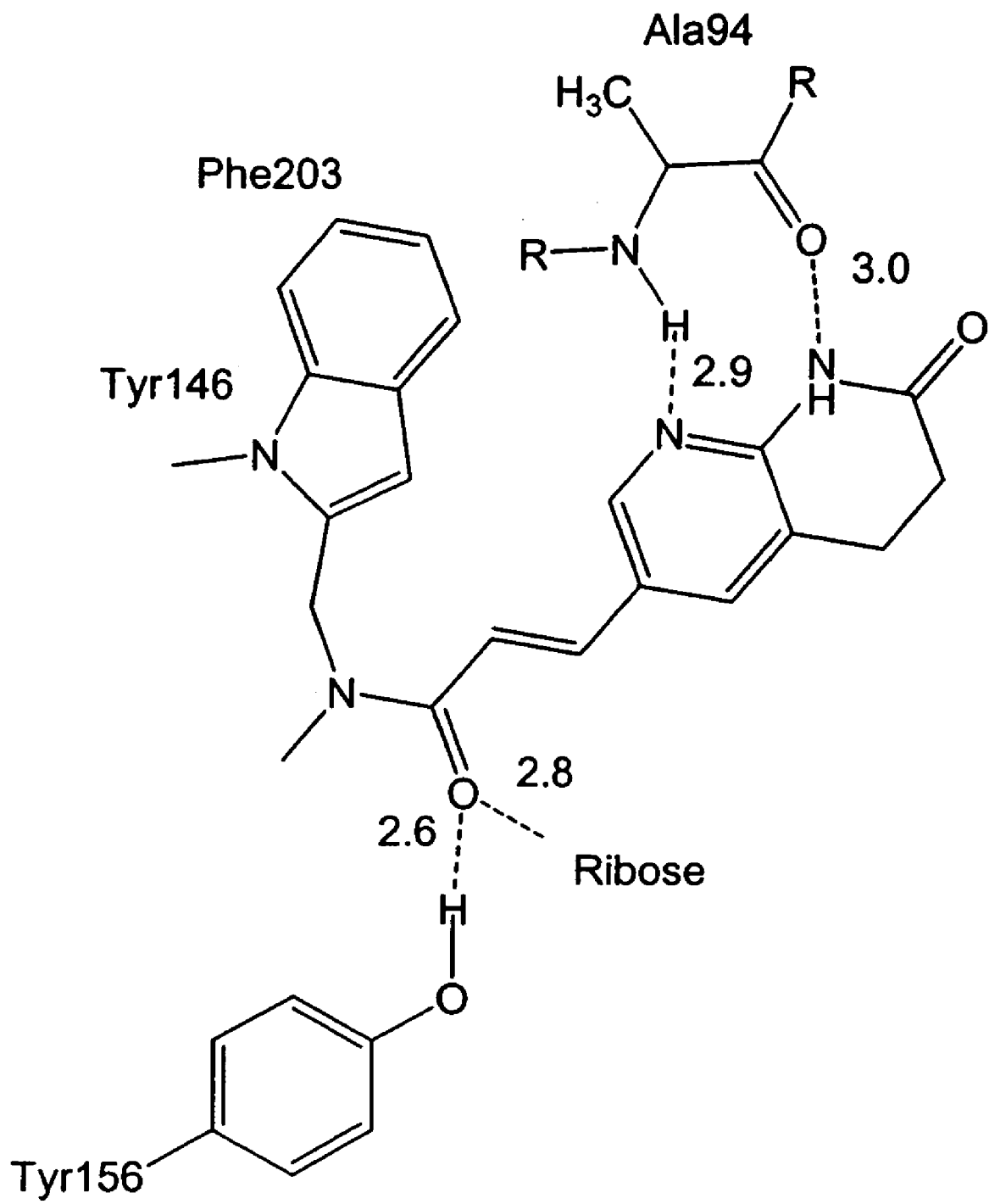
Figure 24B:
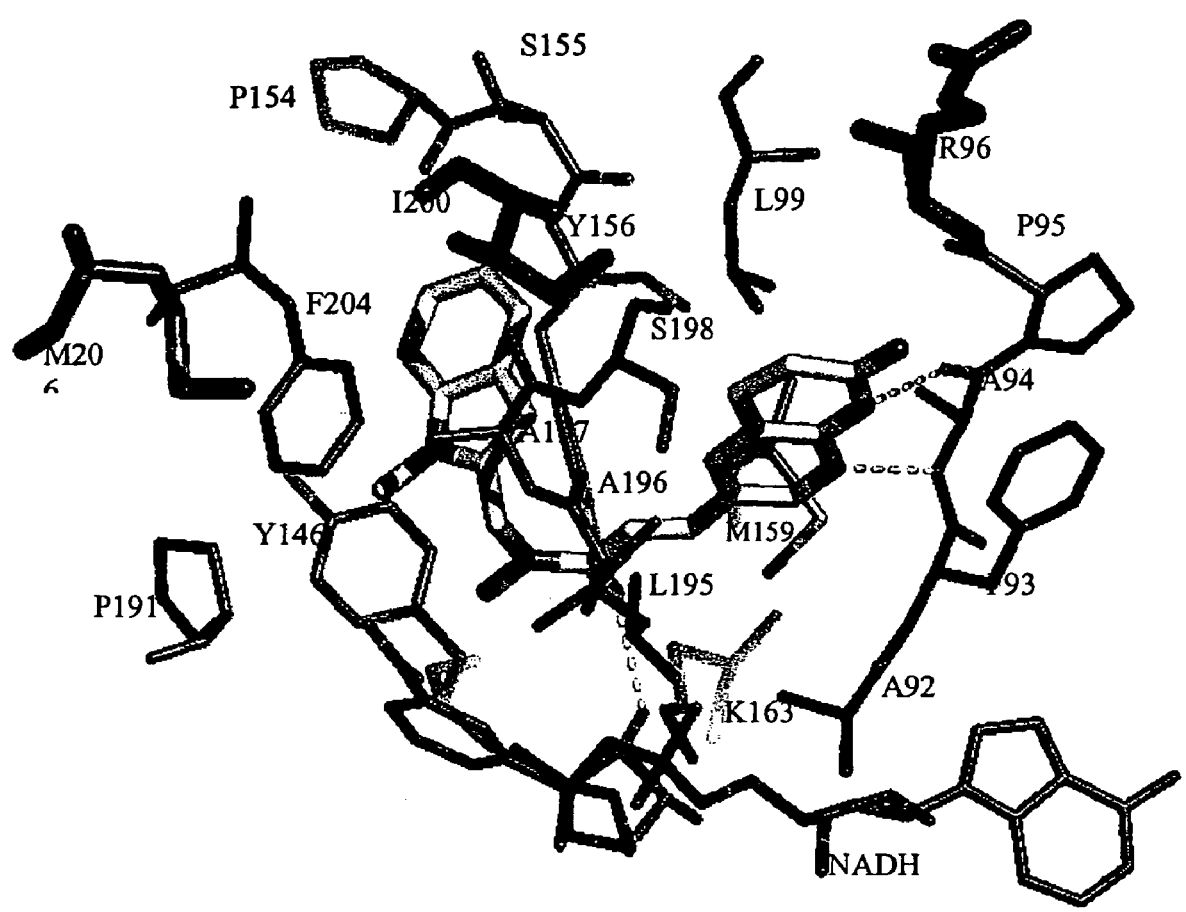

FIG. 24 depicts various views of the inhibitor API-1059 in the *F. tularensis* FabI binding site. FIG. 24A depicts a schematic of the binding of API-1059 in the binding pocket. A94 and Y156 appear to form hydrogen bonds with the inhibitor, while Y146 and F203 appear to form a hydrophobic pocket. FIG. 24B depicts a view of the binding pocket of *F. tularensis* FabI. Hydrogen bonds are shown as dashed lines.

Figure 25:
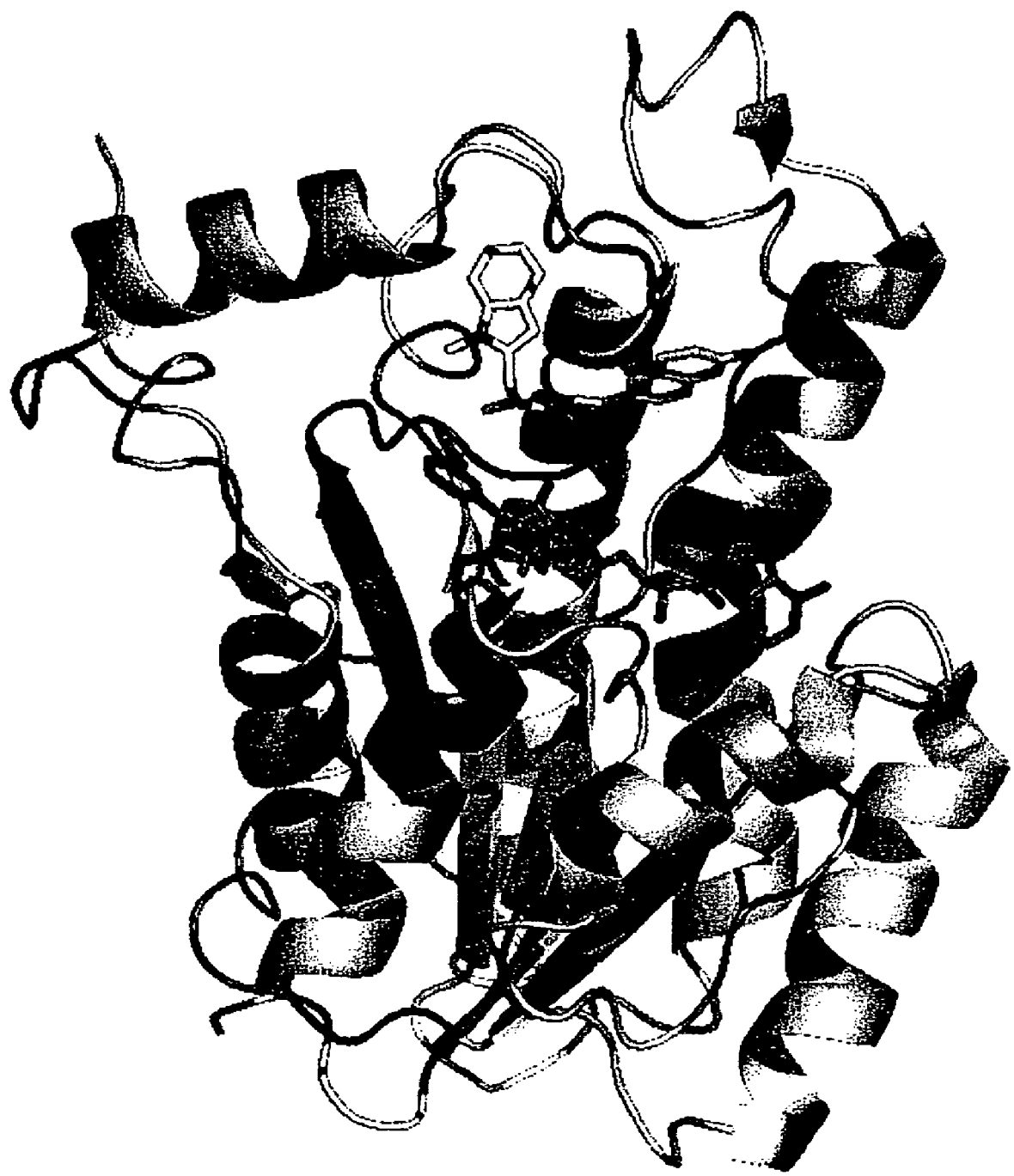

FIG. 25 depicts the conservation of bacterial FabI amino acid sequences mapped onto the *F. tularensis* FabI structure. The amino acid sequences were aligned in ClustalX and the conservation of each position was evaluated in Consurf. Mean conservation between sequences was 0.87, indicating an extremely high degree of sequence conservation overall. This sequence conservation metric was then projected onto the *F. tularensis* FabI API-1059 structure. This analysis shows that the binding site binding site is highly conserved but there are some differences in the residues surrounding the binding pocket.

DETAILED DESCRIPTION OF THE INVENTION

1. Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The term "binding" refers to an association, which may be a stable association, between two molecules, e.g., between a polypeptide of the invention and a binding partner, due to, for example, electrostatic, hydrophobic, ionic and/or hydrogen-bond interactions under physiological conditions.

A "comparison window," as used herein, refers to a conceptual segment of at least 20 contiguous amino acid positions wherein a protein sequence may be compared to a reference sequence of at least 20 contiguous amino acids and wherein the portion of the protein sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods may be identified.

The term "complex" refers to an association between at least two moieties (e.g. chemical or biochemical) that have an affinity for one another. Examples of complexes include associations between antigen/antibodies, lectin/avidin, target polynucleotide/probe oligonucleotide, antibody/anti-antibody, receptor/ligand, enzyme/ligand, polypeptide/polypeptide, polypeptide/polynucleotide, polypeptide/co-factor, polypeptide/substrate, polypeptide/inhibitor, polypeptide/small molecule, and the like. "Member of a complex" refers to one moiety of the complex, such as an antigen or ligand. "Protein complex" or "polypeptide complex" refers to a complex comprising at least one polypeptide.

The term "conserved residue" refers to an amino acid that is a member of a group of amino acids having certain common properties. The term "conservative amino acid substitution" refers to the substitution (conceptually or otherwise) of an amino acid from one such group with a different amino acid from the same group. A functional way to define common properties between individual amino acids is to analyze the normalized frequencies of amino acid changes between corresponding proteins of homologous organisms (Schulz, G. E. and R. H. Schirmer, Principles of Protein Structure, Springer-Verlag). According to such analyses, groups of amino acids may be defined where amino acids within a group exchange preferentially with each other, and therefore resemble each other most in their impact on the overall protein structure (Schulz, G. E. and R. H. Schirmer, Principles of Protein Structure, Springer-Verlag). One example of a set of amino acid groups defined in this manner include: (i) a charged group, consisting of Glu and Asp, Lys, Arg and His, (ii) a positively-charged group, consisting of Lys, Arg and His, (iii) a negatively-charged group, consisting of Glu and Asp, (iv) an aromatic group, consisting of Phe, Tyr and Trp, (v) a nitrogen ring group, consisting of His and Trp, (vi) a large aliphatic nonpolar group, consisting of Val, Leu and Ile, (vii) a slightly-polar group, consisting of Met and Cys, (viii) a small-residue group, consisting of Ser, Thr, Asp, Asn, Gly, Ala, Glu, Gln and Pro, (ix) an aliphatic group consisting of Val, Leu, Ile, Met and Cys, and (x) a small hydroxyl group consisting of Ser and Thr.

The term "domain", when used in connection with a polypeptide, refers to a specific region within such polypeptide that comprises a particular structure or mediates a particular function. In the typical case, a domain of a polypeptide of the invention is a fragment of the polypeptide. In certain instances, a domain is a structurally stable domain, as evidenced, for example, by mass spectroscopy, or by the fact that a modulator may bind to a druggable region of the domain.

The term "druggable region", when used in reference to a polypeptide, nucleic acid, complex and the like, refers to a region of the molecule which is a target or is a likely target for binding a modulator. For a polypeptide, a druggable region generally refers to a region wherein several amino acids of a polypeptide would be capable of interacting with a modulator or other molecule. For a polypeptide or complex thereof, exemplary druggable regions including binding pockets and sites, enzymatic active sites, interfaces between domains of a polypeptide or complex, surface grooves or contours or surfaces of a polypeptide or complex which are capable of participating in interactions with another molecule. In certain instances, the interacting molecule is another polypeptide, which may be naturally-occurring. In other instances, the druggable region is on the surface of the molecule.

Druggable regions may be described and characterized in a number of ways. For example, a druggable region may be characterized by some or all of the amino acids that make up the region, or the backbone atoms thereof, or the side chain atoms thereof (optionally with or without the C$\alpha$ atoms). Alternatively, in certain instances, the volume of a druggable region corresponds to that of a carbon based molecule of at least about 200 amu and often up to about 800 amu. In other instances, it will be appreciated that the volume of such region may correspond to a molecule of at least about 600 amu and often up to about 1600 amu or more.

Alternatively, a druggable region may be characterized by comparison to other regions on the same or other molecules. For example, the term "affinity region" refers to a druggable region on a molecule (such as a polypeptide of the invention) that is present in several other molecules, in so much as the structures of the same affinity regions are sufficiently the same so that they are expected to bind the same or related structural analogs. An example of an affinity region is an ATP-binding site of a protein kinase that is found in several protein kinases (whether or not of the same origin). The term "selectivity region" refers to a druggable region of a molecule that may not be found on other molecules, in so much as the structures of different selectivity regions are sufficiently different so that they are not expected to bind the same or related structural analogs. An exemplary selectivity region is a catalytic domain of a protein kinase that exhibits specificity for one substrate. In certain instances, a single modulator may bind to the same affinity region across a number of proteins that have a substantially similar biological function, whereas the same modulator may bind to only one selectivity region of one of those proteins.

Continuing with examples of different druggable regions, the term "undesired region" refers to a druggable region of a molecule that upon interacting with another molecule results in an undesirable affect. For example, a binding site that oxidizes the interacting molecule (such as P-450 activity) and thereby results in increased toxicity for the oxidized molecule may be deemed a "undesired region". Other examples of potential undesired regions includes regions that upon interaction with a drug decrease the membrane permeability of the drug, increase the excretion of the drug, or increase the blood brain transport of the drug. It may be the case that, in certain circumstances, an undesired region will no longer be deemed an undesired region because the affect of the region will be favorable, e.g., a drug intended to treat a brain condition would benefit from interacting with a region that resulted in increased blood brain transport, whereas the same region could be deemed undesirable for drugs that were not intended to be delivered to the brain.

When used in reference to a druggable region, the "selectivity" or "specificity" of a molecule such as a modulator to a druggable region may be used to describe the binding between the molecule and a druggable region. For example, the selectivity of a modulator with respect to a druggable region may be expressed by comparison to another modulator, using the respective values of Kd (i.e., the dissociation constants for each modulator-druggable region complex) or, in cases where a biological effect is observed below the Kd, the ratio of the respective EC50's (i.e., the concentrations that produce 50% of the maximum response for the modulator interacting with each druggable region).

A "fusion protein" or "fusion polypeptide" refers to a chimeric protein as that term is known in the art and may be constructed using methods known in the art. In many examples of fusion proteins, there are two different polypeptide sequences, and in certain cases, there may be more. The sequences may be linked in frame. A fusion protein may include a domain which is found (albeit in a different protein) in an organism which also expresses the first protein, or it may be an "interspecies", "intergenic", etc. fusion expressed by different kinds of organisms. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. The fusion polypeptides may be fused to the N-terminus, the C-terminus, or the N- and C-terminus of the first polypeptide. Exemplary fusion proteins include polypeptides comprising a glutathione S-transferase tag (GST-tag), histidine tag (His-tag), an immunoglobulin domain or an immunoglobulin binding domain.

The term "gene" refers to a nucleic acid comprising an open reading frame encoding a polypeptide having exon sequences and optionally intron sequences. The term "intron" refers to a DNA sequence present in a given gene which is not translated into protein and is generally found between exons.

The term "having substantially similar biological activity", when used in reference to two polypeptides, refers to a biological activity of a first polypeptide which is substantially similar to at least one of the biological activities of a second polypeptide. A substantially similar biological activity means that the polypeptides carry out a similar function, e.g., a similar enzymatic reaction or a similar physiological process, etc. For example, two homologous proteins may have a substantially similar biological activity if they are involved in a similar enzymatic reaction, e.g., they are both kinases which catalyze phosphorylation of a substrate polypeptide, however, they may phosphorylate different regions on the same protein substrate or different substrate proteins altogether. Alternatively, two homologous proteins may also have a substantially similar biological activity if they are both involved in a similar physiological process, e.g., transcription. For example, two proteins may be transcription factors, however, they may bind to different DNA sequences or bind to different polypeptide interactors. Substantially similar biological activities may also be associated with proteins carrying out a similar structural role, for example, two membrane proteins.

The term "isolated polypeptide" refers to a polypeptide, in certain embodiments prepared from recombinant DNA or RNA, or of synthetic origin, or some combination thereof, which (1) is not associated with proteins that it is normally found with in nature, (2) is isolated from the cell in which it normally occurs, (3) is isolated free of other proteins from the same cellular source, e.g. free of other *F. tularensis* proteins, (4) is expressed by a cell from a different species, or (5) does not occur in nature.

The term "isolated nucleic acid" refers to a polynucleotide of genomic, cDNA, or synthetic origin or some combination there of, which (1) is not associated with the cell in which the "isolated nucleic acid" is found in nature, or (2) is operably linked to a polynucleotide to which it is not linked in nature.

The terms "label" or "labeled" refer to incorporation or attachment, optionally covalently or non-covalently, of a detectable marker into a molecule, such as a polypeptide. Various methods of labeling polypeptides are known in the art and may be used. Examples of labels for polypeptides include, but are not limited to, the following: radioisotopes, fluorescent labels, heavy atoms, enzymatic labels or reporter genes, chemiluminescent groups, biotinyl groups, predetermined polypeptide epitopes recognized by a secondary reporter (e.g., leucine zipper pair sequences, binding sites for secondary antibodies, metal binding domains, epitope tags). Examples and use of such labels are described in more detail below. In some embodiments, labels are attached by spacer arms of various lengths to reduce potential steric hindrance.

The term "mammal" is known in the art, and exemplary mammals include humans, primates, bovines, porcines, canines, felines, and rodents (e.g., mice and rats).

The term "modulation", when used in reference to a functional property or biological activity or process (e.g., enzyme activity or receptor binding), refers to the capacity to either up regulate (e.g., activate or stimulate), down regulate (e.g., inhibit or suppress) or otherwise change a quality of such property, activity or process. In certain instances, such regulation may be contingent on the occurrence of a specific event, such as activation of a signal transduction pathway, and/or may be manifest only in particular cell types.

The term "modulator" refers to a polypeptide, nucleic acid, macromolecule, complex, molecule, small molecule, compound, species or the like (naturally-occurring or non-naturally-occurring), or an extract made from biological materials such as bacteria, plants, fungi, or animal cells or tissues, that may be capable of causing modulation. Modulators may be evaluated for potential activity as inhibitors or activators (directly or indirectly) of a functional property, biological activity or process, or combination of them, (e.g., agonist, partial antagonist, partial agonist, inverse agonist, antagonist, antimicrobial agents, inhibitors of microbial infection or proliferation, and the like) by inclusion in assays. In such assays, many modulators may be screened at one time. The activity of a modulator may be known, unknown or partially known.

The term "motif" refers to an amino acid sequence that is commonly found in a protein of a particular structure or function. Typically, a consensus sequence is defined to represent a particular motif. The consensus sequence need not be strictly defined and may contain positions of variability, degeneracy, variability of length, etc. The consensus sequence may be used to search a database to identify other proteins that may have a similar structure or function due to the presence of the motif in its amino acid sequence. For example, on-line databases may be searched with a consensus sequence in order to identify other proteins containing a particular motif. Various search algorithms and/or programs may be used, including FASTA, BLAST or ENTREZ. FASTA and BLAST are available as a part of the GCG sequence analysis package (University of Wisconsin, Madison, Wis.). ENTREZ is available through the National Center for Biotechnology Information, National Library of Medicine, National Institutes of Health, Bethesda, Md.

The term "naturally-occurring", as applied to an object, refers to the fact that an object may be found in nature. For example, a polypeptide or polynucleotide sequence that is present in an organism (including bacteria) that may be isolated from a source in nature and which has not been intentionally modified by man in the laboratory is naturally-occurring.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "nucleic acid of the invention" refers to a nucleic acid encoding a polypeptide of the invention, e.g., a nucleic acid comprising a sequence consisting of, or consisting essentially of, the polynucleotide sequence set forth in SEQ ID NO: 1. A nucleic acid of the invention may comprise all, or a portion of: the nucleotide sequence of SEQ ID NO: 1; a nucleotide sequence at least 60%, 70%, 80%, 90%, 95%, 96%, 97%, 98% or 99% identical to SEQ ID NO: 1; a nucleotide sequence that hybridizes under stringent conditions to SEQ ID NO: 1; nucleotide sequences encoding polypeptides that are functionally equivalent to polypeptides of the invention; nucleotide sequences encoding polypeptides at least about 60%, 70%, 80%, 85%, 90%, 95%, 98%, 99% homologous or identical with an amino acid sequence of SEQ ID NO: 2; nucleotide sequences encoding polypeptides having an activity of a polypeptide of the invention and having at least about 60%, 70%, 80%, 85%, 90%, 95%, 98%, 99% or more homology or identity with SEQ ID NO: 2; nucleotide sequences that differ by 1 to about 2, 3, 5, 7, 10, 15, 20, 30, 50, 75 or more nucleotide substitutions, additions or deletions, such as allelic variants, of SEQ ID NO: 1; nucleic acids derived from and evolutionarily related to SEQ ID NO: 1; and complements of, and nucleotide sequences resulting from the degeneracy of the genetic code, for all of the foregoing and other nucleic acids of the invention. Nucleic acids of the invention also include homologs, e.g., orthologs and paralogs, of SEQ ID NO: 1 and also variants of SEQ ID NO: 1 which have been codon optimized for expression in a particular organism (e.g., host cell).

The term "operably linked", when describing the relationship between two nucleic acid regions, refers to a juxtaposition wherein the regions are in a relationship permitting them to function in their intended manner. For example, a control sequence "operably linked" to a coding sequence is ligated in such a way that expression of the coding sequence is achieved under conditions compatible with the control sequences, such as when the appropriate molecules (e.g., inducers and polymerases) are bound to the control or regulatory sequence(s).

The term "phenotype" refers to the entire physical, biochemical, and physiological makeup of a cell, e.g., having any one trait or any group of traits.

The term "polypeptide", and the terms "protein" and "peptide" which are used interchangeably herein, refers to a polymer of amino acids. Exemplary polypeptides include gene products, naturally-occurring proteins, homologs, orthologs, paralogs, fragments, and other equivalents, variants and analogs of the foregoing.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus or carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. A fragment can retain one or more of the biological activities of the reference polypeptide. In certain embodiments, a fragment may comprise a druggable region, and optionally additional amino acids on one or both sides of the druggable region, which additional amino acids may number from 5, 10, 15, 20, 30, 40, 50, or up to 100 or more residues. Further, fragments can include a sub-fragment of a specific region, which sub-fragment retains a function of the region from which it is derived. In another embodiment, a fragment may have immunogenic properties.

The term "polypeptide of the invention" refers to a polypeptide comprising the amino acid sequence set forth in SEQ ID NO: 2, or an equivalent or fragment thereof, e.g., a polypeptide comprising a sequence consisting of, or consisting essentially of, the amino acid sequence set forth in SEQ ID NO: 2. Polypeptides of the invention include polypeptides comprising (i) all or a portion of the amino acid sequence set forth in SEQ ID NO: 2; (ii) the amino acid sequence set forth in SEQ ID NO: 2 with 1 to about 2, 3, 5, 7, 10, 15, 20, 30, 50, 75 or more conservative amino acid substitutions; (iii) an amino acid sequence that is at least 60%, 70%, 80%, 90%, 95%, 96%, 97%, 98%, or 99% identical to SEQ ID NO: 2; (iii) an amino acid sequence that is at least 40%, 45%, 50%, 55%, 60%, 65%, 70%, 75%, 80%, 85%, 90%, 95%, or 98% identical to SEQ ID NO: 2, wherein said amino acid sequence includes one or more of the following: SEQ ID NOs: 12, 13, 17, 18, 19, 20, 21, 22, 23, 24, 28, 29, or 30; and functional fragments thereof. Polypeptides of the invention also include homologs, e.g., orthologs and paralogs, of SEQ ID NO: 2.

The term "purified" refers to an object species that is the predominant species present (i.e., on a molar basis it is more abundant than any other individual species in the composition). A "purified fraction" is a composition wherein the object species comprises at least about 50 percent (on a molar basis) of all species present. In making the determination of the purity of a species in solution or dispersion, the solvent or matrix in which the species is dissolved or dispersed is usually not included in such determination; instead, only the species (including the one of interest) dissolved or dispersed are taken into account. Generally, a purified composition will have one species that comprises more than about 80 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification in light of the teachings herein. Purity of a polypeptide may be determined by a number of methods known to those of skill in the art, including for example, amino-terminal amino acid sequence analysis, gel electrophoresis, mass-spectrometry analysis and the methods described in the Exemplification section herein.

The terms "recombinant protein" or "recombinant polypeptide" refer to a polypeptide which is produced by recombinant DNA techniques. An example of such techniques includes the case when DNA encoding the expressed protein is inserted into a suitable expression vector which is in turn used to transform a host cell to produce the protein or polypeptide encoded by the DNA.

A "reference sequence" is a defined sequence used as a basis for a sequence comparison; a reference sequence may be a subset of a larger sequence, for example, as a segment of a full-length protein given in a sequence listing such as SEQ ID NO: 2, or may comprise a complete protein sequence. Generally, a reference sequence is at least 200, 300 or 400 nucleotides in length, frequently at least 600 nucleotides in length, and often at least 800 nucleotides in length (or the protein equivalent if it is shorter or longer in length). Because two proteins may each (1) comprise a sequence (i.e., a portion of the complete protein sequence) that is similar between the two proteins, and (2) may further comprise a sequence that is divergent between the two proteins, sequence comparisons between two (or more) proteins are typically performed by comparing sequences of the two proteins over a "comparison window" to identify and compare local regions of sequence similarity.

The term "regulatory sequence" is a generic term used throughout the specification to refer to polynucleotide sequences, such as initiation signals, enhancers, regulators and promoters, that are necessary or desirable to affect the expression of coding and non-coding sequences to which they are operably linked. Exemplary regulatory sequences are described in Goeddel; *Gene Expression Technology: Methods in Enzymology*, Academic Press, San Diego, Calif. (1990), and include, for example, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. The nature and use of such control sequences may differ depending upon the host organism. In prokaryotes, such regulatory sequences generally include promoter, ribosomal binding site, and transcription termination sequences. The term "regulatory sequence" is intended to include, at a minimum, components whose presence may influence expression, and may also include additional components whose presence is advantageous, for example, leader sequences and fusion partner sequences. In certain embodiments, transcription of a polynucleotide sequence is under the control of a promoter sequence (or other regulatory sequence) which controls the expression of the polynucleotide in a cell-type in which expression is intended. It will also be understood that the polynucleotide can be under the control of regulatory sequences which are the same or different from those sequences which control expression of the naturally-occurring form of the polynucleotide.

The term "reporter gene" refers to a nucleic acid comprising a nucleotide sequence encoding a protein that is readily detectable either by its presence or activity, including, but not limited to, luciferase, fluorescent protein (e.g., green fluorescent protein), chloramphenicol acetyl transferase, β-galactosidase, secreted placental alkaline phosphatase, β-lactamase, human growth hormone, and other secreted enzyme reporters. Generally, a reporter gene encodes a polypeptide not otherwise produced by the host cell, which is detectable by analysis of the cell(s), e.g., by the direct fluorometric, radioisotopic or spectrophotometric analysis of the cell(s) and preferably without the need to kill the cells for signal analysis. In certain instances, a reporter gene encodes an enzyme, which produces a change in fluorometric properties of the host cell, which is detectable by qualitative, quantitative or semiquantitative function or transcriptional activation. Exemplary enzymes include esterases, β-lactamase, phosphatases, peroxidases, proteases (tissue plasminogen activator or urokinase) and other enzymes whose function may be detected by appropriate chromogenic or fluorogenic substrates known to those skilled in the art or developed in the future.

The term "sequence homology" refers to the proportion of base matches between two nucleic acid sequences or the proportion of amino acid matches between two amino acid sequences. When sequence homology is expressed as a percentage, e.g., 50%, the percentage denotes the proportion of matches over the length of sequence from a desired sequence (e.g., SEQ. ID NO: 1) that is compared to some other sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino acid-by-amino acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The term "small molecule" refers to a compound, which has a molecular weight of less than about 5 kD, less than about 2.5 kD, less than about 1.5 kD, or less than about 0.9 kD. Small molecules may be, for example, nucleic acids, peptides, polypeptides, peptide nucleic acids, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention. The term "small organic molecule" refers to a small molecule that is often identified as being an organic or medicinal compound, and does not include molecules that are exclusively nucleic acids, peptides or polypeptides.

The term "soluble" as used herein with reference to a polypeptide of the invention or other protein, means that upon expression in cell culture, at least some portion of the polypeptide or protein expressed remains in the cytoplasmic fraction of the cell and does not fractionate with the cellular debris upon lysis and centrifugation of the lysate. Solubility of a polypeptide may be increased by a variety of art recognized methods, including fusion to a heterologous amino acid sequence, deletion of amino acid residues, amino acid substitution (e.g., enriching the sequence with amino acid residues having hydrophilic side chains), and chemical modification (e.g., addition of hydrophilic groups). The solubility of polypeptides may be measured using a variety of art recognized techniques, including, dynamic light scattering to determine aggregation state, UV absorption, centrifugation to separate aggregated from non-aggregated material, and SDS gel electrophoresis (e.g., the amount of protein in the soluble fraction is compared to the amount of protein in the soluble and insoluble fractions combined). When expressed in a host cell, the polypeptides of the invention may be at least about 1%, 2%, 5%, 10%, 20%, 30%, 40%, 50%, 60%, 70%, 80%, 90% or more soluble, e.g., at least about 1%, 2%, 5%, 10%, 20%, 30%, 40%, 50%, 60%, 70%, 80%, 90% or more of the total amount of protein expressed in the cell is found in the cytoplasmic fraction. In certain embodiments, a one liter culture of cells expressing a polypeptide of the invention will produce at least about 0.1, 0.2, 0.5, 1, 2, 5, 10, 20, 30, 40, 50 milligrams or more of soluble protein. In an exemplary embodiment, a polypeptide of the invention is at least about 10% soluble and will produce at least about 1 milligram of protein from a one liter cell culture.

The term "specifically hybridizes" refers to detectable and specific nucleic acid binding. Polynucleotides, oligonucleotides and nucleic acids of the invention selectively hybridize to nucleic acid strands under hybridization and wash conditions that minimize appreciable amounts of detectable binding to nonspecific nucleic acids. Stringent conditions may be used to achieve selective hybridization conditions as known in the art and discussed herein. Generally, the nucleic acid sequence homology between the polynucleotides, oligonucleotides, and nucleic acids of the invention and a nucleic acid sequence of interest will be at least 30%, 40%, 50%, 60%, 70%, 80%, 85%, 90%, 95%, 98%, 99%, or more. In certain instances, hybridization and washing conditions are performed under stringent conditions according to conventional hybridization procedures and as described further herein.

The terms "stringent conditions" or "stringent hybridization conditions" refer to conditions which promote specific hydribization between two complementary polynucleotide strands so as to form a duplex. Stringent conditions may be selected to be about 5° C. lower than the thermal melting point (Tm) for a given polynucleotide duplex at a defined ionic strength and pH. The length of the complementary polynucleotide strands and their GC content will determine the Tm of the duplex, and thus the hybridization conditions necessary for obtaining a desired specificity of hybridization. The Tm is the temperature (under defined ionic strength and pH) at which 50% of the a polynucleotide sequence hybridizes to a perfectly matched complementary strand. In certain cases it may be desirable to increase the stringency of the hybridization conditions to be about equal to the Tm for a particular duplex.

A variety of techniques for estimating the Tm are available. Typically, G-C base pairs in a duplex are estimated to contribute about 3° C. to the Tm, while A-T base pairs are estimated to contribute about 2° C., up to a theoretical maximum of about 80-100° C. However, more sophisticated models of Tm are available in which G-C stacking interactions, solvent effects, the desired assay temperature and the like are taken into account. For example, probes can be designed to have a dissociation temperature (Td) of approximately 60° C., using the formula: $Td=(((((3 \times \#GC)+(2 \times \#AT)) \times 37)-562)/\#bp)-5$; where #GC, #AT, and #bp are the number of guanine-cytosine base pairs, the number of adenine-thymine base pairs, and the number of total base pairs, respectively, involved in the formation of the duplex.

Hybridization may be carried out in 5×SSC, 4×SSC, 3×SSC, 2×SSC, 1×SSC or 0.2×SSC for at least about 1 hour, 2 hours, 5 hours, 12 hours, or 24 hours. The temperature of the hybridization may be increased to adjust the stringency of the reaction, for example, from about 25° C. (room temperature), to about 45° C., 50° C., 55° C., 60° C., or 65° C. The hybridization reaction may also include another agent affecting the stringency, for example, hybridization conducted in the presence of 50% formamide increases the stringency of hybridization at a defined temperature.

The hybridization reaction may be followed by a single wash step, or two or more wash steps, which may be at the same or a different salinity and temperature. For example, the temperature of the wash may be increased to adjust the stringency from about 25° C. (room temperature), to about 45° C., 50° C., 55° C., 60° C., 65° C., or higher. The wash step may be conducted in the presence of a detergent, e.g., 0.1 or 0.2% SDS. For example, hybridization may be followed by two wash steps at 65° C. each for about 20 minutes in 2×SSC, 0.1% SDS, and optionally two additional wash steps at 65° C. each for about 20 minutes in 0.2×SSC, 0.1% SDS.

Exemplary stringent hybridization conditions include overnight hybridization at 65° C. in a solution comprising, or consisting of, 50% formamide, 10×Denhardt (0.2% Ficoll, 0.2% Polyvinylpyrrolidone, 0.2% bovine serum albumin) and 200 µg/mL of denatured carrier DNA, e.g., sheared salmon sperm DNA, followed by two wash steps at 65° C. each for about 20 minutes in 2×SSC, 0.1% SDS, and two wash steps at 65° C. each for about 20 minutes in 0.2×SSC, 0.1% SDS.

Hybridization may consist of hybridizing two nucleic acids in solution, or a nucleic acid in solution to a nucleic acid attached to a solid support, e.g., a filter. When one nucleic acid is on a solid support, a prehybridization step may be conducted prior to hybridization. Prehybridization may be carried out for at least about 1 hour, 3 hours or 10 hours in the same solution and at the same temperature as the hybridization solution (without the complementary polynucleotide strand).

Appropriate stringency conditions are known to those skilled in the art or may be determined experimentally by the skilled artisan. See, for example, Current Protocols in Molecular Biology, John Wiley & Sons, N.Y. (1989), 6.3.1-12.3.6; Sambrook et al., 1989, Molecular Cloning, A Laboratory Manual, Cold Spring Harbor Press, N.Y; S. Agrawal (ed.) Methods in Molecular Biology, volume 20; Tijssen (1993) Laboratory Techniques in biochemistry and molecular biology-hybridization with nucleic acid probes, e.g., part I chapter 2 "Overview of principles of hybridization and the strategy of nucleic acid probe assays", Elsevier, New York; and Tibanyenda, N. et al., Eur. J. Biochem. 139:19 (1984) and Ebel, S. et al., Biochem. 31:12083 (1992).

As applied to proteins, the term "substantial identity" means that two protein sequences, when optimally aligned, such as by the programs GAP or BESTFIT using default gap weights, typically share at least about 70 percent sequence identity, alternatively at least about 80, 85, 90, 95 percent sequence identity or more. In certain instances, residue positions that are not identical differ by conservative amino acid substitutions, which are described above.

The term "structural motif", when used in reference to a polypeptide, refers to a polypeptide that, although it may have different amino acid sequences, may result in a similar structure, wherein by structure is meant that the motif forms generally the same tertiary structure, or that certain amino acid residues within the motif, or alternatively their backbone or side chains (which may or may not include the Cα atoms of the side chains) are positioned in a like relationship with respect to one another in the motif.

The term "test compound" refers to a molecule to be tested by one or more screening method(s) as a putative modulator of a polypeptide of the invention or other biological entity or process. A test compound is usually not known to bind to a target of interest. The term "control test compound" refers to a compound known to bind to the target (e.g., a known agonist, antagonist, partial agonist or inverse agonist). The term "test compound" does not include a chemical added as a control condition that alters the function of the target to determine signal specificity in an assay. Such control chemicals or conditions include chemicals that 1) nonspecifically or substantially disrupt protein structure (e.g., denaturing agents (e.g., urea or guanidinium), chaotropic agents, sulfhydryl reagents (e.g., dithiothreitol and β-mercaptoethanol), and proteases), 2) generally inhibit cell metabolism (e.g., mitochondrial uncouplers) and 3) non-specifically disrupt electrostatic or hydrophobic interactions of a protein (e.g., high salt concentrations, or detergents at concentrations sufficient to non-specifically disrupt hydrophobic interactions). Further, the term "test compound" also does not include compounds known to be unsuitable for a therapeutic use for a particular indication due to toxicity of the subject. In certain embodiments, various predetermined concentrations of test compounds are used for screening such as 0.01 μM, 0.1 μM, 1.0 μM, and 10.0 μM. Examples of test compounds include, but are not limited to, peptides, nucleic acids, carbohydrates, and small molecules. The term "novel test compound" refers to a test compound that is not in existence as of the filing date of this application. In certain assays using novel test compounds, the novel test compounds comprise at least about 50%, 75%, 85%, 90%, 95% or more of the test compounds used in the assay or in any particular trial of the assay.

The term "therapeutically effective amount" refers to that amount of a modulator, drug or other molecule which is sufficient to effect treatment when administered to a subject in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "transfection" means the introduction of a nucleic acid, e.g., an expression vector, into a recipient cell, which in certain instances involves nucleic acid-mediated gene transfer. The term "transformation" refers to a process in which a cell's genotype is changed as a result of the cellular uptake of exogenous nucleic acid. For example, a transformed cell may express a recombinant form of a polypeptide of the invention or antisense expression may occur from the transferred gene so that the expression of a naturally-occurring form of the gene is disrupted.

The term "transgene" means a nucleic acid sequence, which is partly or entirely heterologous to a transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene may include one or more regulatory sequences and any other nucleic acids, such as introns, that may be necessary for optimal expression.

The term "transgenic animal" refers to any animal, for example, a mouse, rat or other non-human mammal, a bird or an amphibian, in which one or more of the cells of the animal contain heterologous nucleic acid introduced by way of human intervention, such as by transgenic techniques well known in the art. The nucleic acid is introduced into the cell, directly or indirectly, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of a protein. However, transgenic animals in which the recombinant gene is silent are also contemplated.

The term "vector" refers to a nucleic acid capable of transporting another nucleic acid to which it has been linked. One type of vector which may be used in accord with the invention is an episome, i.e., a nucleic acid capable of extra-chromosomal replication. Other vectors include those capable of autonomous replication and expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer to circular double stranded DNA molecules which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

2. Polypeptides of the Invention

A variety of embodiments including soluble, purified and/or isolated forms of the polypeptides of the invention are provided. Milligram quantities of an exemplary polypeptide of the invention, SEQ ID NO: 2 (optionally with a tag, and optionally labeled), have been isolated in a highly purified form. Expressing and purifying polypeptides of the invention in quantities that equal or exceed the quantity of polypeptide(s) of the invention expressed and purified as provided in the Exemplification section below (or smaller amount(s) thereof, such as 25%, 33%, 50% or 75% of the amount(s) so expressed and/or purified) are provided.

In one aspect, an isolated polypeptide is provided comprising (a) the amino acid sequence set forth in SEQ ID NO: 2, (b) the amino acid sequence set forth in SEQ ID NO: 2 with 1 to about 20 conservative amino acid substitutions, deletions or additions, (c) an amino acid sequence that is at least 90% identical to SEQ ID NO: 2 or (d) a functional fragment of a polypeptide having an amino acid sequence set forth in (a), (b) or (c). In another aspect, a composition comprising such an isolated polypeptide and less than about 10%, or alternatively 5%, or alternatively 1%, contaminating biological macromolecules or polypeptides is provided.

In certain embodiments, a polypeptide of the invention is a fusion protein containing a domain which increases its solubility and/or facilitates its purification, identification, detection, and/or structural characterization. Exemplary domains, include, for example, glutathione S-transferase (GST), protein A, protein G, calmodulin-binding peptide, thioredoxin, maltose binding protein, HA, myc, poly arginine, poly His, poly His-Asp or FLAG fusion proteins and tags. Additional exemplary domains include domains that alter protein localization in vivo, such as signal peptides, type III secretion system-targeting peptides, transcytosis domains, nuclear localization signals, etc. In various embodiments, a polypeptide of the invention may comprise one or more heterologous fusions. Polypeptides may contain multiple copies of the same fusion domain or may contain fusions to two or more different domains. The fusions may occur at the N-terminus of the polypeptide, at the C-terminus of the polypeptide, or at both the N- and C-terminus of the polypeptide. It is also within the scope of the invention to include linker sequences between a polypeptide of the invention and the fusion domain in order to facilitate construction of the fusion protein or to optimize protein expression or structural constraints of the fusion protein. In another embodiment, the polypeptide may be constructed so as to contain protease cleavage sites between the fusion polypeptide and polypeptide of the invention in order to remove the tag after protein expression or thereafter. Examples of suitable endoproteases, include, for example, Factor Xa and TEV proteases.

In another embodiment, a polypeptide of the invention may be modified so that its rate of traversing the cellular membrane is increased. For example, the polypeptide may be fused to a second peptide which promotes "transcytosis," e.g., uptake of the peptide by cells. The peptide may be a portion of the HIV transactivator (TAT) protein, such as the fragment corresponding to residues 37-62 or 48-60 of TAT, portions which have been observed to be rapidly taken up by a cell in vitro (Green and Loewenstein, (1989) Cell 55:1179-1188). Alternatively, the internalizing peptide may be derived from the *Drosophila antennapedia* protein, or homologs thereof. The 60 amino acid long homeodomain of the homeo-protein antennapedia has been demonstrated to translocate through biological membranes and can facilitate the translocation of heterologous polypeptides to which it is coupled. Thus, polypeptides may be fused to a peptide consisting of about amino acids 42-58 of *Drosophila antennapedia* or shorter fragments for transcytosis (Derossi et al. (1996) *J Biol Chem* 271:18188-18193; Derossi et al. (1994) *JBiol Chem* 269: 10444-10450; and Perez et al. (1992) *J Cell Sci* 102:717-722). The transcytosis polypeptide may also be a non-naturally-occurring membrane-translocating sequence (MTS), such as the peptide sequences disclosed in U.S. Pat. No. 6,248,558.

In another embodiment, a polypeptide of the invention is labeled with an isotopic label to facilitate its detection and or structural characterization using nuclear magnetic resonance or another applicable technique. Exemplary isotopic labels include radioisotopic labels such as, for example, potassium-40 ($^{40}$K), carbon-14 ($^{14}$C), tritium ($^{3}$H), sulphur-35 ($^{35}$S), phosphorus-32 ($^{32}$P), technetium-99m ($^{99m}$Tc), thallium-201 ($^{201}$Tl), gallium-67 ($^{67}$Ga), indium-111 ($^{111}$In), iodine-123 ($^{123}$I), iodine-131 ($^{131}$I), yttrium-90 ($^{90}$Y), samarium-153 ($^{153}$Sm), rhenium-186 ($^{186}$Re), rhenium-188 ($^{188}$Re), dysprosium-165 ($^{165}$Dy) and holmium-166 ($^{166}$Ho). The isotopic label may also be an atom with non zero nuclear spin, including, for example, hydrogen-1 ($^{1}$H), hydrogen-2 ($^{2}$H), hydrogen-3 ($^{3}$H), phosphorous-31 ($^{31}$P), sodium-23 ($^{23}$Na), nitrogen-14 ($^{14}$N), nitrogen-15 ($^{15}$N), carbon-13 ($^{13}$C) and fluorine-19 ($^{19}$F). In certain embodiments, the polypeptide is uniformly labeled with an isotopic label, for example, wherein at least 50%, 70%, 80%, 90%, 95%, or 98% of the possible labels in the polypeptide are labeled, e.g., wherein at least 50%, 70%, 80%, 90%, 95%, or 98% of the nitrogen atoms in the polypeptide are $^{15}$N, and/or wherein at least 50%, 70%, 80%, 90%, 95%, or 98% of the carbon atoms in the polypeptide are $^{13}$C, and/or wherein at least 50%, 70%, 80%, 90%, 95%, or 98% of the hydrogen atoms in the polypeptide are $^{2}$H. In other embodiments, the isotopic label is located in one or more specific locations within the polypeptide, for example, the label may be specifically incorporated into one or more of the leucine residues of the polypeptide. The invention also encompasses the embodiment wherein a single polypeptide comprises two, three or more different isotopic labels, for example, the polypeptide comprises both $^{15}$N and $^{13}$C labeling.

In yet another embodiment, the polypeptides of the invention are labeled to facilitate structural characterization using x-ray crystallography or another applicable technique. Exemplary labels include heavy atom labels such as, for example, cobalt, selenium, krypton, bromine, strontium, molybdenum, ruthenium, rhodium, palladium, silver, cadmium, tin, iodine, xenon, barium, lanthanum, cerium, praseodymium, neodymium, samarium, europium, gadolinium, terbium, dysprosium, holmium, erbium, thulium, ytterbium, lutetium, tantalum, tungsten, rhenium, osmium, iridium, platinum, gold, mercury, thallium, lead, thorium and uranium. In an exemplary embodiment, the polypeptide is labeled with selenomethionine.

A variety of methods are available for preparing a polypeptide with a label, such as a radioisotopic label or heavy atom label. For example, in one such method, an expression vector comprising a nucleic acid encoding a polypeptide is introduced into a host cell, and the host cell is cultured in a cell culture medium in the presence of a source of the label, thereby generating a labeled polypeptide. As indicated above, the extent to which a polypeptide may be labeled may vary.

In still another embodiment, the polypeptides of the invention are labeled with a fluorescent label to facilitate their detection, purification, or structural characterization. In an exemplary embodiment, a polypeptide of the invention is fused to a heterologous polypeptide sequence which produces a detectable fluorescent signal, including, for example, green fluorescent protein (GFP), enhanced green fluorescent protein (EGFP), *Renilla Reniformis* green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED).

In other embodiments, polypeptides of the invention may be immobilized onto a solid surface, including, microtiter plates, slides, beads, films, etc. The polypeptides of the invention may be immobilized onto a "chip" as part of an array. An array, having a plurality of addresses, may comprise one or more polypeptides of the invention in one or more of those addresses. In one embodiment, the chip comprises one or more polypeptides of the invention as part of an array of *F. tularensis* polypeptide sequences.

In other embodiments, polypeptides of the invention may be immobilized onto a solid surface, including, plates, microtiter plates, slides, beads, particles, spheres, films, strands, precipitates, gels, sheets, tubing, containers, capillaries, pads, slices, etc. The polypeptides of the invention may be immobilized onto a "chip" as part of an array. An array, having a plurality of addresses, may comprise one or more polypeptides of the invention in one or more of those addresses. In one embodiment, the chip comprises one or more polypeptides of the invention as part of an array that contains at least some polypeptide sequences from *F. tularensis*.

In still other embodiments, polypeptide sequences of the invention may be provided in computer readable format. A database comprising the polypeptide sequences of the invention is also provided.

In other embodiments, polypeptides of the invention may be contained within a vessels useful for manipulation of the polypeptide sample. For example, the polypeptides of the invention may be contained within a microtiter plate to facilitate detection, screening or purification of the polypeptide. The polypeptides may also be contained within a syringe as a container suitable for administering the polypeptide to a subject in order to generate antibodies or as part of a vaccination regimen. The polypeptides may also be contained within an NMR tube in order to enable characterization by nuclear magnetic resonance techniques.

In still other embodiments, crystallized polypeptides of the invention and crystallized polypeptides which have been mounted for examination by x-ray crystallography are provided as described further below. In certain instances, a polypeptide of the invention in crystal form may be single crystals of various dimensions (e.g., micro-crystals) or may be an aggregate of crystalline material. In another aspect, a crystallized complex including a polypeptide of the invention and one or more of the following: a co-factor (such as a salt, metal, nucleotide, oligonucleotide or polypeptide), a modulator, or a small molecule is provided. In another aspect, a crystallized complex including a polypeptide of the invention and any other molecule or atom (such as a metal ion) that associates with the polypeptide in vivo is provided.

In certain embodiments, polypeptides of the invention may be synthesized a chemically, ribosomally in a cell free system, or ribosomally within a cell. Chemical synthesis of polypeptides of the invention may be carried out using a variety of art recognized methods, including stepwise solid phase synthesis, semi-synthesis through the conformationally-assisted re-ligation of peptide fragments, enzymatic ligation of cloned or synthetic peptide segments, and chemical ligation. Native chemical ligation employs a chemoselective reaction of two unprotected peptide segments to produce a transient thioester-linked intermediate. The transient thioester-linked intermediate then spontaneously undergoes a rearrangement to provide the full length ligation product having a native peptide bond at the ligation site. Full length ligation products are chemically identical to proteins produced by cell free synthesis. Full length ligation products may be refolded and/or oxidized, as allowed, to form native disulfide-containing protein molecules. (see e.g., U.S. Pat. Nos. 6,184,344 and 6,174,530; and T. W. Muir et al., Curr. Opin. Biotech. (1993): vol. 4, p 420; M. Miller, et al., Science (1989): vol. 246, p 1149; A. Wlodawer, et al., Science (1989): vol. 245, p 616; L. H. Huang, et al., Biochemistry (1991): vol. 30, p 7402; M. Schnlzer, et al., Int. J. Pept. Prot. Res. (1992): vol. 40, p 180-193; K. Rajarathnam, et al., Science (1994): vol. 264, p 90; R. E. Offord, "Chemical Approaches to Protein Engineering", in Protein Design and the Development of New therapeutics and Vaccines, J. B. Hook, G. Poste, Eds., (Plenum Press, New York, 1990) pp. 253-282; C. J. A. Wallace, et al., J. Biol. Chem. (1992): vol. 267, p 3852; L. Abrahmsen, et al., Biochemistry (1991): vol. 30, p 4151; T. K. Chang, et al., Proc. Natl. Acad. Sci. USA (1994) 91: 12544-12548; M. Schnlzer, et al., Science (1992): vol., 3256, p 221; and K. Akaji, et al., Chem. Pharm. Bull. (Tokyo) (1985) 33: 184).

In certain embodiments, it may be advantageous to provide naturally-occurring or experimentally-derived homologs of a polypeptide of the invention. Such homologs may function in a limited capacity as a modulator to promote or inhibit a subset of the biological activities of the naturally-occurring form of the polypeptide. Thus, specific biological effects may be elicited by treatment with a homolog of limited function, and with fewer side effects relative to treatment with agonists or antagonists which are directed to all of the biological activities of a polypeptide of the invention. For instance, antagonistic homologs may be generated which interfere with the ability of the wild-type polypeptide of the invention to associate with certain proteins, but which do not substantially interfere with the formation of complexes between the native polypeptide and other cellular proteins.

Polypeptides may be derived from the full-length polypeptides of the invention. Isolated peptidyl portions of those polypeptides may be obtained by screening polypeptides recombinantly produced from the corresponding fragment of the nucleic acid encoding such polypeptides. In addition, fragments may be chemically synthesized using techniques known in the art such as conventional Merrifield solid phase f-Moc or t-Boc chemistry. For example, proteins may be arbitrarily divided into fragments of desired length with no overlap of the fragments, or may be divided into overlapping fragments of a desired length. The fragments may be produced (recombinantly or by chemical synthesis) and tested to identify those peptidyl fragments having a desired property, for example, the capability of functioning as a modulator of the polypeptides of the invention. In an illustrative embodiment, peptidyl portions of a protein of the invention may be tested for binding activity, as well as inhibitory ability, by expression as, for example, thioredoxin fusion proteins, each of which contains a discrete fragment of a protein of the invention (see, for example, U.S. Pat. Nos. 5,270,181 and 5,292,646; and PCT publication WO94/02502).

In another embodiment, truncated polypeptides may be prepared. Truncated polypeptides have from 1 to 20 or more amino acid residues removed from either or both the N- and C-termini. Such truncated polypeptides may prove more amenable to expression, purification or characterization than the full-length polypeptide. For example, truncated polypeptides may prove more amenable than the full-length polypeptide to crystallization, to yielding high quality diffracting crystals or to yielding an HSQC spectrum with high intensity peaks and minimally overlapping peaks. In addition, the use of truncated polypeptides may also identify stable and active domains of the full-length polypeptide that may be more amenable to characterization.

It is also possible to modify the structure of the polypeptides of the invention for such purposes as enhancing therapeutic or prophylactic efficacy, or stability (e.g., ex vivo shelf life, resistance to proteolytic degradation in vivo, etc.). Such modified polypeptides, when designed to retain at least one activity of the naturally-occurring form of the protein, are considered "functional equivalents" of the polypeptides described in more detail herein. Such modified polypeptides may be produced, for instance, by amino acid substitution, deletion, or addition, which substitutions may consist in whole or part by conservative amino acid substitutions.

For instance, it is reasonable to expect that an isolated conservative amino acid substitution, such as replacement of a leucine with an isoleucine or valine, an aspartate with a glutamate, a threonine with a serine, will not have a major affect on the biological activity of the resulting molecule. Whether a change in the amino acid sequence of a polypeptide results in a functional homolog may be readily determined by assessing the ability of the variant polypeptide to produce a response similar to that of the wild-type protein. Polypeptides in which more than one replacement has taken place may readily be tested in the same manner.

Methods of generating sets of combinatorial mutants of polypeptides of the invention are provided, as well as truncation mutants, and is especially useful for identifying potential variant sequences (e.g. homologs). The purpose of screening such combinatorial libraries is to generate, for example, homologs which may modulate the activity of a polypeptide of the invention, or alternatively, which possess novel activities altogether. Combinatorially-derived homologs may be generated which have a selective potency relative to a naturally-occurring protein. Such homologs may be used in the development of therapeutics.

Likewise, mutagenesis may give rise to homologs which have intracellular half-lives dramatically different than the corresponding wild-type protein. For example, the altered protein may be rendered either more stable or less stable to proteolytic degradation or other cellular process which result in destruction of, or otherwise inactivation of the protein. Such homologs, and the genes which encode them, may be utilized to alter protein expression by modulating the half-life of the protein. As above, such proteins may be used for the development of therapeutics or treatment.

In similar fashion, protein homologs may be generated by the present combinatorial approach to act as antagonists, in that they are able to interfere with the activity of the corresponding wild-type protein.

In a representative embodiment of this method, the amino acid sequences for a population of protein homologs are aligned, preferably to promote the highest homology possible. Such a population of variants may include, for example, homologs from one or more species, or homologs from the same species but which differ due to mutation. Amino acids which appear at each position of the aligned sequences are selected to create a degenerate set of combinatorial sequences. In certain embodiments, the combinatorial library is produced by way of a degenerate library of genes encoding a library of polypeptides which each include at least a portion of potential protein sequences. For instance, a mixture of synthetic oligonucleotides may be enzymatically ligated into gene sequences such that the degenerate set of potential nucleotide sequences are expressible as individual polypeptides, or alternatively, as a set of larger fusion proteins (e.g. for phage display).

There are many ways by which the library of potential homologs may be generated from a degenerate oligonucleotide sequence. Chemical synthesis of a degenerate gene sequence may be carried out in an automatic DNA synthesizer, and the synthetic genes may then be ligated into an appropriate vector for expression. One purpose of a degenerate set of genes is to provide, in one mixture, all of the sequences encoding the desired set of potential protein sequences. The synthesis of degenerate oligonucleotides is well known in the art (see for example, Narang, S A (1983) *Tetrahedron* 39:3; Itakura et al., (1981) *Recombinant DNA, Proc.* 3rd Cleveland Sympos. Macromolecules, ed. AG Walton, Amsterdam: Elsevier pp. 273-289; Itakura et al., (1984) *Annu. Rev. Biochem.* 53:323; Itakura et al., (1984) *Science* 198:1056; Ike et al., (1983) *Nucleic Acid Res.* 11:477). Such techniques have been employed in the directed evolution of other proteins (see, for example, Scott et al., (1990) *Science* 249:386-390; Roberts et al., (1992) *PNAS USA* 89:2429-2433; Devlin et al., (1990) *Science* 249: 404-406; Cwirla et al., (1990) *PNAS USA* 87: 6378-6382; as well as U.S. Pat. Nos. 5,223,409, 5,198,346, and 5,096,815).

Alternatively, other forms of mutagenesis may be utilized to generate a combinatorial library. For example, protein homologs (both agonist and antagonist forms) may be generated and isolated from a library by screening using, for example, alanine scanning mutagenesis and the like (Ruf et al., (1994) *Biochemistry* 33:1565-1572; Wang et al., (1994) *J. Biol. Chem.* 269:3095-3099; Balint et al., (1993) *Gene* 137: 109-118; Grodberg et al., (1993) *Eur. J. Biochem.* 218:597-601; Nagashima et al., (1993) *J. Biol. Chem.* 268:2888-2892; Lowman et al., (1991) *Biochemistry* 30:10832-10838; and Cunningham et al., (1989) *Science* 244:1081-1085), by linker scanning mutagenesis (Gustin et al., (1993) *Virology* 193: 653-660; Brown et al., (1992) *Mol. Cell. Biol.* 12:2644-2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11-19); or by random mutagenesis (Miller et al., (1992) A Short Course in Bacterial Genetics, CSHL Press, Cold Spring Harbor, N.Y.; and Greener et al., (1994) *Strategies in Mol Biol* 7:32-34). Linker scanning mutagenesis, particularly in a combinatorial setting, is an attractive method for identifying truncated forms of proteins that are bioactive.

A wide range of techniques are known in the art for screening gene products of combinatorial libraries made by point mutations and truncations, and for screening cDNA libraries for gene products having a certain property. Such techniques will be generally adaptable for rapid screening of the gene libraries generated by the combinatorial mutagenesis of protein homologs. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high throughput analysis as necessary to screen large numbers of degenerate sequences created by combinatorial mutagenesis techniques.

In an illustrative embodiment of a screening assay, candidate combinatorial gene products are displayed on the surface of a cell and the ability of particular cells or viral particles to bind to the combinatorial gene product is detected in a "panning assay". For instance, the gene library may be cloned into the gene for a surface membrane protein of a bacterial cell (Ladner et al., WO 88/06630; Fuchs et al., (1991) *Bio/Technology* 9:1370-1371; and Goward et al., (1992) *TIBS* 18:136-140), and the resulting fusion protein detected by panning, e.g. using a fluorescently labeled molecule which binds the cell surface protein, e.g. FITC-substrate, to score for potentially functional homologs. Cells may be visually inspected and separated under a fluorescence microscope, or, when the morphology of the cell permits, separated by a fluorescence-activated cell sorter. This method may be used to identify substrates or other polypeptides that can interact with a polypeptide of the invention.

In similar fashion, the gene library may be expressed as a fusion protein on the surface of a viral particle. For instance, in the filamentous phage system, foreign peptide sequences may be expressed on the surface of infectious phage, thereby conferring two benefits. First, because these phage may be applied to affinity matrices at very high concentrations, a large number of phage may be screened at one time. Second, because each infectious phage displays the combinatorial gene product on its surface, if a particular phage is recovered from an affinity matrix in low yield, the phage may be amplified by another round of infection. The group of almost identical *E. coli* filamentous phages M13, fd, and fl are most often used in phage display libraries, as either of the phage gIII or gVII coat proteins may be used to generate fusion proteins without disrupting the ultimate packaging of the viral particle (Ladner et al., PCT publication WO 90/02909; Garrard et al., PCT publication WO 92/09690; Marks et al., (1992) *J. Biol. Chem.* 267:16007-16010; Griffiths et al., (1993) *EMBO J.* 12:725-734; Clackson et al., (1991) *Nature* 352:624-628; and Barbas et al., (1992) *PNAS USA* 89:4457-4461). Other phage coat proteins may be used as appropriate.

The polypeptides of the invention may be reduced to generate mimetics, e.g. peptide or non-peptide agents, which are able to mimic binding of the authentic protein to another cellular partner. Such mutagenic techniques as described above, as well as the thioredoxin system, are also particularly useful for mapping the determinants of a protein which participates in a protein-protein interaction with another protein. To illustrate, the critical residues of a protein which are involved in molecular recognition of a substrate protein may be determined and used to generate peptidomimetics that may bind to the substrate protein. The peptidomimetic may then be used as an inhibitor of the wild-type protein by binding to the substrate and covering up the critical residues needed for interaction with the wild-type protein, thereby preventing interaction of the protein and the substrate. By employing, for example, scanning mutagenesis to map the amino acid residues of a protein which are involved in binding a substrate polypeptide, peptidomimetic compounds may be generated which mimic those residues in binding to the substrate. For instance, non-hydrolyzable peptide analogs of such residues may be generated using benzodiazepine (e.g., see Freidinger et al., in *Peptides: Chemistry and Biology*, G. R. Marshall ed., ESCOM Publisher: Leiden, Netherlands, 1988), azepine (e.g., see Huffman et al., in *Peptides: Chemistry and Biology*, G. R. Marshall ed., ESCOM Publisher: Leiden, Netherlands, 1988), substituted gamma lactam rings (Garvey et al., in *Peptides: Chemistry and Biology*, G. R. Marshall ed., ESCOM Publisher: Leiden, Netherlands, 1988), keto-methylene pseudopeptides (Ewenson et al., (1986) *J. Med. Chem.* 29:295; and Ewenson et al., in *Peptides: Structure and Function* (Proceedings of the 9th American Peptide Symposium) Pierce Chemical Co. Rockland, Ill., 1985), β-turn dipeptide cores (Nagai et al., (1985) *Tetrahedron Lett* 26:647; and Sato et al., (1986) *J Chem Soc Perkin Trans* 1:1231), and β-aminoalcohols (Gordon et al., (1985) *Biochem Biophys Res Commun* 126:419; and Dann et al., (1986) *Biochem Biophys Res Commun* 134:71).

The activity of a polypeptide of the invention may be identified and/or assayed using a variety of methods well known to the skilled artisan. For example, information about the activity of non-essential genes may be assayed by creating a null mutant strain of bacteria expressing a mutant form of, or lacking expression of, a protein of interest. The resulting phenotype of the null mutant strain may provide information about the activity of the mutated gene product. Essential genes may be studied by creating a bacterial strain with a conditional mutation in the gene of interest. The bacterial strain may be grown under permissive and non-permissive conditions and the change in phenotype under the non-permissive conditions may be used to identify and/or assay the activity of the gene product.

In an alternative embodiment, the activity of a protein may be assayed using an appropriate substrate or binding partner or other reagent suitable to test for the suspected activity. For catalytic activity, the assay is typically designed so that the enzymatic reaction produces a detectable signal. For example, mixture of a kinase with a substrate in the presence of $^{32}P$ will result in incorporation of the $^{32}P$ into the substrate. The labeled substrate may then be separated from the free $^{32}P$ and the presence and/or amount of radiolabeled substrate may be detected using a scintillation counter or a phosphorimager. Similar assays may be designed to identify and/or assay the activity of a wide variety of enzymatic activities. Based on the teachings herein, the skilled artisan would readily be able to develop an appropriate assay for a polypeptide of the invention.

In another embodiment, the activity of a polypeptide of the invention may be determined by assaying for the level of expression of RNA and/or protein molecules. Transcription levels may be determined, for example, using Northern blots, hybridization to an oligonucleotide array or by assaying for the level of a resulting protein product. Translation levels may be determined, for example, using Western blotting or by identifying a detectable signal produced by a protein product (e.g., fluorescence, luminescence, enzymatic activity, etc.). Depending on the particular situation, it may be desirable to detect the level of transcription and/or translation of a single gene or of multiple genes.

Alternatively, it may be desirable to measure the overall rate of DNA replication, transcription and/or translation in a cell. In general this may be accomplished by growing the cell in the presence of a detectable metabolite which is incorporated into the resultant DNA, RNA, or protein product. For example, the rate of DNA synthesis may be determined by growing cells in the presence of BrdU which is incorporated into the newly synthesized DNA. The amount of BrdU may then be determined histochemically using an anti-BrdU antibody.

In general, the biological activity of a polypeptide encoded by SEQ ID NO. 1, and possibly other polypeptides of the invention, is an enoyl-ACP reductase having the gene designation of FabI. In one aspect, the present invention contemplates a polypeptide having biological activity, or is a component of a protein complex having biological activity, substantially similar to or identical to a FabI polypeptide. Alternatively, the polypeptide catalyzes, or is a component of a protein complex that catalyzes, a reaction that is substantially the same type of, or is the same as, the reaction catalyzed by FabI. Other biological activities of polypeptides of the invention are described herein, or will be reasonably apparent to those skilled in the art in light of the present disclosure.

Although the overall pathway of saturated fatty acid biosynthesis is similar in all organisms, the fatty acid synthase (FAS) systems vary considerably with respect to their structural organization. Thus in Type I FAS systems, found in vertebrates and yeasts, the necessary enzymes required for fatty acid synthesis are present on one or two polypeptide chains respectively. In contrast, in Type II systems found in most bacteria and plants, each step in the pathway is catalysed by a separate mono-functional enzyme. It would therefore appear that significant selectivity of inhibition of the bacterial and mammalian enzymes is possible.

Fab I functions as an enoyl-acyl carrier protein (ACP) reductase in the final step of the four reactions involved in each cycle of bacterial fatty acid biosynthesis. The first step is catalysed by β-ketoacyl-ACP synthase, which condenses malonyl-ACP with acetyl-CoA (FabH, synthase III). In subsequent rounds malonyl-ACP is condensed with the growing-chain acyl-ACP (FabB and FabF, synthases I and II respectively).

The second step in the elongation cycle is ketoester reduction by NADPH-dependent β-ketoacyl-ACP reductase (FabG). Subsequent dehydration by β-hydroxyacyl-ACP dehydrase (either FabA or FabZ) leads to trans-2-enoyl-ACP which is in turn converted to acyl-ACP by NADH-dependent enoyl-ACP reductase (Fab I). Further rounds of this cycle, adding two carbon atoms per cycle, eventually lead to palmitoyl-ACP (16C) where upon the cycle is stopped largely due to feedback inhibition of Fab I by palmitoyl-ACP. Fab I is therefore a major biosynthetic enzyme which is also a key regulatory point in the overall synthetic pathway.

It has been shown that diazaborine antibiotics inhibit fatty acid, phospholipid and lipopolysaccharide (LPS) biosynthesis and it has also been shown that the antibacterial target of these compounds is Fab I. Inhibition of Fab I either by diazaborine or by raising the temperature in Fab I temperature sensitive mutants to non-permissive conditions is lethal, thus demonstrating that Fab I is essential to the survival of bacterial organisms. Additionally, laboratory generated point mutations in the Fab I gene lead to diazaborine resistant *E. coli*.

Bacterial FabI polypeptides have a low percent identity to a mammalian 2,4-dienoyl-coenzyme A reductase. This mammalian homolog differs from Fab I in that it is involved in the β-oxidation of polyunsaturated enoyl-CoAs and utilizes NADPH as cofactor rather than NADH. Therefore, there is significant potential for selective inhibition of FabI.

There is an unmet need for developing new classes of antibiotic compounds. Clearly, there is also a need for factors, such as FabI, that may be used to screen compounds for antibiotic activity, such as a simple high through-put assay for screening inhibitors of FAS. Such factors may also be used to determine their roles in pathogenesis of infection, dysfunction and disease. Identification and characterization of such factors, which can play a role in preventing, ameliorating or correcting infections, dysfunctions or diseases are critical steps in making important discoveries to improve human health.

For all of the foregoing reasons, the polypeptides of the present invention are potentially valuable targets for therapeutics and diagnostics.

3. Nucleic Acids of the Invention

Isolated nucleic acids are also provided For example, an isolated nucleic acid is provided comprising (a) the nucleotide sequence of SEQ ID NO: 1, (b) a nucleotide sequence at least 80%, 85%, 90%, 95%, 98%, 99% or more identical to SEQ ID NO: 1, (c) a nucleotide sequence that hybridizes under stringent conditions to SEQ ID NO: 1, or (d) the complement of the nucleotide sequence of (a), (b) or (c). In certain embodiments, nucleic acids of the invention may be labeled, with for example, a radioactive, chemiluminescent or fluorescent label.

In another aspect, isolated nucleic acids are provided that specifically hybridize under stringent conditions to at least ten nucleotides of SEQ ID NO: 1, or the complement thereof, which nucleic acid can specifically detect or amplify SEQ ID NO: 1, or the complement thereof. In yet another aspect, the present invention contemplates such an isolated nucleic acid comprising a nucleotide sequence encoding a fragment of SEQ ID NO: 2 at least 8 residues in length. A method of hybridizing an oligonucleotide with a nucleic acid of the invention may comprise: (a) providing a single-stranded oligonucleotide at least eight nucleotides in length, the oligonucleotide being complementary to a portion of a nucleic acid of the invention; and (b) contacting the oligonucleotide with a sample comprising a nucleic acid of the acid under conditions that permit hybridization of the oligonucleotide with the nucleic acid of the invention.

Isolated nucleic acids which differ from the nucleic acids of the invention due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the polypeptides of the invention will exist. One skilled in the art will appreciate that these variations in one or more nucleotides (from less than 1% up to about 3 or 5% or possibly more of the nucleotides) of the nucleic acids encoding a particular protein of the invention may exist among a given species due to natural allelic variation. Any and all such nucleotide variations and resulting amino acid polymorphisms are within the scope of this invention.

Bias in codon choice within genes in a single species appears related to the level of expression of the protein encoded by that gene. Accordingly, the invention encompasses nucleic acid sequences which have been optimized for improved expression in a host cell by altering the frequency of codon usage in the nucleic acid sequence to approach the frequency of preferred codon usage of the host cell. Due to codon degeneracy, it is possible to optimize the nucleotide sequence without affecting the amino acid sequence of an encoded polypeptide. Accordingly, any nucleotide sequence that encodes all or a substantial portion of the amino acid sequence set forth in SEQ ID NO: 2, or other polypeptides of the invention is within the scope of the invention.

Nucleic acids encoding proteins derived from *F. tularensis* and which have amino acid sequences evolutionarily related to a polypeptide of the invention are provided, wherein "evolutionarily related to", refers to proteins having different amino acid sequences which have arisen naturally (e.g. by allelic variance or by differential splicing), as well as mutational variants of the proteins of the invention which are derived, for example, by combinatorial mutagenesis.

Fragments of the polynucleotides of the invention encoding a biologically active portion of the subject polypeptides are also within the scope of the invention. As used herein, a fragment of a nucleic acid of the invention encoding an active portion of a polypeptide of the invention refers to a nucleotide sequence having fewer nucleotides than 4 the nucleotide sequence encoding the full length amino acid sequence of a polypeptide of the invention, for example, SEQ ID NO: 2, and which encodes a polypeptide which retains at least a portion of a biological activity of the full-length protein as defined herein, or alternatively, which is functional as a modulator of the biological activity of the full-length protein. For example, such fragments include a polypeptide containing a domain of the full-length protein from which the polypeptide is derived that mediates the interaction of the protein with another molecule (e.g., polypeptide, DNA, RNA, etc.). In another embodiment, the present invention contemplates an isolated nucleic acid that encodes a polypeptide having a biological activity of a FabI polypeptide.

Nucleic acids within the scope of the invention may also contain linker sequences, modified restriction endonuclease sites and other sequences useful for molecular cloning, expression or purification of such recombinant polypeptides.

A nucleic acid encoding a polypeptide of the invention may be obtained from mRNA or genomic DNA from any organism in accordance with protocols described herein, as well as those generally known to those skilled in the art. A cDNA encoding a polypeptide of the invention, for example, may be obtained by isolating total mRNA from an organism, e.g. a bacteria, virus, mammal, etc. Double stranded cDNAs may then be prepared from the total mRNA, and subsequently inserted into a suitable plasmid or bacteriophage vector using any one of a number of known techniques. A gene encoding a polypeptide of the invention may also be cloned using established polymerase chain reaction techniques in accordance with the nucleotide sequence information provided by the invention. In one aspect, methods for amplification of a nucleic acid of the invention, or a fragment thereof may comprise: (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample comprising a nucleic acid comprising the nucleic acid of the invention under conditions which permit amplification of the region located between the pair of oligonucleotides, thereby amplifying the nucleic acid.

Another aspect relates to the use of nucleic acids of the invention in "antisense therapy". As used herein, antisense therapy refers to administration or in situ generation of oligonucleotide probes or their derivatives which specifically hybridize or otherwise bind under cellular conditions with the cellular mRNA and/or genomic DNA encoding one of the polypeptides of the invention so as to inhibit expression of that polypeptide, e.g. by inhibiting transcription and/or translation. The binding may be by conventional base pair complementarity, or, for example, in the case of binding to DNA duplexes, through specific interactions in the major groove of the double helix. In general, antisense therapy refers to the range of techniques generally employed in the art, and includes any therapy which relies on specific binding to oligonucleotide sequences.

An antisense construct of the present invention may be delivered, for example, as an expression plasmid which, when transcribed in the cell, produces RNA which is complementary to at least a unique portion of the mRNA which encodes a polypeptide of the invention. Alternatively, the antisense construct may be an oligonucleotide probe which is generated ex vivo and which, when introduced into the cell causes inhibition of expression by hybridizing with the mRNA and/or genomic sequences encoding a polypeptide of the invention. Such oligonucleotide probes may be modified oligonucleotides which are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by van der Krol et al., (1988) *Biotechniques* 6:958-976; and Stein et al., (1988) *Cancer Res* 48:2659-2668.

In a further aspect, double stranded small interfering RNAs (siRNAs), and methods for administering the same are provided. siRNAs decrease or block gene expression. While not wishing to be bound by theory, it is generally thought that siRNAs inhibit gene expression by mediating sequence specific mRNA degradation. RNA interference (RNAi) is the process of sequence-specific, post-transcriptional gene silencing, particularly in animals and plants, initiated by double-stranded RNA (dsRNA) that is homologous in sequence to the silenced gene (Elbashir et al. Nature 2001; 411(6836): 494-8). Accordingly, it is understood that siRNAs and long dsRNAs having substantial sequence identity to all or a portion of SEQ ID NO: 1 may be used to inhibit the expression of a nucleic acid of the invention, and particularly when the polynucleotide is expressed in a mammalian or plant cell.

The nucleic acids of the invention may be used as diagnostic reagents to detect the presence or absence of the target DNA or RNA sequences to which they specifically bind, 4 such as for determining the level of expression of a nucleic acid of the invention. In one aspect, methods for detecting the presence of a nucleic acid of the invention or a portion thereof in a sample may comprise: (a) providing an oligonucleotide at least eight nucleotides in length, the oligonucleotide being complementary to a portion of a nucleic acid of the invention; (b) contacting the oligonucleotide with a sample comprising at least one nucleic acid under conditions that permit hybridization of the oligonucleotide with a nucleic acid comprising a nucleotide sequence complementary thereto; and (c) detecting hybridization of the oligonucleotide to a nucleic acid in the sample, thereby detecting the presence of a nucleic acid of the invention or a portion thereof in the sample. In another aspect, methods for detecting the presence of a nucleic acid of the invention or a portion thereof in a sample may comprise: (a) providing a pair of single stranded oligonucleotides, each of which is at least eight nucleotides in length, complementary to sequences of a nucleic acid of the invention, and wherein the sequences to which the oligonucleotides are complementary are at least ten nucleotides apart; and (b) contacting the oligonucleotides with a sample comprising at least one nucleic acid under hybridization conditions; (c) amplifying the nucleotide sequence between the two oligonucleotide primers; and (d) detecting the presence of the amplified sequence, thereby detecting the presence of a nucleic acid comprising the nucleic acid of the invention or a portion thereof in the sample.

The subject nucleic acid may be provided in an expression vector comprising a nucleotide sequence encoding a polypeptide of the invention and operably linked to at least one regulatory sequence. It should be understood that the design of the expression vector may depend on such factors as the choice of the host cell to be transformed and/or the type of protein desired to be expressed. The vector's copy number, the ability to control that copy number and the expression of any other protein encoded by the vector, such as antibiotic markers, should be considered.

The subject nucleic acids may be used to cause expression and over-expression of a polypeptide of the invention in cells propagated in culture, e.g. to produce proteins or polypeptides, including fusion proteins or polypeptides.

Host cells may be transfected with a recombinant gene in order to express a polypeptide of the invention. The host cell may be any prokaryotic or eukaryotic cell. For example, a polypeptide of the invention may be expressed in bacterial cells, such as *E. coli*, insect cells (baculovirus), yeast, or mammalian cells. In those instances when the host cell is human, it may or may not be in a live subject. Other suitable host cells are known to those skilled in the art. Additionally, the host cell may be supplemented with tRNA molecules not typically found in the host so as to optimize expression of the polypeptide. Other methods suitable for maximizing expression of the polypeptide will be known to those in the art.

Methods of producing the polypeptides of the invention are also provided. For example, a host cell transfected with an expression vector encoding a polypeptide of the invention may be cultured under appropriate conditions to allow expression of the polypeptide to occur. The polypeptide may be secreted and isolated from a mixture of cells and medium containing the polypeptide. Alternatively, the polypeptide may be retained cytoplasmically and the cells harvested, lysed and the protein isolated.

A cell culture includes host cells, media and other byproducts. Suitable media for cell culture are well known in the art. The polypeptide may be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of a polypeptide of the invention.

Thus, a nucleotide sequence encoding all or a selected portion of polypeptide of the invention, may be used to produce a recombinant form of the protein via microbial or eukaryotic cellular processes. Ligating the sequence into a polynucleotide construct, such as an expression vector, and transforming or transfecting into hosts, either eukaryotic (yeast, avian, insect or mammalian) or prokaryotic (bacterial cells), are standard procedures. Similar procedures, or modifications thereof, may be employed to prepare recombinant polypeptides of the invention by microbial means or tissue-culture technology.

Expression vehicles for production of a recombinant protein include plasmids and other vectors. For instance, suitable vectors for the expression of a polypeptide of the invention include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., (1983) in *Experimental Manipulation of Gene Expression*, ed. M. Inouye Academic Press, p. 83). These vectors may replicate in *E. coli* due the presence of the pBR322 ori, and in *S. cerevisiae* due to the replication determinant of the yeast 2 micron plasmid. In addition, drug resistance markers such as ampicillin may be used.

In certain embodiments, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see *Molecular Cloning A Laboratory Manual*, 2nd Ed., ed. by Sambrook, Fritsch and Maniatis (Cold Spring Harbor Laboratory Press, 1989) Chapters 16 and 17. In some instances, it may be desirable to express the recombinant protein by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In another variation, protein production may be achieved using in vitro translation systems. In vitro translation systems are, generally, a translation system which is a cell-free extract containing at least the minimum elements necessary for translation of an RNA molecule into a protein. An in vitro translation system typically comprises at least ribosomes, tRNAs, initiator methionyl-tRNAMet, proteins or complexes involved in translation, e.g., eIF2, eIF3, the cap-binding (CB) complex, comprising the cap-binding protein (CBP) and eukaryotic initiation factor 4F (eIF4F). A variety of in vitro translation systems are well known in the art and include commercially available kits. Examples of in vitro translation systems include eukaryotic lysates, such as rabbit reticulocyte lysates, rabbit oocyte lysates, human cell lysates, insect cell lysates and wheat germ extracts. Lysates are commercially available from manufacturers such as Promega Corp., Madison, Wis.; Stratagene, La Jolla, Calif.; Amersham, Arlington Heights, Ill.; and GIBCO/BRL, Grand Island, N.Y. In vitro translation systems typically comprise macromolecules, such as enzymes, translation, initiation and elongation factors, chemical reagents, and ribosomes. In addition, an in vitro transcription system may be used. Such systems typically comprise at least an RNA polymerase holoenzyme, ribonucleotides and any necessary transcription initiation, elongation and termination factors. In vitro transcription and translation may be coupled in a one-pot reaction to produce proteins from one or more isolated DNAs.

When expression of a carboxy terminal fragment of a polypeptide is desired, i.e. a truncation mutant, it may be necessary to add a start codon (ATG) to the oligonucleotide fragment containing the desired sequence to be expressed. It is well known in the art that a methionine at the N-terminal position may be enzymatically cleaved by the use of the enzyme methionine aminopeptidase (MAP). MAP has been cloned from *E. coli* (Ben-Bassat et al., (1987) *J. Bacteriol.* 169:751-757) and *Salmonella typhimurium* and its in vitro activity has been demonstrated on recombinant proteins (Miller et al., (1987) *PNAS USA* 84:2718-1722). Therefore, removal of an N-terminal methionine, if desired, may be achieved either in vivo by expressing such recombinant polypeptides in a host which produces MAP (e.g., *E. coli* or CM89 or *S. cerevisiae*), or in vitro by use of purified MAP (e.g., procedure of Miller et al.).

Coding sequences for a polypeptide of interest may be incorporated as a part of a fusion gene including a nucleotide sequence encoding a different polypeptide. The present invention contemplates an isolated nucleic acid comprising a nucleic acid of the invention and at least one heterologous sequence encoding a heterologous peptide linked in frame to the nucleotide sequence of the nucleic acid of the invention so as to encode a fusion protein comprising the heterologous polypeptide. The heterologous polypeptide may be fused to (a) the C-terminus of the polypeptide encoded by the nucleic acid of the invention, (b) the N-terminus of the polypeptide, or (c) the C-terminus and the N-terminus of the polypeptide. In certain instances, the heterologous sequence encodes a polypeptide permitting the detection, isolation, solubilization and/or stabilization of the polypeptide to which it is fused. In still other embodiments, the heterologous sequence encodes a polypeptide selected from the group consisting of a polyHis tag, myc, HA, GST, protein A, protein G, calmodulin-binding peptide, thioredoxin, maltose-binding protein, poly arginine, poly His-Asp, FLAG, a portion of an immunoglobulin protein, and a transcytosis peptide.

Fusion expression systems can be useful when it is desirable to produce an immunogenic fragment of a polypeptide of the invention. For example, the VP6 capsid protein of rotavirus may be used as an immunologic carrier protein for portions of polypeptide, either in the monomeric form or in the form of a viral particle. The nucleic acid sequences corresponding to the portion of a polypeptide of the invention to which antibodies are to be raised may be incorporated into a fusion gene construct which includes coding sequences for a late vaccinia virus structural protein to produce a set of recombinant viruses expressing fusion proteins comprising a portion of the protein as part of the virion. The Hepatitis B surface antigen may also be utilized in this role as well. Similarly, chimeric constructs coding for fusion proteins containing a portion of a polypeptide of the invention and the poliovirus capsid protein may be created to enhance immunogenicity (see, for example, EP Publication NO: 0259149; and Evans et al., (1989) *Nature* 339:385; Huang et al., (1988) *J. Virol.* 62:3855; and Schlienger et al., (1992) *J. Virol.* 66:2).

Fusion proteins may facilitate the expression and/or purification of proteins. For example, a polypeptide of the invention may be generated as a glutathione-S-transferase (GST) fusion protein. Such GST fusion proteins may be used to simplify purification of a polypeptide of the invention, such as through the use of glutathione-derivatized matrices (see, for example, *Current Protocols in Molecular Biology*, eds. Ausubel et al., (N.Y.: John Wiley & Sons, 1991)). In another embodiment, a fusion gene coding for a purification leader sequence, such as a poly-(His)/enterokinase cleavage site sequence at the N-terminus of the desired portion of the recombinant protein, may allow purification of the expressed fusion protein by affinity chromatography using a $Ni^{2+}$ metal resin. The purification leader sequence may then be subsequently removed by treatment with enterokinase to provide the purified protein (e.g., see Hochuli et al., (1987) *J. Chromatography* 411: 177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene may be synthesized by conventional techniques including automated DNA synthesizers. Alternatively, PCR amplification of gene fragments may be carried out using anchor primers which give rise to complementary overhangs between two consecutive gene fragments which may subsequently be annealed to generate a chimeric gene sequence (see, for example, *Current Protocols in Molecular Biology*, eds. Ausubel et al., John Wiley & Sons: 1992).

Transgenic non-human animals having cells which harbor a transgene comprising a nucleic acid of the invention are also provided In other embodiments, nucleic acids of the invention may be immobilized onto a solid surface, including, plates, microtiter plates, slides, beads, particles, spheres, films, strands, precipitates, gels, sheets, tubing, containers, capillaries, pads, slices, etc. The nucleic acids of the invention may be immobilized onto a chip as part of an array. The array may comprise one or more polynucleotides of the invention as described herein. In one embodiment, the chip comprises one or more polynucleotides of the invention as part of an array of *F. tularensis* polynucleotide sequences.

In still other embodiments, the sequence of a nucleic acid of the invention may be provided in computer readable format. Databases comprising the sequence of a nucleic acid of the invention are also provided.

4. Homology Searching of Nucleotide and Polypeptide Sequences

The nucleotide or amino acid sequences of the invention, including those set forth in the appended Figures, may be used as query sequences against databases such as GenBank, SwissProt, PDB, BLOCKS, and Pima II. These databases contain previously identified and annotated sequences that may be searched for regions of homology (similarity) using BLAST, which stands for Basic Local Alignment Search Tool (Altschul S F (1993) J Mol Evol 36:290-300; Altschul, S F et al (1990) J Mol Biol 215:403-10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992; Protein Engineering 5:35-51) may be used when dealing with primary sequence patterns and secondary structure gap penalties. In the usual course using BLAST, sequences have lengths of at least 49 nucleotides and no more than 12% uncalled bases (where N is recorded rather than A, C, G, or T).

The BLAST approach, as detailed in Karlin and Altschul (1993; Proc Nat Acad Sci 90:5873-7) searches matches between a query sequence and a database sequence, to evaluate the statistical significance of any matches found, and to report only those matches which satisfy the user-selected threshold of significance. The threshold is typically set at about 10-25 for nucleotides and about 3-15 for peptides.

5. Analysis of Protein Properties (a) Analysis of Proteins by Mass Spectrometry

Typically, protein characterization by mass spectroscopy first requires protein isolation followed by either chemical or enzymatic digestion of the protein into smaller peptide fragments, whereupon the peptide fragments may be analyzed by mass spectrometry to obtain a peptide map. Mass spectrometry may also be used to identify post-translational modifications (e.g., phosphorylation, etc.) of a polypeptide.

Various mass spectrometers may be used within the present invention. Representative examples include: triple quadrupole mass spectrometers, magnetic sector instruments (magnetic tandem mass spectrometer, JEOL, Peabody, Mass.), ionspray mass spectrometers (Bruins et al., Anal Chem. 59:2642-2647, 1987), electrospray mass spectrometers (including tandem, nano- and nano-electrospray tandem) (Fenn et al., Science 246:64-71, 1989), laser desorption time-of-flight mass spectrometers (Karas and Hillenkamp, Anal. Chem. 60:2299-2301, 1988), and a Fourier Transform Ion Cyclotron Resonance Mass Spectrometer (Extrel Corp., Pittsburgh, Mass.).

MALDI ionization is a technique in which samples of interest, in this case peptides and proteins, are co-crystallized with an acidified matrix. The matrix is typically a small molecule that absorbs at a specific wavelength, generally in the ultraviolet (UV) range, and dissipates the absorbed energy thermally. Typically a pulsed laser beam is used to transfer energy rapidly (i.e., a few ns) to the matrix. This transfer of energy causes the matrix to rapidly dissociate from the MALDI plate surface and results in a plume of matrix and the co-crystallized analytes being transferred into the gas phase. MALDI is considered a "soft-ionization" method that typically results in singly-charged species in the gas phase, most often resulting from a protonation reaction with the matrix. MALDI may be coupled in-line with time of flight (TOF) mass spectrometers. TOF detectors are based on the principle that an analyte moves with a velocity proportional to its mass. Analytes of higher mass move slower than analytes of lower mass and thus reach the detector later than lighter analytes. The present invention contemplates a composition comprising a polypeptide of the invention and a matrix suitable for mass spectrometry. In certain instances, the matrix is a nicotinic acid derivative or a cinnamic acid derivative.

MALDI-TOF MS is easily performed with modern mass spectrometers. Typically the samples of interest, in this case peptides or proteins, are mixed with a matrix and spotted onto a polished stainless steel plate (MALDI plate). Commercially available MALDI plates can presently hold up to 1536 samples per plate. Once spotted with sample, the MALDI sample plate is then introduced into the vacuum chamber of a MALDI mass spectrometer. The pulsed laser is then activated and the mass to charge ratios of the analytes are measured utilizing a time of flight detector. A mass spectrum representing the mass to charge ratios of the peptides/proteins is generated.

As mentioned above, MALDI can be utilized to measure the mass to charge ratios of both proteins and peptides. In the case of proteins, a mixture of intact protein and matrix are co-crystallized on a MALDI target (Karas, M. and Hillenkamp, F. Anal. Chem. 1988, 60 (20) 2299-2301). The spectrum resulting from this analysis is employed to determine the molecular weight of a whole protein. This molecular weight can then be compared to the theoretical weight of the protein and utilized in characterizing the analyte of interest, such as whether or not the protein has undergone post-translational modifications (e.g., example phosphorylation).

In certain embodiments, MALDI mass spectrometry is used for determination of peptide maps of digested proteins. The peptide masses are measured accurately using a MALDI-TOF or a MALDI-Q-Star mass spectrometer, with detection precision down to the low ppm (parts per million) level. The ensemble of the peptide masses observed in a protein digest, such as a tryptic digest, may be used to search protein/DNA databases in a method called peptide mass fingerprinting. In this approach, protein entries in a database are ranked according to the number of experimental peptide masses that match the predicted trypsin digestion pattern. Commercially available software utilizes a search algorithm that provides a scoring scheme based on the size of the databases, the number of matching peptides, and the different peptides. Depending on the number of peptides observed, the accuracy of the measurement, and the size of the genome of the particular species, unambiguous protein identification may be obtained.

Statistical analysis may be performed upon each protein match to determine the validity of the match. Typical constraints include error tolerances within 0.1 Da for monoisotopic peptide masses, cysteines may be alkylated and searched as carboxyamidomethyl modifications, 0 or 1 missed enzyme cleavages, and no methionine oxidations allowed. Identified proteins may be stored automatically in a relational database with software links to SDS-PAGE images and ligand sequences. Often even a partial peptide map is specific enough for identification of the protein. If no protein match is found, a more error-tolerant search can be used, for example using fewer peptides or allowing a larger margin error with respect to mass accuracy.

Other mass spectroscopy methods such as tandem mass spectrometry or post source decay may be used to obtain sequence information about proteins that cannot be identified by peptide mass mapping, or to confirm the identity of proteins that are tentatively identified by an error-tolerant peptide mass search described above. (Griffin et al, Rapid Commun. Mass. Spectrom. 1995, 9, 1546-51).

(b) Analysis of Proteins by Nuclear Magnetic Resonance (NMR)

NMR may be used to characterize the structure of a polypeptide in accordance with the methods of the invention. In particular, NMR can be used, for example, to determine the three dimensional structure, the conformational state, the aggregation level, the state of protein folding/unfolding or the dynamic properties of a polypeptide. For example, the present invention contemplates a method for determining three dimensional structure information of a polypeptide of the invention, the method comprising: (a) generating a purified isotopically labeled polypeptide of the invention; and (b) subjecting the polypeptide to NMR spectroscopic analysis, thereby determining information about its three dimensional structure.

Interaction between a polypeptide and another molecule can also be monitored using NMR. Thus, the invention encompasses methods for detecting, designing and characterizing interactions between a polypeptide and another molecule, including polypeptides, nucleic acids and small molecules, utilizing NMR techniques. For example, methods for determining three dimensional structure information of a polypeptide of the invention, or a fragment thereof, while the polypeptide is complexed with another molecule, may comprise: (a) generating a purified isotopically labeled polypeptide of the invention, or a fragment thereof; (b) forming a complex between the polypeptide and the other molecule; and (c) subjecting the complex to NMR spectroscopic analysis, thereby determining information about the three dimensional structure of the polypeptide. In another aspect, methods for identifying compounds that bind to a polypeptide of the invention, or a fragment thereof, may comprise: (a) generating a first NMR spectrum of an isotopically labeled polypeptide of the invention, or a fragment thereof; (b) exposing the polypeptide to one or more chemical compounds; (c) generating a second NMR spectrum of the polypeptide which has been exposed to one or more chemical compounds; and (d) comparing the first and second spectra to determine differences between the first and the second spectra, wherein the differences are indicative of one or more compounds that have bound to the polypeptide.

Briefly, the NMR technique involves placing the material to be examined (usually in a suitable solvent) in a powerful magnetic field and irradiating it with radio frequency (rf) electromagnetic radiation. The nuclei of the various atoms will align themselves with the magnetic field until energized by the rf radiation. They then absorb this resonant energy and re-radiate it at a frequency dependent on i) the type of nucleus and ii) its atomic environment. Moreover, resonant energy may be passed from one nucleus to another, either through bonds or through three-dimensional space, thus giving information about the environment of a particular nucleus and nuclei in its vicinity.

However, it is important to recognize that not all nuclei are NMR active. Indeed, not all isotopes of the same element are active. For example, whereas "ordinary" hydrogen, $^1H$, is NMR active, heavy hydrogen (deuterium), $^2H$, is not active in the same way. Thus, any material that normally contains $^1H$ hydrogen may be rendered "invisible" in the hydrogen NMR spectrum by replacing all or almost all the $^1H$ hydrogens with $^2H$. It is for this reason that NMR spectroscopic analyses of water-soluble materials frequently are performed in $^2H_2O$ (or deuterium) to eliminate the water signal.

Conversely, "ordinary" carbon, $^{12}$C, is NMR inactive whereas the stable isotope, $^{13}$C, present to about 1% of total carbon in nature, is active. Similarly, while "ordinary" nitrogen, $^{14}$N, is NMR active, it has undesirable properties for NMR and resonates at a different frequency from the stable isotope $^{15}$N, present to about 0.4% of total nitrogen in nature.

By labeling proteins with $^{15}$N and 15N/$^{13}$C, it is possible to conduct analytical NMR of macromolecules with weights of 15 kD and 40 kD, respectively. More recently, partial deuteration of the protein in addition to $^{13}$C- and $^{15}$N-labeling has increased the possible weight of proteins and protein complexes for NMR analysis still further, to approximately 60-70 kD. See Shan et al., J. Am. Chem. Soc., 118:6570-6579 (1996); L. E. Kay, Methods Enzymol., 339:174-203 (2001); and K. H. Gardner & L. E. Kay, Annu Rev Biophys Biomol Struct., 27:357-406 (1998); and references cited therein.

Isotopic substitution may be accomplished by growing a bacterium or yeast or other type of cultured cells, transformed by genetic engineering to produce the protein of choice, in a growth medium containing $^{13}$C-, $^{15}$N- and/or $^2$H-labeled substrates. In certain instances, bacterial growth media consists of $^{13}$C-labeled glucose and/or $^{15}$N-labeled ammonium salts dissolved in $D_2O$ where necessary. Kay, L. et al., Science, 249:411 (1990) and references therein and Bax, A., J. Am. Chem. Soc., 115, 4369 (1993). More recently, isotopically labeled media especially adapted for the labeling of bacterially produced macromolecules have been described. See U.S. Pat. No. 5,324,658.

The goal of these methods has been to achieve universal and/or random isotopic enrichment of all of the amino acids of the protein. By contrast, other methods allow only certain residues to be relatively enriched in $^1$H, $^2$H, $^{13}$C and $^{15}$N. For example, Kay et al., J. Mol. Biol., 263, 627-636 (1996) and Kay et al., J. Am. Chem. Soc., 119, 7599-7600 (1997) have described methods whereby isoleucine, alanine, valine and leucine residues in a protein may be labeled with $^2$H, $^3$C and $^{15}$N, and may be specifically labeled with $^1$H at the terminal methyl position. In this way, study of the proton-proton interactions between some amino acids may be facilitated. Similarly, a cell-free system has been described by Yokoyama et al., J. Biomol. NMR, 6(2), 129-134 (1995), wherein a transcription-translation system derived from $E.$ $coli$ was used to express human Ha-Ras protein incorporating $^{15}$N into serine and/or aspartic acid.

Techniques for producing isotopically labeled proteins and macromolecules, such as glycoproteins, in mammalian or insect cells have been described. See U.S. Pat. Nos. 5,393,669 and 5,627,044; Weller, C. T., Biochem., 35, 8815-23 (1996) and Lustbader, J. W., J. Biomol. NMR, 7, 295-304 (1996). Other methods for producing polypeptides and other molecules with labels appropriate for NMR are known in the art.

A variety of solvents which are appropriate for NMR may be used. For $^1$H NMR, a deuterium lock solvent may be used. Exemplary deuterium lock solvents include acetone ($CD_3COCD_3$), chloroform ($CDCl_3$), dichloro methane ($CD_2Cl_2$), methylnitrile ($CD_3CN$), benzene ($C_6D_6$), water ($D_2O$), diethylether (($CD_3CD_2)_2O$), dimethylether (($CD_3)_2O$), N,N-dimethylformamide (($CD_3)_2NCDO$), dimethyl sulfoxide ($CD_3SOCD_3$), ethanol ($CD_3CD_2OD$), methanol ($CD_3OD$), tetrahydrofuran ($C_4D_8O$), toluene ($C_6D_5CD_3$), pyridine ($C_5D_5N$) and cyclohexane ($C_6H_{12}$). For example, a composition comprising a polypeptide of the invention and a deuterium lock solvent is provided.

The 2-dimensional $^1$H-$^{15}$N HSQC (Heteronuclear Single Quantum Correlation) spectrum provides a diagnostic fingerprint of conformational state, aggregation level, state of protein folding, and dynamic properties of a polypeptide (Yee et al, PNAS 99, 1825-30 (2002)). Polypeptides in aqueous solution usually populate an ensemble of 3-dimensional structures which can be determined by NMR. When the polypeptide is a stable globular protein or domain of a protein, then the ensemble of solution structures is one of very closely related conformations. In this case, one peak is expected for each non-proline residue with a dispersion of resonance frequencies with roughly equal intensity. Additional pairs of peaks from side-chain $NH_2$ groups are also often observed, and correspond to the approximate number of Gln and Asn residues in the protein. This type of HSQC spectra usually indicates that the protein is amenable to structure determination by NMR methods.

If the HSQC spectrum shows well-dispersed peaks but there are either too few or too many in number, and/or the peak intensities differ throughout the spectrum, then the protein likely does not exist in a single globular conformation. Such spectral features are indicative of conformational heterogeneity with slow or nonexistent inter-conversion between states (too many peaks) or the presence of dynamic processes on an intermediate timescale that can broaden and obscure the NMR signals. Proteins with this type of spectrum can sometimes be stabilized into a single conformation by changing either the protein construct, the solution conditions, temperature or by binding of another molecule.

The $^1$H-$^{15}$N HSQC can also indicate whether a protein has formed large nonspecific aggregates or has dynamic properties. Alternatively, proteins that are largely unfolded, e.g., having very little regular secondary structure, result in $^1$H-$^{15}$N HSQC spectra in which the peaks are all very narrow and intense, but have very little spectral dispersion in the $^{15}$N-dimension. This reflects the fact that many or most of the amide groups of amino acids in unfolded polypeptides are solvent exposed and experience similar chemical environments resulting in similar $^1$H chemical shifts.

The use of the $^1$H-$^{15}$N HSQC, can thus allow the rapid characterization of the conformational state, aggregation level, state of protein folding, and dynamic properties of a polypeptide. Additionally, other 2D spectra such as $^1$H-$^{13}$C HSQC, or HNCO spectra can also be used in a similar manner. Further use of the $^1$H-$^{15}$N HSQC combined with relaxation measurements can reveal the molecular rotational correlation time and dynamic properties of polypeptides. The rotational correlation time is proportional to size of the protein and therefore can reveal if it forms specific homo-oligomers such as homodimers, homotetramers, etc.

The structure of stable globular proteins can be determined through a series of well-described procedures. For a general review of structure determination of globular proteins in solution by NMR spectroscopy, see Wüthrich, Science 243: 45-50 (1989). See also, Billeter et al., J. Mol. Biol. 155: 321-346 (1982). Current methods for structure determination usually require the complete or nearly complete sequence-specific assignment of $^1$H-resonance frequencies of the protein and subsequent identification of approximate inter-hydrogen distances (from nuclear Overhauser effect (NOE) spectra) for use in restrained molecular dynamics calculations of the protein conformation. One approach for the analysis of NMR resonance assignments was first outlined by Wüthrich, Wagner and co-workers (Wüthrich, "NMR or proteins and nucleic acids" Wiley, New York, N.Y. (1986); Wüthrich, Science 243: 45-50 (1989); Billeter et al., J. Mol. Biol. 155: 321-346 (1982)). Newer methods for determining the structures of globular proteins include the use of residual dipolar coupling restraints (Tian et al., J Am Chem. Soc. 2001 Nov. 28; 123 (47):11791-6; Bax et al, Methods Enzymol. 2001; 339:127-74) and empirically derived conformational restraints (Zweckstetter & Bax, J Am Chem. Soc. 2001 Sep. 26; 123 (38):9490-1). It has also been shown that it may be possible to determine structures of globular proteins using only un-assigned NOE measurements. NMR may also be used to determine ensembles of many inter-converting, unfolded conformations (Choy and Forman-Kay, J Mol. Biol. 2001 May 18; 308(5):1011-32).

NMR analysis of a polypeptide in the presence and absence of a test compound (e.g., a polypeptide, nucleic acid or small molecule) may be used to characterize interactions between a polypeptide and another molecule. Because the $^1$H-$^{15}$N HSQC spectrum and other simple 2D NMR experiments can be obtained very quickly (on the order of minutes depending on protein concentration and NMR instrumentation), they are very useful for rapidly testing whether a polypeptide is able to bind to another molecule. Changes in the resonance frequency (in one or both dimensions) of one or more peaks in the HSQC spectrum indicate an interaction with another molecule. Often only a subset of the peaks will have changes in resonance frequency upon binding to another molecule, allowing one to map onto the structure those residues directly involved in the interaction or involved in conformational changes as a result of the interaction. If the interacting molecule is relatively large (protein or nucleic acid) the peak widths will also broaden due to the increased rotational correlation time of the complex. In some cases the peaks involved in the interaction may actually disappear from the NMR spectrum if the interacting molecule is in intermediate exchange on the NMR timescale (i.e., exchanging on and off the polypeptide at a frequency that is similar to the resonance frequency of the monitored nuclei).

To facilitate the acquisition of NMR data on a large number of compounds (e.g., a library of synthetic or naturally-occurring small organic compounds), a sample changer may be employed. Using the sample changer, a larger number of samples, numbering 60 or more, may be run unattended. To facilitate processing of the NMR data, computer programs are used to transfer and automatically process the multiple one-dimensional NMR data.

In one embodiment, screening methods for identifying small molecules capable of interacting with a polypeptide of the invention are provided. In one example, the screening process begins with the generation or acquisition of either a $T_2$-filtered or a diffusion-filtered one-dimensional proton spectrum of the compound or mixture of compounds. Means for generating $T_2$-filtered or diffusion-filtered one-dimensional proton spectra are well known in the art (see, e.g., S. Meiboom and D. Gill, Rev. Sci. Instrum. 29:688 (1958), S. J. Gibbs and C. S. Johnson, Jr. J. Main. Reson. 93:395-402 (1991) and A. S. Altieri, et al. J. Am. Chem. Soc. 117: 7566-7567 (1995)).

Following acquisition of the first spectrum for the molecules, the $^{15}$N- or $^{13}$C-labeled polypeptide is exposed to one or more molecules. Where more than one test compound is to be tested simultaneously, it is preferred to use a library of compounds such as a plurality of small molecules. Such molecules are typically dissolved in perdeuterated dimethylsulfoxide. The compounds in the library may be purchased from vendors or created according to desired needs.

Individual compounds may be selected inter alia on the basis of size and molecular diversity for maximizing the possibility of discovering compounds that interact with widely diverse binding sites of a polypeptide of the invention.

The NMR screening process may utilize a range of test compound concentrations, e.g., from about 0.05 to about 1.0 mM. At those exemplary concentrations, compounds which are acidic or basic may significantly change the pH of buffered protein solutions. Chemical shifts are sensitive to pH changes as well as direct binding interactions, and false-positive chemical shift changes, which are not the result of test compound binding but of changes in pH, may therefore be observed. It may therefore be necessary to ensure that the pH of the buffered solution does not change upon addition of the test compound.

Following exposure of the test compounds to a polypeptide (e.g., the target molecule for the experiment) a second one-dimensional $T_2$- or diffusion-filtered spectrum is generated. For the $T_2$-filtered approach, that second spectrum is generated in the same manner as set forth above. The first and second spectra are then compared to determine whether there are any differences between the two spectra. Differences in the one-dimensional $T_2$-filtered spectra indicate that the compound is binding to, or otherwise interacting with, the target molecule. Those differences are determined using standard procedures well known in the art. For the diffusion-filtered method, the second spectrum is generated by looking at the spectral differences between low and high gradient strengths—thus selecting for those compounds whose diffusion rates are comparable to that observed in the absence of target molecule.

To discover additional molecules that bind to the protein, molecules are selected for testing based on the structure/activity relationships from the initial screen and/or structural information on the initial leads when bound to the protein. By way of example, the initial screening may result in the identification of compounds, all of which contain an aromatic ring. The second round of screening would then use other aromatic molecules as the test compounds.

In another embodiment, the methods may utilize a process for detecting the binding of one ligand to a polypeptide in the presence of a second ligand. In accordance with this embodiment, a polypeptide is bound to the second ligand before exposing the polypeptide to the test compounds.

For more information on NMR methods encompassed by the present invention, see also: U.S. Pat. Nos. 5,668,734; 6,194,179; 6,162,627; 6,043,024; 5,817,474; 5,891,642; 5,989,827; 5,891,643; 6,077,682; WO 00/05414; WO 99/22019; Cavanagh, et al., Protein NMR Spectroscopy, Principles and Practice, 1996, Academic Press; Clore, et al., NMR of Proteins. In Topics in Molecular and Structural Biology, 1993, S, Neidle, Fuller, W., and Cohen, J. S., eds., Macmillan Press, Ltd., London; and Christendat et al., Nature Structural Biology 7: 903-909 (2000).

(c) Analysis of Proteins by X-ray Crystallography (i) X-ray Structure Determination Exemplary methods for obtaining the three dimensional structure of the crystalline form of a molecule or complex are described herein and, in view of this specification, variations on these methods will be apparent to those skilled in the art (see Ducruix and Geige 1992, LRL Press, Oxford, England).

A variety of methods involving x-ray crystallography are contemplated by the present invention. For example, a crystallized polypeptide of the invention, or a fragment thereof, may be produced by: (a) introducing into a host cell an expression vector comprising a nucleic acid encoding for a polypeptide of the invention, or a fragment thereof; (b) culturing the host cell in a cell culture medium to express the polypeptide or fragment; (c) isolating the polypeptide or fragment from the cell culture; and (d) crystallizing the polypeptide or fragment thereof. Alternatively, the three dimensional structure of a crystallized polypeptide of the invention, or a fragment thereof, may be determined by: (a) crystallizing a polypeptide of the invention, or a fragment thereof, such that the crystals will diffract x-rays to a resolution of 3.5 Å or better; and (b) analyzing the polypeptide or fragment by x-ray diffraction to determine the three-dimensional structure of the crystallized polypeptide.

X-ray crystallography techniques generally require that the protein molecules be available in the form of a crystal. Crystals may be grown from a solution containing a purified polypeptide of the invention, or a fragment thereof (e.g., a stable domain), by a variety of conventional processes. These processes include, for example, batch, liquid, bridge, dialysis, vapour diffusion (e.g., hanging drop or sitting drop methods). (See for example, McPherson, 1982 John Wiley, New York; McPherson, 1990, Eur. J. Biochem. 189: 1-23; Webber. 1991, Adv. Protein Chem. 41:1-36).

In certain embodiments, native crystals of the invention may be grown by adding precipitants to the concentrated solution of the polypeptide. The precipitants are added at a concentration just below that necessary to precipitate the protein. Water may be removed by controlled evaporation to produce precipitating conditions, which are maintained until crystal growth ceases.

The formation of crystals is dependent on a number of different parameters, including pH, temperature, protein concentration, the nature of the solvent and precipitant, as well as the presence of added ions or ligands to the protein. In addition, the sequence of the polypeptide being crystallized will have a significant affect on the success of obtaining crystals. Many routine crystallization experiments may be needed to screen all these parameters for the few combinations that might give crystal suitable for x-ray diffraction analysis (See, for example, Jancarik, J & Kim, S. H., J. Appl. Cryst. 1991 24: 409-411).

Crystallization robots may automate and speed up the work of reproducibly setting up large number of crystallization experiments. Once some suitable set of conditions for growing the crystal are found, variations of the condition may be systematically screened in order to find the set of conditions which allows the growth of sufficiently large, single, well ordered crystals. In certain instances, a polypeptide of the invention is co-crystallized with a compound that stabilizes the polypeptide.

A number of methods are available to produce suitable radiation for x-ray diffraction. For example, x-ray beams may be produced by synchrotron rings where electrons (or positrons) are accelerated through an electromagnetic field while traveling at close to the speed of light. Because the admitted wavelength may also be controlled, synchrotrons may be used as a tunable x-ray source (Hendrickson W A., Trends Biochem Sci 2000 December; 25(12):637-43). For less conventional Laue diffraction studies, polychromatic x-rays covering a broad wavelength window are used to observe many diffraction intensities simultaneously (Stoddard, B. L., Curr. Opin. Struct Biol 1998 October; 8(5):612-8). Neutrons may also be used for solving protein crystal structures (Gutberlet T, Heinemann U & Steiner M., Acta Crystallogr D 2001; 57: 349-54).

Before data collection commences, a protein crystal may be frozen to protect it from radiation damage. A number of different cryo-protectants may be used to assist in freezing the crystal, such as methyl pentanediol (MPD), isopropanol, ethylene glycol, glycerol, formate, citrate, mineral oil, or a low-molecular-weight polyethylene glycol (PEG). The present invention contemplates a composition comprising a polypeptide of the invention and a cryo-protectant. As an alternative to freezing the crystal, the crystal may also be used for diffraction experiments performed at temperatures above the freezing point of the solution. In these instances, the crystal may be protected from drying out by placing it in a narrow capillary of a suitable material (generally glass or quartz) with some of the crystal growth solution included in order to maintain vapour pressure.

X-ray diffraction results may be recorded by a number of ways know to one of skill in the art. Examples of area electronic detectors include charge coupled device detectors, multi-wire area detectors and phosphoimager detectors (Amemiya, Y, 1997. Methods in Enzymology, Vol. 276. Academic Press, San Diego, pp. 233-243; Westbrook, E. M., Naday, I. 1997. Methods in Enzymology, Vol. 276. Academic Press, San Diego, pp. 244-268; 1997. Kahn, R. & Fourme, R. Methods in Enzymology, Vol. 276. Academic Press, San Diego, pp. 268-286).

A suitable system for laboratory data collection might include a Bruker AXS Proteum R system, equipped with a copper rotating anode source, Confocal Max-Flux™ optics and a SMART 6000 charge coupled device detector. Collection of x-ray diffraction patterns are well documented by those skilled in the art (See, for example, Ducruix and Geige, 1992, IRL Press, Oxford, England).

The theory behind diffraction by a crystal upon exposure to x-rays is well known. Because phase information is not directly measured in the diffraction experiment, and is needed to reconstruct the electron density map, methods that can recover this missing information are required. One method of solving structures ab initio are the real/reciprocal space cycling techniques. Suitable real/reciprocal space cycling search programs include shake-and-bake (Weeks C M, DeTitta G T, Hauptman H A, Thuman P, Miller R Acta Crystallogr A 1994; V50: 210-20).

Other methods for deriving phases may also be needed. These techniques generally rely on the idea that if two or more measurements of the same reflection are made where strong, measurable, differences are attributable to the characteristics of a small subset of the atoms alone, then the contributions of other atoms can be, to a first approximation, ignored, and positions of these atoms may be determined from the difference in scattering by one of the above techniques. Knowing the position and scattering characteristics of those atoms, one may calculate what phase the overall scattering must have had to produce the observed differences.

One version of this technique is isomorphous replacement technique, which requires the introduction of new, well ordered, x-ray scatterers into the crystal. These additions are usually heavy metal atoms, (so that they make a significant difference in the diffraction pattern); and if the additions do not change the structure of the molecule or of the crystal cell, the resulting crystals should be isomorphous. Isomorphous replacement experiments are usually performed by diffusing different heavy-metal metals into the channels of a pre-existing protein crystal. Growing the crystal from protein that has been soaked in the heavy atom is also possible (Petsko, G. A., 1985. Methods in Enzymology, Vol. 114. Academic Press, Orlando, pp. 147-156). Alternatively, the heavy atom may also be reactive and attached covalently to exposed amino acid side chains (such as the sulfur atom of cysteine) or it may be associated through non-covalent interactions. It is sometimes possible to replace endogenous light metals in metalloproteins with heavier ones, e.g., zinc by mercury, or calcium by samarium (Petsko, G. A., 1985. Methods in Enzymology, Vol. 114. Academic Press, Orlando, pp. 147-156). Exemplary sources for such heavy compounds include, without limitation, sodium bromide, sodium selenate, trimethyl lead acetate, mercuric chloride, methyl mercury acetate, platinum tetracyanide, platinum tetrachloride, nickel chloride, and europium chloride.

A second technique for generating differences in scattering involves the phenomenon of anomalous scattering. X-rays that cause the displacement of an electron in an inner shell to a higher shell are subsequently rescattered, but there is a time lag that shows up as a phase delay. This phase delay is observed as a (generally quite small) difference in intensity between reflections known as Friedel mates that would be identical if no anomalous scattering were present. A second effect related to this phenomenon is that differences in the intensity of scattering of a given atom will vary in a wavelength dependent manner, given rise to what are known as dispersive differences. In principle anomalous scattering occurs with all atoms, but the effect is strongest in heavy atoms, and may be maximized by using x-rays at a wavelength where the energy is equal to the difference in energy between shells. The technique therefore requires the incorporation of some heavy atom much as is needed for isomorphous replacement, although for anomalous scattering a wider variety of atoms are suitable, including lighter metal atoms (copper, zinc, iron) in metallo-proteins. One method for preparing a protein for anomalous scattering involves replacing the methionine residues in whole or in part with selenium containing seleno-methionine. Soaks with halide salts such as bromides and other non-reactive ions may also be effective (Dauter Z, Li M, Wlodawer A., Acta Crystallogr D 2001; 57: 239-49).

In another process, known as multiple anomalous scattering or MAD, two to four suitable wavelengths of data are collected. (Hendrickson, W. A. and Ogata, C. M. 1997 Methods in Enzymology 276, 494-523). Phasing by various combinations of single and multiple isomorphous and anomalous scattering are possible too. For example, SIRAS (single isomorphous replacement with anomalous scattering) utilizes both the isomorphous and anomalous differences for one derivative to derive phases. More traditionally, several different heavy atoms are soaked into different crystals to get sufficient phase information from isomorphous differences while ignoring anomalous scattering, in the technique known as multiple isomorphous replacement (MIR) (Petsko, G. A., 1985. Methods in Enzymology, Vol. 114. Academic Press, Orlando, pp. 147-156).

Additional restraints on the phases may be derived from density modification techniques. These techniques use either generally known features of electron density distribution or known facts about that particular crystal to improve the phases. For example, because protein regions of the crystal scatter more strongly than solvent regions, solvent flattening/flipping may be used to adjust phases to make solvent density a uniform flat value (Zhang, K. Y. J., Cowtan, K. and Main, P. Methods in Enzymology 277, 1997 Academic Press, Orlando pp 53-64). If more than one molecule of the protein is present in the asymmetric unit, the fact that the different molecules should be virtually identical may be exploited to further reduce phase error using non-crystallographic symmetry averaging (Villieux, F. M. D. and Read, R. J. Methods in Enzymology 277, 1997 Academic Press, Orlando pp 18-52). Suitable programs for performing these processes include DM and other programs of the CCP4 suite (Collaborative Computational Project, Number 4. 1994. Acta Cryst. D50, 760-763) and CNX.

The unit cell dimensions, symmetry, vector amplitude and derived phase information can be used in a Fourier transform function to calculate the electron density in the unit cell, i.e., to generate an experimental electron density map. This may be accomplished using programs of the CNX or CCP4 packages. The resolution is measured in Ångstrom (Å) units, and is closely related to how far apart two objects need to be before they can be reliably distinguished. The smaller this number is, the higher the resolution and therefore the greater the amount of detail that can be seen. Preferably, crystals of the invention diffract x-rays to a resolution of better than about 4.0, 3.5, 3.0, 2.5, 2.0, 1.5, 1.0, 0.5 Å or better.

As used herein, the term "modeling" includes the quantitative and qualitative analysis of molecular structure and/or function based on atomic structural information and interaction models. The term "modeling" includes conventional numeric-based molecular dynamic and energy minimization models, interactive computer graphic models, modified molecular mechanics models, distance geometry and other structure-based constraint models.

Model building may be accomplished by either the crystallographer using a computer graphics program such as TURBO or O (Jones, T A. et al., Acta Crystallogr. A47, 100-119, 1991) or, under suitable circumstances, by using a fully automated model building program, such as wARP (Anastassis Perrakis, Richard Morris & Victor S. Lamzin; Nature Structural Biology, May 1999 Volume 6 Number 5 pp 458-463) or MAID (Levitt, D. G., Acta Crystallogr. D 2001 V57: 1013-9). This structure may be used to calculate model-derived diffraction amplitudes and phases. The model-derived and experimental diffraction amplitudes may be compared and the agreement between them can be described by a parameter referred to as R-factor. A high degree of correlation in the amplitudes corresponds to a low R-factor value, with 0.0 representing exact agreement and 0.59 representing a completely random structure. Because the R-factor may be lowered by introducing more free parameters into the model, an unbiased, cross-correlated version of the R-factor known as the R-free gives a more objective measure of model quality. For the calculation of this parameter a subset of reflections (generally around 10%) are set aside at the beginning of the refinement and not used as part of the refinement target. These reflections are then compared to those predicted by the model (Kleywegt G J, Brunger A T, Structure 1996 Aug. 15; 4(8): 897-904).

The model may be improved using computer programs that maximize the probability that the observed data was produced from the predicted model, while simultaneously optimizing the model geometry. For example, the CNX program may be used for model refinement, as can the XPLOR program (1992, Nature 355:472-475, G. N. Murshudov, A. A. Vagin and E. J. Dodson, (1997) Acta Cryst. D 53, 240-255). In order to maximize the convergence radius of refinement, simulated annealing refinement using torsion angle dynamics may be employed in order to reduce the degrees of freedom of motion of the model (Adams P D, Pannu N S, Read R J, Brunger A T., Proc Natl Acad Sci U S A 1997 May 13; 94(10):5018-23). Where experimental phase information is available (e.g. where MAD data was collected) Hendrickson-Lattman phase probability targets may be employed. Isotropic or anisotropic domain, group or individual temperature factor refinement, may be used to model variance of the atomic position from its mean. Well defined peaks of electron density not attributable to protein atoms are generally modeled as water molecules. Water molecules may be found by manual inspection of electron density maps, or with automatic water picking routines. Additional small molecules, including ions, cofactors, buffer molecules or substrates may be included in the model if sufficiently unambiguous electron density is observed in a map.

In general, the R-free is rarely as low as 0.15 and may be as high as 0.35 or greater for a reasonably well-determined protein structure. The residual difference is a consequence of approximations in the model (inadequate modeling of residual structure in the solvent, modeling atoms as isotropic Gaussian spheres, assuming all molecules are identical rather than having a set of discrete conformers, etc.) and errors in the data (Lattman EE., Proteins 1996; 25: i-ii). In refined structures at high resolution, there are usually no major errors in the orientation of individual residues, and the estimated errors in atomic positions are usually around 0.1-0.2 up to 0.3 Å.

The three dimensional structure of a new crystal may be modeled using molecular replacement. The term "molecular replacement" refers to a method that involves generating a preliminary model of a molecule or complex whose structure coordinates are unknown, by orienting and positioning a molecule whose structure coordinates are known within the unit cell of the unknown crystal, so as best to account for the observed diffraction pattern of the unknown crystal. Phases may then be calculated from this model and combined with the observed amplitudes to give an approximate Fourier synthesis of the structure whose coordinates are unknown. This, in turn, can be subject to any of the several forms of refinement to provide a final, accurate structure of the unknown crystal. Lattman, E., "Use of the Rotation and Translation Functions", in Methods in Enzymology, 115, pp. 55-77 (1985); M. G. Rossmann, ed., "The Molecular Replacement Method", Int. Sci. Rev. Ser., No. 13, Gordon & Breach, New York, (1972).

Commonly used computer software packages for molecular replacement are CNX, X-PLOR (Brunger 1992, Nature 355: 472-475), AMoRE (Navaza, 1994, Acta Crystallogr. A50:157-163), the CCP4 package, the MERLOT package (P. M. D. Fitzgerald, J. Appl. Cryst., Vol. 21, pp. 273-278, 1988) and XTALVIEW (McCree et al (1992) J. Mol. Graphics. 10: 44-46). The quality of the model may be analyzed using a program such as PROCHECK or 3D-Profiler (Laskowski et al 1993 J. Appl. Cryst. 26:283-291; Luthy R. et al, Nature 356: 83-85, 1992; and Bowie, J. U. et al, Science 253: 164-170, 1991).

Homology modeling (also known as comparative modeling or knowledge-based modeling) methods may also be used to develop a three dimensional model from a polypeptide sequence based on the structures of known proteins. The method utilizes a computer model of a known protein, a computer representation of the amino acid sequence of the polypeptide with an unknown structure, and standard computer representations of the structures of amino acids. This method is well known to those skilled in the art (Greer, 1985, Science 228, 1055; Bundell et al 1988, Eur. J. Biochem. 172, 513; Knighton et al., 1992, Science 258:130-135, http://biochem.vt.edu/courses/-modeling/homology.htn). Computer programs that can be used in homology modeling are QUANTA and the Homology module in the Insight II modeling package distributed by Molecular Simulations Inc, or MODELLER (Rockefeller University, www.iucr.ac.uk/sinris-top/logical/prg-modeller.html).

Once a homology model has been generated it is analyzed to determine its correctness. A computer program available to assist in this analysis is the Protein Health module in QUANTA which provides a variety of tests. Other programs that provide structure analysis along with output include PROCHECK and 3D-Profiler (Luthy R. et al, Nature 356: 83-85, 1992; and Bowie, J. U. et al, Science 253: 164-170, 1991). Once any irregularities have been resolved, the entire structure may be further refined.

Other molecular modeling techniques may also be employed in accordance with this invention. See, e.g., Cohen, N. C. et al, J. Med. Chem., 33, pp. 883-894 (1990). See also, Navix, M. A. and M. A. Marko, Current Opinions in Structural Biology, 2, pp. 202-210 (1992).

Under suitable circumstances, the entire process of solving a crystal structure may be accomplished in an automated fashion by a system such as ELVES (ucxray.berkeley.edu/~jamesh/elves/index.html) with little or no user intervention.

(ii) X-Ray Structure

Methods for determining some or all of the structural coordinates for amino acids of a polypeptide of the invention, or a complex thereof are provided.

In another aspect, methods for identifying a druggable region of a polypeptide of the invention are provided. For example, one such method includes: (a) obtaining crystals of a polypeptide of the invention or a fragment thereof such that the three dimensional structure of the crystallized protein can be determined to a resolution of 3.5 Å or better; (b) determining the three dimensional structure of the crystallized polypeptide or fragment using x-ray diffraction; and (c) identifying a druggable region of a polypeptide of the invention based on the three-dimensional structure of the polypeptide or fragment.

A three dimensional structure of a molecule or complex may be described by the set of atoms that best predict the observed diffraction data (that is, which possesses a minimal R value). Files may be created for the structure that defines each atom by its chemical identity, spatial coordinates in three dimensions, root mean squared deviation from the mean observed position and fractional occupancy of the observed position.

Those of skill in the art understand that a set of structure coordinates for an protein, complex or a portion thereof, is a relative set of points that define a shape in three dimensions. Thus, it is possible that an entirely different set of coordinates could define a similar or identical shape. Moreover, slight variations in the individual coordinates may have little affect on overall shape. Such variations in coordinates may be generated because of mathematical manipulations of the structure coordinates. For example, structure coordinates could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little affect on overall shape. If such variations are within an acceptable standard error as compared to the original coordinates, the resulting three-dimensional shape is considered to be structurally equivalent. It should be noted that slight variations in individual structure coordinates of a polypeptide of the invention or a complex thereof would not be expected to significantly alter the nature of modulators that could associate with a druggable region thereof. Thus, for example, a modulator that bound to the active site of a polypeptide of the invention would also be expected to bind to or interfere with another active site whose structure coordinates define a shape that falls within the acceptable error.

A crystal structure of the present invention may be used to make a structural or computer model of the polypeptide, complex or portion thereof. A model may represent the secondary, tertiary and/or quaternary structure of the polypeptide, complex or portion. The configurations of points in space derived from structure coordinates according to the invention can be visualized as, for example, a holographic image, a stereodiagram, a model or a computer-displayed image, and the invention thus includes such images, diagrams or models.

(iii) Structural Equivalents

Various computational analyses can be used to determine whether a molecule or the active site portion thereof is structurally equivalent with respect to its three-dimensional structure, to all or part of a structure of a polypeptide of the invention or a portion thereof.

For the purpose of this invention, any molecule or complex or portion thereof, that has a root mean square deviation of conserved residue backbone atoms (N, C$\alpha$, C, O) of less than about 1.75 Å, when superimposed on the relevant backbone atoms described by the reference structure coordinates of a polypeptide of the invention, is considered "structurally equivalent" to the reference molecule. That is to say, the crystal structures of those portions of the two molecules are substantially identical, within acceptable error. Alternatively, the root mean square deviation may be is less than about 1.50, 1.40, 1.25, 1.0, 0.75, 0.5 or 0.35 Å.

The term "root mean square deviation" is understood in the art and means the square root of the arithmetic mean of the squares of the deviations. It is a way to express the deviation or variation from a trend or object.

In another aspect, a scalable three-dimensional configuration of points, at least a portion of said points, and preferably all of said points, derived from structural coordinates of at least a portion of a polypeptide of the invention and having a root mean square deviation from the structure coordinates of the polypeptide of the invention of less than 1.50, 1.40, 1.25, 1.0, 0.75, 0.5 or 0.35 Å is provided. In certain embodiments, the portion of a polypeptide of the invention is 25%, 33%, 50%, 66%, 75%, 85%, 90% or 95% or more of the amino acid residues contained in the polypeptide.

In another aspect, a molecule or complex including a druggable region of a polypeptide of the invention is provided, the druggable region being defined by a set of points having a root mean square deviation of less than about 1.75 Å from the structural coordinates for points representing (a) the backbone atoms of the amino acids contained in a druggable region of a polypeptide of the invention, (b) the side chain atoms (and optionally the C$\alpha$ atoms) of the amino acids contained in such druggable region, or (c) all the atoms of the amino acids contained in such druggable region. In certain embodiments, only a portion of the amino acids of a druggable region may be included in the set of points, such as 25%, 33%, 50%, 66%, 75%, 85%, 90% or 95% or more of the amino acid residues contained in the druggable region. In certain embodiments, the root mean square deviation may be less than 1.50, 1.40, 1.25, 1.0, 0.75, 0.5, or 0.35 Å. In still other embodiments, instead of a druggable region, a stable domain, fragment or structural motif is used in place of a druggable region.

(iv) Machine Displays and Machine Readable Storage Media

Machine-readable storage media are provided, including a data storage material encoded with machine readable data which, when using a machine programmed with instructions for using said data, displays a graphical three-dimensional representation of any of the molecules or complexes, or portions, thereof, of this invention. In another embodiment, the graphical three-dimensional representation of such molecule, complex or portion thereof includes the root mean square deviation of certain atoms of such molecule by a specified amount, such as the backbone atoms by less than 0.8 Å. In another embodiment, a structural equivalent of such molecule, complex, or portion thereof, may be displayed. In another embodiment, the portion may include a druggable region of the polypeptide of the invention.

According to one embodiment, a computer for determining at least a portion of the structure coordinates corresponding to x-ray diffraction data obtained from a molecule or complex is provided, wherein said computer includes: (a) a machine-readable data storage medium comprising a data storage material encoded with machine-readable data, wherein said data comprises at least a portion of the structural coordinates of a polypeptide of the invention; (b) a machine-readable data storage medium comprising a data storage material encoded with machine-readable data, wherein said data comprises x-ray diffraction data from said molecule or complex; (c) a working memory for storing instructions for processing said machine-readable data of (a) and (b); (d) a central-processing unit coupled to said working memory and to said machine-readable data storage medium of (a) and (b) for performing a Fourier transform of the machine readable data of (a) and for processing said machine readable data of (b) into structure coordinates; and (e) a display coupled to said central-processing unit for displaying said structure coordinates of said molecule or complex. In certain embodiments, the structural coordinates displayed are structurally equivalent to the structural coordinates of a polypeptide of the invention.

In an alternative embodiment, the machine-readable data storage medium includes a data storage material encoded with a first set of machine readable data which includes the Fourier transform of the structure coordinates of a polypeptide of the invention or a portion thereof, and which, when using a machine programmed with instructions for using said data, can be combined with a second set of machine readable data including the x-ray diffraction pattern of a molecule or complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, touch screens, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of an active site of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

In one embodiment, computer readable storage media comprising structural data are provided, wherein the data include the identity and three-dimensional coordinates of a polypeptide of the invention or portion thereof. In another aspect, a database comprising the identity and three-dimensional coordinates of a polypeptide of the invention or a portion thereof is provided, for example, a database comprising a portion or all of the atomic coordinates of a polypeptide of the invention or portion thereof.

(v) Structurally Similar Molecules and Complexes

Structural coordinates for a polypeptide of the invention can be used to aid in obtaining structural information about another molecule or complex. This method of the invention allows determination of at least a portion of the three-dimensional structure of molecules or molecular complexes which contain one or more structural features that are similar to structural features of a polypeptide of the invention. Similar structural features can include, for example, regions of amino acid identity, conserved active site or binding site motifs, and similarly arranged secondary structural elements (e.g., α helices and β sheets). Many of the methods described above for determining the structure of a polypeptide of the invention may be used for this purpose as well.

As used herein, "structural homolog" is a polypeptide that contains one or more amino acid substitutions, deletions, additions, or rearrangements with respect to the amino acid sequence of SEQ ID NO: 2 or other polypeptides of the invention, but that, when folded into its native conformation, exhibits or is reasonably expected to exhibit at least a portion of the tertiary (three-dimensional) structure of the polypeptide encoded by SEQ ID NO: 2 or such other polypeptide of the invention. For example, structurally homologous molecules can contain deletions or additions of one or more contiguous or noncontiguous amino acids, such as a loop or a domain. Structurally homologous molecules also include modified polypeptide molecules that have been chemically or enzymatically derivatized at one or more constituent amino acids, including side chain modifications, backbone modifications, and N- and C-terminal modifications including acetylation, hydroxylation, methylation, amidation, and the attachment of carbohydrate or lipid moieties, cofactors, and the like.

By using molecular replacement, all or part of the structure coordinates of a polypeptide of the invention can be used to determine the structure of a crystallized molecule or complex whose structure is unknown more quickly and efficiently than attempting to determine such information ab initio. For example, in one embodiment this invention provides a method of utilizing molecular replacement to obtain structural information about a molecule or complex whose structure is unknown including: (a) crystallizing the molecule or complex of unknown structure; (b) generating an x-ray diffraction pattern from said crystallized molecule or complex; and (c) applying at least a portion of the structure coordinates for a polypeptide of the invention to the x-ray diffraction pattern to generate a three-dimensional electron density map of the molecule or complex whose structure is unknown.

In another aspect, methods are provided for generating a preliminary model of a molecule or complex whose structure coordinates are unknown, by orienting and positioning the relevant portion of a polypeptide of the invention within the unit cell of the crystal of the unknown molecule or complex so as best to account for the observed x-ray diffraction pattern of the crystal of the molecule or complex whose structure is unknown.

Structural information about a portion of any crystallized molecule or complex that is sufficiently structurally similar to a portion of a polypeptide of the invention may be resolved by this method. In addition to a molecule that shares one or more structural features with a polypeptide of the invention, a molecule that has similar bioactivity, such as the same catalytic activity, substrate specificity or ligand binding activity as a polypeptide of the invention, may also be sufficiently structurally similar to a polypeptide of the invention to permit use of the structure coordinates for a polypeptide of the invention to solve its crystal structure.

In another aspect, the method of molecular replacement is utilized to obtain structural information about a complex containing a polypeptide of the invention, such as a complex between a modulator and a polypeptide of the invention (or a domain, fragment, ortholog, homolog etc. thereof). In certain instances, the complex includes a polypeptide of the invention (or a domain, fragment, ortholog, homolog etc. thereof) co-complexed with a modulator. For example, in one embodiment, the present invention contemplates a method for making a crystallized complex comprising a polypeptide of the invention, or a fragment thereof, and a compound having a molecular weight of less than 5 kDa, the method comprising: (a) crystallizing a polypeptide of the invention such that the crystals will diffract x-rays to a resolution of 3.5 Å or better; and (b) soaking the crystal in a solution comprising the compound having a molecular weight of less than 5 kDa, thereby producing a crystallized complex comprising the polypeptide and the compound.

Using homology modeling, a computer model of a structural homolog or other polypeptide can be built or refined without crystallizing the molecule. For example, in another aspect, the present invention provides a computer-assisted method for homology modeling a structural homolog of a polypeptide of the invention including: aligning the amino acid sequence of a known or suspected structural homolog with the amino acid sequence of a polypeptide of the invention and incorporating the sequence of the homolog into a model of a polypeptide of the invention derived from atomic structure coordinates to yield a preliminary model of the homolog; subjecting the preliminary model to energy minimization to yield an energy minimized model; remodeling regions of the energy minimized model where stereochemistry restraints are violated to yield a final model of the homolog.

In another embodiment, methods are provided for determining the crystal structure of a homolog of a polypeptide having SEQ ID NO: 2, or equivalent thereof, the method comprising: (a) providing the three dimensional structure of a crystallized polypeptide having SEQ ID NO: 2, or a fragment thereof; (b) obtaining crystals of a homologous polypeptide comprising an amino acid sequence that is at least 80% identical to the amino acid sequence set forth in SEQ ID NO: 2 such that the three dimensional structure of the crystallized homologous polypeptide may be determined to a resolution of 3.5 Å or better; and (c) determining the three dimensional structure of the crystallized homologous polypeptide by x-ray crystallography based on the atomic coordinates of the three dimensional structure provided in step (a). In certain instances of the foregoing method, the atomic coordinates for the homologous polypeptide have a root mean square deviation from the backbone atoms of the polypeptide having SEQ ID NO: 2, or a fragment thereof, of not more than 1.5 Å for all backbone atoms shared in common with the homologous polypeptide and the polypeptide having SEQ ID NO: 2, or a fragment thereof (vi) NMR Analysis Using X-ray Structural Data In another aspect, the structural coordinates of a known crystal structure may be applied to nuclear magnetic resonance data to determine the three dimensional structures of polypeptides with uncharacterized or incompletely characterized structure. (See for example, Wuthrich, 1986, John Wiley and Sons, New York: 176-199; Pflugrath et al., 1986, J. Molecular Biology 189: 383-386; Kline et al., 1986 J. Molecular Biology 189:377-382). While the secondary structure of a polypeptide may often be determined by NMR data, the spatial connections between individual pieces of secondary structure are not as readily determined. The structural coordinates of a polypeptide defined by x-ray crystallography can guide the NMR spectroscopist to an understanding of the spatial interactions between secondary structural elements in a polypeptide of related structure. Information on spatial interactions between secondary structural elements can greatly simplify NOE data from two-dimensional NMR experiments. In addition, applying the structural coordinates after the determination of secondary structure by NMR techniques simplifies the assignment of NOE's relating to particular amino acids in the polypeptide sequence.

In an embodiment, methods are provided for determining three dimensional structures of polypeptides with unknown structures, by applying the structural coordinates of a crystal of the present invention to nuclear magnetic resonance data of the unknown structure. This method comprises the steps of: (a) determining the secondary structure of an unknown structure using NMR data; and (b) simplifying the assignment of through-space interactions of amino acids. The term "through-space interactions" defines the orientation of the secondary structural elements in the three dimensional structure and the distances between amino acids from different portions of the amino acid sequence. The term "assignment" defines a method of analyzing NMR data and identifying which amino acids give rise to signals in the NMR spectrum.

For all of this section on x-ray crystallography, see also Brooks et al. (1983) *J Comput Chem* 4:187-217; Weiner et al (1981) *J Comput. Chem.* 106: 765; Eisenfield et al. (1991) *Am J Physiol* 261:C376-386; Lybrand (1991) *J Pharm Belg* 46:49-54; Froimowitz (1990) *Biotechniques* 8:640-644; Burbam et al. (1990) *Proteins* 7:99-111; Pedersen (1985) *Environ Health Perspect* 61:185-190; and Kini et al. (1991) *J Biomol Struct Dyn* 9:475-488; Ryckaert et al. (1977) *J Comput Phys* 23:327; Van Gunsteren et al. (1977) *Mol Phys* 34:1311; Anderson (1983) *J Comput Phys* 52:24; J. Mol. Biol. 48: 442-453, 1970; Dayhoff et al., Meth. Enzymol. 91: 524-545, 1983; Henikoff and Henikoff, Proc. Nat. Acad. Sci. USA 89: 10915-10919, 1992; J. Mol. Biol. 233: 716-738, 1993; Methods in Enzymology, Volume 276, Macromolecular crystallography, Part A, ISBN 0-12-182177-3 and Volume 277, Macromolecular crystallography, Part B, ISBN 0-12-182178-1, Eds. Charles W. Carter, Jr. and Robert M. Sweet (1997), Academic Press, San Diego; Pfuetzner, et al., J. Biol. Chem. 272: 430-434 (1997).

6. Interacting Proteins

Methods are provided for isolating specific protein interactors of a polypeptide of the invention, and complexes comprising a polypeptide of the invention and one or more interacting proteins. In one aspect, the present invention contemplates an isolated protein complex comprising a polypeptide of the invention and at least one protein that interacts with the polypeptide of the invention. The protein may be naturally-occurring. The interacting protein may be of *F. tularensis* origin. Alternatively, the interacting protein may be of mammalian origin or human origin. Either the polypeptide of the invention or the interacting protein or both may be a fusion protein.

A method for identifying a protein capable of interacting with a polypeptide of the invention or a fragment thereof may comprise: (a) exposing a sample to a solid substrate coupled to a polypeptide of the invention or a fragment thereof under conditions which promote protein-protein interactions; (b) washing the solid substrate so as to remove any polypeptides interacting non-specifically with the polypeptide or fragment; (c) eluting the polypeptides which specifically interact with the polypeptide or fragment; and (d) identifying the interacting protein. The sample may be an extract of *F. tularensis*, a mammalian cell extract, a human cell extract, a purified protein (or a fragment thereof), or a mixture of purified proteins (or fragments thereof). The interacting protein may be identified by a number of methods, including mass spectrometry or protein sequencing.

In another aspect, ta method for identifying a protein capable of interacting with a polypeptide of present invention or a fragment thereof may comprise: (a) subjecting a sample to protein-affinity chromatography on multiple columns, the columns having a polypeptide of the invention or a fragment thereof coupled to the column matrix in varying concentrations, and eluting bound components of the extract from the columns; (b) separating the components to isolate a polypeptide capable of interacting with the polypeptide or fragment; and (c) analyzing the interacting protein by mass spectrometry to identify the interacting protein. In certain instances, the foregoing method will use polyacrylamide gel electrophoresis without SDS.

In another aspect, methods for identifying a protein capable of interacting with a polypeptide of the invention may comprise: (a) subjecting a cellular extract or extracellular fluid to protein-affinity chromatography on multiple columns, the columns having a polypeptide of the invention or a fragment thereof coupled to the column matrix in varying concentrations, and eluting bound components of the extract from the columns; (b) gel-separating the components to isolate an interacting protein; wherein the interacting protein is observed to vary in amount in direct relation to the concentration of coupled polypeptide or fragment; (c) digesting the interacting protein to give corresponding peptides; (d) analyzing the peptides by MALDI-TOF mass spectrometry or post source decay to determine the peptide masses; and (d) performing correlative database searches with the peptide, or peptide fragment, masses, whereby the interacting protein is identified based on the masses of the peptides or peptide fragments. The foregoing method may include the further step of including the identifies of any interacting proteins into a relational database.

In another aspect, methods for identifying modulators of a protein complex may comprise: (a) contacting a protein complex comprising a polypeptide of the invention and an interacting protein with one or more test compounds; and (b) determining the effect of the test compound on (i) the activity of the protein complex, (ii) the amount of the protein complex, (iii) the stability of the protein complex, (iv) the conformation of the protein complex, (v) the activity of at least one polypeptide included in the protein complex, (vi) the conformation of at least one polypeptide included in the protein complex, (vii) the intracellular localization of the protein complex or a component thereof, (viii) the transcription level of a gene dependent on the complex, and/or (ix) the level of second messenger levels in a cell; thereby identifying modulators of the protein complex. The foregoing method may be carried out in vitro or in vivo as appropriate.

Typically, it will be desirable to immobilize a polypeptide of the invention to facilitate separation of complexes comprising a polypeptide of the invention from uncomplexed forms of the interacting proteins, as well as to accommodate automation of the assay. The polypeptide of the invention, or ligand, may be immobilized onto a solid support (e.g., column matrix, microtiter plate, slide, etc.). In certain embodiments, the ligand may be purified. In certain instances, a fusion protein may be provided which adds a domain that permits the ligand to be bound to a support.

In various in vitro embodiments, the set of proteins engaged in a protein-protein interaction comprises a cell extract, a clarified cell extract, or a reconstituted protein mixture of at least semi-purified proteins. By semi-purified, it is meant that the proteins utilized in the reconstituted mixture have been previously separated from other cellular or viral proteins. For instance, in contrast to cell lysates, the proteins involved in a protein-protein interaction are present in the mixture to at least about 50% purity relative to all other proteins in the mixture, and more preferably are present in greater, even 90-95%, purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure activity resulting from the given protein-protein interaction.

Complex formation involving a polypeptide of the invention and another component polypeptide or a substrate polypeptide, may be detected by a variety of techniques. For instance, modulation in the formation of complexes can be quantitated using, for example, detectably labeled proteins (e.g. radiolabeled, fluorescently labeled, or enzymatically labeled), by immunoassay, or by chromatographic detection.

Assays are also provided for identifying molecules which are modulators of a protein-protein interaction involving a polypeptide of the invention, or are a modulator of the role of the complex comprising a polypeptide of the invention in the infectivity or pathogenicity of $F.$ $tularensis$. In one embodiment, the assay detects agents which inhibit formation or stabilization of a protein complex comprising a polypeptide of the invention and one or more additional proteins. In another embodiment, the assay detects agents which modulate the intrinsic biological activity of a protein complex comprising a polypeptide of the invention, such as an enzymatic activity, binding to other cellular components, cellular compartmentalization, signal transduction, and the like. Such modulators may be used, for example, in the treatment of $F.$ $tularensis$ related diseases or disorders. In certain embodiments, the compound is a mechanism based inhibitor which chemically alters one member of a protein-protein interaction involving a polypeptide of the invention and which is a specific inhibitor of that member, e.g. has an inhibition constant about 10-fold, 100-fold, or 1000-fold different compared to homologous proteins.

In one embodiment, proteins that interact with a polypeptide of the invention may be isolated using immunoprecipitation. A polypeptide of the invention may be expressed in $F.$ $tularensis$, or in a heterologous system. The cells expressing a polypeptide of the invention are then lysed under conditions which maintain protein-protein interactions, and complexes comprising a polypeptide of the invention are isolated. For example, a polypeptide of the invention may be expressed in mammalian cells, including human cells, in order to identify mammalian proteins that interact with a polypeptide of the invention and therefore may play a role in $F.$ $tularensis$ infectivity or proliferation. In one embodiment, a polypeptide of the invention is expressed in the cell type for which it is desirable to find interacting proteins. For example, a polypeptide of the invention may be expressed in $F.$ $tularensis$ in order to find $F.$ $tularensis$ derived interacting proteins.

In an alternative embodiment, a polypeptide of the invention is expressed and purified and then mixed with a potential interacting protein or mixture of proteins to identify complex formation. The potential interacting protein may be a single purified or semi-purified protein, or a mixture of proteins, including a mixture of purified or semi-purified proteins, a cell lysate, a clarified cell lysate, a semi-purified cell lysate, etc.

In certain embodiments, it may be desirable to use a tagged version of a polypeptide of the invention in order to facilitate isolation of complexes from the reaction mixture. Suitable tags for immunoprecipitation experiments include HA, myc, FLAG, HIS, GST, protein A, protein G, etc. Immunoprecipitation from a cell lysate or other protein mixture may be carried out using an antibody specific for a polypeptide of the invention or using an antibody which recognizes a tag to which a polypeptide of the invention is fused (e.g., anti-HA, anti-myc, anti-FLAG, etc.). Antibodies specific for a variety of tags are known to the skilled artisan and are commercially available from a number of sources. In the case where a polypeptide of the invention is fused to a H is, GST, or protein A/G tag, immunoprecipitation may be carried out using the appropriate affinity resin (e.g., beads functionalized with Ni, glutathione, Fc region of IgG, etc.). Test compounds which modulate a protein-protein interaction involving a polypeptide of the invention may be identified by carrying out the immunoprecipitation reaction in the presence and absence of the test agent and comparing the level and/or activity of the protein complex between the two reactions.

In another embodiment, proteins that interact with a polypeptide of the invention may be identified using affinity chromatography. Some examples of such chromatography are described in U.S. Ser. No. 09/727,812, filed Nov. 30, 2000, and the PCT Application filed Nov. 30, 2001 and entitled "Methods for Systematic Identification of Protein-Protein Interactions and other Properties", which claims priority to such U.S. application.

In one aspect, for affinity chromatography using a solid support, a polypeptide of the invention or a fragment thereof may be attached by a variety of means known to those of skill in the art. For example, the polypeptide may be coupled directly (through a covalent linkage) to commercially available pre-activated resins as described in Formosa et al., Methods in Enzymology 1991, 208, 24-45; Sopta et al, J. Biol. Chem. 1985, 260, 10353-60; Archambault et al., Proc. Natl. Acad. Sci. USA 1997, 94, 14300-5. Alternatively, the polypeptide may be tethered to the solid support through high affinity binding interactions. If the polypeptide is expressed fused to a tag, such as GST, the fusion tag can be used to anchor the polypeptide to the matrix support, for example Sepharose beads containing immobilized glutathione. Solid supports that take advantage of these tags are commercially available.

In another aspect, the support to which a polypeptide may be immobilized is a soluble support, which may facilitate certain steps performed in the methods of the present invention. For example, the soluble support may be soluble in the conditions employed to create a binding interaction between a target and the polypeptide, and then used under conditions in which it is a solid for elution of the proteins or other biological materials that bind to a polypeptide.

The concentration of the coupled polypeptide may have an affect on the sensitivity of the method. In certain embodiments, to detect interactions most efficiently, the concentration of the polypeptide bound to the matrix should be at least 10-fold higher than the $K_d$ of the interaction. Thus, the concentration of the polypeptide bound to the matrix should be highest for the detection of the weakest protein-protein interactions. However, if the concentration of the immobilized polypeptide is not as high as may be ideal, it may still be possible to observe protein-protein interactions of interest by, for example, increasing the concentration of the polypeptide or other moiety that interacts with the coupled polypeptide. The level of detection will of course vary with each different polypeptide, interactor, conditions of the assay, etc. In certain instances, the interacting protein binds to the polypeptide with a $K_d$ of about $10^{-5}$ M to about $10^{-8}$ M or $10^{-10}$ M.

In another aspect, the coupling may be done at various ratios of the polypeptide to the resin. An upper limit of the protein: resin ratio may be determined by the isoelectric point and the ionic nature of the protein, although it may be possible to achieve higher polypeptide concentrations by use of various methods.

In certain embodiments, several concentrations of the polypeptide immobilized on a solid or soluble support may be used. One advantage of using multiple concentrations, although not a requirement, is that one may be able to obtain an estimate for the strength of the protein-protein interaction that is observed in the affinity chromatography experiment. Another advantage of using multiple concentrations is that a binding curve which has the proper shape may indicate that the interaction that is observed is biologically important rather than a spurious interaction with denatured protein.

In one example of such an embodiment, a series of columns may be prepared with varying concentrations of polypeptide (mg polypeptide/mL resin volume). The number of columns employed may be between 2 to 8, 10, 12, 15, 25 or more, each with a different concentration of attached polypeptide. Larger numbers of columns may be used if appropriate for the polypeptide being examined, and multiple columns may be used with the same concentration as any methods may require. In certain embodiments, 4 to 6 columns are prepared with varying concentrations of polypeptide. In another aspect of this embodiment, two control columns may be prepared: one that contains no polypeptide and a second that contains the highest concentration of polypeptide but is not treated with extract. After elution of the columns and separation of the eluent components (by one of the methods described below), it may be possible to distinguish the interacting proteins (if any) from the non-specific bound proteins as follows. The concentration of the interacting proteins, as determined by the intensity of the band on the gel, will increase proportionally to the increase in polypeptide concentration but will be missing from the second control column. This allows for the identification of unknown interacting proteins.

The methods may be used for small-scale analysis. A variety of column sizes, types, and geometries may be used. In addition, other vessel shapes and sizes having a smaller scale than is usually found in laboratory experiments may be used as well, including a plurality of wells in a plate. For high throughput analysis, it is advantageous to use small volumes, from about 20, 30, 50, 80 or 100 µL. Larger or small volumes may be used, as necessary, and it may be possible to achieve high throughput analysis using them. The entire affinity chromatography procedure may be automated by assembling the micro-columns into an array (e.g. with 96 micro-column arrays).

A variety of materials may be used as the source of potential interacting proteins. In one embodiment, a cellular extract or extracellular fluid may be used. The choice of starting material for the extract may be based upon the cell or tissue type or type of fluid that would be expected to contain proteins that interact with the target protein. Micro-organisms or other organisms are grown in a medium that is appropriate for that organism and can be grown in specific conditions to promote the expression of proteins that may interact with the target protein. Exemplary starting material that may be used to make a suitable extract are: 1) one or more types of tissue derived from an animal, plant, or other multi-cellular organism, 2) cells grown in tissue culture that were derived from an animal or human, plant or other source, 3) micro-organisms grown in suspension or non-suspension cultures, 4) virus-infected cells, 5) purified organelles (including, but not restricted to nuclei, mitochondria, membranes, Golgi, endoplasmic reticulum, lysosomes, or peroxisomes) prepared by differential centrifugation or another procedure from animal, plant or other kinds of eukaryotic cells, 6) serum or other bodily fluids including, but not limited to, blood, urine, semen, synovial fluid, cerebrospinal fluid, amniotic fluid, lymphatic fluid or interstitial fluid. In other embodiments, a total cell extract may not be the optimal source of interacting proteins. For example, if the ligand is known to act in the nucleus, a nuclear extract can provide a 10-fold enrichment of proteins that are likely to interact with the ligand. In addition, proteins that are present in the extract in low concentrations may be enriched using another chromatographic method to fractionate the extract before screening various pools for an interacting protein.

Extracts are prepared by methods known to those of skill in the art. The extracts may be prepared at a low temperature (e.g., 4° C.) in order to retard denaturation or degradation of proteins in the extract. The pH of the extract may be adjusted to be appropriate for the body fluid or tissue, cellular, or organellar source that is used for the procedure (e.g. pH 7-8 for cytosolic extracts from mammals, but low pH for lysosomal extracts). The concentration of chaotropic or non-chaotropic salts in the extracting solution may be adjusted so as to extract the appropriate sets of proteins for the procedure. Glycerol may be added to the extract, as it aids in maintaining the stability of many proteins and also reduces background non-specific binding. Both the lysis buffer and column buffer may contain protease inhibitors to minimize proteolytic degradation of proteins in the extract and to protect the polypeptide. Appropriate co-factors that could potentially interact with the interacting proteins may be added to the extracting solution. One or more nucleases or another reagent may be added to the extract, if appropriate, to prevent protein-protein interactions that are mediated by nucleic acids. Appropriate detergents or other agents may be added to the solution, if desired, to extract membrane proteins from the cells or tissue. A reducing agent (e.g. dithiothreitol or 2-mercaptoethanol or glutathione or other agent) may be added. Trace metals or a chelating agent may be added, if desired, to the extracting solution.

Usually, the extract is centrifuged in a centrifuge or ultracentrifuge or filtered to provide a clarified supernatant solution. This supernatant solution may be dialyzed using dialysis tubing, or another kind of device that is standard in the art, against a solution that is similar to, but may not be identical with, the solution that was used to make the extract. The extract is clarified by centrifugation or filtration again immediately prior to its use in affinity chromatography.

In some cases, the crude lysate will contain small molecules that can interfere with the affinity chromatography. This can be remedied by precipitating proteins with ammonium sulfate, centrifugation of the precipitate, and re-suspending the proteins in the affinity column buffer followed by dialysis. An additional centrifugation of the sample may be needed to remove any particulate matter prior to application to the affinity columns.

The amount of cell extract applied to the column may be important for any embodiment. If too little extract is applied to the column and the interacting protein is present at low concentration, the level of interacting protein retained by the column may be difficult to detect. Conversely, if too much extract is applied to the column, protein may precipitate on the column or competition by abundant interacting proteins for the limited amount of protein ligand may result in a difficulty in detecting minor species.

The columns functionalized with a polypeptide of the invention are loaded with protein extract from an appropriate source that has been dialyzed against a buffer that is consistent with the nature of the expected interaction. The pH, salt concentrations and the presence or absence of reducing and chelating agents, trace metals, detergents, and co-factors may be adjusted according to the nature of the expected interaction. Most commonly, the pH and the ionic strength are chosen so as to be close to physiological for the source of the extract. The extract is most commonly loaded under gravity onto the columns at a flow rate of about 4-6 column volumes per hour, but this flow rate can be adjusted for particular circumstances in an automated procedure.

The volume of the extract that is loaded on the columns can be varied but is most commonly equivalent to about 5 to 10 column volumes. When large volumes of extract are loaded on the columns, there is often an improvement in the signal-to-noise ratio because more protein from the extract is available to bind to the protein ligand, whereas the background binding of proteins from the extract to the solid support saturates with low amounts of extract.

A control column may be included that contains the highest concentration of protein ligand, but buffer rather than extract is loaded onto this column. The elutions (eluates) from this column will contain polypeptide that failed to be attached to the column in a covalent manner, but no proteins that are derived from the extract.

The columns may be washed with a buffer appropriate to the nature of the interaction being analyzed, usually, but not necessarily, the same as the loading buffer. An elution buffer with an appropriate pH, glycerol, and the presence or absence of reducing agent, chelating agent, cofactors, and detergents are all important considerations. The columns may be washed with anywhere from about 5 to 20 column volumes of each wash buffer to eliminate unbound proteins from the natural extract. The flow rate of the wash is usually adjusted to about 4 to 6 column volumes per hour by using gravity or an automated procedure, but other flow rates are possible in specific circumstances.

In order to elute the proteins that have been retained by the column, the interactions between the extract proteins and the column ligand should be disrupted. This is performed by eluting the column with a solution of salt or detergent. Retention of activity by the eluted proteins may require the presence of glycerol and a buffer of appropriate pH, as well as proper choices of ionic strength and the presence or absence of appropriate reducing agent, chelating agent, trace metals, cofactors, detergents, chaotropic agents, and other reagents. If physical identification of the bound proteins is the objective, the elution may be performed sequentially, first with buffer of high ionic strength and then with buffer containing a protein denaturant, most commonly, but not restricted to sodium dodecyl sulfate (SDS), urea, or guanidine hydrochloride. In certain instances, the column is eluted with a protein denaturant, particularly SDS, for example as a 1% SDS solution. Using only the SDS wash, and omitting the salt wash, may result in SDS-gels that have higher resolution (sharper bands with less smearing). Also, using only the SDS wash results in half as many samples to analyze. The volume of the eluting solution may be varied but is normally about 2 to 4 column volumes. For 20 mL columns, the flow rate of the eluting procedures are most commonly about 4 to 6 column volumes per hour, under gravity, but can be varied in an automated procedure.

The proteins from the extract that were bound to and are eluted from the affinity columns may be most easily resolved for identification by an electrophoresis procedure, but this procedure may be modified, replaced by another suitable method, or omitted. Any of the denaturing or non-denaturing electrophoresis procedures that are standard in the art may be used for this purpose, including SDS-PAGE, gradient gels, capillary electrophoresis, and two-dimensional gels with isoelectric focusing in the first dimension and SDS-PAGE in the second. Typically, the individual components in the column eluent are separated by polyacrylamide gel electrophoresis.

After electrophoresis, protein bands or spots may be visualized using any number of methods know to those of skill in the art, including staining techniques such as Coomassie blue or silver staining, or some other agent that is standard in the art. Alternatively, autoradiography can be used for visualizing proteins isolated from organisms cultured on media containing a radioactive label, for example $^{35}SO_4^{2-}$ or $^{35}[S]$methionine, that is incorporated into the proteins. The use of radioactively labeled extract allows a distinction to be made between extract proteins that were retained by the column and proteolytic fragments of the ligand that may be released from the column.

Protein bands that are derived from the extract (i.e. it did not elute from the control column that was not loaded with protein from the extract) and bound to an experimental column that contained polypeptide covalently attached to the solid support, and did not bind to a control column that did not contain any polypeptide, may be excised from the stained electrophoretic gel and further characterized.

To identify the protein interactor by mass spectrometry, it may be desirable to reduce the disulfide bonds of the protein followed by alkylation of the free thiols prior to digestion of the protein with protease. The reduction may be performed by treatment of the gel slice with a reducing agent, for example with dithiothreitol, whereupon, the protein is alkylated by treating the gel slice with a suitable alkylating agent, for example iodoacetamide.

Prior to analysis by mass spectrometry, the protein may be chemically or enzymatically digested. The protein sample in the gel slice may be subjected to in-gel digestion. Shevchenko A. et al., Mass Spectrometric Sequencing of Proteins from Silver Stained Polyacrylamide Gels. Analytical Chemistry 1996, 58, 850-858. One method of digestion is by treatment with the enzyme trypsin. The resulting peptides are extracted from the gel slice into a buffer.

The peptide fragments may be purified, for example by use of chromatography. A solid support that differentially binds the peptides and not the other compounds derived from the gel slice, the protease reaction or the peptide extract may be used. The peptides may be eluted from the solid support into a small volume of a solution that is compatible with mass spectrometry (e.g. 50% acetonitrile/0.1% trifluoroacetic acid).

The preparation of a protein sample from a gel slice that is suitable for mass spectrometry may also be done by an automated procedure.

Peptide samples derived from gel slices may be analyzed by any one of a variety of techniques in mass spectrometry as further described above. This technique may be used to assign function to an unknown protein based upon the known function of the interacting protein in the same or a homologous/orthologous organism.

Eluates from the affinity chromatography columns may also be analyzed directly without resolution by electrophoretic methods, by proteolytic digestion with a protease in solution, followed by applying the proteolytic digestion products to a reverse phase column and eluting the peptides from the column.

In yet another embodiment, proteins that interact with a polypeptide of the invention may be identified using an interaction trap assay (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696).

In another embodiment, methods may make use of chimeric genes which express hybrid proteins. To illustrate, a first hybrid gene comprises the coding sequence for a DNA-binding domain of a transcriptional activator fused in frame to the coding sequence for a "bait" protein, e.g., a polypeptide of the invention of sufficient length to bind to a potential interacting protein. The second hybrid protein encodes a transcriptional activation domain fused in frame to a gene encoding a "fish" protein, e.g., a potential interacting protein of sufficient length to interact with a polypeptide of the invention portion of the bait fusion protein. If the bait and fish proteins are able to interact, e.g., form a protein-protein interaction, they bring into close proximity the two domains of the transcriptional activator. This proximity causes transcription of a reporter gene which is operably linked to a transcriptional regulatory site responsive to the transcriptional activator, and expression of the reporter gene can be detected and used to score for the interaction of the bait and fish proteins.

Methods may include providing a host cell, typically a yeast cell, e.g., Kluyverei lactis, Schizosaccharomyces pombe, Ustilago maydis, Saccharomyces cerevisiae, Neurospora crassa, Aspergillus niger, Aspergillus nidulans, Pichia pastoris, Candida tropicalis, and Hansenula polymorpha, though most preferably S. cerevisiae or S. pombe. The host cell contains a reporter gene having a binding site for the DNA-binding domain of a transcriptional activator used in the bait protein, such that the reporter gene expresses a detectable gene product when the gene is transcriptionally activated. The first chimeric gene may be present in a chromosome of the host cell, or as part of an expression vector.

The host cell also contains a first chimeric gene which is capable of being expressed in the host cell. The gene encodes a chimeric protein, which comprises (a) a DNA-binding domain that recognizes the responsive element on the reporter gene in the host cell, and (b) a bait protein (e.g., a polypeptide of the invention).

A second chimeric gene is also provided which is capable of being expressed in the host cell, and encodes the "fish" fusion protein. In one embodiment, both the first and the second chimeric genes are introduced into the host cell in the form of plasmids. Preferably, however, the first chimeric gene is present in a chromosome of the host cell and the second chimeric gene is introduced into the host cell as part of a plasmid.

The DNA-binding domain of the first hybrid protein and the transcriptional activation domain of the second hybrid protein may be derived from transcriptional activators having separable DNA-binding and transcriptional activation domains. For instance, these separate DNA-binding and transcriptional activation domains are known to be found in the yeast GAL4 protein, and are known to be found in the yeast GCN4 and ADR1 proteins. Many other proteins involved in transcription also have separable binding and transcriptional activation domains which make them useful for the present invention, and include, for example, the LexA and VP16 proteins. It will be understood that other (substantially) transcriptionally-inert DNA-binding domains may be used in the subject constructs; such as domains of ACE1, λcI, lac repressor, jun or fos. In another embodiment, the DNA-binding domain and the transcriptional activation domain may be from different proteins. The use of a LexA DNA binding domain provides certain advantages. For example, in yeast, the LexA moiety contains no activation function and has no known affect on transcription of yeast genes. In addition, use of LexA allows control over the sensitivity of the assay to the level of interaction (see, for example, the Brent et al. PCT publication WO94/10300).

In certain embodiments, any enzymatic activity associated with the bait or fish proteins is inactivated, e.g., dominant negative or other mutants of a protein-protein interaction component can be used.

Continuing with the illustrative example, a polypeptide of the invention-mediated interaction, if any, between the bait and fish fusion proteins in the host cell, causes the activation domain to activate transcription of the reporter gene. The method is carried out by introducing the first chimeric gene and the second chimeric gene into the host cell, and subjecting that cell to conditions under which the bait and fish fusion proteins and are expressed in sufficient quantity for the reporter gene to be activated. The formation of a protein complex containing a polypeptide of the invention results in a detectable signal produced by the expression of the reporter gene.

In still further embodiments, the protein-protein interaction of interest is generated in whole cells, taking advantage of cell culture techniques to support the subject assay. For example, the protein-protein interaction of interest can be constituted in a prokaryotic or eukaryotic cell culture system. Advantages to generating the protein complex in an intact cell includes the ability to screen for inhibitors of the level or activity of the complex which are functional in an environment more closely approximating that which therapeutic use of the inhibitor would require, including the ability of the agent to gain entry into the cell. Furthermore, certain of the in vivo embodiments of the assay are amenable to high throughput analysis of candidate agents.

The components of the protein complex comprising a polypeptide of the invention can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein. Moreover, in the whole cell embodiments of the subject assay, the reporter gene construct can provide, upon expression, a selectable marker. Such embodiments of the subject assay are particularly amenable to high through-put analysis in that proliferation of the cell can provide a simple measure of the protein-protein interaction.

The amount of transcription from the reporter gene may be measured using any method known to those of skill in the art to be suitable. For example, specific mRNA expression may be detected using Northern blots or specific protein product may be identified by a characteristic stain, western blots or an intrinsic activity. In certain embodiments, the product of the reporter gene is detected by an intrinsic activity associated with that product. For instance, the reporter gene may encode a gene product that, by enzymatic activity, gives rise to a detection signal based on color, fluorescence, or luminescence.

The interaction trap assay of the invention may also be used to identify test agents capable of modulating formation of a complex comprising a polypeptide of the invention. In general, the amount of expression from the reporter gene in the presence of the test compound is compared to the amount of expression in the same cell in the absence of the test compound. Alternatively, the amount of expression from the reporter gene in the presence of the test compound may be compared with the amount of transcription in a substantially identical cell that lacks a component of the protein-protein interaction involving a polypeptide of the invention.

7. Antibodies

Another aspect pertains to antibodies specifically reactive with a polypeptide of the invention. For example, by using peptides based on a polypeptide of the invention, e.g., having an amino acid sequence of SEQ ID NO: 2 or an immunogenic fragment thereof, antisera or monoclonal antibodies may be made using standard methods. An exemplary immunogenic fragment may contain eight, ten or more consecutive amino acid residues of SEQ ID NO: 2.

The term "antibody" as used herein is intended to include fragments thereof which are also specifically reactive with a polypeptide of the invention. Antibodies can be fragmented using conventional techniques and the fragments screened for utility in the same manner as is suitable for whole antibodies. For example, F(ab')$_2$ fragments can be generated by treating antibody with pepsin. The resulting F(ab')$_2$ fragment can be treated to reduce disulfide bridges to produce Fab' fragments. The antibody of the present invention is further intended to include bispecific and chimeric molecules, as well as single chain (scFv) antibodies. Also included are trimeric antibodies, humanized antibodies, human antibodies, and single chain antibodies. All of these modified forms of antibodies as well as fragments of antibodies are intended to be included in the term "antibody".

In one aspect, a purified antibody is provided that binds specifically to a polypeptide of the invention and which does not substantially cross-react with a protein which is less than about 80%, or less than about 90%, identical to SEQ ID NO: 2. In another aspect, the present invention contemplates an array comprising a substrate having a plurality of address, wherein at least one of the addresses has disposed thereon a purified antibody that binds specifically to a polypeptide of the invention.

Antibodies may be elicited by methods known in the art. For example, a mammal such as a mouse, a hamster or rabbit may be immunized with an immunogenic form of a polypeptide of the invention (e.g., an antigenic fragment which is capable of eliciting an antibody response). Alternatively, immunization may occur by using a nucleic acid of the acid, which presumably in vivo expresses the polypeptide of the invention giving rise to the immunogenic response observed. Techniques for conferring immunogenicity on a protein or peptide include conjugation to carriers or other techniques well known in the art. For instance, a peptidyl portion of a polypeptide of the invention may be administered in the presence of adjuvant. The progress of immunization may be monitored by detection of antibody titers in plasma or serum. Standard ELISA or other immunoassays may be used with the immunogen as antigen to assess the levels of antibodies.

Following immunization, antisera reactive with a polypeptide of the invention may be obtained and, if desired, polyclonal antibodies isolated from the serum. To produce monoclonal antibodies, antibody producing cells (lymphocytes) may be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) *Nature,* 256: 495-497), as the human B cell hybridoma technique (Kozbar et al., (1983) *Immunology Today,* 4: 72), and the EBV-hybridoma technique to produce human monoclonal antibodies (Cole et al., (1985) *Monoclonal Antibodies and Cancer Therapy*, Alan R. Liss, Inc. pp. 77-96). Hybridoma cells can be screened immunochemically for production of antibodies specifically reactive with the polypeptides of the invention and the monoclonal antibodies isolated.

Antibodies directed against the polypeptides of the invention can be used to selectively block the action of the polypeptides of the invention. Antibodies against a polypeptide of the invention may be employed to treat infections, particularly bacterial infections and diseases. For example, methods for treating a subject suffering from a *F. tularensis* related disease or disorder may comprise administering to an animal having the condition a therapeutically effective amount of a purified antibody that binds specifically to a polypeptide of the invention. In another example, methods for inhibiting SEQ ID NO: 2 dependent growth or infectivity of *F. tularensis* may comprise contacting *F. tularensis* with a purified antibody that binds specifically to a polypeptide of the invention.

In one embodiment, antibodies reactive with a polypeptide of the invention are used in the immunological screening of cDNA libraries constructed in expression vectors, such as λgt11, λgt18-23, λZAP, and λORF8. Messenger libraries of this type, having coding sequences inserted in the correct reading frame and orientation, can produce fusion proteins. For instance, λgt11 will produce fusion proteins whose amino termini consist of β-galactosidase amino acid sequences and whose carboxy termini consist of a foreign polypeptide. Antigenic epitopes of a polypeptide of the invention can then be detected with antibodies, as, for example, reacting nitrocellulose filters lifted from phage infected bacterial plates with an antibody specific for a polypeptide of the invention. Phage scored by this assay can then be isolated from the infected plate. Thus, homologs of a polypeptide of the invention can be detected and cloned from other sources.

Antibodies may be employed to isolate or to identify clones expressing the polypeptides to purify the polypeptides by affinity chromatography.

In other embodiments, the polypeptides of the invention may be modified so as to increase their immunogenicity. For example, a polypeptide, such as an antigenically or immunologically equivalent derivative, may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

In other embodiments, the antibodies of the invention, or variants thereof, are modified to make them less immunogenic when administered to a subject. For example, if the subject is human, the antibody may be "humanized"; where the complimentarily determining region(s) of the hybridoma-derived antibody has been transplanted into a human monoclonal antibody, for example as described in Jones, P. et al. (1986), Nature 321, 522-525 or Tempest et al. (1991) Biotechnology 9, 266-273. Also, transgenic mice, or other mammals, may be used to express humanized antibodies. Such humanization may be partial or complete.

The use of a nucleic acid of the invention in genetic immunization may employ a suitable delivery method such as direct injection of plasmid DNA into muscles (Wolff et al., Hum Mol Genet. 1992, 1:363, Manthorpe et al., Hum. Gene Ther. 1963:4, 419), delivery of DNA complexed with specific protein carriers (Wu et al., J Biol. Chem. 1989: 264,16985), coprecipitation of DNA with calcium phosphate (Benvenisty & Reshef, PNAS USA, 1986:83,9551), encapsulation of DNA in various forms of liposomes (Kaneda et al., Science 1989:243,375), particle bombardment (Tang et al., Nature 1992, 356:152, Eisenbraun et al., DNA Cell Biol 1993, 12:791) and in vivo infection using cloned retroviral vectors (Seeger et al., PNAS USA 1984:81,5849).

8. Diagnostic Assays

Methods for detecting the presence of F. tularensis in a biological sample are provided. Detection of F. tularensis in a subject, particularly a mammal, and especially a human, will provide a diagnostic method for diagnosis of a F. tularensis related disease or disorder. In general, the method involves contacting the biological sample with a compound or an agent capable of detecting a polypeptide of the invention or a nucleic acid of the invention. The term "biological sample" when used in reference to a diagnostic assay is intended to include tissues, cells and biological fluids isolated from a subject, as well as tissues, cells and fluids present within a subject.

The detection methods may be used to detect the presence of F. tularensis in a biological sample in vitro as well as in vivo. For example, in vitro techniques for detection of a nucleic acid of the invention include Northern hybridizations and in situ hybridizations. In vitro techniques for detection of polypeptides of the invention include enzyme linked immunosorbent assays (ELISAs), Western blots, immunoprecipitations, immunofluorescence, radioimmunoassays and competitive binding assays. Alternatively, polypeptides of the invention can be detected in vivo in a subject by introducing into the subject a labeled antibody specific for a polypeptide of the invention. For example, the antibody can be labeled with a radioactive marker whose presence and location in a subject can be detected by standard imaging techniques. It may be possible to use all of the diagnostic methods disclosed herein for pathogens in addition to F. tularensis.

Nucleic acids for diagnosis may be obtained from an infected individual's cells and tissues, such as bone, blood, muscle, cartilage, and skin. Nucleic acids, e.g., DNA and RNA, may be used directly for detection or may be amplified, e.g., enzymatically by using PCR or other amplification technique, prior to analysis. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing a nucleic acid, e.g., amplified DNA, to a nucleic acid of the invention, which nucleic acid may be labeled. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g. Myers et al., Science, 230: 1242 (1985). Sequence changes at specific locations also may be revealed by nuclease protection assays, such as RNase and S1 protection or a chemical cleavage method. See, e.g., Cotton et al., Proc. Natl. Acad. Sci., USA, 85: 4397-4401 (1985).

Agents for detecting a nucleic acid of the invention, e.g., comprising the sequence set forth in SEQ ID NO: 1, include labeled or labelable nucleic acid probes capable of hybridizing to a nucleic acid of the invention. The nucleic acid probe can comprise, for example, the full length sequence of a nucleic acid of the invention, or an equivalent thereof, or a portion thereof, such as an oligonucleotide of at least 15, 30, 50, 100, 250 or 500 nucleotides in length and sufficient to specifically hybridize under stringent conditions to SEQ ID NO: 1, or the complement thereof. Agents for detecting a polypeptide of the invention, e.g., comprising an amino acid sequence of SEQ ID NO: 2, include labeled or labelable antibodies capable of binding to a polypeptide of the invention. Antibodies may be polyclonal, or alternatively, monoclonal. An intact antibody, or a fragment thereof (e.g., Fab or F(ab')$_2$) can be used. Labeling the probe or antibody also encompasses direct labeling of the probe or antibody by coupling (e.g., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In certain embodiments, detection of a nucleic acid of the invention in a biological sample involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) PNAS 91:360-364), the latter of which can be particularly useful for distinguishing between orthologs of polynucleotides of the invention (see Abravaya et al. (1995) Nucleic Acids Res. 23:675-682). This method can include the steps of collecting a sample of cells from a patient, isolating nucleic acid (e.g., genomic, mRNA or both) from the cells of the sample, contacting the nucleic acid sample with one or more primers which specifically hybridize to a nucleic acid of the invention under conditions such that hybridization and amplification of the polynucleotide (if present) occurs, and detecting the presence or absence of an amplification product, or detecting the size of the amplification product and comparing the length to a control sample.

In one aspect, methods for detecting the presence of *F. tularensis* in a sample may comprise: (a) providing a sample to be tested for the presence of *F. tularensis*; (b) contacting the sample with an antibody reactive against eight consecutive amino acid residues of SEQ ID NO: 2 under conditions which permit association between the antibody and its ligand; and (c) detecting interaction of the antibody with its ligand, thereby detecting the presence of *F. tularensis* in the sample.

In another aspect, methods for detecting the presence of *F. tularensis* in a sample, may comprise: (a) providing a sample to be tested for the presence of *F. tularensis*; (b) contacting the sample with an antibody that binds specifically to a polypeptide of the invention under conditions which permit association between the antibody and its ligand; and (c) detecting interaction of the antibody with its ligand, thereby detecting the presence of *F. tularensis* in the sample.

In yet another example, methods for diagnosing a patient suffering from a *F. tularensis* related disease or disorder may comprise: (a) obtaining a biological sample from a patient; (b) detecting the presence or absence of a polypeptide of the invention, or a nucleic acid encoding a polypeptide of the invention, in the sample; and (c) diagnosing a patient suffering from a *F. tularensis* related disease or disorder based on the presence of a polypeptide of the invention, or a nucleic acid encoding a polypeptide of the invention, in the patient sample.

The diagnostic assays may also be used to monitor the effectiveness of an anti-*F. tularensis* treatment in an individual suffering from an *F. tularensis* related disease or disorder. For example, the presence and/or amount of a nucleic acid of the invention or a polypeptide of the invention can be detected in an individual suffering from an *F. tularensis* related disease or disorder before and after treatment with anti-*F. tularensis* therapeutic agent. Any change in the level of a polynucleotide or polypeptide of the invention after treatment of the individual with the therapeutic agent can provide information about the effectiveness of the treatment course. In particular, no change, or a decrease, in the level of a polynucleotide or polypeptide of the invention present in the biological sample will indicate that the therapeutic is successfully combating the *F. tularensis* related disease or disorder.

Kits for detecting the presence of *F. tularensis* in a biological sample are also provided. For example, the kit can comprise a labeled or labelable compound or agent capable of detecting a polynucleotide or polypeptide of the invention in a biological sample; means for determining the amount of *F. tularensis* in the sample; and means for comparing the amount of *F. tularensis* in the sample with a standard. The compound or agent can be packaged in a suitable container. The kit can further comprise instructions for using the kit to detect a polynucleotide or polypeptide of the invention.

9. Drug Discovery

Modulators to polypeptides of the invention and other structurally related molecules, and complexes containing the same, may be identified and developed as set forth below and otherwise using techniques and methods known to those of skill in the art. The modulators may be employed, for instance, to inhibit and treat *F. tularensis* associated diseases or conditions, such as tularemia, or other diseases or disorders associated with an *F. tularensis* infection, such as, for example, infection of the lymph nodes, lungs and pleura, spleen, liver, and/or kidney, upper respiratory problems, bronchitis, and pleuropneumonitis.

A variety of methods for inhibiting the growth or infectivity of *F. tularensis* are contemplated. For example, exemplary methods involve contacting *F. tularensis* with a polypeptide of the invention that modulates the same or another polypeptide from such pathogen, a nucleic acid encoding such polypeptide of the invention, or a compound thought or shown to be effective against such pathogen.

For example, in one aspect, methods for treating a patient suffering from an infection of *F. tularensis* may comprise administering to the patient an amount of a SEQ ID NO: 2 inhibitor effective to inhibit the expression and/or activity of a polypeptide of the invention. In certain instances, the animal is a human or a livestock animal such as a cow, pig, goat or sheep. A method for treating a subject suffering from a *F. tularensis* related disease or disorder is provided, comprising administering to an animal having the condition a therapeutically effective amount of a molecule identified using one of the methods of the present invention.

Any molecule that is shown to modulate the activity of a polypeptide of the invention is within the scope of the present invention.

In another embodiment, inhibitors, modulators of the subject polypeptides, or biological complexes containing them, may be used in the manufacture of a medicament for any number of uses, including, for example, treating any disease or other treatable condition of a patient (including humans and animals), and particularly a disease caused by *F. tularensis*, such as, for example, one of the following: tularemia, or other diseases or disorders associated with an *F. tularensis* infection, such as, for example, infection of the lymph nodes, lungs and pleura, spleen, liver, and/or kidney, upper respiratory problems, bronchitis, and pleuropneumonitis.

(a) Drug Design

A number of techniques can be used to screen, identify, select and design chemical entities capable of associating with polypeptides of the invention, structurally homologous molecules, and other molecules. Knowledge of the structure for a polypeptide of the invention, determined in accordance with the methods described herein, permits the design and/or identification of molecules and/or other modulators which have a shape complementary to the conformation of a polypeptide of the invention, or more particularly, a druggable region thereof. It is understood that such techniques and methods may use, in addition to the exact structural coordinates and other information for a polypeptide of the invention, structural equivalents thereof described above (including, for example, those structural coordinates that are derived from the structural coordinates of amino acids contained in a druggable region as described above).

The term "chemical entity," as used herein, refers to chemical compounds, complexes of two or more chemical compounds, and fragments of such compounds or complexes. In certain instances, it is desirable to use chemical entities exhibiting a wide range of structural and functional diversity, such as compounds exhibiting different shapes (e.g., flat aromatic rings(s), puckered aliphatic rings(s), straight and branched chain aliphatics with single, double, or triple bonds) and diverse functional groups (e.g., carboxylic acids, esters, ethers, amines, aldehydes, ketones, and various heterocyclic rings).

In one aspect, the method of drug design generally includes computationally evaluating the potential of a selected chemical entity to associate with any of the molecules or complexes of the present invention (or portions thereof). For example, this method may include the steps of (a) employing computational means to perform a fitting operation between the selected chemical entity and a druggable region of the molecule or complex; and (b) analyzing the results of said fitting operation to quantify the association between the chemical entity and the druggable region.

A chemical entity may be examined either through visual inspection or through the use of computer modeling using a docking program such as GRAM, DOCK, or AUTODOCK (Dunbrack et al., Folding & Design, 2:27-42 (1997)). This procedure can include computer fitting of chemical entities to a target to ascertain how well the shape and the chemical structure of each chemical entity will complement or interfere with the structure of the subject polypeptide (Bugg et al., Scientific American, Dec.: 92-98 (1993); West et al., TIPS, 16:67-74 (1995)). Computer programs may also be employed to estimate the attraction, repulsion, and steric hindrance of the chemical entity to a druggable region, for example. Generally, the tighter the fit (e.g., the lower the steric hindrance, and/or the greater the attractive force) the more potent the chemical entity will be because these properties are consistent with a tighter binding constant. Furthermore, the more specificity in the design of a chemical entity the more likely that the chemical entity will not interfere with related proteins, which may minimize potential side-effects due to unwanted interactions.

A variety of computational methods for molecular design, in which the steric and electronic properties of druggable regions are used to guide the design of chemical entities, are known: Cohen et al. (1990) *J. Med. Cam.* 33: 883-894; Kuntz et al. (1982) *J. Mol. Biol.* 161: 269-288; DesJarlais (1988) *J. Med. Cam.* 31: 722-729; Bartlett et al. (1989) *Spec. Publ., Roy. Soc. Chem.* 78: 182-196; Goodford et al. (1985) *J. Med. Cam.* 28: 849-857; and Desjarlais et al. *J. Med. Cam.* 29: 2149-2153. Directed methods generally fall into two categories: (1) design by analogy in which 3-D structures of known chemical entities (such as from a crystallographic database) are docked to the druggable region and scored for goodness-of-fit; and (2) de novo design, in which the chemical entity is constructed piece-wise in the druggable region. The chemical entity may be screened as part of a library or a database of molecules. Databases which may be used include ACD (Molecular Designs Limited), NCl (National Cancer Institute), CCDC (Cambridge Crystallographic Data Center), CAST (Chemical Abstract Service), Derwent (Derwent Information Limited), Maybridge (Maybridge Chemical Company Ltd), Aldrich (Aldrich Chemical Company), DOCK (University of California in San Francisco), and the Directory of Natural Products (Chapman & Hall). Computer programs such as CONCORD (Tripos Associates) or DB-Converter (Molecular Simulations Limited) can be used to convert a data set represented in two dimensions to one represented in three dimensions.

Chemical entities may be tested for their capacity to fit spatially with a druggable region or other portion of a target protein. As used herein, the term "fits spatially" means that the three-dimensional structure of the chemical entity is accommodated geometrically by a druggable region. A favorable geometric fit occurs when the surface area of the chemical entity is in close proximity with the surface area of the druggable region without forming unfavorable interactions. A favorable complementary interaction occurs where the chemical entity interacts by hydrophobic, aromatic, ionic, dipolar, or hydrogen donating and accepting forces. Unfavorable interactions may be steric hindrance between atoms in the chemical entity and atoms in the druggable region.

If a model is a computer model, the chemical entities may be positioned in a druggable region through computational docking. If, on the other hand, the model of the present invention is a structural model, the chemical entities may be positioned in the druggable region by, for example, manual docking. As used herein the term "docking" refers to a process of placing a chemical entity in close proximity with a druggable region, or a process of finding low energy conformations of a chemical entity/druggable region complex.

In an illustrative embodiment, the design of potential modulator begins from the general perspective of shape complimentary for the druggable region of a polypeptide of the invention, and a search algorithm is employed which is capable of scanning a database of small molecules of known three-dimensional structure for chemical entities which fit geometrically with the target druggable region. Most algorithms of this type provide a method for finding a wide assortment of chemical entities that are complementary to the shape of a druggable region of the subject polypeptide. Each of a set of chemical entities from a particular data-base, such as the Cambridge Crystallographic Data Bank (CCDB) (Allen et al. (1973) *J. Chem. Doc.* 13: 119), is individually docked to the druggable region of a polypeptide of the invention in a number of geometrically permissible orientations with use of a docking algorithm. In certain embodiments, a set of computer algorithms called DOCK, can be used to characterize the shape of invaginations and grooves that form the active sites and recognition surfaces of the druggable region (Kuntz et al. (1982) *J. Mol. Biol.* 161: 269-288). The program can also search a database of small molecules for templates whose shapes are complementary to particular binding sites of a polypeptide of the invention (DesJarlais et al. (1988) *J Med Chem* 31: 722-729).

The orientations are evaluated for goodness-of-fit and the best are kept for further examination using molecular mechanics programs, such as AMBER or CHARMM. Such algorithms have previously proven successful in finding a variety of chemical entities that are complementary in shape to a druggable region.

Goodford (1985, *J Med Chem* 28:849-857) and Boobbyer et al. (1989, *J Med Chem* 32:1083-1094) have produced a computer program (GRID) which seeks to determine regions of high affinity for different chemical groups (termed probes) of the druggable region. GRID hence provides a tool for suggesting modifications to known chemical entities that might enhance binding. It may be anticipated that some of the sites discerned by GRID as regions of high affinity correspond to "pharmacophoric patterns" determined inferentially from a series of known ligands. As used herein, a "pharmacophoric pattern" is a geometric arrangement of features of chemical entities that is believed to be important for binding. Attempts have been made to use pharmacophoric patterns as a search screen for novel ligands (Jakes et al. (1987) *J Mol Graph* 5:41-48; Brint et al. (1987) *J Mol Graph* 5:49-56; Jakes et al. (1986) *J Mol Graph* 4:12-20).

Yet a further embodiment utilizes a computer algorithm such as CLIX which searches such databases as CCDB for chemical entities which can be oriented with the druggable region in a way that is both sterically acceptable and has a high likelihood of achieving favorable chemical interactions between the chemical entity and the surrounding amino acid residues. The method is based on characterizing the region in terms of an ensemble of favorable binding positions for different chemical groups and then searching for orientations of the chemical entities that cause maximum spatial coincidence of individual candidate chemical groups with members of the ensemble. The algorithmic details of CLIX is described in Lawrence et al. (1992) *Proteins* 12:31-41.

In this way, the efficiency with which a chemical entity may bind to or interfere with a druggable region may be tested and optimized by computational evaluation. For example, for a favorable association with a druggable region, a chemical entity must preferably demonstrate a relatively small difference in energy between its bound and fine states (i.e., a small deformation energy of binding). Thus, certain, more desirable chemical entities will be designed with a deformation energy of binding of not greater than about 10 kcal/mole, and more preferably, not greater than 7 kcal/mole. Chemical entities may interact with a druggable region in more than one conformation that is similar in overall binding energy. In those cases, the deformation energy of binding is taken to be the difference between the energy of the free entity and the average energy of the conformations observed when the chemical entity binds to the target.

In this way, computer-assisted methods for identifying or designing a potential modulator of the activity of a polypeptide of the invention are provided, including: supplying a computer modeling application with a set of structure coordinates of a molecule or complex, the molecule or complex including at least a portion of a druggable region from a polypeptide of the invention; supplying the computer modeling application with a set of structure coordinates of a chemical entity; and determining whether the chemical entity is expected to bind to the molecule or complex, wherein binding to the molecule or complex is indicative of potential modulation of the activity of a polypeptide of the invention.

In another aspect, a computer-assisted method for identifying or designing a potential modulator to a polypeptide of the invention is provided, supplying a computer modeling application with a set of structure coordinates of a molecule or complex, the molecule or complex including at least a portion of a druggable region of a polypeptide of the invention; supplying the computer modeling application with a set of structure coordinates for a chemical entity; evaluating the potential binding interactions between the chemical entity and active site of the molecule or molecular complex; structurally modifying the chemical entity to yield a set of structure coordinates for a modified chemical entity, and determining whether the modified chemical entity is expected to bind to the molecule or complex, wherein binding to the molecule or complex is indicative of potential modulation of the polypeptide of the invention.

In one embodiment, a potential modulator can be obtained by screening a peptide library (Scott and Smith, Science, 249:386-390 (1990); Cwirla et al., Proc. Natl. Acad. Sci., 87:6378-6382 (1990); Devlin et al., Science, 249:404-406 (1990)). A potential modulator selected in this manner could then be systematically modified by computer modeling programs until one or more promising potential drugs are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). Alternatively a potential modulator may be selected from a library of chemicals such as those that can be licensed from third parties, such as chemical and pharmaceutical companies. A third alternative is to synthesize the potential modulator de novo.

For example, in certain embodiments, methods for making a potential modulator for a polypeptide of the invention may comprise synthesizing a chemical entity or a molecule containing the chemical entity to yield a potential modulator of a polypeptide of the invention, the chemical entity having been identified during a computer-assisted process including supplying a computer modeling application with a set of structure coordinates of a molecule or complex, the molecule or complex including at least one druggable region from a polypeptide of the invention; supplying the computer modeling application with a set of structure coordinates of a chemical entity; and determining whether the chemical entity is expected to bind to the molecule or complex at the active site, wherein binding to the molecule or complex is indicative of potential modulation. This method may further include the steps of evaluating the potential binding interactions between the chemical entity and the active site of the molecule or molecular complex and structurally modifying the chemical entity to yield a set of structure coordinates for a modified chemical entity, which steps may be repeated one or more times.

Once a potential modulator is identified, it can then be tested in any standard assay for the macromolecule depending of course on the macromolecule, including in high throughput assays. Further refinements to the structure of the modulator will generally be necessary and can be made by the successive iterations of any and/or all of the steps provided by the particular screening assay, in particular further structural analysis by e.g., $^{15}$N NMR relaxation rate determinations or x-ray crystallography with the modulator bound to the subject polypeptide. These studies may be performed in conjunction with biochemical assays.

Once identified, a potential modulator may be used as a model structure, and analogs to the compound can be obtained. The analogs are then screened for their ability to bind the subject polypeptide. An analog of the potential modulator might be chosen as a modulator when it binds to the subject polypeptide with a higher binding affinity than the predecessor modulator.

In a related approach, iterative drug design is used to identify modulators of a target protein. Iterative drug design is a method for optimizing associations between a protein and a modulator by determining and evaluating the three dimensional structures of successive sets of protein/modulator complexes. In iterative drug design, crystals of a series of protein/modulator complexes are obtained and then the three-dimensional structures of each complex is solved. Such an approach provides insight into the association between the proteins and modulators of each complex. For example, this approach may be accomplished by selecting modulators with inhibitory activity, obtaining crystals of this new protein/modulator complex, solving the three dimensional structure of the complex, and comparing the associations between the new protein/modulator complex and previously solved protein/modulator complexes. By observing how changes in the modulator affected the protein/modulator associations, these associations may be optimized.

In addition to designing and/or identifying a chemical entity to associate with a druggable region, as described above, the same techniques and methods may be used to design and/or identify chemical entities that either associate, or do not associate, with affinity regions, selectivity regions or undesired regions of protein targets. By such methods, selectivity for one or a few targets, or alternatively for multiple targets, from the same species or from multiple species, can be achieved.

For example, a chemical entity may be designed and/or identified for which the binding energy for one druggable region, e.g., an affinity region or selectivity region, is more favorable than that for another region, e.g., an undesired region, by about 20%, 30%, 50% to about 60% or more. It may be the case that the difference is observed between (a) more than two regions, (b) between different regions (selectivity, affinity or undesirable) from the same target, (c) between regions of different targets, (d) between regions of homologs from different species, or (e) between other combinations. Alternatively, the comparison may be made by reference to the Kd, usually the apparent Kd, of said chemical entity with the two or more regions in question.

In another aspect, prospective modulators are screened for binding to two nearby druggable regions on a target protein. For example, a modulator that binds a first region of a target polypeptide does not bind a second nearby region. Binding to the second region can be determined by monitoring changes in a different set of amide chemical shifts in either the original screen or a second screen conducted in the presence of a modulator (or potential modulator) for the first region. From an analysis of the chemical shift changes, the approximate location of a potential modulator for the second region is identified. Optimization of the second modulator for binding to the region is then carried out by screening structurally related compounds (e.g., analogs as described above). When modulators for the first region and the second region are identified, their location and orientation in the ternary complex can be determined experimentally. On the basis of this structural information, a linked compound, e.g., a consolidated modulator, is synthesized in which the modulator for the first region and the modulator for the second region are linked. In certain embodiments, the two modulators are covalently linked to form a consolidated modulator. This consolidated modulator may be tested to determine if it has a higher binding affinity for the target than either of the two individual modulators. A consolidated modulator is selected as a modulator when it has a higher binding affinity for the target than either of the two modulators. Larger consolidated modulators can be constructed in an analogous manner, e.g., linking three modulators which bind to three nearby regions on the target to form a multilinked consolidated modulator that has an even higher affinity for the target than the linked modulator. In this example, it is assumed that is desirable to have the modulator bind to all the druggable regions. However, it may be the case that binding to certain of the druggable regions is not desirable, so that the same techniques may be used to identify modulators and consolidated modulators that show increased specificity based on binding to at least one but not all druggable regions of a target.

A number of methods that use drug design as described above may be used. For example, in one aspect, methods for designing a candidate compound for screening for inhibitors of a polypeptide of the invention may comprise: (a) determining the three dimensional structure of a crystallized polypeptide of the invention or a fragment thereof; and (b) designing a candidate inhibitor based on the three dimensional structure of the crystallized polypeptide or fragment.

In another aspect, methods for identifying a potential inhibitor of a polypeptide of the invention may comprise: (a) providing the three-dimensional coordinates of a polypeptide of the invention or a fragment thereof; (b) identifying a druggable region of the polypeptide or fragment; and (c) selecting from a database at least one compound that comprises three dimensional coordinates which indicate that the compound may bind the druggable region; (d) wherein the selected compound is a potential inhibitor of a polypeptide of the invention.

In another aspect, methods for identifying a potential modulator of a molecule comprising a druggable region similar to that of SEQ ID NO: 2 may comprise: (a) using the atomic coordinates of amino acid residues from SEQ ID NO: 2, or a fragment thereof, ±a root mean square deviation from the backbone atoms of the amino acids of not more than 1.5 Å, to generate a three-dimensional structure of a molecule comprising a druggable region that is a portion of SEQ ID NO: 2; (b) employing the three dimensional structure to design or select the potential modulator; (c) synthesizing the modulator; and (d) contacting the modulator with the molecule to determine the ability of the modulator to interact with the molecule.

In another aspect, an apparatus for determining whether a compound is a potential inhibitor of a polypeptide having SEQ ID NO: 2 may comprise: (a) a memory that comprises: (i) the three dimensional coordinates and identities of the atoms of a polypeptide of the invention or a fragment thereof that form a druggable site; and (ii) executable instructions; and (b) a processor that is capable of executing instructions to: (i) receive three-dimensional structural information for a candidate compound; (ii) determine if the three-dimensional structure of the candidate compound is complementary to the structure of the interior of the druggable site; and (iii) output the results of the determination.

In another aspect, methods for designing a potential compound for the prevention or treatment of *F. tularensis* related disease or disorder may comprise: (a) providing the three dimensional structure of a crystallized polypeptide of the invention, or a fragment thereof; (b) synthesizing a potential compound for the prevention or treatment of *F. tularensis* related disease or disorder based on the three dimensional structure of the crystallized polypeptide or fragment; (c) contacting a polypeptide of the present invention or an *F. tularensis* with the potential compound; and (d) assaying the activity of a polypeptide of the present invention, wherein a change in the activity of the polypeptide indicates that the compound may be useful for prevention or treatment of a *F. tularensis* related disease or disorder.

In another aspect, methods for designing a potential compound for the prevention or treatment of *F. tularensis* related disease or disorder may comprise: (a) providing structural information of a druggable region derived from NMR spectroscopy of a polypeptide of the invention, or a fragment thereof; (b) synthesizing a potential compound for the prevention or treatment of *F. tularensis* related disease or disorder based on the structural information; (c) contacting a polypeptide of the present invention or an *F. tularensis* with the potential compound; and (d) assaying the activity of a polypeptide of the present invention, wherein a change in the activity of the polypeptide indicates that the compound may be useful for prevention or treatment of a *F. tularensis* related disease or disorder.

(b) In Vitro Assays

Polypeptides of the invention may be used to assess the activity of small molecules and other modulators in in vitro assays. In one embodiment of such an assay, agents are identified which modulate the biological activity of a protein, protein-protein interaction of interest or protein complex, such as an enzymatic activity, binding to other cellular components, cellular compartmentalization, signal transduction, and the like. In certain embodiments, the test agent is a small organic molecule.

Assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

Methods of screening compounds to identify those which modulate the action of polypeptides of the invention, or polynucleotides encoding the same, are provided. The method of screening may involve high-throughput techniques. For example, to screen for modulators, a synthetic reaction mix, a cellular compartment, such as a membrane, cell envelope or cell wall, or a preparation of any thereof, comprising a polypeptide of the invention and a labeled substrate or ligand of such polypeptide is incubated in the absence or the presence of a candidate molecule that may be a modulator of a polypeptide of the invention. The ability of the candidate molecule to modulate a polypeptide of the invention is reflected in decreased binding of the labeled ligand or decreased production of product from such substrate. Detection of the rate or level of production of product from substrate may be enhanced by using a reporter system. Reporter systems that may be useful in this regard include but are not limited to colorimetric labeled substrate converted into product, a reporter gene that is responsive to changes in a nucleic acid of the invention or polypeptide activity, and binding assays known in the art.

Another example of an assay for a modulator of a polypeptide of the invention is a competitive assay that combines a polypeptide of the invention and a potential modulator with molecules that bind to a polypeptide of the invention, recombinant molecules that bind to a polypeptide of the invention, natural substrates or ligands, or substrate or ligand mimetics, under appropriate conditions for a competitive inhibition assay. Polypeptides of the invention can be labeled, such as by radioactivity or a calorimetric compound, such that the number of molecules of a polypeptide of the invention bound to a binding molecule or converted to product can be determined accurately to assess the effectiveness of the potential modulator.

A number of methods for identifying a molecule which modulates the activity of a polypeptide are known in the art. For example, in one such method, a subject polypeptide is contacted with a test compound, and the activity of the subject polypeptide in the presence of the test compound is determined, wherein a change in the activity of the subject polypeptide is indicative that the test compound modulates the activity of the subject polypeptide. In certain instances, the test compound agonizes the activity of the subject polypeptide, and in other instances, the test compound antagonizes the activity of the subject polypeptide.

In another example, a compound which modulates SEQ ID NO: 2 dependent growth or infectivity of *F. tularensis* may be identified by (a) contacting a polypeptide of the invention with a test compound; and (b) determining the activity of the polypeptide in the presence of the test compound, wherein a change in the activity of the polypeptide is indicative that the test compound may modulate the growth or infectivity of *F. tularensis*.

In an exemplary embodiment, the activity of a Fab I polypeptide may be measured using either crotonoyl-CoA (CCA) or crotonoyl-ACP as a substrate (Bergler, et al, (1994), *J. Biol. Chem.* 269, 5493-5496) and monitoring the decrease in absorbance at 340 nm due to the consumption of NADH. Crotonoyl-ACP is available from Sigma (C6146). A diazaborine derivative may be used as a positive control, this should be readily available via a 2 step synthesis with publicly available starting materials using methods known in the art. Test compounds may be added to this assay to determine whether they agonize or antagonize enzymatic activity. Exemplary activities of a FabI polypeptide that may be monitored in connection with assays for identifying modulators of a FabI polypeptide, include, for example, reduction of enoyl-ACP, crotonyl-CoA or crotonyl-ACP, uncompetitive inhibition by Apo-ACP versus NADH (Ki(app)), competitive inhibition by Apo-ACP versus crotonoyl CoA, induction of negative cooperativity with respect to CCA binding, use of NADH and NADPH as substrates by Fab I, binding of NADH and NADPH by FabI, oxidation of NADH and NADPH by FabI, ratio of Kmapp for NADH as compared to NADPH, use of NADH and crotonoyl CoA as substrates by Fab I in a sequential kinetic mechanism, sequential binding of NADH and crotonoyl CoA by Fab I, increasing inhibition of FabI by saturated fatty acyl CoA's of increasing chain length, feedback regulatory mechanism of Fab I by saturated fatty acyl CoA's, competitive inhibition by palmitoyl CoA versus crotonoyl CoA, competitive inhibition by palmitoyl CoA versus crotonoyl CoA modulation through binding of multiple palmitoyl CoA molecules to Fab I, binding of multiple palmitoyl CoA molecules to Fab I, negative cooperativity in the binding of CCA, formation of an dimeric quaternary structure, formation of an tetrameric quaternary structure formation of an oligomeric quaternary structure, binding of Fab I by pseudo-product inhibitors beta-NADP+ or palmitoyl coA, or NADH binding to Fab I prior to or simultaneous with ACP binding.

(c) In Vivo Assays

Animal models of bacterial infection and/or disease may be used as an in vivo assay for evaluating the effectiveness of a potential drug target in treating or preventing diseases or disorders. A number of suitable animal models are described briefly below, however, these models are only examples and modifications, or completely different animal models, may be used in accord with the methods of the invention.

(i) Mouse Soft Tissue Model

The mouse soft tissue infection model is a sensitive and effective method for measurement of bacterial proliferation. In these models (Vogelman et al., 1988, J. Infect. Dis. 157: 287-298) anesthetized mice are infected with the bacteria in the muscle of the hind thigh. The mice can be either chemically immune compromised (e.g., cytoxan treated at 125 mg/kg on days −4, −2, and 0) or immunocompetent. The dose of microbe necessary to cause an infection is variable and depends on the individual microbe, but commonly is on the order of $10^5$-$10^6$ colony forming units per injection for bacteria. A variety of mouse strains are useful in this model although Swiss Webster and DBA2 lines are most commonly used. Once infected the animals are conscious and show no overt ill effects of the infections for approximately 12 hours. After that time virulent strains cause swelling of the thigh muscle, and the animals can become bacteremic within approximately 24 hours. This model most effectively measures proliferation of the microbe, and this proliferation is measured by sacrifice of the infected animal and counting colonies from homogenized thighs.

(ii) Diffusion Chamber Model

A second model useful for assessing the virulence of microbes is the diffusion chamber model (Malouin et al., 1990, Infect. Immun. 58: 1247-1253; Doy et al., 1980, J. Infect. Dis. 2: 39-51; Kelly et al., 1989, Infect. Immun. 57: 344-350. In this model rodents have a diffusion chamber surgically placed in the peritoneal cavity. The chamber consists of a polypropylene cylinder with semipermeable membranes covering the chamber ends. Diffusion of peritoneal fluid into and out of the chamber provides nutrients for the microbes. The progression of the "infection" may be followed by examining growth, the exoproduct production or RNA messages. The time experiments are done by sampling multiple chambers.

(iii) Endocarditis Model

For bacteria, an important animal model effective in assessing pathogenicity and virulence is the endocarditis model (J. Santoro and M. E. Levinson, 1978, Infect. Immun. 19: 915-918). A rat endocarditis model can be used to assess colonization, virulence and proliferation.

(iv) Osteomyelitis Model

A fourth model useful in the evaluation of pathogenesis is the osteomyelitis model (Spagnolo et al., 1993, Infect.

Immun. 61: 5225-5230). Rabbits are used for these experiments. Anesthetized animals have a small segment of the tibia removed and microorganisms are microinjected into the wound. The excised bone segment is replaced and the progression of the disease is monitored. Clinical signs, particularly inflammation and swelling are monitored. Termination of the experiment allows histolic and pathologic examination of the infection site to complement the assessment procedure.

(v) Murine Septic Arthritis Model

A fifth model relevant to the study of microbial pathogenesis is a murine septic arthritis model (Abdelnour et al., 1993, Infect. Immun. 61: 3879-3885). In this model mice are infected intravenously and pathogenic organisms are found to cause inflammation in distal limb joints. Monitoring of the inflammation and comparison of inflammation vs. inocula allows assessment of the virulence of related strains.

(vi) Bacterial Peritonitis Model

Finally, bacterial peritonitis offers rapid and predictive data on the virulence of strains (M. G. Bergeron, 1978, Scand. J. Infect. Dis. Suppl. 14: 189-206; S. D. Davis, 1975, Antimicrob. Agents Chemother. 8: 50-53). Peritonitis in rodents, such as mice, can provide essential data on the importance of targets. The end point may be lethality or clinical signs can be monitored. Variation in infection dose in comparison to outcome allows evaluation of the virulence of individual strains.

A variety of other in vivo models are available and may be used when appropriate for specific pathogens or specific test agents. For example, target organ recovery assays (Gordee et al., 1984, J. Antibiotics 37:1054-1065; Bannatyne et al., 1992, Infect. 20:168-170) may be useful for fungi and for bacterial pathogens which are not acutely virulent to animals.

It is also relevant to note that the species of animal used for an infection model, and the specific genetic make-up of that animal, may contribute to the effective evaluation of the effects of a particular test agent. For example, immuno-incompetent animals may, in some instances, be preferable to immuno-competent animals. For example, the action of a competent immune system may, to some degree, mask the effects of the test agent as compared to a similar infection in an immuno-incompetent animal. In addition, many opportunistic infections, in fact, occur in immuno-compromised patients, so modeling an infection in a similar immunological environment is appropriate.

10. Vaccines

There are provided products, compositions and methods for raising immunological response against a pathogen, especially *F. tularensis*. In one aspect, a polypeptide of the invention or a nucleic acid of the invention, or an antigenic fragment thereof, may be administered to a subject, optionally with a booster, adjuvant, or other composition that stimulates immune responses.

Another aspect relates to a method for inducing an immunological response in an individual, particularly a mammal which comprises inoculating the individual with a polypeptide of the invention and/or a nucleic acid of the invention, adequate to produce antibody and/or T cell immune response to protect said individual from infection, particularly bacterial infection and most particularly *F. tularensis* infection. Also provided are methods whereby such immunological response slows bacterial replication. Yet another aspect relates to a method of inducing immunological response in an individual which comprises delivering to such individual a nucleic acid vector, sequence or ribozyme to direct expression of a polypeptide of the invention and/or a nucleic acid of the invention in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect relates to an immunological composition that when introduced into an individual, preferably a human, capable of having induced within it an immunological response, induces an immunological response in such individual to a nucleic acid of the invention and/or a polypeptide encoded therefrom, wherein the composition comprises a recombinant nucleic acid of the invention and/or polypeptide encoded therefrom and/or comprises DNA and/or RNA which encodes and expresses an antigen of said nucleic acid of the invention, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

Another embodiment relates to compositions comprising a polypeptide of the invention and an adjuvant. The adjuvant can be any vehicle which would typically enhance the antigenicity of a polypeptide, e.g., minerals (for instance, alum, aluminum hydroxide or aluminum phosphate), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, liposomes, or any of the other adjuvants known in the art. A polypeptide of the invention can be emulsified with, absorbed onto, or coupled with the adjuvant.

A polypeptide of the invention may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, may further comprise an antigenic co-protein, such as lipoprotein D from *Hemophilus* influenzae, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of a polypeptide of the invention.

Provided are compositions, particularly vaccine compositions, and methods comprising the polypeptides and/or polynucleotides of the invention and immunostimulatory DNA sequences, such as those described in Sato, Y. et al. Science 273: 352 (1996).

Also, provided are methods using the described polynucleotide or particular fragments thereof, which have been shown to encode non-variable regions of bacterial cell surface proteins, in polynucleotide constructs used in such genetic immunization experiments in animal models of infection with *F. tularensis*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *F. tularensis* infection, in mammals, particularly humans.

A polypeptide of the invention may be used as an antigen for vaccination of a host to produce specific antibodies which protect against invasion of bacteria, for example by blocking adherence of bacteria to damaged tissue.

11. Array Analysis

Subject nucleic acids may be used in arrays to assess gene expression, for example in arrays for *F. tularensis*. Another aspect contemplates using the subject nucleic acids to interact with probes contained on arrays.

In one aspect, an array comprising a substrate having a plurality of addresses is provided, wherein at least one of the addresses has disposed thereon a capture probe that can specifically bind to a nucleic acid of the invention. Methods for detecting expression of a nucleotide sequence which encodes a polypeptide of the invention, or a fragment thereof, may use the foregoing array by: (a) providing a sample comprising at least one mRNA molecule; (b) exposing the sample to the array under conditions which promote hybridization between the capture probe disposed on the array and a nucleic acid complementary thereto; and (c) detecting hybridization between an mRNA molecule of the sample and the capture probe disposed on the array, thereby detecting expression of a sequence which encodes for a polypeptide of the invention, or a fragment thereof.

Arrays are often divided into microarrays and macroarrays, where microarrays have a much higher density of individual probe species per area. Microarrays may have as many as 1000 or more different probes in a 1 $cm^2$ area. There is no concrete cut-off to demarcate the difference between micro- and macroarrays, and both types of arrays are contemplated for use with the invention.

Microarrays are known in the art and generally consist of a surface to which probes that correspond in sequence to gene products (e.g., cDNAs, mRNAs, oligonucleotides) are bound at known positions. In one embodiment, the microarray is an array (e.g., a matrix) in which each position represents a discrete binding site for a product encoded by a gene (e.g., a protein or RNA), and in which binding sites are present for products of most or almost all of the genes in the organism's genome. In certain embodiments, the binding site or site is a nucleic acid or nucleic acid analogue to which a particular cognate cDNA can specifically hybridize. The nucleic acid or analogue of the binding site may be, e.g., a synthetic oligomer, a full-length cDNA, a less-than full length cDNA, or a gene fragment.

Although in certain embodiments the microarray contains binding sites for products of all or almost all genes in the target organism's genome, such comprehensiveness is not necessarily required. Usually the microarray will have binding sites corresponding to at least 100, 500, 1000, 4000 genes or more. In certain embodiments, arrays will have anywhere from about 50, 60, 70, 80, 90, or even more than 95% of the genes of a particular organism represented. The microarray typically has binding sites for genes relevant to testing and confirming a biological network model of interest. Several exemplary human microarrays are publicly available.

The probes to be affixed to the arrays are typically polynucleotides. These DNAs can be obtained by, e.g., polymerase chain reaction (PCR) amplification of gene segments from genomic DNA, cDNA (e.g., by RT-PCR), or cloned sequences. PCR primers are chosen, based on the known sequence of the genes or cDNA, that result in amplification of unique fragments (e.g., fragments that do not share more than 10 bases of contiguous identical sequence with any other fragment on the microarray). Computer programs are useful in the design of primers with the required specificity and optimal amplification properties. See, e.g., Oligo pl version 5.0 (National Biosciences). In an alternative embodiment, the binding (hybridization) sites are made from plasmid or phage clones of genes, cDNAs (e.g., expressed sequence tags), or inserts therefrom (Nguyen et al., 1995, Genomics 29:207-209).

A number of methods are known in the art for affixing the nucleic acids or analogues to a solid support that makes up the array (Schena et al., 1995, Science 270:467-470; DeRisi et al., 1996, Nature Genetics 14:457-460; Shalon et al., 1996, Genome Res. 6:639-645; and Schena et al., 1995, Proc. Natl. Acad. Sci. USA 93:10539-11286).

Another method for making microarrays is by making high-density oligonucleotide arrays (Fodor et al., 1991, Science 251:767-773; Pease et al.; 1994, Proc. Natl. Acad. Sci. USA 91:5022-5026; Lockhart et al., 1996, Nature Biotech 14:1675; U.S. Pat. Nos. 5,578,832; 5,556,752; and 5,510,270; Blanchard et al., 1996, 11: 687-90).

Other methods for making microarrays, e.g., by masking (Maskos and Southern, 1992, Nuc. Acids Res. 20:1679-1684), may also be used. In principal, any type of array, for example, dot blots on a nylon hybridization membrane (see Sambrook et al., Molecular Cloning—A Laboratory Manual (2nd Ed.), Vol. 1-3, Cold Spring Harbor Laboratory, Cold Spring Harbor, N.Y., 1989), could be used, although, as will be recognized by those of skill in the art.

The nucleic acids to be contacted with the microarray may be prepared in a variety of ways, and may include nucleotides of the subject invention. Such nucleic acids are often labeled fluorescently. Nucleic acid hybridization and wash conditions are chosen so that the population of labeled nucleic acids will specifically hybridize to appropriate, complementary nucleic acids affixed to the matrix. Non-specific binding of the labeled nucleic acids to the array can be decreased by treating the array with a large quantity of non-specific DNA—a so-called "blocking" step.

When fluorescently labeled probes are used, the fluorescence emissions at each site of a transcript array may be detected by scanning confocal laser microscopy. When two fluorophores are used, a separate scan, using the appropriate excitation line, is carried out for each of the two fluorophores used. Fluorescent microarray scanners are commercially available from Affymetrix, Packard BioChip Technologies, BioRobotics and many other suppliers. Signals are recorded, quantitated and analyzed using a variety of computer software.

According to the methods, the relative abundance of an mRNA in two cells or cell lines is scored as a perturbation and its magnitude determined (i.e., the abundance is different in the two sources of mRNA tested), or as not perturbed (i.e., the relative abundance is the same). As used herein, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Present detection methods allow reliable detection of difference of an order of about 2-fold to about 5-fold, but more sensitive methods are expected to be developed.

In addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

In certain embodiments, the data obtained from such experiments reflects the relative expression of each gene represented in the microarray. Expression levels in different samples and conditions may now be compared using a variety of statistical methods.

12. Pharmaceutical Compositions

Pharmaceutical compositions include any modulator identified according to the present invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. The term parenteral as used herein includes subcutaneous, intracutaneous, intravenous, intramuscular, intra articular, intrasynovial, intrasternal, intrathecal, intralesional, and intracranial injection or infusion techniques.

Dosage levels of between about 0.01 and about 100 mg/kg body weight per day, preferably between about 0.5 and about 75 mg/kg body weight per day of the modulators described herein are useful for the prevention and treatment of disease and conditions, including *F. tularensis* mediated diseases and conditions. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

13. Antimicrobial Agents

The polypeptides of the invention may be used to develop antimicrobial agents for use in a wide variety of applications. The uses are as varied as surface disinfectants, topical pharmaceuticals, personal hygiene applications (e.g., antimicrobial soap, deodorant or the like), additives to cell culture medium, and systemic pharmaceutical products. Antimicrobial agents of the invention may be incorporated into a wide variety of products and used to treat an already existing microbial infection/contamination or may be used prophylactically to suppress future infection/contamination.

The antimicrobial agents may be administered to a site, or potential site, of infection/contamination in either a liquid or solid form. Alternatively, the agent may be applied as a coating to a surface of an object where microbial growth is undesirable using nonspecific absorption or covalent attachment. For example, implants or devices (such as linens, cloth, plastics, heart pacemakers, surgical stents, catheters, gastric tubes, endotracheal tubes, prosthetic devices) can be coated with the antimicrobials to minimize adherence or persistence of bacteria during storage and use. The antimicrobials may also be incorporated into such devices to provide slow release of the agent locally for several weeks during healing. The antimicrobial agents may also be used in association with devices such as ventilators, water reservoirs, air-conditioning units, filters, paints, or other substances. Antimicrobials may also be given orally or systemically after transplantation, bone replacement, during dental procedures, or during implantation to prevent colonization with bacteria.

In another embodiment, subject antimicrobial agents may be used as a food preservative or in treating food products to eliminate potential pathogens. The latter use might be targeted to the fish and poultry industries that have serious problems with enteric pathogens which cause severe human disease. In a further embodiment, the agents of the invention may be used as antimicrobials for food crops, either as agents to reduce post harvest spoilage or to enhance host resistance. The antimicrobials may also be used as preservatives in processed foods either alone or in combination with antibacterial food additives such as lysozymes.

In another embodiment, the antimicrobials of the invention may be used as an additive to culture medium to prevent or eliminate infection of cultured cells with a pathogen.

14. OTHER EMBODIMENTS

In addition to the other embodiments, aspects and objects disclosed herein, including the claims appended hereto, the following paragraphs set forth additional, non-limiting embodiments and other aspects of the present invention (with all references to paragraphs contained in this section referring to other paragraphs set forth in this section):

1. A composition comprising an isolated, recombinant polypeptide, wherein the polypeptide comprises: (a) an amino acid sequence set forth in SEQ ID NO: 2; (b) an amino acid sequence having at least about 95% identity with the amino acid sequence set forth in SEQ ID NO: 2; or (c) an amino acid sequence encoded by a polynucleotide that hybridizes under stringent conditions to the complementary strand of a polynucleotide having SEQ ID NO: 1 and has at least one biological activity of FabI from *F. tularensis*; and wherein the polypeptide of (a), (b) or (c) is at least about 90% pure in a sample of the composition.

2. The composition of paragraph 1, wherein the polypeptide is at least about 95% pure as determined by gel electrophoresis.

3. The composition of paragraph 1, wherein the polypeptide is purified to essential homogeneity.

4. The composition of paragraph 1, wherein at least about two-thirds of the polypeptide in the sample is soluble.

5. The composition of paragraph 1, wherein the polypeptide is fused to at least one heterologous polypeptide that increases the solubility or stability of the polypeptide.

6. The composition of paragraph 1, which further comprises a matrix suitable for mass spectrometry.

7. The composition of paragraph 6, wherein the matrix is a nicotinic acid derivative or a cinnamic acid derivative.

8. A sample comprising an isolated, recombinant polypeptide, wherein the polypeptide comprises: (a) an amino acid sequence set forth in SEQ ID NO: 2; (b) an amino acid sequence having at least about 95% identity with the amino acid sequence set forth in SEQ ID NO: 2; or (c) an amino acid sequence encoded by a polynucleotide that hybridizes under stringent conditions to the complementary strand of a polynucleotide having SEQ ID NO: 1 and has at least one biological activity of FabI from *F. tularensis*; and wherein the polypeptide of (a), (b) or (c) is labeled with a heavy atom.

9. The sample of paragraph 8, wherein the heavy atom is one of the following: cobalt, selenium, krypton, bromine, strontium, molybdenum, ruthenium, rhodium, palladium, silver, cadmium, tin, iodine, xenon, barium, lanthanum, cerium, praseodymium, neodymium, samarium, europium, gadolinium, terbium, dysprosium, holmium, erbium, thulium, ytterbium, lutetium, tantalum, tungsten, rhenium, osmium, iridium, platinum, gold, mercury, thallium, lead, thorium and uranium.

10. The sample of paragraph 8, wherein the polypeptide is labeled with seleno-methionine.

11. The sample of paragraph 8, further comprising a cryoprotectant.

12. The sample of paragraph 11, wherein the cryo-protectant is one of the following: methyl pentanediol, isopropanol, ethylene glycol, glycerol, formate, citrate, mineral oil and a low-molecular-weight polyethylene glycol.

13. A crystallized, recombinant polypeptide comprising: (a) an amino acid sequence set forth in SEQ ID NO: 2; (b) an amino acid sequence having at least about 95% identity with the amino acid sequence set forth in SEQ ID NO: 2; or (c) an amino acid sequence encoded by a polynucleotide that hybridizes under stringent conditions to the complementary strand of a polynucleotide having SEQ ID NO: 1 and has at least one biological activity of FabI from *F. tularensis*; wherein the polypeptide of (a), (b) or (c) is in crystal form.

14. A crystallized complex comprising the crystallized, recombinant polypeptide of paragraph 13 and a co-factor, wherein the complex is in crystal form.

15. A crystallized complex comprising the crystallized, recombinant polypeptide of paragraph 13 and a small organic molecule, wherein the complex is in crystal form.

16. The crystallized, recombinant polypeptide of paragraph 13, which diffracts x-rays to a resolution of about 3.5 Å or better.

17. The crystallized, recombinant polypeptide of paragraph 13, wherein the polypeptide comprises at least one heavy atom label.

18. The crystallized, recombinant polypeptide of paragraph 17, wherein the polypeptide is labeled with seleno-methionine.

19. A method for designing a modulator for the prevention or treatment of *F. tularensis* related disease or disorder, comprising:
(a) providing a three-dimensional structure for a crystallized, recombinant polypeptide of paragraph 13;
(b) identifying a potential modulator for the prevention or treatment of *F. tularensis* related disease or disorder by reference to the three-dimensional structure;
(c) contacting a polypeptide of the composition of paragraph 1 or *F. tularensis* with the potential modulator; and
(d) assaying the activity of the polypeptide or determining the viability of *F. tularensis* after contact with the modulator, wherein a change in the activity of the polypeptide or the viability of *F. tularensis* indicates that the modulator may be useful for prevention or treatment of a *F. tularensis* related disease or disorder.

20. A sample comprising an isolated, recombinant polypeptide, wherein the polypeptide comprises: (a) an amino acid sequence set forth in SEQ ID NO: 2; (b) an amino acid sequence having at least about 95% identity with the amino acid sequence set forth in SEQ ID NO: 2; or (c) an amino acid sequence encoded by a polynucleotide that hybridizes under stringent conditions to the complementary strand of a polynucleotide having SEQ ID NO: 1 and has at least one biological activity of FabI from *F. tularensis*; and wherein the polypeptide of (a), (b) or (c) is enriched in at least one NMR isotope.

21. The sample of paragraph 20, wherein the NMR isotope is one of the following: hydrogen-1 ($^1$H), hydrogen-2 ($^2$H), hydrogen-3 ($^3$H), phosphorous-31 ($^{31}$p), sodium-23 ($^{23}$Na), nitrogen-14 ($^{14}$N), nitrogen-15 ($^{15}$N), carbon-13 ($^{13}$C) and fluorine-19 ($^{19}$F).

22. The sample of paragraph 20, further comprising a deuterium lock solvent.

23. The sample of paragraph 22, wherein the deuterium lock solvent is one of the following: acetone ($CD_3COCD_3$), chloroform ($CDCl_3$), dichloro methane ($CD_2Cl_2$), methylnitrile ($CD_3CN$), benzene ($C_6D_6$), water ($D_2O$), diethylether (($CD_3CD_2)_2O$), dimethylether (($CD_3)_2O$), N,N-dimethylformamide (($CD_3)_2NCDO$), dimethyl sulfoxide ($CD_3SOCD_3$), ethanol ($CD_3CD_2OD$), methanol ($CD_3OD$), tetrahydrofuran ($C_4D_8O$), toluene ($C_6D_5CD_3$), pyridine ($C_5D_5N$) and cyclohexane ($C_6H_{12}$).

24. The sample of paragraph 20, which is contained within an NMR tube.

25. A method for identifying small molecules that bind to a polypeptide of the composition of paragraph 1, comprising:
(a) generating a first NMR spectrum of an isotopically labeled polypeptide of the composition of paragraph 1;
(b) exposing the polypeptide to one or more small molecules;
(c) generating a second NMR spectrum of the polypeptide which has been exposed to one or more small molecules; and
(d) comparing the first and second spectra to determine differences between the first and the second spectra, wherein the differences are indicative of one or more small molecules that have bound to the polypeptide.

26. A host cell comprising a nucleic acid encoding a polypeptide comprising: (a) an amino acid sequence set forth in SEQ ID NO: 2; (b) an amino acid sequence having at least about 95% identity with the amino acid sequence set forth in SEQ ID NO: 2; or (c) an amino acid sequence encoded by a polynucleotide that hybridizes under stringent conditions to the complementary strand of a polynucleotide having SEQ ID NO: 1 and has at least one biological activity of FabI from *F. tularensis*; wherein a culture of the host cell produces at least about 1 mg of the polypeptide per liter of culture and the polypeptide is at least about one-third soluble as measured by gel electrophoresis.

27. An isolated, recombinant polypeptide, comprising: (a) an amino acid sequence having at least about 90% identity with the amino acid sequence set forth in SEQ ID NO: 4; or (b) an amino acid sequence encoded by a polynucleotide that hybridizes under stringent conditions to the complementary strand of a polynucleotide having SEQ ID NO: 1 and has at least one biological activity of FabI from *F. tularensis*; and wherein the polypeptide comprises one or more of the following amino acid residues at the specified position of the polypeptide: A92, R96, P154, S155, P191, S198, L195, A94, F203, Y146, Y156, I200, S201, M206, A196, M153, M159, L99, F93, K163, I192, K193, T194, L195, A196, A197, S198, G199, I200, S201, or N202.

28. A method for obtaining structural information of a crystallized polypeptide, the method comprising:
(a) crystallizing a recombinant polypeptide, wherein the polypeptide comprises: (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*; and wherein the crystallized polypeptide is capable of diffracting X-rays to a resolution of 3.5 Å or better; and
(b) analyzing the crystallized polypeptide by X-ray diffraction to determine the three-dimensional structure of at least a portion of the crystallized polypeptide.

29. The method of paragraph 28, wherein the three-dimensional structure of the portion of the crystallized polypeptide is determined to a resolution of 3.5 Å or better.

30. A method for identifying a druggable region of a polypeptide, the method comprising:

(a) obtaining crystals of a polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*, such that the three dimensional structure of the crystallized polypeptide may be determined to a resolution of 3.5 Å or better;

(b) determining the three dimensional structure of the crystallized polypeptide using X-ray diffraction; and (c) identifying a druggable region of the crystallized polypeptide based on the three-dimensional structure of the crystallized polypeptide.

31. The method of paragraph 30, wherein the druggable region is an active site.

32. The method of paragraph 31, wherein the druggable region is on the surface of the polypeptide.

33. Crystalline FabI from *F. tularensis* comprising a crystal having unit cell dimensions a=b=130.072 Å, c=88.436 Å, $\alpha=\gamma=90°$, $\beta=120°$, with space group $P6_222$.

34. A crystallized polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*; wherein the crystal has a $P6_222$ space group.

35. A crystallized polypeptide comprising a structure of a polypeptide that is defined by a substantial portion of the atomic coordinates set forth in FIG. 20.

36. A method for determining the crystal structure of a homolog of a polypeptide, the method comprising:

(a) providing the three dimensional structure of a first crystallized polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*;

(b) obtaining crystals of a second polypeptide comprising an amino acid sequence that is at least 70% identical to the amino acid sequence set forth in SEQ ID NO: 2, such that the three dimensional structure of the second crystallized polypeptide may be determined to a resolution of 3.5 Å or better; and (c) determining the three dimensional structure of the second crystallized polypeptide by x-ray crystallography based on the atomic coordinates of the three dimensional structure provided in step (a).

37. The method of paragraph 36, wherein the atomic coordinates for the second crystallized polypeptide have a root mean square deviation from the backbone atoms of the first polypeptide of not more than 1.0 Å for all backbone atoms shared in common with the first polypeptide and the second polypeptide.

38. A method for homology modeling a homolog of FabI from *F. tularensis*, comprising:

(a) aligning the amino acid sequence of a homolog of FabI from *F. tularensis* with an amino acid sequence of SEQ ID NO: 2 and incorporating the sequence of the homolog of FabI from *F. tularensis* into a model of FabI from *F. tularensis* derived from structure coordinates as listed in FIG. 20 to yield a preliminary model of the homolog of FabI from *F. tularensis*;

(b) subjecting the preliminary model to energy minimization to yield an energy minimized model;

(c) remodeling regions of the energy minimized model where stereochemistry restraints are violated to yield a final model of the homolog of FabI from *F. tularensis*.

39. A method for obtaining structural information about a molecule or a molecular complex of unknown structure comprising:

(a) crystallizing the molecule or molecular complex;

(b) generating an x-ray diffraction pattern from the crystallized molecule or molecular complex;

(c) applying at least a portion of the structure coordinates set forth in FIG. 20 to the x-ray diffraction pattern to generate a three-dimensional electron density map of at least a portion of the molecule or molecular complex whose structure is unknown.

40. A method for attempting to make a crystallized complex comprising a polypeptide and a modulator having a molecular weight of less than 5 kDa, the method comprising:

(a) crystallizing a polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*; such that crystals of the crystallized polypeptide will diffract x-rays to a resolution of 5 Å or better; and (b) soaking the crystals in a solution comprising a potential modulator having a molecular weight of less than 5 kDa.

41. A method for incorporating a potential modulator in a crystal of a polypeptide, comprising placing a crystal of FabI from *F. tularensis* having unit cell dimensions a=b=130.072 Å, c=88.436 Å, $\alpha=\gamma=90°$, $\beta=120°$, with space group $P6_222$ in a solution comprising the potential modulator.

42. A computer readable storage medium comprising digitally encoded structural data, wherein the data comprises structural coordinates as listed in FIG. 20 for the backbone atoms of at least about six amino acid residues from a druggable region of FabI from *F. tularensis*.

43. A scalable three-dimensional configuration of points, at least a portion of the points derived from some or all of the structure coordinates as listed in FIG. 20 for a plurality of amino acid residues from a druggable region of FabI from *F. tularensis*.

44. The scalable three-dimensional configuration of points of paragraph 43, wherein the structure coordinates as listed in FIG. 20 for the backbone atoms of at least about five amino acid residues from a druggable region of FabI from *F. tularensis* are used to derive part or all of the portion of points.

45. The scalable three-dimensional configuration of points of paragraph 43, wherein the structure coordinates as listed in FIG. 20 for the backbone and optionally the side chain atoms of at least about ten amino acid residues from a druggable region of FabI from *F. tularensis* are used to derive part or all of the portion of points.

46. The scalable three-dimensional configuration of points of paragraph 43, wherein the structure coordinates as listed in FIG. 20 for the backbone atoms of at least about fifteen amino acid residues from a druggable region of FabI from *F. tularensis* are used to derive part or all of the portion of points.

47. The scalable three-dimensional configuration of points of paragraph 43, wherein substantially all of the points are derived from structure coordinates as listed in FIG. 20.

48. The scalable three-dimensional configuration of points of paragraph 43, wherein the structure coordinates as listed in FIG. 20 for the atoms of the amino acid residues from any of the above-described druggable regions of FabI from *F. tularensis* are used to derive part or all of the portion of points:

49. A scalable three-dimensional configuration of points, comprising points having a root mean square deviation of less than about 1.0 Å from the three dimensional coordinates as listed in FIG. 20 for the backbone atoms of at least five amino acid residues, wherein the five amino acid residues are from a druggable region of FabI from *F. tularensis*.

50. The scalable three-dimensional configuration of points of paragraph 49, wherein any point-to-point distance, calculated from the three dimensional coordinates as listed in FIG. 20, between one of the backbone atoms for one of the five amino acid residues and another backbone atom of a different one of the five amino acid residues is not more than about 10 Å.

51. A scalable three-dimensional configuration of points comprising points having a root mean square deviation of less than about 1.0 Å from the three dimensional coordinates as listed in FIG. 20 for the atoms of the amino acid residues from any of the above-described druggable regions of FabI from *F. tularensis:*

52. A computer readable storage medium comprising digitally encoded structural data, wherein the data comprise the identity and three-dimensional coordinates as listed in FIG. 20 for the atoms of the amino acid residues from any of the above-described druggable regions of FabI from *F. tularensis:*

53. A scalable three-dimensional configuration of points, wherein the points have a root mean square deviation of less than about 1.0 Å from the three dimensional coordinates as listed in FIG. 20 for the atoms of the amino acid residues from any of the above-described druggable regions of FabI from *F. tularensis*, wherein up to one amino acid residue in each of the regions may have a conservative substitution thereof.

54. A scalable three-dimensional configuration of points derived from a druggable region of a polypeptide, wherein the points have a root mean square deviation of less than about 1.0 Å from the three dimensional coordinates as listed in FIG. 20 for the backbone atoms of at least ten amino acid residues that participate in the intersubunit contacts of FabI from *F. tularensis*.

55. A computer-assisted method for identifying an inhibitor of the activity of FabI from *F. tularensis*, comprising:

(a) supplying a computer modeling application with a set of structure coordinates as listed in FIG. 20 for the atoms of the amino acid residues from any of the above-described druggable regions of FabI from *F. tularensis* so as to define part or all of a molecule or complex;

(b) supplying the computer modeling application with a set of structure coordinates of a chemical entity; and (c) determining whether the chemical entity is expected to bind to or interfere with the molecule or complex.

56. The method of paragraph 55, wherein determining whether the chemical entity is expected to bind to or interfere with the molecule or complex comprises performing a fitting operation between the chemical entity and a druggable region of the molecule or complex, followed by computationally analyzing the results of the fitting operation to quantify the association between the chemical entity and the druggable region.

57. The method of paragraph 55, further comprising screening a library of chemical entities.

58. A computer-assisted method for designing an inhibitor of FabI activity comprising:

(a) supplying a computer modeling application with a set of structure coordinates having a root mean square deviation of less than about 1.0 Å from the structure coordinates as listed in FIG. 20 for the atoms of the amino acid residues from any of the above-described druggable regions of FabI from *F. tularensis* so as to define part or all of a molecule or complex;

(b) supplying the computer modeling application with a set of structure coordinates for a chemical entity;

(c) evaluating the potential binding interactions between the chemical entity and the molecule or complex;

(d) structurally modifying the chemical entity to yield a set of structure coordinates for a modified chemical entity; and (e) determining whether the modified chemical entity is an inhibitor expected to bind to or interfere with the molecule or complex, wherein binding to or interfering with the molecule or molecular complex is indicative of potential inhibition of FabI activity.

59. The method of paragraph 58, wherein determining whether the modified chemical entity is an inhibitor expected to bind to or interfere with the molecule or complex comprises performing a fitting operation between the chemical entity and the molecule or complex, followed by computationally analyzing the results of the fitting operation to evaluate the association between the chemical entity and the molecule or complex.

60. The method of paragraph 58, wherein the set of structure coordinates for the chemical entity is obtained from a chemical library.

61. A computer-assisted method for designing an inhibitor of FabI activity de novo comprising:

(a) supplying a computer modeling application with a set of three-dimensional coordinates derived from the structure coordinates as listed in FIG. 20 for the atoms of the amino acid residues from any of the above-described druggable regions of FabI from *F. tularensis* so as to define part or all of a molecule or complex;

(b) computationally building a chemical entity represented by a set of structure coordinates; and (c) determining whether the chemical entity is an inhibitor expected to bind to or interfere with the molecule or complex, wherein binding to or interfering with the molecule or complex is indicative of potential inhibition of FabI activity.

62. The method of paragraph 61, wherein determining whether the chemical entity is an inhibitor expected to bind to or interfere with the molecule or complex comprises performing a fitting operation between the chemical entity and a druggable region of the molecule or complex, followed by computationally analyzing the results of the fitting operation to quantify the association between the chemical entity and the druggable region.

63. The method of any of paragraphs 55, 58 or 61, further comprising supplying or synthesizing the potential inhibitor, then assaying the potential inhibitor to determine whether it inhibits FabI activity.

64. A method for identifying a potential modulator for the prevention or treatment of a *F. tularensis* related disease or disorder, the method comprising:

(a) providing the three dimensional structure of a crystallized polypeptide comprising: (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*;

(b) obtaining a potential modulator for the prevention or treatment of *F. tularensis* related disease or disorder based on the three dimensional structure of the crystallized polypeptide;

(c) contacting the potential modulator with a second polypeptide comprising: (i) an amino acid sequence set forth in SEQ ID NO: 2; (ii) an amino acid sequence having at least about 95% identity with the amino acid sequence set forth in SEQ ID NO: 2; or (iii) an amino acid sequence encoded by a polynucleotide that hybridizes under stringent conditions to the complementary strand of a polynucleotide having SEQ ID NO: 1 and has at least one biological activity of FabI from *F. tularensis*; which second polypeptide may optionally be the same as the crystallized polypeptide; and (d) assaying the activity of the second polypeptide, wherein a change in the activity of the second polypeptide indicates that the compound may be useful for prevention or treatment of a *F. tularensis* related disease or disorder.

65. A method for designing a candidate modulator for screening for inhibitors of a polypeptide, the method comprising:

(a) providing the three dimensional structure of a druggable region of a polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*; and (b) designing a candidate modulator based on the three dimensional structure of the druggable region of the polypeptide.

66. A method for identifying a potential modulator of a polypeptide from a database, the method comprising:

(a) providing the three-dimensional coordinates for a plurality of the amino acids of a polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*;

(b) identifying a druggable region of the polypeptide; and (c) selecting from a database at least one potential modulator comprising three dimensional coordinates which indicate that the modulator may bind or interfere with the druggable region.

67. The method of paragraph 66, wherein the modulator is a small molecule.

68. A method for preparing a potential modulator of a druggable region contained in a polypeptide, the method comprising:

(a) using the atomic coordinates for the backbone atoms of at least about six amino acid residues from a polypeptide of SEQ ID NO: 4, with a±a root mean square deviation from the backbone atoms of the amino acid residues of not more than 1.0 Å, to generate one or more three-dimensional structures of a molecule comprising a druggable region from the polypeptide;

(b) employing one or more of the three dimensional structures of the molecule to design or select a potential modulator of the druggable region; and (c) synthesizing or obtaining the modulator.

69. An apparatus for determining whether a compound is a potential modulator of a polypeptide, the apparatus comprising:

(a) a memory that comprises:

(i) the three dimensional coordinates and identities of at least about fifteen atoms from a druggable region of a polypeptide comprising (1) an amino acid sequence set forth in SEQ ID NO: 2; (2) an amino acid sequence having at least about 95% identity with the amino acid sequence set forth in SEQ ID NO: 2; or (3) an amino acid sequence encoded by a polynucleotide that hybridizes under stringent conditions to the complementary strand of a polynucleotide having SEQ ID NO: 1 and has at least one biological activity of FabI from *F. tularensis*;

(ii) executable instructions; and (b) a processor that is capable of executing instructions to:

(i) receive three-dimensional structural information for a candidate modulator;

(ii) determine if the three-dimensional structure of the candidate modulator is complementary to the three dimensional coordinates of the atoms from the druggable region; and (iii) output the results of the determination.

70. A method for making an inhibitor of FabI activity, the method comprising chemically or enzymatically synthesizing a chemical entity to yield an inhibitor of FabI activity, the chemical entity having been identified during a computer-assisted process comprising supplying a computer modeling application with a set of structure coordinates of a molecule or complex, the molecule or complex comprising at least a portion of at least one druggable region from FabI from *F. tularensis*; supplying the computer modeling application with a set of structure coordinates of a chemical entity; and determining whether the chemical entity is expected to bind or to interfere with the molecule or complex at a druggable region, wherein binding to or interfering with the molecule or complex is indicative of potential inhibition of FabI activity.

71. A computer readable storage medium comprising digitally encoded data, wherein the data comprises structural coordinates for a druggable region that is structurally homologous to the structure coordinates as listed in FIG. 20 for a druggable region of FabI from *F. tularensis*.

72. A computer readable storage medium comprising digitally encoded structural data, wherein the data comprise a majority of the three-dimensional structure coordinates as listed in FIG. 20.

73. The computer readable storage medium of paragraph 72, further comprising the identity of the atoms for the majority of the three-dimensional structure coordinates as listed in FIG. 20.

74. The computer readable storage medium of paragraph 72, wherein the data comprise substantially all of the three-dimensional structure coordinates as listed in FIG. 20.

75. An isolated polypeptide comprising an amino acid sequence that is at least 80% identical to SEQ ID NO: 2 over its entire length and wherein said polypeptide includes SEQ ID NO: 22.

76. An isolated polypeptide comprising an amino acid sequence that is at least 80% identical to SEQ ID NO: 2 over its entire length and wherein said polypeptide includes SEQ ID NO: 23.

77. A isolated polypeptide comprising: (a) an amino acid sequence set forth in SEQ ID NO: 2; (b) an amino acid sequence having at least about 95% identity with the amino acid sequence set forth in SEQ ID NO: 2; or (c) an amino acid sequence encoded by a polynucleotide that hybridizes under stringent conditions to the complementary strand of a polynucleotide having SEQ ID NO: 1, wherein said polypeptide has at least one biological activity of a FabI polypeptide.

78. The isolated polypeptide of any one of paragraphs 75-77, wherein said polypeptide has at least one biological activity of a FabI polypeptide.

79. The isolated polypeptide of paragraph 78, wherein said polypeptide is capable of reducing crotonyl-CoA or crotonyl-ACP.

80. The isolated polypeptide of any one of paragraphs 75-77, wherein said polypeptide is fused to at least one heterologous polypeptide that increases the solubility or stability of the polypeptide.

81. A composition comprising the isolated polypeptide of any one of paragraphs 75-77, wherein said polypeptide is at least about 90% pure in a sample of the composition.

82. A composition comprising the isolated polypeptide of any one of paragraphs 75-77, wherein at least about two-thirds of the polypeptide in the sample is soluble.

83. The isolated polypeptide of any one of paragraphs 75-77, wherein said polypeptide further comprises a label.

84. The isolated polypeptide of paragraph 83, wherein said label is a heavy atom label, seleno-methionine, an isotopic label, a fluorescent label, or an antigenic label.

85. The isolated polypeptide of any one of paragraphs 75-77, wherein said polypeptide is combined with a matrix suitable for mass spectrometry, a cryo-protectant, a deuterium lock solvent, or an adjuvent.

86. An isolated nucleic acid comprising (a) a nucleotide sequence that encodes a polypeptide comprising an amino acid sequence that is at least 40% identical to SEQ ID NO: 2 over its entire length and wherein said polypeptide includes SEQ ID NO: 21, (b) a nucleotide sequence that encodes a polypeptide comprising an amino acid sequence that is at least 60% identical to SEQ ID NO: 2 over its entire length and wherein said polypeptide includes SEQ ID NO: 22, or (c) a nucleotide sequence that encodes an amino acid sequence having at least about 95% identity with the amino acid sequence set forth in SEQ ID NO: 2.

87. An isolated nucleic acid that hybridizes under stringent conditions to nucleic acid sequence set forth in SEQ ID NO: 1.

88. The isolated nucleic acid of any one of paragraphs 86 or 87, wherein said nucleic acid encodes a polypeptide having at least one biological activity of a FabI polypeptide.

89. A vector comprising the isolated nucleic acid of any one of paragraphs 86 or 87.

90. A host cell comprising the isolated nucleic acid of any one of paragraphs 86 or 87.

91. The host cell of paragraph 90, wherein a culture of the host cell produces at least about 1 mg of the polypeptide per liter of culture and the polypeptide is at least about one-third soluble as measured by gel electrophoresis.

92. An antibody that binds to a polypeptide having SEQ ID NO: 2.

93. The antibody of paragraph 92, wherein said antibody does not significantly cross react with a FabI polypeptide from a species other than *F. tularensis*.

94. The antibody of paragraph 93, wherein said antibody does not significantly cross react with a FabI polypeptide having less than 80% identity with SEQ ID NO: 2.

95. A method for screening for a modulator of a FabI polypeptide comprising:
contacting an isolated FabI polypeptide according to any one of paragraphs 75-77 with a candidate compound; and
detecting a change in an activity of said FabI polypeptide.

96. The method of paragraph 95, wherein said activity of said FabI polypeptide is one or more of the following: reduction of enoyl-ACP, crotonyl-CoA or crotonyl-ACP, uncompetitive inhibition by Apo-ACP versus NADH (Ki(app)), competitive inhibition by Apo-ACP versus crotonoyl CoA, induction of negative cooperativity with respect to CCA binding, use of NADH and NADPH as substrates by Fab I, binding of NADH and NADPH by FabI, oxidation of NADH and NADPH by FabI, ratio of Kmapp for NADH as compared to NADPH, use of NADH and crotonoyl CoA as substrates by Fab I in a sequential kinetic mechanism, sequential binding of NADH and crotonoyl CoA by Fab I, increasing inhibition of FabI by saturated fatty acyl CoA's of increasing chain length, feedback regulatory mechanism of Fab I by saturated fatty acyl CoA's, competitive inhibition by palmitoyl CoA versus crotonoyl CoA, competitive inhibition by palmitoyl CoA versus crotonoyl CoA modulation through binding of multiple palmitoyl CoA molecules to Fab I, binding of multiple palmitoyl CoA molecules to Fab I, negative cooperativity in the binding of CCA, formation of an dimeric quaternary structure, formation of an tetrameric quaternary structure formation of an oligomeric quaternary structure, binding of Fab I by pseudo-product inhibitors beta-NADP+ or palmitoyl coA, or NADH binding to Fab I prior to or simultaneous with ACP binding.

97. The method of paragraph 95, wherein said modulator is agonist of said FabI polypeptide.

98. The method of paragraph 95, wherein said modulator is antagonist of said FabI polypeptide.

99. The method of paragraph 96, wherein said activity of said FabI polypeptide is reduction of enoyl-ACP, crotonyl-CoA or crotonyl-ACP.

100. The method of paragraph 99, wherein said contacting is carried out in the presence of NADPH or NADH.

101. The method of paragraph 99, wherein said detecting step comprises: (i) measuring the rate of reduction of enoyl-ACP, crotonyl-CoA or crotonyl-ACP, (ii) measuring a change in light absorption for at least two time point, or (iii) assaying the concentration of NADH.

EXEMPLIFICATION

The invention now being generally described, it will be more readily understood by reference to the following examples which are included merely for purposes of illustration of certain aspects and embodiments of the present invention, and are not intended to limit the invention in any way.

*Francisella* tularensis is a small, nonmotile, aerobic, gram-negative coccobacillus and is the causative agent of tularemia, an infrequent disease of the northern hemisphere (Ellis et al. 2002). Naturally, tularemia is a disease transmitted to humans through contact with wild animals, arthropod hosts, and water. The human infection may be prolonged and difficult to treat, and has a high mortality rate, estimated up to 10% with some serovars. There are approximately 200 natural cases of tularemia in the United States annually (Morb Mortal Wkly Rep 1998; 46:71-80).

*F. tularensis* multiplies within macrophages, and is a facultative intracellular bacterium. The major target organs are the lymph nodes, lungs and pleura, spleen, liver, and kidney. Untreated, bacilli inoculated into skin or mucous membranes multiply, spread to regional lymph nodes and further multiply, and then may disseminate to organs throughout the body (Ellis et al. 2002). The initial tissue reaction is focal tissue injury consisting of large accumulations of polymorphonuclear leukocytes, leading to large granuloma-like lesions.

Before the advent of antibiotics, the overall mortality rate for the more virulent Type A strain infections was 5-15%, but mortality rates have been as high as 30-60% for the untreated pneumonic and more severe systemic forms of the disease. With treatment, the most recent mortality rates in the US have been 2% (Ellis et al. 2002). *F. tularensis* Type B infections are rarely fatal.

The genome of *F. tularensis* is approximately 2 million nucleotides in length; two efforts are underway to sequence *F. tularensis* genomes. A genome project to sequence the *F. tularensis* Live Vaccine Strain (LVS) has been initiated by the Department of Energy Joint Genome Institute (bbrp.llnl.gov/bbrp/html/microbe.html). No sequence information is yet available from this project. A second genome project to sequence the *F. tularensis* strain Schu 4 has been funded (Prior et al. 2001). Preliminary sequence information is available on the project's web site (artedi.ebc.uu.se/Projects/Francisella/). Within this sequence, portions of the probable *F. tularensis* fabI gene have been found.

*F. tularensis* is difficult to culture on standard media, however modified media have been devised (Baker et al. 1985), which allow recovery of isolates from blood, ulcers, conjunctival exudates, sputum, gastric washings, and pharyngeal exudates. Infection of laboratory personnel is a substantial risk, and routine culture is not recommended (Baker et al. 1985). Confirmation of *F. tularensis* can be done by antigen recognition assays and polymerase chain reaction (Ellis et al. 2002).

Streptomycin is the antibacterial of choice for the treatment for natural infections. The drug is bactericidal for *F. tularensis* and patients normally respond within 48 hours of administration. Gentamicin, which is more widely available and can be used intravenously, is an alternative. Other agents with less clinical experience that have activity against *F. tularensis* are fluoroquinolones and doxycycline. Tetracycline and chloramphenicol are bacteriostatic against *F. tularensis*, and treatment failures and relapses are reported with these antibiotics. In mass causality settings, ciprofloxacin and doxycycline are the suggested antibacterial treatments of choice (Ellis et al. 2002).

In the United States, a live-attenuated vaccine derived from the avirulent LVS has been used to protect laboratory personnel routinely working with *F. tularensis*. This vaccine is not currently registered, but available from the US military services. Given the short incubation period of tularemia and incomplete protection of current vaccines against inhalational tularemia, vaccination is not recommended for post-exposure prophylaxis.

*Francisella* tularensis, the organism that causes tularemia, is one of the most infectious pathogenic bacteria known, requiring inoculation or inhalation of as few as 10 organisms to cause disease. It is considered to be a dangerous potential biological weapon and of greater threat than anthrax, because of its extreme infectivity, ease of dissemination, and substantial capacity to cause illness and death (Center for Civilian Biodefense Strategies).

The Working Group on Civilian Biodefense believes that of the various possible ways that *F. tularensis* could be used as a weapon, an aerosol release would cause the greatest adverse medical and public health consequences (Dennis et al. 2001).

A World Health Organization (WHO) expert committee reported in 1970 that if 50 kg of virulent *F. tularensis* was dispersed as an aerosol over a metropolitan area with a population of 5 million there would an estimated 250,000 incapacitating casualties, including 19,000 deaths.

Aerosol dissemination of *F. tularensis* in a populated area would be expected to result in the abrupt onset of large numbers of cases of acute, non-specific febrile illness beginning 3 to 5 days later (incubation range, 1-14 days), with pleuropneumonitis developing in a significant proportion of cases over the ensuing days and weeks. At first, this could be difficult to distinguish from a natural outbreak of community acquired influenza or atypical pneumonia (Dennis et al. 2001). The large numbers of patients afflicted, rapid progression of disease from upper respiratory problems to bronchitis to pleuropneumonitis and systemic infection would quickly alert authorities of an unexpected public health event and bioterrorism as a possible cause (Dennis et al. 2001). Treatment of confirmed patients infected with *F. tularensis* would most likely require intra-venous (IV) agents in a hospital setting, due to the life-threatening pneumonia that occurs in a high proportion of cases. In addition, safe, effective oral agents would be needed to distribute to the population for post-exposure prophylaxis, due to the highly infectious nature of *Francisella*.

Engineered, antibiotic resistant forms of *F. tularensis* are an additional threat. Transformed plasmids have been engineered to express chloramphenicol and tetracycline resistance in *F. tularensis* (Pavlov et al. 1996). Virulent, streptomycin-resistant *F. tularensis* strains have been examined in biowarfare agent studies both in the United States and the Soviet Union (Sawyer et al. 1966).

One approach to combat microbial infection is the inhibition of enzymes involved in bacterial fatty acid biosynthesis (FAB). Fatty acid biosynthesis in bacteria is essential to the production of a number of lipid-containing components including the cell membrane. The bacterial fatty acid synthase system (FASII) utilizes discrete monofunctional enzymes that operate in conjunction with acyl carrier protein (ACP)-associated substrates. Mammalian fatty acid synthase (FASI) differs from FASII in that lipid biosynthesis is mediated by a single multifunctional enzyme-ACP complex. The differences in prokaryote and eukaryote fatty acid biosynthesis offer an attractive opportunity for selective FASII inhibition.

FabI is an enoyl-ACP reductase (ENR) that catalyzes the ultimate and rate-limiting step of the chain elongation process of FASII. The reaction involves the conjugate reduction of an enoyl-ACP to the corresponding acyl-ACP using the cofactor NAD(P)H as a hydride source. Reports describing the antibacterial agents isoniazid, diazaboranes, and triclosan as inhibitors of bacterial enoyl-ACP reductase support a FabI-targeted approach to antibacterial drug therapy.

In addition to FabI, FabK and FabL, which are other bacterial enoyl-ACP reductases expressed in several bacterial species may replace or augment FabI. FabK is a flavoprotein resistant to triclosan. It has been shown to be the only enoyl ACP-reductase in *Streptococcus pneumoniae* and to exist together with FabI in *Enterococcus faecalis*. The third enoyl-reductase, FabL, is present along with FabI in *Bacillus subtilus*. Therefore, an inhibitor designed to selectively target a single bacterial enoyl-ACP reductase may have a narrow spectrum of antimicrobial activity, whereas an inhibitor targeting multiple enoyl ACP-reductases may have a broader spectrum of activity.

One of the most important features of any drug is its ability to discriminate between a target enzyme and its counterpart in the host. To this end, significant differences in enzymes which carry out the same reaction afford attractive opportunities for drug development. A particular attractive area of metabolism where this has proved to be the case is in fatty acid biosynthesis.

Example 1

Isolation and Cloning of Nucleic Acid

The nucleotide sequence of the *F. tularensis* FabI gene was identified within genome sequencing project results available at artedi.ebc.uu.se/Projects/Francisella by tblastn analysis using the *E. coli* protein sequence. Oligonucleotide primers were designed to allow expression of untagged, amino terminal his-tagged, and carboxyl terminal his-tagged proteins using the pPW2 and pPW4 expression vectors. The sequences for the oligonucleotide primers are shown in FIG. 15 (SEQ ID NOs: 31 and 32). These primers were used to construct N-terminal His-tagged *F. tularensis* FabI (hisFt FabI) in the pPW2 vector, untagged *F. tularensis* FabI (Ft FabI) in the pPW4 vector, and C-terminal His-tagged *F. tularensis* FabI (C-hisFt FabI) in the pPW4 vector.

PCR reactions for each nucleotide sequence were performed using 1 uL of resuspended heat killed *F. tularensis* lyophilized cell pellet (Francis Nano, BC, Canada) and 2 units of high fidelity Platinum Pfx (invitrogen). The thermocycling conditions for the PCR process include a DNA melting step at 94° C. for 45 sec., a primer annealing step at 55° C. for 45 sec, and an extension step at 68° C. for 2 min 30 sec. After 30 cycles, a final blocking step at 72° C. for 9 min was carried out. The amplified nucleic acid product was isolated from the PCR cocktail using silica-gel membrane based column chromatography (Qiagen). The quality of the PCR product was assessed by resolving an aliquot of amplified product on a 1% agarose gel and quantified spectrophotometrically at $A_{260}$ or by visualizing the resolved products with ethidium bromide and a 302 nm UV-B light source.

The PCR product for each subject nucleic acid sequences was directionally cloned into the polylinker region of pPW2 and pPW4 using 1 unit T4 DNA ligase (Invitrogen). After the ligation reaction, the DNA was transformed into competent *E. coli* cells (strain BL21-GOLD (Stratagene) or DHSalpha (Invitrogen)) via heat shock as described in Sambrook, et. al., Molecular Cloning: A Laboratory Manual, $2^{nd}$ ed., Cold Spring Harbor Laboratory Press, Cold Spring Harbor, N.Y. (1989). Colony isolation and DNA extraction followed by PCR analysis with oligonucleotides complementary to the vector indicated that the expression vectors contained the Ft FabI gene. The positive transformants containing the 3 expression vectors were analyzed using standard test expression techniques, and the Ft FabI protein was observed in the soluble fraction of cell lysates.

The identified constructs producing soluble Ft FabI protein were sequenced, and the sequencing analysis demonstrated consensus between the expression construct and the genomic sequencing data.

Example 2

Cell Growth and Solubility

(a) Cell Growth

BL21(DE3) *E. coli* cells containing expression plasmids were grown at 37° C. to an $OD_{600}$ of approximately 3.82 in 1 L of Terrific Broth supplemented with 100 ug/mL ampicillin (hisFt FabI), or 50 ug/mL kanamycin (Ft FabI, C-hisFt FabI). The temperature was reduced to 15° C. and IPTG was added to a final concentration of 0.5 mM. The cells were incubated for 16 hours and harvested by centrifugation at 3000 rpm (Beckman J6M). Cells containing native expressed proteins were resuspended in lysis buffer (50 mM Tris pH 7.5) containing 0.5 mM PMSF and 1 mM benzamidine, and cells containing his tag fusion proteins were resuspended in binding buffer (50 mM HEPES pH 7.5, 500 mM NaCl, 5 mM imidazole, and 5% glycerol) containing 0.5 mM PMSF and 1 mM benzamidine. Cell suspensions were stored frozen at −70° C.

(b) Method One for Determining Protein Solubility Levels

The cells are harvested by centrifugation and subjected to a freeze/thaw cycle. The cells are lysed using detergent, sonication, or incubation with lysozyme. Total and soluble proteins are assayed using a 26-well BioRad Criterion gel running system. The proteins are stained with an appropriate dye (Coomassie, Silver stain, or Sypro-Red) and visualized with the appropriate visualization system. Typically, recombinant protein is seen as a prominent band in the lanes of the gel representing the soluble fraction.

(c) Method Two for Determining Protein Solubility Levels

The soluble and insoluble fractions (in the presence of 6M urea) of the cell pellet are bound to the appropriate affinity column. The purified proteins from both fractions are analysed by SDS-PAGE and the levels of protein in the soluble fraction are determined.

Example 3

Native Protein Expression

The expression construct clone encoding the soluble polypeptide having the amino acid sequence of SEQ ID NO: 4 is introduced into an expression host. The resultant cell line is then grown in culture. The method of growth is dependant on whether the protein to be purified is a native protein or a labeled protein. For native and $^{15}N$ labeled protein production, a Gold-pUBS520 (as described above), BL21-Gold (DE3) Codon-Plus (RIL) or (RP), or BL21 STAR *E. Coli* cell line is used. For generating proteins metabolically labeled with selenium, the clone is introduced into a strain called B834 (Novagen). The methods for expressing labeled polypeptides of the invention are described in the Examples that follow.

In one method for expressing an unlabeled polypeptide of the invention, 2 L LB cultures or 1 L TB cultures are inoculated with a 1% (v/v) starter culture ($OD_{600}$ of 0.8). The cultures are shaken at 37° C. and 200 rpm and grown to an $OD_{600}$ of 0.6-0.8 followed by induction with 0.5 mM IPTG at 15° C. and 200 rpm for at least 10 hours or at 25° C. for 4 hours.

The cells are harvested by centrifugation and the pellets are resuspended in 25 mL HEPES buffer (50 mM, pH 7.5), supplemented with 100 μL of protease inhibitors (PMSF and benzamidine (Sigma)) and flash-frozen in liquid nitrogen.

Alternatively, for an unlabeled polypeptide of the invention, a starter culture is prepared in a 300 mL Tunair flask (Shelton Scientific) by adding 20 mL of medium having 47.6 g/L of Terrific Broth and 1.5% glycerol in $dH_2O$ followed by autoclaving for 30 minutes at 121° C. and 15 psi. When the broth cools to room temperature, the medium is supplemented with 6.3 µM $CoCl_2\cdot 6H_2O$, 33.2 µM $MnSO_4\cdot 5H_2O$, 5.9 µM $CuCl_2\cdot 2H_2O$, 8.1 µM $H_3BO_3$, 8.3 µM $Na_2MoO_4\cdot 2H_2O$, 7 µM $ZnSO_4\cdot 7H_2O$, 108 µM $FeSO_4\cdot 7H_2O$, 68 µM $CaCl_2\cdot 2H_2O$, 4.1 µM $AlCl_3\cdot 6H_2O$, 8.4 µM $NiCl_2\cdot 6H_2O$, 1 mM $MgSO_4$, 0.5% v/v of Kao and Michayluk vitamins mix (Sigma; Cat. No. K3129), 25 µg/mL Carbenicillin, and 50 µg/mL Kanamycin. The medium is then inoculated with several colonies of the freshly transformed expression construct of interest. The culture is incubated at 37° C. and 260 rpm for about 3 hours and then transferred to a 2.5 L Tunair Flask containing 1 L of the above media. The 1 L culture is then incubated at 37° C. with shaking at 230-250 rpm on an orbital shaker having a 1 inch orbital diameter. When the culture reaches an $OD_{600}$ of 3-6 it is induced with 0.5 mM IPTG. The induced culture is then incubated at 15° C. with shaking at 230-250 rpm or faster for about 6-15 hours. The cells are harvested by centrifugation at 3500 rpm at 4° C. for 20 minutes and the cell pellet is resuspended in 15 mL ice cold binding buffer (Hepes 50 mM, pH 7.5) and 100 µL of protease inhibitors (50 mM PMSF and 100 mM Benzamidine, stock concentration) and flash frozen.

Example 4

Expression of Selmet Labeled Polypeptides

The freshly transformed cell, harboring a plasmid with a nucleic acid encoding a polypeptide of the invention, is inoculated into 20 mL of NMM (New Minimal Medium) and shaken at 37° C. for 8-9 hours. This culture is then transferred into a 6 L Erlenmeyer flask containing 2 L of minimum medium (M9). The media is supplemented with all amino acids except methionine. All amino acids are added as a solution except for Tyrosine, Tryptophan and Phenylalanine which are added to the media in powder format. As well the media is supplemented with $MgSO_4$ (2 mM final concentration), $FeSO_4\cdot 7H_2O$ (25 mg/L final concentration), Glucose (0.4% final concentration), $CaCl_2$ (0.1 mM final concentration) and Seleno-L-Methionine (40 mg/L final concentration). When the $OD_{600}$ of the cell culture reaches 0.8-0.9, IPTG (0.4 mM final concentration) is added to the medium for protein induction, and the cell culture is kept shaking at 15° C. for 10 hours. The cells are harvested by centrifugation at 3500 rpm at 4° C. for 20 minutes and the cell pellet is resuspended in 15 mL cold binding buffer (Hepes 50 mM, pH 7.5) and 100 µL of protease inhibitors (PMSF and Benzamidine) and flash frozen.

Alternatively, a starter culture is prepared in a 300 mL Tunair flask (Shelton Scientific) by adding 50 mL of sterile medium having 10% 10XM9 (37.4 mM $NH_4Cl$ (Sigma; Cat. No. A4514), 44 mM $KH_2PO_4$ (Bioshop, Ontario, Canada; Cat. No. PPM 302), 96 mM $Na_2HPO_4$ (Sigma; Cat. No. S2429256), and 96 mM $Na_2HPO_4\cdot 7H_2O$ (Sigma; Cat. No. S9390) final concentration), 450 µM alanine, 190 µM arginine, 302 µM asparagine, 300 µM aspartic acid, 330 µM cysteine, 272 µM glutamic acid, 274 µM glutamine, 533 µM glycine, 191 µM histidine, 305 µM isoleucine, 305 µM leucine, 220 µM lysine, 242 µM phenylalanine, 348 µM proline, 380 µM serine, 336 µM threonine, 196 µM tryptophan, 220 µM tyrosine, and 342 µM valine, 204 µM Seleno-L-Methionine (Sigma; Cat. No. S3132), 0.5% v/v of Kao and Michayluk vitamins mix (Sigma; Cat. No. K3129), 2 mM $MgSO_4$ (Sigma; Cat. No. M7774), 90 µM $FeSO_4\cdot 7H_2O$ (Sigma; Cat. No. F8633), 0.4% glucose (Sigma; Cat. No. G-5400), 100 µM $CaCl_2$ (Bioshop, Ontario, Canada; Cat. No. CCL 302), 50 µg/mL Ampicillin, and 50 µg/mL Kanamycin in $dH_2O$. The medium is then inoculated with several colonies of E. coli B834 cells (Novagen) freshly transformed with an expression construct clone encoding the polypeptide of interest. The culture is then incubated at 37° C. and 200 rpm until it reaches an $OD_{600}$ of 1 and is then transferred to a 2.5 L Tunair Flask containing 1 L of the above media. The 1 L culture is incubated at 37° C. with shaking at 200 rpm until the culture reaches an $OD_{600}$ of 0.6-0.8 and is then induced with 0.5 mM IPTG. The induced culture is incubated overnight at 15° C. with shaking at 200 rpm. The cells are harvested by centrifugation at 4200 rpm at 4° C. for 20 minutes and the cell pellet is resuspended in 15 mL ice cold binding buffer (Hepes 50 mM, pH 7.5) and 100 µL of protease inhibitors (50 mM PMSF and 100 mM Benzamidine, stock concentration) and flash frozen.

Alternatively, the cell harboring a plasmid with a nucleic acid encoding a polypeptide of the invention is inoculated into 10 mL of M9 minimum medium and kept shaking at 37° C. for 8-9 hours. This culture is then transferred into a 2 L Baffled Flask (Corning) containing 1 L minimum medium. The media is supplemented with all amino acids except methionine. All are added as a solution, except for Phenylalanine, Alanine, Valine, Leucine, Isoleucine, Proline, and Tryptophan which are added to the media in powder format. As well the media is supplemented with $MgSO_4$ (2 mM final concentration), $FeSO_4\cdot 7H_2O$ (25 mg/L final concentration), Glucose (0.5% final concentration), $CaCl_2$ (0.1 mM final concentration) and Seleno-Methionine (50 mg/L final concentration). When the $OD_{600}$ of the cell culture reaches 0.8-0.9, IPTG (0.8 mM final concentration) is added to the medium for protein induction, and the cell culture is kept shaking at 25° C. for 4 hours. The cells are harvested by centrifuged at 3500 rpm at 4° C. for 20 minutes and the cell pellet is resuspended in 10 mL cold binding buffer (Hepes 50 mM, pH 7.5) and 100 µL of protease inhibitors (PMSF and Benzamidine) and flash frozen.

Example 5

Expression of $^{15}N$ Labeled Polypeptides

The cell, harboring a plasmid with a nucleic acid encoding a polypeptide of the invention, is inoculated into 2 L of minimal media (containing $^{15}N$ isotope, Cambridge Isotope Lab) in a 6 L Erlenmeyer flask. The minimal media is supplemented with 0.01 mM $ZnSO_4$, 0.1 mM $CaCl_2$, 1 mM $MgSO_4$, 5 mg/L Thiamine.HCl, and 0.4% glucose. The 2 L culture is grown at 37° C. and 200 rpm to an $OD_{600}$ of between 0.7-0.8. The culture is then induced with 0.5 mM IPTG and allowed to shake at 15° C. for 14 hours. The cells are harvested by centrifugation and the cell pellet is resuspended in 15 mL cold binding buffer and 100 µL of protease inhibitor and flash frozen. The protein is then purified as described below.

Alternatively, the freshly transformed cell, harboring a plasmid with the gene of interest, is inoculated into 10 mL of M9 media (with $^{15}N$ isotope) and supplemented with 0.01 mM $ZnSO_4$, 0.1 mM $CaCl_2$, 1 mM $MgSO_4$, 5 mg/L Thiamine.HCl, and 0.4% glucose. After 8-10 hours of growth at 37° C., the culture is transferred to a 2 L Baffled flask (Corning) containing 990 mL of the same media. When $OD_{600}$ of the culture is between 0.7-0.8, protein production is initiated by adding IPTG to a final concentration of 0.8 mM and lowering the temperature to 25° C. After 4 hours of incubation at this temperature, the cells are harvested, and the cell pellet is resuspended in 10 mL cold binding buffer (Hepes 50 mM, pH 7.5) and 100 µL of protease inhibitor and flash frozen.

Example 6

Purification of Untagged Polypeptides

Cells containing Ft FabI were thawed on ice and lysed by sonication (3×30 seconds on ice), additional PMSF (0.5 mM) and benzamidine (1 mM) were added along with a complete protease inhibitor tablet, and the lysate was clarified by centrifugation at 24,000 rpm (Beckman J-251, GA-25.50 rotor) for one hour at 4° C. The soluble protein (FIG. 16) was applied to a Blue Sepharose FF column (~30 mL, 25/20 column, Biorad) equilibrated with 100 mL Buffer A (50 mM Tris-HCl pH 7.5, 50 mM NaCl). The column was then washed with 1 L of Buffer A, and eluted with Buffer A containing 0.8 M NaCl. The eluate was monitored using Bradford Biorad reagent. Fractions containing Ft FabI were pooled and dialyzed overnight against 50 mM Tris pH 7.5, 100 mM NaCl. The dialyzed protein was filtered and applied to a Resource Q column (6 mL, 1.6×3.0 cm, Pharmacia) at 6 ml/min equilibrated in Buffer A containing 150 mM NaCl, washed with 3 column volumes (CV) of the same buffer and eluted with a linear gradient to Buffer A containing 1 M NaCl. The flow-through and the fractions were analyzed by SDS-PAGE and the appropriate fractions were pooled. Based on the SDS-PAGE gel the protein was observed in the flow-through indicating that Ft FabI did not bind to the column. Subsequently, the flow-through fractions were pooled and applied to a Resource S column (6 mL, 1.6×3.0 cm, Pharmacia) at 6 mL/min equilibrated in Buffer A containing 150 mM NaCl, washed with 3 CV of the same buffer and eluted with a linear gradient to Buffer A containing 1 M NaCl. Once again the protein failed to bind to the column and was collected in the flow-through fractions. The pooled flow-through fractions were concentrated to 20 mL and split into two loads in order to be applied at 2 mL/min to a gel filtration column (Pharmacia, SD200HR 20/200) pre-equilibrated in Crystal Buffer (10 mM Hepes, 500 mM NaCl), two peaks of interest were observed from the gel filtration column, one corresponding to monomer and the second corresponding to multimer. Fractions containing monomer and mulitmer FabI were analyzed using SDS-PAGE, pooled and concentrated. Crystallization and biochemical assays received aliquots. Crystallization was given protein concentrated to >20 mg/mL while biochemical assays received protein at 5 mg/mL with 20% glycerol. All aliquots were stored at −70° C. Protein yield, concentration, and purity are shown in FIG. 17.

Example 7

Purification of His-tagged Polypeptides

Cells containing N-terminal or C-terminal His-tagged Ft FabI were thawed on ice and lysed in the presence of 0.5% CHAPS, 0.2 mM PMSF, 0.5 mM benzamidine, and 250 units of benzonase (Novagen, Wis.) in binding buffer (50 mM HEPES pH 7.5, 500 mM NaCl, 5 mM imidazole, and 5% glycerol) by sonication (Branson, V W R) on ice, centrifuged at 24,000 rpm (Beckman J-251, GA-25.50 rotor), and the clarified cell lysates were applied to a 20 mL DE52 column (Whatman, UK). The flow through from the ion exchange column was applied to 5 mL of metal chelate chromatography resin (Superflow, Qiagen) charged with $Ni^{2+}$. The column was washed with 4 column volumes of binding buffer, 20 column volumes of wash buffer (lysis buffer containing 30 mM imidazole), and eluted with 4-6 column volumes of elution buffer (lysis buffer containing 250 mM imidazole). The elution fractions containing the protein of interest were pooled and dialyzed overnight against Crystal Buffer (10 mM Hepes, 500 mM NaCl) and concentrated. Crystallization and biochemical assays received aliquots. Crystallization was given protein concentrated to >20 mg/mL while biochemical assays received protein at 5 mg/mL with 20% glycerol. All aliquots were stored at −70° C. The samples are assayed by SDS-PAGE and stained with Coomassie Blue, with protein purity determined by visual staining. Protein yield, concentration, and purity are shown in FIG. 17.

Two methods may be used to remove the His tag located at either the C or N-terminus. In certain instances, the His tag may not be removed. In method one, a sample of purified polypeptide is supplemented with 2.5 mM $CaCl_2$ and an appropriate amount of thrombin (the amount added will vary depending on the activity of the enzyme preparation) and incubated for ~20-30 minutes on ice in order to remove the His tag. In method two, a sample of purified polypeptide is combined with thirty units of recombinant TEV protease in 50 mM TRIS HCl pH=8.0, 0.5 mM EDTA and 1 mM DTT, followed by incubation at 4° C. overnight, to remove the His tag.

The protein sample is then dialyzed in dialysis buffer (10 mM HEPES, pH 7.5, 5% glycerol (v/v) and 0.5 M NaCl) for at least 8 hours using a Slide-A-Lyzer (Pierce) appropriate for the molecular weight of the recombinant protein. An aliquot of the cleaved and dialyzed samples is then assayed by SDS-PAGE and stained with Coomassie Blue to determine the purity of the protein and the success of cleavage.

The remainder of the sample is centrifuged at 2700 rpm at 4° C. for 10-15 minutes to remove any precipitant and supplemented with 100 μL of protease inhibitor cocktail (0.1 M benzamidine and 0.05 M PMSF) (NO Bioshop). The protein is then applied to a second Ni-NTA column (~8 mL of resin) to remove the His-tags and eluted with binding buffer or wash buffer until no more protein is eluting off the column as assayed using the Bradford reagent. The eluted sample is supplemented with 1 mM EDTA and 0.6 mM of DTT and concentrated to a final volume of ~15 mL using a Millipore Concentrator with an appropriately sized filter at 2700 rpm at 4° C. The samples are then dialyzed overnight against crystallization buffer and concentrated to final volume of 0.3-0.7 mL.

Example 8

Enzymatic Characterization

The purified constructs of Ft FabI were characterized for co-factor and enzyme concentration dependence to identify optimal assay conditions. First the substrates NADH and NADPH, were titrated from 0 to 1000 μM to determine the natural substrate for Ft FabI. NADH was identified as the preferred substrate and an enzyme titration was performed with all Ft FabI constructs to determine the optimal enzyme concentration for further analysis.

The assays were performed in half area plates in 100 ul volumes containing 100 mM NaADA, pH 6.5, 4% glycerol, 50 uM NADH and 25 uM crotonyl-ACP at 30° C. titrating enzyme from 1000 nM to 2.5 nM. Based on the enzyme titrations N-terminal His-tagged Ft FabI was chosen for future experimentation at the optimal concentration of 25 mM.

Addition of NADH was used to initiate the assay and the reaction was monitored by absorbance at 340 nm. Linear and cubic curve fitting was used to determine the initial velocity.

The effect of substrate concentration on enzyme activity was determined along with the Ft FabI enzyme oxidation and reductase properties. The $K_m$ was determined for NADH (34.7 uM) and crotonyl-ACP (4.4 uM) based on the substrate titrations. The $V_{max}$ was determined to be 2.39 umoles NADH/min/mg with a turnover number of 71.5 $min^{-1}$. These kinetic values are comparable to the kinetic values previously determined for *S. aureus* FabI. Based on these values the concentrations of substrate for the enzymatic assay were chosen to be 25 uM crotonyl-ACP and 50 uM NADH.

The intrinsic NADH oxidase activity was evaluated for Ft FabI through an NADH titration of the enzyme in the presence and absence of the substrate crotonyl-ACP. A significant oxidase activity was observed at high NADH concentrations (greater than 100 uM). The overall oxidase and the intrinsic oxidase in the absence of crotonyl-ACP substrate were used to obtain the NADH reductase activity of Ft FabI. The percentage of NADH converted was calculated for each method of NADH consumption. Total NADH oxidation consumed 75.2% of the available NADH, Ft FabI intrinsic oxidation consumed 23.6% and Ft FabI reductase activity consumed 51.8% of the available NADH which was equal to 100% of the available crotonyl-ACP. The derived reductase activity was used to determine the kinetic parameters.

| | FabI Orthologue | |
|---|---|---|
| | *F. tularensis* | *S. aureus* |
| Specific Activity (umoles/min/mg) | 0.56 | 0.41 |
| Km (NADH) uM | 34.7 | 37.3 |
| Km (crotonyl-ACP) uM | 4.4 | 7.5 |
| Vmax (umoles NADH/min/mg) | 2.39 | 4.29 |
| Kcat ($min^{-1}$) | 71.6 | 124.3 |

Inhibition of *F. Tularensis* FabI

Ft FabI is an antimicrobial target for the discovery of compounds effective for the inhibition of *Franciscella tularensis* cell growth. To identify potential Ft FabI inhibitors, 48 compounds were selected for dose response analysis. The dose response assay used the optimal assay conditions described above and titrated the compounds from 30 to 0.025 uM. Ft FabI $IC_{50}$ results varied from 0.006 uM to 36.15 uM. The $IC_{50}$ value for the compound that was co-crystallized with Ft FabI was 0.047 uM.

Antimicrobial Testing

Two strains of *F. tularensis* (strain 17135 and 17137) were evaluated for susceptibility to 12 compounds using a standard minimum inhibitor concentration (MIC) assay. Resultant MIC values ranged from 0.12 ug/mL to 16 ug/mL for both strains. The MIC values for the compound that was co-crystallized with Ft FabI was 0.5 ug/mL for strain 17135 and 2 ug/mL for strain 17137.

Example 9

Mass Spectrometry Analysis via Fingerprint Mapping

A gel slice from a purification protocol described above containing a polypeptide of the invention is cut into 1 mm cubes and 10 to 20 µL of 1% acetic acid is added. After washing with 100-150 µL HPLC grade water and removal of the liquid, acetonitrile (~200 µL, approximately 3 to 4 times the volume of the gel particles) is added followed by incubation at room temperature for 10 to 15 minutes with vortexing. A second acetonitrile wash may be required to completely dehydrate the gel particles. The protein in the gel particles is reduced at 50 degrees Celsius using 10 mM dithiothreitol (in 100 mM ammonium bicarbonate) and then alkylated at room temperature in the dark using 55 mM iodoacetamide (in 100 mM ammonium bicarbonate). The gel particles are rinsed with a minimal volume of 100 mM ammonium bicarbonate before a trypsin (50 mM ammonium bicarbonate, 5 mM $CaCl_2$, and 12.5 ng/µL trypsin) solution is added. The gel particles are left on ice for 30 to 45 minutes (after 20 minutes incubation more trypsin solution is added). The excess trypsin solution is removed and 10 to 15 µL digestion buffer without trypsin is added to ensure the gel particles remain hydrated during digestion. After digestion at 37° C., the supernatant is removed from the gel particles. The peptides are extracted from the gel particles with 2 changes of 100 µL of 100 mM ammonium bicarbonate with shaking for 45 minutes and pooled with the initial gel supernatant. The extracts are acidified to 1% (v/v) with 100% acetic acid.

The tryptic peptides are purified with a C18 reverse phase resin. 250 µL of dry resin is washed twice with methanol and twice with 75% acetonitrile/1% acetic acid. A 5:1 slurry of solvent:resin is prepared with 75% acetonitrile/1% acetic acid. To the extracted peptides, 2 µL of the resin slurry is added and the solution is shaken for 30 minutes at room temperature. The supernatant is removed and replaced with 200 µL of 2% acetonitrile/1% acetic acid and shaken for 5-15 minutes. The supernatant is removed and the peptides are eluted from the resin with 15 µL of 75% acetonitrile/1% acetic acid with shaking for about 5 minutes. The peptide and slurry mixture is applied to a filter plate and centrifuged, and the filtrate is collected and stored at −70° C. until use.

Alternatively, the tryptic peptides are purified using Zip-$Tip_{C18}$ (Millipore, Cat # ZTC18S960). The ZipTips are first pre-wetted by aspirating and dispensing 100% methanol. The tips are then washed with 2% acetonitrile/1% acetic acid (5 times), followed by 65% acetonitrile/1% acetic (5 times) and returned to 2% acetonitrile/1% acetic acid (10 times). The digested peptides are bound to the ZipTips by aspirating and dispensing the samples 5 times. Salts are removed by washing ZipTips with 2% acetonitrile/1% acetic acid (5 times). 10 µL of 65% acetonitrile/1% acetic acid is collected by the ZipTips and dispensed into a 96-well microtitre plate.

Analytical samples containing tryptic peptides are subjected to MALDI-TOF mass spectrometry. Samples are mixed 1:1 with a matrix of α-cyano-4-hydroxy-trans-cinnamic acid. The sample/matrix mixture is spotted on to the MALDI sample plate with a robot, either a Gilson 215 liquid handler or BioMek FX laboratory automation workstation (Beckman). The sample/matrix mixture is allowed to dry on the plate and is then introduced into the mass spectrometer. Analysis of the peptides in the mass spectrometer is conducted using both delayed extraction mode (400 ns delay) and an ion reflector to ensure high resolution of the peptides.

Internally-calibrated tryptic peptide masses are searched against databases using a correlative mass matching algorithm. The ProteoMetrics software package (ProteoMetrics) is utilized for batch database searching of tryptic peptide mass spectra. Statistical analysis is performed on each protein match to determine its validity. Typical search constraints include error tolerances within 0.1 Da for monoisotopic peptide masses, carboxyamidomethylation of cysteines, no oxidation of methionines allowed, and 0 or 1 missed enzyme cleavages. The software calculates the probability that a candidate in the database search is the protein being analyzed, which is expressed as the Z-score. The Z-score is the distance to the population mean in unit of standard deviation and corresponds to the percentile of the search in the random match population. If a search is in the 95th percentile, for example, about 5% of random matches could yield a higher Z-score than the search. A Z-score of 1.282 for a search indicates that the search is in the 90th percentile, a Z-score of 1.645 indicates that the search is in the 95th percentile, a Z-score of 2.326 indicates that the search is in the 99th percentile, and a Z-score of 3.090 indicates that the search is in the 99.9th percentile.

Example 10

Mass Spectrometry Analysis via High Mass

A matrix solution of 25 mg/mL of 3,5-dimethoxy-4-hydroxycinnamic acid (sinapinic acid) in 66% (v/v) acetonitrile/ 1% (v/v) acetic acid is prepared along with an internal calibrant of carbonic anhydrase. On to a stainless steel polished MALDI target, 1.5 µL of a protein solution (concentration of 2 µg/µL) is spotted, followed immediately by 1.5 µL of matrix. 3 µL of 40% (v/v) acetonitrile/1% (v/v) acetic acid is then added to each spot has dried. The sample is either spotted manually or utilizing a Gilson 215 liquid handler or BioMek FX laboratory automation workstation (Beckman). The MALDI-TOF instrument utilizes positive ion and linear detection modes. Spectra are acquired automatically over a mass to charge range from 0-150,000 Da, pulsed ion extraction delay is set at 200 ns, and 600 summed shots of 50-shot steps are completed.

The theoretical molecular weight of the protein for MALDI-TOF is determined from its amino acid sequence, taking into account any purification tag or residue thereof still present and any labels (e.g., selenomethionine or $^{15}N$). To account for $^{15}N$ incorporation, an amount equal to the theoretical molecular weight of the protein divided by 70 is added. The mass of water is subtracted from the overall molecular weight. The MALDI-TOF spectrum is calibrated with the internal calibrant of carbonic anhydrase (observed as either $[MH^+_{avg}]$ 29025 or $[MH_2^{2+}]$ 14513).

Example 11

Method One for Isolating and Identifying Interacting Proteins (a) Method One for Preparation of Affinity Column Micro-columns are prepared using forceps to bend the ends of P200 pipette tips and adding 10 µL of glass beads to act as a column frit. Six micro-columns are required for every polypeptide to be studied. The micro-columns are placed in a 96-well plate that has 1 mL wells. Next, a series of solutions of the polypetide having SEQ ID NO: 4 or other polypeptide of the invention, prepared and purified as described above and with a GST tag on either terminus, is prepared so as to give final amounts of 0, 0.1, 0.5, 1.0, and 2.0 mg of ligand per mL of resin volume.

A slurry of Glutathione-Sepharose 4B (Amersham) is prepared and 0.5 mL slurry/ligand is removed (enough for six 40-µg aliquots of resin). Using a glass frit Buchner funnel, the resin is washed sequentially with three 10 mL portions each of distilled $H_2O$ and 1 M ACB (20 mM HEPES pH 7.9, 1 M NaCl, 10% glycerol, 1 mM DTT, and 1 mM EDTA). The Glutathione-Sepharose 4B is completely drained of buffer, but not dried. The Glutathione-Sepharose 4B is resuspended as a 50% slurry in 1 M ACB and 80 µL is added to each micro-column to obtain 40 µg/column. The buffer containing the ligand concentration series is added to the columns and allowed to flow by gravity. The resin and ligand are allowed to cross-link overnight at 4° C. In the morning, micro-columns are washed with 100 µL of 1 M ACB and allowed to flow by gravity. This is repeated twice more and the elutions are tested for cross-linking efficiency by measuring the amount of unbound ligand. After washing, the micro-columns are equilibrated using 200 µL of 0.1 M ACB (20 mM HEPES pH 7.5, 0.1 M NaCl, 10% glycerol, 1 mM DTT, 1 mM EDTA).

In another method, the recombinant GST fusion protein can be replaced by a hexa-histidine fusion peptide for use with NTA-Agarose (Qiagen) as the solid support. No adaptation to the above protocol is required for the substitution of NTA agarose for GST Sepharose except that the recombinant protein requires a six histidine fusion peptide in place of the GST fusion.

(b) Method Two for Preparation of Affinity Column

In an alternative method, GST-Sepharose 4B may be replaced by Affi-gel 10 Gel (Bio-Rad). The column resin for affinity chromatography could also be Affigel 10 resin which allows for covalent attachment of the protein ligand to the micro affinity column. An adaptation to the above protocol for the use of this resin is a pre-wash of the resin with 100% isopropanol. No fusion peptides or proteins are required for the use of Affigel 10 resin.

(c) Bacterial Extract Preparation

Bacterial cell extracts from *F. tularensis* are prepared from cell pellets using a Bead-Beater apparatus (Bio-spec Products Inc.) and zirconia beads (0.1 mm diameter). The bacterial cell pellet is suspended (~6 g) is suspended in 3 pellet volumes (~20 mL final volume) of 20 mM HEPES pH 7.5, 150 mM NaCl, 10% glycerol, 10 mM $MgSO_4$, 10 mM $CaCl_2$, 1 mM DTT, 1 mM PMSF, 1 mM benzamidine, 40 μg/mL RNAse A, 75 units/mL S1 nuclease, and 40 units/mL DNAse 1. The cells are lysed with 10 pulses of 30 sec between 90 sec pauses at a temperature of −5° C. The lysate is separated from the zirconia beads using a standard column apparatus. The lysate is centrifuged at 20000 rpm (48000×g) in a Beckman JA25.50 rotor. The supernatant is removed and dialyzed overnight at 4° C. against dialysis buffer (20 mM HEPES pH 7.5, 10% glycerol, 1 mM DTT, 1 mM EDTA, 100 mM NaCl, 10 mM $MgSO_4$, 10 mM $CaCl_2$, 1 mM benzamidine, and 1 mM PMSF). The dialyzed protein extract is removed from the dialysis tubing and frozen in one mL aliquots at −70° C.

(d) HeLa Cell Extract Preparation

A HeLa cell extract is prepared in the presence of protease inhibitors. Approximately 30 g of Hela cells are submitted to a freeze/thaw cycle and then divided into two tubes. To each tube 20 mL of Buffer A (10 mM HEPES pH 7.9, 1.5 mM MgCl, 10 mM KCl, 0.5 mM DTT, 0.5 mM PMSF) and a protease inhibitor cocktail are added. The cell suspension is homogenized with 10 strokes (2×5 strokes) to lyse the cells. Buffer B (15 mL per tube) is added (50 mM HEPES pH 7.9, 1.5 mM MgCl, 1.26 M NaCl, 0.5 mM DTT, 0.5 mM PMSF, 0.5 mM EDTA, 75% glycerol) to each tube followed by a second round of homogenization (2×5 strokes). The lysates are stirred on ice for 30 minutes followed by centrifugation 37,000 rpm for 3 hr at 4° C. in a Ti70 fixed angle Beckman rotor. The supernatant is removed and dialyzed overnight in a 10,000 Mr dialysis membrane against dialysis buffer (20 mM HEPES pH 7.9, 10% glycerol, 1 mM DTT, 1 mM EDTA, and 1 M NaCl. The dialyzed protein extract is removed from the dialysis tubing and frozen in one mL aliquots at −70° C.

(e) Affinity Chromatography

Cell extract is thawed and diluted to 5 mg/mL prior to loading 5 column volumes onto each micro-column. Each column is washed with 5 column volumes of 0.1 M ACB. This washing is repeated once. Each column is then washed with 5 column volumes of 0.1 M ACB containing 0.1% Triton X-100. The columns are eluted with 4 column volumes of 1% sodium dodecyl sulfate into a 96 well PCR plate. To each eluted fraction is added one-tenth volume of 10-fold concentrated loading buffer for SDS-PAGE.

(f) Resolution of the Eluted Proteins and Detection of Bound Proteins

The components of the eluted samples are resolved on SDS-polyacrylamide gels containing 13.8% polyacrylamide using the Laemmli buffer system and stained with silver nitrate. The bands containing the interacting protein are excised with a clean scalpel. The gel volume is kept to a minimum by cutting as close to the band as possible. The gel slice is placed into one well of a low protein binding, 96-well round-bottom plate. To the gel slices is added 20 µL of 1% acetic acid.

Example 12

Method Two for Isolating and Identifying Interacting Proteins

Interacting proteins may be isolated using immunoprecipitation. Naturally-occurring bacterial or eukaryotic cells are grown in defined growth conditions or the cells can be genetically manipulated with a protein expression vector. The protein expression vector is used to transiently transfect the cDNA of interest into eukaryotic or prokaryotic cells and the protein is expressed for up to 24 or 48 hours. The cells are harvested and washed three times in sterile 20 mM HEPES (pH7.4)/Hanks balanced salts solution (H/H). The cells are finally resuspended in culture media and incubated at 37° C. for 4-8 hr.

The harvested cells may be subjected to one or more culture conditions that may alter the protein profile of the cells for a given period of time. The cells are collected and washed with ice-cold H/H that includes 10 mM sodium pyrophosphate, 10 mM sodium fluoride, 10 mM EDTA, and 1 mM sodium orthovanadate. The cells are then lysed in lysis buffer (50 mM Tris-HCl (pH 8.0), 150 mM NaCl, 1% Triton X-100, 10 mM sodium pyrophosphate, 10 mM sodium fluoride, 10 mM EDTA, 1 mM sodium orthovanadate, 1 µg/mL PMSF, 1 µg/mL aprotinin, 1 µg/mL leupeptin, and 1 µg/mL pepstatin A) by gentle mixing, and placed on ice for 5 minutes. After lysis, the lysate is transferred to centrifuge tubes and centrifuged in an ultracentrifuge at 75000 rpm for 15 min at 4° C. The supernatant is transferred to eppendorf tubes and pre-cleared with 10 µL of rabbit pre-immune antibody on a rotator at 4° C. for 1 hr. Forty 1 L of protein A-Sepharose (Amersham) is then added and incubated at 4° C. overnight on a rotator.

The protein A-Sepharose beads are harvested and the supernatant removed to a fresh eppendorf tube. Immune antibody is added to supernatant and rotated for 1 hr at 4° C. Thirty µL of protein A-Sepharose is then added and the mixture is further rotated at 4° C. for 1 hr. The beads are harvested and the supernatant is aspirated. The beads are washed three times with 50 mM Tris (pH 8.0), 150 mM NaCl, 0.1% Triton X-100, 10 mM sodium fluoride, 10 mM sodium pyrophosphate, 10 mM sodium orthovanadate, and 10 mM EDTA. Dry the beads with a 50 µL Hamilton syringe. Laemmli loading buffer containing 100 mM DTT is added to the beads and samples are boiled for 5 min. The beads are spun down and the supernatant is loaded onto SDS-PAGE gels. Comparison of the control and experimental samples allows for the selection of polypeptides that interact with the protein of interest.

Example 13

Sample for Mass Spectrometry of Interacting Proteins

The gel slices are cut into 1 mm cubes and 10 to 20 µL of 1% acetic acid is added. The gel particles are washed with 100-150 µL of HPLC grade water (5 minutes with occasional mixing), briefly centrifuged, and the liquid is removed. Acetonitrile (200 µL, approximately 3 to 4 times the volume of the gel particles) is added followed by incubation at room temperature for 10 to 15 minutes with vortexing. A second acetonitrile wash may be required to completely dehydrate the gel particles. The sample is briefly centrifuged and all the liquid is removed.

The protein in the gel particles is reduced at 50 degrees Celsius using 10 mM dithiothreitol (in 100 mM ammonium bicarbonate) for 30 minutes and then alkylated at room temperature in the dark using 55 mM iodoacetamide (in 100 mM ammonium bicarbonate). The gel particles are rinsed with a minimal volume of 100 mM ammonium bicarbonate before a trypsin (50 mM ammonium bicarbonate, 5 mM $CaCl_2$, and 12.5 ng/µL trypsin) solution is added. The gel particles are left on ice for 30 to 45 minutes (after 20 minutes incubation more trypsin solution is added). The excess trypsin solution is removed and 10 to 15 µL digestion buffer without trypsin is added to ensure the gel particles remain hydrated during digestion. The samples are digested overnight at 37° C.

The following day, the supernatant is removed from the gel particles. The peptides are extracted from the gel particles with 2 changes of 100 µL of 100 mM ammonium bicarbonate with shaking for 45 minutes and pooled with the initial gel supernatant. The extracts are acidified to 1% (v/v) with 100% acetic acid.

(a) Method One for Purification of Tryptic Peptides

The tryptic peptides are purified with a C18 reverse phase resin. 250 µL of dry resin is washed twice with methanol and twice with 75% acetonitrile/1% acetic acid. A 5:1 slurry of solvent:resin is prepared with 75% acetonitrile/1% acetic acid. To the extracted peptides, 2 µL of the resin slurry is added and the solution is shaken at moderate speed for 30 minutes at room temperature. The supernatant is removed and replaced with 200 µL of 2% acetonitrile/1% acetic acid and shaken for 5-15 minutes with moderate speed. The supernatant is removed and the peptides are eluted from the resin with 15 µL of 75% acetonitrile/1% acetic acid with shaking for about 5 minutes. The peptide and slurry mixture is applied to a filter plate and centrifuged for 1-2 minutes at 1000 rpm, the filtrate is collected and stored at −70° C. until use.

(b) Method Two for Purification of Tryptic Peptides

Alternatively, the tryptic peptides may be purified using $ZipTip_{C18}$ (Millipore, Cat # ZTC18S960). The ZipTips are first pre-wetted by aspirating and dispensing 100% methanol 5 times. The tips are then washed with 2% acetonitrile/1% acetic acid (5 times), followed by 65% acetonitrile/1% acetic (5 times) and returned to 2% acetonitrile/1% acetic acid (5 times). The ZipTips are replaced in their rack and the residual solvent is eliminated. The ZipTips are washed again with 2% acetonitrile/1% acetic acid (5 times). The digested peptides are bound to the ZipTips by aspirating and dispensing the samples 5 times. Salts are removed by washing ZipTips with 2% acetonitrile/1% acetic acid (5 times). 10 µL of 65% acetonitrile/1% acetic acid is collected by the ZipTips and dispensed into a 96-well microtiter plate. 1 µL of sample and 1 µL of matrix are spotted on a MALDI-TOF sample plate for analysis.

Example 14

Mass Spectrometric Analysis of Interacting Proteins (a) Method One for Analysis of Tryptic Peptides Analytical samples containing tryptic peptides are subjected to Matrix Assisted Laser Desorption/Ionization Time Of Flight (MALDI-TOF) mass spectrometry. Samples are mixed 1:1 with a matrix of α-cyano-4-hydroxy-trans-cinnamic acid. The sample/matrix mixture is spotted on to the MALDI sample plate with a robot. The sample/matrix mixture is allowed to dry on the plate and is then introduced into the mass spectrometer. Analysis of the peptides in the mass spectrometer is conducted using both delayed extraction mode and an ion reflector to ensure high resolution of the peptides.

Internally-calibrated tryptic peptide masses are searched against both in-house proprietary and public databases using a correlative mass matching algorithm. Statistical analysis is performed on each protein match to determine its validity. Typical search constraints include error tolerances within 0.1 Da for monoisotopic peptide masses and carboxyamidomethylation of cysteines. Identified proteins are stored automatically in a relational database with software links to SDS-PAGE images and ligand sequences.

(b) Method Two for Analysis of Tryptic Peptides

Alternatively, samples containing tryptic peptides are analyzed with an ion trap instrument. The peptide extracts are first dried down to approximately 1 µL of liquid. To this, 0.1% trifluoroacetic acid (TFA) is added to make a total volume of approximately 5 µL. Approximately 1-2 µL of sample are injected onto a capillary column (C8, 150 µm ID, 15 cm long) and run at a flow rate of 800 mL/min. using the following gradient program:

| Time (minutes) | % Solvent A | % Solvent B |
| --- | --- | --- |
| 0 | 95 | 5 |
| 30 | 65 | 35 |
| 40 | 20 | 80 |
| 41 | 95 | 5 |

Where Solvent A is composed of water/0.5% acetic acid and Solvent B is acetonitrile/0.5% acetic acid. The majority of the peptides will elute between the 20-40% acetonitrile gradient. Two types of data from the eluting HPLC peaks are acquired with the ion trap mass spectrometer. In the $MS^1$ dimension, the mass to charge range for scanning is set at 400-1400—this will determine the parent ion spectrum. Secondly, the instrument has $MS^2$ capabilities whereby it will acquire fragmentation spectra of any parent ions whose intensities are detected to be greater than a predetermined threshold (Mann and Wilm, *Anal Chem* 66(24): 4390-4399 (1994)). A significant amount of information is collected for each protein sample as both a parent ion spectrum and many daughter ion spectra are generated with this instrumentation.

All resulting mass spectra are submitted to a database search algorithm for protein identification. A correlative mass algorithm is utilized along with a statistical verification of each match to identify a protein's identification (Ducret A, et al., *Protein Sci* 7(3): 706-719 (1998)). This method proves much more robust than MALDI-TOF mass spectrometry for identifying the components of complex mixtures of proteins.

Example 15

NMR Analysis

Purified protein sample is centrifuged at 13,000 rpm for 10 minutes with a bench-top microcentrifuge to eliminate any precipitated protein. The supernatant is then transferred into a clean tube and the sample volume is measured. If the sample volume is less than 450 µL, an appropriate amount of crystal buffer is added to the sample to reach that volume. Then 50 µL of $D_2O$ (99.9%) is added to the sample to make an NMR sample of 500 µL. The usual concentration of the protein sample is usually approximately 1 mmol or greater.

NMR screening experiments are performed on a Bruker AV600 spectrometer equipped with a cryoprobe, or other equivalent instrumentation. Ail spectra are recorded at 25° C. Standard 1D proton pulse sequence with presaturation is used for 1D screening. Normally, a sweepwidth of 6400 Hz, and eight or sixteen scans are used, although different pulse sequences are known to those of skill in the art and may be readily determined. For $^1H$, $^{15}N$ HSQC experiments, a pulse sequence with "flip-back" water suppression may be used. Typically, sweep widths of 8000 Hz and 2000 Hz are used for F2 and F1 dimension, respectively. Four to sixteen scans are normally adequate. The data is then processed on a Sun Ultra 5 computer with NMR pipe software.

Example 16

X-Ray Crystallography (a) Crystallization

Suitable crystals for x-ray experimentation were obtained by sitting drop vapor diffusion against a 100 µL reservoir solution containing 2.5 M ammonium sulfate, 0.1 M sodium acetate pH 4.5, and 0.2 M lithium sulfate in a 96 well sitting plate format. 1.5 µL of 15 mg/mL protein mixed with 1.5 mM NADH, 1/200 DTT and 1.5 mM API-1059 and 1.5 µL reservoir solutions were set in each drop. The crystals were soaked for 1 minute in a solution consisting of three parts mother liquor (from the well of the drop) to one part ethylene glycol, and were then frozen at 100K in a cold gas stream. The crystal diffracted to 2.4 Å. Data was collected from these crystals on a Bruker diffractometer equipped with Osmic confocal lenses and a SMART 6000 CCD. Data was processed using the Proteum software suite, integrated using Saint, and scaled using Proscale. Crystals proved to be of the space group $P6_222$ with cell dimensions a=b=130.072 Å, c=88.436 Å, α=β90°, γ=120°.

(b) Co-Crystallization

A variety of methods known in the art may be used for preparation of co-crystals comprising the subject polypeptides and one or more compounds that interact with the subject polypeptides, such as, for example, an inhibitor, co-factor, substrate, polynucleotide, polypeptide, and/or other molecule. In one exemplary method, crystals of the subject polypeptide may be soaked, for an appropriate period of time, in a solution containing a compound that interacts with a subject polypeptide. In another method, solutions of the subject polypeptide and/or compound that interacts with the subject polypeptide may be prepared for crystallization as described above and mixed into the above-described sitting drops. In certain embodiments, the molecule to be co-crystallized with the subject polypeptide may be present in the buffer in the sitting drop prior to addition of the solution comprising the subject polypeptide. In other embodiments, the subject polypeptide may be mixed with another molecule before adding the mixture to the sitting drop. Based on the teachings herein, one of skill in the art may determine the co-crystallization method yielding a co-crystal comprising the subject polypeptide.

(c) Heavy Atom Substitution

For preparation of crystals containing heavy atoms, crystals of the subject polypeptide may be soaked in a solution of a compound containing the appropriate heavy atom for such period as time as may be experimentally determined as necessary to obtain a useful heavy atom derivative for x-ray purposes. Likewise, for other compounds that may be of interest, including, for example, inhibitors or other molecules that interact with the subject polypeptide, crystals of the subject polypeptide may be soaked in a solution of such compound for an appropriate period of time.

(d) Data Collection and Processing

The *F. tularensis* FabI complex structure was solved by molecular replacement using the coordinates of the protein monomer of the *E. coli* FabI (sequence identity 57.7%) as the search model for molecular replacement using CNX. Five percent of the reflections were randomly excluded from the refinement and used to monitor Rfree in CNX (Brunger 1998). The structure was rebuilt using XtalView (McRee 1999). Refinement of the model using CCP4 (Collaborative Computational Project 1994) was alternated with manual inspection and rebuilding of the model using XtalView (McRee 1999). After several cycles of refinement and manual rebuilding, almost all of the protein has been modeled, with the exception of residue 1, the N terminal histidine tag and residues 257-260. In addition to the protein chain, it was found that a NADH molecule and the inhibitor API-1059 are visible in each of the active sites. 244 solvent molecules were picked manually using a combination of sigma A weighted 2Fo-Fc and Fo-Fc maps.

Table 1 (FIG. 19) contains a summary of the crystallographic data. Structure solution and refined statistics are reported in Table 2, also contained in FIG. 19. FIG. 20 contains a list of the atomic coordinates of the subject polypeptide and other molecules contained in the crystal. FIG. 21 to FIG. 25 depict various features of the crystal structure and other properties of a subject polypeptide.

(e) Analysis of the X-ray Structure of the Subject Polypeptide

General Description of Structure

The functional *F. tularensis* FabI protein is monomeric in a solution of 10 mM HEPES pH 7.5, and 500 mM NaCl. There is a monomer in the asymmetric unit, with symmetry related molecules forming a tetramer. A large portion of each subunit of the tetramer is involved in intramolecular contacts. Two long helices from each of the monomers are involved in the formation of the tetramer.

Each FabI subunit forms a single domain, with a core region which supports the cofactor. The overall fold of *F. tularensis* FabI is composed of a seven-stranded parallel β-sheet flanked on each side by three α-helices with a further helix lying at the C terminus of the β-sheet. The NADH cofactor is bound in an extended conformation at the COOH-terminal end of the β-sheet, with the nicotinamide ring lying deep in a pocket on the enzyme surface. A loop of the protein, termed here as the flipping loop (residues 193-203), covers the binding pocket. This configuration forms a deep crevice, hiding the inhibitor in the substrate binding site.

Structurally, FabI appears to be a typical example of the short-chain dehydrogenase/reductase (SDR) family. This family contains a wide variety of enzymes in organisms ranging from bacteria to mammals. These molecules share the common function of adding or removing hydrogen in a NAD(H)— or NADP(H)-dependent manner from specific substrates. These proteins, containing approximately 250 amino acids, have been observed to exist as tetramers and have an α/β structure with the signature Rossmann fold motif. This Rossmann fold creates a "topological switch point" at the carboxy termini of two central, strands, and the cleft formed at this point creates a nucleotide-binding site which binds the cofactor. Although members of this family are believed to be involved in a wide variety of biological processes and share a common fold, each is specific for a certain substrate. Substrate specificity is dictated by differences in amino acid sequence, particularly at the active site for substrate recognition.

Flexibility of the Flipping Loop

The electron density for a "flipping loop" is visible in the *S. aureus* FabI complex structure, which forms a slightly opened helix-turn-helix conformation, and encompasses part of the inhibitor binding site. The flipping loop may be mobile and in this case, the ternary complex may help to order this part of the molecule. The structure of the ternary *E. coli* FabI A138G-NAD1-thienodiazaborine complex revealed that the part of the chain comprising the flipping loop is significantly shifted from the position observed in the binary complexes with NAD+ or NADH. In the new *F. tularensis* crystal form, this loop adopts a regular helical conformation, which forms an additional edge of the diazaborine-binding site and makes it less accessible to the solvent. This conformation also draws the residues A240 and A241 closer to the diazaborine so that now both their side-chain and main-chain atoms make extensive van der Waals contacts with the edge of the fused rings of the inhibitor.

The flipping loop may present a druggable region, and a modulator may be designed to affect its function, for example, to prevent it from moving.

Substrate Binding Site

Most proteins of the SDR family contain the highly conserved catalytic $YX_3K$ sequence motif which is usually present near the carboxy terminus of an α-helix. FabI however does not contain this sequence motif. Instead, the orientation of Y156 and K163 in the structure mimic those of the tyrosine and lysine involved in the $YX_3K$ motif of the other proteins in the SDR family. Although the precise catalytic mechanism mediated by these residues is a matter of debate, it appears that the tyrosine and lysine residues are involved in actual catalysis. According to this scheme, K163 and Y156 cooperate to catalyze a syn addition of hydrogen via a 2-Re, 3-Si attack on the double bond of crotonyl-ACP. This involves the hydride transfer from the C4 position of the NADH to the C-3 position at the double bond in the enoyl substrate, which leads to the formation of an enolate anion intermediate which can then be protonated on the oxygen atom to form an enol. Subsequent tautomerization of the enol appears to lead to the production of the reduced acyl product. K163 (K163 in *E. coli*) is thought to be to stabilize the negative charge of the transition state and Y156 (Y156 in *E. coli*) is thought to be the proton donor to the enolate anion. Both of these residues are conserved in the sequences of a number of bacterial FabIs. The substrate binding site may present a druggable region.

Inhibitor Binding to *F. tularensis* FabI

*F. tularensis* FabI has a "U-shaped" binding site available for inhibitor or substrate binding above the cofactor NADH. This binding site may present a druggable region. One side of the cavity is open and exposed to solvent (termed here as the right hand side, above the adenine ribose of the NADH) and the other side contains a small opening (termed here as the left hand side, above the nicotinamide ring of NADH). Overall, the pocket is hydrophobic in nature, with many aromatic residues clustered on the left hand side of the binding pocket (FIGS. 23 and 24).

The specificity of API-1059 is evident in the binding mode between the inhibitor and protein molecule. The linking amide carbonyl, of the inhibitor is well-positioned for a hydrogen bond interaction with the 2'-hydroxyl of NADH and the hydroxyl of Y156 (FIG. 24). The central cis-amide fragment appears to participate in a π-stacking interaction with the nicotinamide portion of NADH. The right hand side of the molecule makes specific, directional interactions with the protein while the left hand side of the molecule is nestled in a hydrophobic pocket. The peptide backbone of A94 is involved in hydrogen bond interactions that bind both the pyridylamine and the N-acyl hydrogen of the naphthyridinone functionality. The indole portion of the left hand side of API-1059 is flanked by lipophilic residues (M206, F203, Y156 and Y146) creating tight hydrophobic packing. Ordered solvent molecules are found on either side of the inhibitor, with solvent molecules on the left hand side forming a hydrogen bonding network with the protein.

Based on the structure of API-1059 in *F. tularensis* FabI, improved modulators may be rationally designed. The residues involved in API-1059 binding may comprise a druggable region.

Other Inhibitors of FabI

One approach to combat microbial infection is the inhibition of enzymes involved in bacterial fatty acid biosynthesis (FAB). Fatty acid biosynthesis in bacteria is essential to the production of a number of lipid-containing components including the cell membrane. The bacterial fatty acid synthase system (FASII) utilizes discrete monofunctional enzymes that operate in conjunction with acyl carrier protein (ACP)-associated substrates. Mammalian fatty acid synthase (FASI) differs from FASII in that lipid biosynthesis is mediated by a single multifunctional enzyme-ACP complex. The differences in prokaryote and eukaryote fatty acid biosynthesis offer an attractive opportunity for selective FASII inhibition.

In addition to FabI, FabK and FabL are other bacterial enoyl-ACP reductases expressed in several bacterial species replacing or augmenting FabI. FabK is a flavoprotein resistant to triclosan. It has been shown to be the only enoyl ACP-reductase in *Streptococcus pneumoniae* and to exist together with FabI in *Enterococcus faecalis*. The third enoyl-reductase, FabL, is present along with FabI in *Bacillus subtilus*. Therefore, an inhibitor designed to selectively target a single bacterial enoyl-ACP reductase would be expected to have a narrow spectrum of antimicrobial activity, whereas an inhibitor targeting multiple enoyl ACP-reductases should have a broader spectrum of activity.

One of the most important features of any drug is its ability to discriminate between the target enzyme and its counterpart in the host. To this end, significant differences in enzymes which carry out the same reaction afford attractive opportunities for drug development. A particular attractive area of metabolism where this has proved to be the case is in fatty acid biosynthesis.

FabI is an enoyl-ACP reductase (ENR) that catalyzes the ultimate and rate-limiting step of the chain elongation process of FASII. The reaction involves the conjugate reduction of an enoyl-ACP to the corresponding acyl-ACP using the cofactor NAD(P)H as a hydride source. Reports describing the antibacterial agents isoniazid, diazaboranes, and triclosan as inhibitors of bacterial enoyl-ACP reductase support a FabI-targeted approach to antibacterial drug therapy.

The study of FabI as a drug target has gained much attention in connection with the discovery that three distinctly different synthetic anti-bacterial drugs, isoniazid, diazaborine, and triclosan block lipid biosynthesis in bacteria by inhibiting FabI. Generating three novel lead compounds from a compound collection (1,4-disubstituted imidazole, 2,9-disubstituted 1,2,3,4-tetrahydropyrido[3,4-b]indole and benzodiazepine) involved a combination of iterative medicinal chemistry and structure based design.

Two series of small molecule-FabI inhibitors were optimized from screening leads obtained from a proprietary compound collection. Additional research from the group that performed this work led to the discovery of an aminopyridine-based FabI inhibitor that exhibits in vivo efficacy against *S. aureus*. The discovery of a naphthyridinone-based series of FabI inhibitors by the same group demonstrates the ability to generate improvements in potency, spectrum, and in vivo efficacy over previously reported selective FASII inhibitors. Significantly, selected compounds from this novel class of inhibitors display dual FabI/FabK inhibition.

The crystal structure of the *E. coli* enoyl reductase-NAD+ triclosan complex shows that unlike diazaborines and isoniazid that bind to the cofactor NADH covalently, triclosan interacts with both the enzyme and the cofactor in a noncovalent fashion. The potent noncovalent interactions ~$IC_{50}$ of 120 nm have been mainly attributed to the face-to-face stacking of its phenol ring to the nicotinamide ring, and the hydrogen bonds between the phenolic hydroxyl and the hydroxyls of Tyr156 and 29 nicotinamide ribose (*E. coli* numbering). Additional interactions with the flipping active site loop is crucial for defining the molecular basis for triclosan's potent inhibitory activity.

The key pharmacophoric elements required for selective FabI inhibition in the series of aminopyridine-based FabI inhibitors have been identified by structure-activity relationship (SAR) analysis. A bicyclic aromatic structure, preferably indole, is linked at the 2' or 3' position to a methylamide via a methylene linker. The amide functionality is connected to the 5-position of a 2-aminopyridine through an (E)-olefin. Substitution on the indole moiety is limited to small lipophilic functionality, and substitution on the olefin results in a loss of enzyme inhibitory activity. The most accessible site for further chemical manipulation on the aminopyridine moiety is at the 3-position, and this is where optimization to the naphthyridinone-based series occurred.

An X-ray cocrystallization study with naphthyridinone 29 (FabI *E. coli* $IC_{50}$) 0.07 mM) and *E. coli* FabI NADH(PDB ID: IMFP) reveals the key binding interactions. As expected, the binding characteristics of 29 are quite similar to those previously described for compound 4 (PDB ID: 1LXC) and for triclosan (PDB ID: 1C14; 112Z). The linking amide carbonyl of 29 is well-positioned for an H-bond interaction with the 2'-hydroxyl of NADH and the hydroxyl of Y156 (*E. coli* numbering). The central cis-amide fragment of 29 appears to participate in a n-stacking interaction with the nicotinamide portion of NADH as seen for compound 4. A95 is involved in H-bond interactions that bind both the pyridylamine and the N-acyl hydrogen of the naphthyridinone functionality. The contribution of the naphthyridinone carbonyl of 29 is not apparent in the crystal structure. The indole portion of inhibitor 29 is flanked by lipophilic residues (M206, F203, Y156, Y146; *E. coli* numbering) creating tight hydrophobic packing. Substitution at indole sites other than 1', 2', and 7' of 29 would appear to create unfavorable steric interactions with neighboring backbone residues. Similar observations for other FabI inhibitors in this region of the active site have been described.

An extensive characterization of the biological activities of these series of compounds, and in particular compound API-1135, has been discussed in Payne, Miller et al. 2002. Together, these studies support a mode of action (MOA) for these compounds as fatty acid synthesis (FASII) inhibitors. A tertiary profile was run with selected naphthyridinones against a panel of clinical isolates of *S. aureus* that were resistant to different classes of currently available antibiotics. Several naphthyridinones displayed levels of inhibition better than marketed antibiotics, with compound API-1135 achieving MIC90s>500-fold lower than those exhibited by the commercial antibiotics tested. In in vivo studies, following oral administration at 50 mg/kg, API-1135 was found to be effective in a rat groin abcess model (infected with the MRSA strain WCUH29), providing a 3.5-log reduction in bacterial counts relative to untreated controls.

The clinically relevant (F204C) mutation in the active site of *S. aureus* FabI (F203C in *E. coli*) negatively affects triclosan potency, but has no significant effect on the MIC of the naphthyridinone series of compounds. In general, the antibacterial potency of the indole naphthyridinones remains relatively unaffected by the active-site mutations that confer susceptibility to triclosan.

Resistance to the diazaborines arises from a missense mutation in the fabi gene that leads to the expression of a FabIG93S mutant protein. Similarly, the fabi analog in *Mycobacterium tuberculosis*, the inhA gene, encodes a cellular target for isoniazid and ethionamide. A point mutation in the inhA gene confers resistance to the drugs. Structural studies on diazaborine-bound *E. coli* FabI elucidated the mechanism by which diazaborine inhibits bacterial enoyl-ACP reductase and also threw light onto the molecular nature of the *E. coli* FabI G93S mutant's resistance to diazaborines. These studies indicate that a G93S substitution puts the larger amino acid side chain at the position where it would clash with the sulfonyl oxygens of the diazaborine molecule.

The foregoing information may aid in the design or optimization of *F. tularensis*-specific Fab I inhibitors which may target a druggable region, for example, such as those described above.

Comparison to Other FabI

Several other structures of FabI complexed with various inhibitors and structures of various other FabI (and related proteins) have been solved. If the conservation of bacterial FabI amino acid sequences are mapped onto the *F. tularensis* FabI structure (FIG. 25), variability is tolerated in many areas of the structure. Most residues near the binding pocket are fairly well conserved, but some areas are variable among bacterial species. Although the residues involved in hydrogen bonding with the inhibitor are conserved, changes in the residues encompassing the binding pocket will considerably alter the size and shape of the pocket. Any differences in side chains also change the distribution of potential interaction sites for inhibitors.

For example, in the *F. tularensis* structure, there are specific residues which are different in the other bacterial species which create a specific constellation of residues for the binding pocket. In particular, certain residues on the flipping loop are different in each bacterial species. S201, S198 and A197 have a high degree of variability, where a variety of residues can be present (i.e. glycine to aspartic acid). I200 and A196 have a moderate degree of variability, so the changes here are restricted to more conservative substitutions (i.e. valine to isoleucine).

A change in side chain may create differences in the binding pocket as the flipping loop closes around the inhibitor. Regions containing such differences may comprise druggable regions. On the other hand, similarity in residues in the binding pocket may allow the design of broad spectrum inhibitors. Common elements found in each species, even if the particular structure is unknown can be utilized to design inhibitors which interact specifically in this family of proteins. If alternate residues are modeled using the *F. tularensis* FabI structure as a base, inhibitors could be designed so they are complementary to a variety of bacterial species.

Table 3 summarizes and compares residues that may comprise druggable regions in *F. tularensis* FabI with those in FabI from other species:

TABLE 3

Potentially Druggable Residues in the Catalytic Domains of FabI

| Location | *F. tularensis* average conservation | *F. tularensis* | *S. aureus* | *E. coli* | *H. pylori* |
|---|---|---|---|---|---|
| Binding site[1] | 0.935 | A92 | A95 | G93 | A93 |
| Binding site | 0.560 | R96 | M99 | G97 | K97 |
| Binding site | 0.906 | P154 | Q155 | P154 | A153 |
| Binding site | 0.877 | S155 | N156 | N155 | H154 |
| Binding site | 1.000 | P191 | P192 | P191 | P190 |
| Binding site | 0.872 | S198 | K199 | S198 | S197 |
| Binding site | 1.000 | L195 | L196 | L195 | L194 |
| Binding site | 1.000 | A94 | A97 | A95 | A95 |
| Binding site | 1.000 | F203 | F204 | F203 | F202 |
| Binding site | 1.000 | Y146 | Y147 | Y146 | Y145 |
| Binding site | 1.000 | Y156 | Y157 | Y156 | Y155 |
| Binding site | 0.960 | I200 | V201 | I200 | I199 |

TABLE 3-continued

Potentially Druggable Residues in the Catalytic Domains of FabI

| Location | F. tularensis average conservation | F. tularensis | S. aureus | E. coli | H. pylori |
|---|---|---|---|---|---|
| Binding site | 0.681 | S201 | G202 | K201 | A200 |
| Binding site | 0.986 | M206 | I207 | M206 | I205 |
| Binding site | 0.967 | A196 | S197 | A196 | A195 |
| Binding site | 0.950 | M153 | V154 | I153 | M152 |
| Binding site | 1.000 | M159 | M160 | M159 | M158 |
| Binding site | 1.000 | L99 | L102 | L100 | L100 |
| Binding site | 1.000 | F93 | F96 | F94 | F94 |
| Binding site | 1.000 | K163 | K164 | K163 | K162 |
| Flipping loop |  | 192 IKTLAASGISN 202 | 193 IRTLSAKGVGG 203 | 192 IRTLAASGIKD 202 | 191 IRTLASSGIAD 201 |

[1] Binding site of the inhibitor and not residues involved in binding NADH

Based in part on the structural information described above, in one aspect, druggable regions of a subject polypeptide or other FabI comprising the majority of the amino acid residues contained in any of the above-described druggable regions are provided. In certain embodiments, the druggable region comprises a binding or active site. In some embodiments, the binding site may be comprised of at least one of residues selected from the group consisting of: A92, R96, P154, S155, P191, S198, L195, A94, F203, Y146, Y156, I200, S201, M206, A196, M153, M159, L99, F93, and K163. In yet another embodiment, the binding site may be comprised of at least one of S201, S198 and A197. In still other embodiments, the binding site may be comprised of at least one of I200 and A196. In another embodiment, the druggable region may be comprised of residues in the NADPH binding region. In still another embodiment, the druggable region may be comprised of residues in the inhibitor binding region, such as, for example, M206, F203, Y156 and Y146. In another embodiment, the druggable region may be comprised of residues of the flipping loop, such as, for example I192, K193, T194, L195, A196, A197, S198, G199, I200, S201, or N202.

In another aspect, modulators that interact with a druggable region of FabI, such as an active or binding site, are provided. Further, modulators that interact with the flipping loop are provided. For example, such modulators may preclude the flipping loop from moving.

Example 17

Annotations

The functional annotation is arrived at by comparing the amino acid sequence of the ORF against all available ORFs in the NCBI database using BLAST. The closest match is selected to provide the probable function of the polypeptide having the sequence of SEQ ID NO: 2.

The COGs database (Tatusov R L, Koonin E V, Lipman D J. Science 1997; 278 (5338) 631-37) classifies proteins encoded in twenty-one completed genomes on the basis of sequence similarity. Members of the same Cluster of Orthologous Group, ("COG"), are expected to have the same or similar domain architecture and the same or substantially similar biological activity. The database may be used to predict the function of uncharacterised proteins through their homology to characterized proteins. The COGs database may be searched from NCBI's website (http://www.ncbi.nlm.nih.gov/COG/) to determine functional annotation descriptions, such as "information storage and processing" (translation, ribosomal structure and biogenesis, transcription, DNA replication, recombination and repair); "cellular processes" (cell division and chromosome partitioning, post-translational modification, protein turnover, chaperones, cell envelope biogenesis, outer membrane, cell motility and secretion, inorganic ion transport and metabolism, signal transduction mechanisms); or "metabolism" (energy production and conversion, carbohydrate transport and metabolism, amino acid transport and metabolism, nucleotide transport and metabolism, coenzyme metabolism, lipid metabolism). For certain polypeptides, there is no entry available.

Example 18

Essential Gene Analysis

SEQ ID NO: 2 is compared to a number of publicly available "essential genes" lists to determine whether that protein is encoded by an essential gene. An example of such a list is descended from a free release at the www.shigen.ni.ac.jp PEC (profiling of E. coli chromosome) site, www.shigen.nig.ac.jp/ecoli/pec/. The list is prepared as follows: a wildcard search for all genes in class "essential" yields the list of essential E. coli proteins encoded by essential genes, which number 230. These 230 hits are pruned by comparing against an NCBI E. coli genome. Only 216 of the 230 genes on the list are found in the NCBI genome. These 216 are termed the essential-216-ecoli list. The essential-216-ecoli list is used to garner "essential" genes lists for other microbial genomes by blasting. For instance, formatting the 216-ecoli as a BLAST database, then BLASTing a genome (e.g. S. aureus) against it, elucidates all S. aureus genes with significant homology to a gene in the 216-essential list. SEQ ID NO: 2 is compared against the appropriate list and a match with a score of $e^{-25}$ or better is considered an essential gene according to that list. In addition to the list described above, other lists of essential genes are publicly available or may be determined by methods disclosed publicly, and such lists and methods are considered in deciding whether a gene is essential. See, for example, Thanassi et al., Nucleic Acids Res 2002 Jul. 15; 30(14):3152-62; Forsyth et al., Mol Microbiol 2002 March; 43(6):1387-400; Ji et al., Science 2001 Sep. 21; 293(5538): 2266-9; Sassetti et al., Proc Natl Acad Sci USA 2001 Oct. 23; 98(22):12712-7; Reich et al., J Bacteriol 1999 August; 181 (16):4961-8; Akerley et al., Proc Natl Acad Sci USA 2002 Jan. 22; 99(2):966-71). Also, other methods are known in the art for determining whether a gene is essential, such as that disclosed in U.S. patent application Ser. No. 10/202,442 (filed Jul. 24, 2002).

Example 19

PDB Analysis

SEQ ID NO: 2 is compared against the amino acid sequences in a database of proteins whose structures have been solved and released to the PDB (protein data bank). The identity/information about the top PDB homolog (most similar "hit", if any; a PDB entry is only considered a hit if the score is $e^{-4}$ or better) is annotated, and the percent similarity and identity between SEQ ID NO: 2 and the closest hit is calculated.

Example 20

Virtual Genome Analysis

VGDB or VG is a queryable collection of microbial genome databases annotated with biophysical and protein information. The organisms present in VG include:

| File | GRAM | Species | Source | Genome file date |
|---|---|---|---|---|
| ecoli.faa | G− | Escherichia coli | NCBI | Nov. 18, 1998 |
| hpyl.faa | G− | Helicobacter pylori | NCBI | Apr. 19, 1999 |
| paer.faa | G− | Pseudomonas aeruginosa | NCBI | Sep. 22, 2000 |
| ctra.faa | G− | Chlamydia trachomatis | NCBI | Dec. 22, 1999 |
| hinf.faa | G− | Haemophilus influenzae | NCBI | Nov. 26, 1999 |
| nmen.faa | G− | Neisseria meningitidis | NCBI | Dec. 28, 2000 |
| rpxx.faa | G− | Rickettsia prowazekii | NCBI | Dec. 22, 1999 |
| bbur.faa | G− | Borrelia burgdorferi | NCBI | Nov. 11, 1998 |
| bsub.faa | G+ | Bacillus subtilis | NCBI | Dec. 1, 1999 |
| staph.faa | G+ | Staphylococcus aureus | TIGR | Mar. 8, 2001 |
| spne.faa | G+ | Streptococcus pneumoniae | TIGR | Feb. 22, 2001 |
| mgen.faa | G+ | Mycoplasma genitalium | NCBI | Nov. 23, 1999 |
| efae.faa | G+ | Enterococcus faecalis | TIGR | Mar. 8, 2001 |

The VGDB comprises 13 microbial genomes, annotated with biophysical information (pI, MW, etc), and a wealth of other information. These 13 organism genomes are stored in a single flatfile (the VGDB) against which PSI-blast queries can be done.

SEQ ID NO: 2 is queried against the VGDB to determine whether this sequence is found, conserved, in many microbial genomes. There are certain criteria that must be met for a positive hit to be returned (beyond the criteria inherent in a basic PSI-blast).

When an ORF is queried it may have a maximum of 13 VG-organism hits. A hit is classified as such as long as it matches the following criteria: Minimum Length (as percentage of query length): 75 (Ensure hit protein is at least 75% as long as query); Maximum Length (as percentage of query length): 125 (Ensure hit protein is no more than 125% as long as query); eVal:−10 (Ensure hit has an e-Value of e-10 or better); Id %:>:25 (Ensure hit protein has at least 25% identity to query). The e-Value is a standard parameter of BLAST sequence comparisons, and represents a measure of the similarity between two sequences based on the likelihood that any similarities between the two sequences could have occurred by random chance alone. The lower the e-Value, the less likely that the similarities could have occurred randomly and, generally, the more similar the two sequences are.

Example 21

Epitopic Regions

The three most likely epitopic regions of a polypeptide having SEQ ID NO: 2 are predicted using the semi-empirical method of Kolaskar and Tongaonkar (FEBS Letters 1990 v276 172-174), the software package called Protean (DNAS-TAR), or MacVectors's Protein analysis tools (Accerlyrs). The antigenic propensity of each amino acid is calculated by the ratio between frequency of occurrence of amino acids in 169 antigenic determinants experimentally determined and the calculated frequency of occurrence of amino acids at the surface of protein.

EQUIVALENTS

The present invention provides among other things, novel proteins, protein structures and protein-protein interactions. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

All publications and patents mentioned herein, including those items listed below, are hereby incorporated by reference in their entirety as if each individual publication or patent was specifically and individually indicated to be incorporated by reference. In case of conflict, the present application, including any definitions herein, will control. To the extent that any U.S. Provisional Patent Applications to which this patent application claims priority incorporate by reference another U.S. Provisional Patent Application, such other U.S. Provisional Patent Application is not incorporated by reference herein unless this patent application expressly incorporates by reference, or claims priority to, such other U.S. Provisional Patent Application.

Also incorporated by reference in their entirety are any polynucleotide and polypeptide sequences which reference an accession number correlating to an entry in a public database, such as those maintained by The Institute for Genomic Research (TIGR) (www.tigr.org) and/or the National Center for Biotechnology Information (NCBI) (www.ncbi.nlm.nih.gov).

Also incorporated by reference are the following: U.S. Pat. No. 6,432,670, WO 00/70017. WO 01/30988, WO 02/31128, WO 00/45168, WO 00/79238, WO 00/77712, EP 1047108, EP 1047107, WO 00/72004, WO 00/73787, WO00/67017, WO 00/48004, WO 01/48209, WO 00/45168, WO 00/45164, U.S. Ser. No. 09/720,272; PCT/CA99/00640; U.S. patent application Ser. Nos. 10/097,125 (filed Mar. 12, 2002); 10/097,193 (filed Mar. 12, 2002); 10/202,442 (filed Jul. 24, 2002); 10/097,194 (filed Mar. 12, 2002); 09/671,817 (filed Sep. 17, 2000); 09/965,654 (filed Sep. 27, 2001); 09/727,812 (filed Nov. 30, 2000); 10/409,620 (filed Apr. 8, 2003); 10/246,812 (filed Sep. 18, 2002); U.S. Pat. Nos. 6,451,591; 6,254,833; 6,232,114; 6,229,603; 6,221,612; 6,214,563; 6,200,762; 6,171,780; 6,143,492; 6,124,128; 6,107,477; D428157; 6,063,338; 6,004,808; 5,985,214; 5,981,200; 5,928,888; 5,910,287; 6,248,550; 6,232,114; 6,229,603; 6,221,612; 6,214,563; 6,200,762; 6,197,928; 6,180,411; 6,171,780; 6,150,176; 6,140,132; 6,124,128; 6,107,066; 6,270,988; 6,077,707; 6,066,476; 6,063,338; 6,054,321; 6,054,271; 6,046,925; 6,031,094; 6,008,378; 5,998,204; 5,981,200; 5,955,604; 5,955,453; 5,948,906; 5,932,474; 5,925,558;

5,912,137; 5,910,287; 5,866,548; 6,214,602; 5,834,436; 5,777,079; 5,741,657; 5,693,521; 5,661,035; 5,625,048; 5,602,258; 5,552,555; 5,439,797; 5,374,710; 5,296,703; 5,283,433; 5,141,627; 5,134,232; 5,049,673; 4,806,604; 4,689,432; 4,603,209; 6,217,873; 6,174,530; 6,168,784; 6,271,037; 6,228,654; 6,184,344; 6,040,133; 5,910,437; 5,891,993; 5,854,389; 5,792,664; 6,248,558; 6,341,256; 5,854,922; and 5,866,343.

Armon, A., et al. (2001) *J Mol Biol* 307: 447-463; Baker, C. N., et al. (1985) *J Clin Microbiol* 22: 212-215; Baldock, C., et al. (1998) *J Mol Biol* 284: 1529-1546; Brunger, A. T., et al. (1998) *Acta Crystallogr. D. Biol. Crystallogr.* 54: 905-921; Chen, Z., et al. (1993) *Biochemistry* 32: 3342-3346; Collaborative Computational Project, N. 1994. The CCP4 Suite: Programs for Protein Crystallography. *Acta Cryst.* D: 760-763; Delano, W. L. (2002) *The PyMOL Molecular Graphics System*. DeLano Scientific, San Carlos, Calif., USA; Dennis, D. T., et al. (2001) *Jama* 285: 2763-2773; Ellis, J., et al. *Clin Microbiol Rev* 15: 631-646; Glaser, F., et al. (2003) *Bioinformatics* 19: 163-164; McRee, D. E. (1999) *J Struct Biol* 125: 156-165; Pavlov, V. M., et al. (1996) *FEMS Immunol Med Microbiol* 13: 253-256; Prior, R. G., et al. (2001) *J Appl Microbiol* 91: 614-620; Roujeinikova, A., et al. (1999) *Biol Chem* 274: 30811-30817; Saito, K., et al. (1981) *Eur J Biochem* 116: 581-586; Sawyer, W. D., et al (1966) *Bacteriol Rev* 30: 542-550.

Lonsdale, et al, (2001), DDT 6: 537-544; Rock, C. & Cronan, J. (1996) *Biochimica et Biophysica Acta* 1302: 1-16; Jackowski, S. (1992); Heath, et al, (1996), *J. Biol. Chem.* 271: 1833-1836; Baldock, C., J., et al. (1996), *Science* 274(5295): 2107-10; Baldock, C., J. et al. (1998), *J Mol Biol* 284(5): 1529-46; Bergler, H., et al. (1994), *J Biol Chem* 269(8): 5493-6; Chen, Z., et al. (1993), *Biochemistry* 32(13): 3342-6; Fan, F., K., et al. (2002), 46(11): 3343-7; Fisher, M., et al. (2000), *Structure Fold Des* 8(4): 339-47; Heath, R. J., et al. (2000), *J Biol Chem* 275(7): 4654-9; Heath, R. J., et al. (1999), *J Biol Chem* 274(16): 111110-4; Heerding, D. A., et al. (2001), *Bioorg Med Chem Lett* 11(16): 2061-5; Kissinger, C. R., et al. (1999), *Acta Crystallogr D Biol Crystallogr* 55 (Pt 2): 484-91; Levy, C. W., et al. (2001), *J Mol Biol* 309(1): 171-80; Levy, C. W., et al. (1999), *Nature* 398(6726): 383-4; McMurry, L. M., et al. (1998), *Nature* 394(6693): 531-2; Miller, W., et al. (2002), *J Med Chem* 45(15): 3246-56; Payne, D. J., et al. (2002), *Antimicrob Agents Chemother* 46(10): 3118-24; Perozzo, R., et al. (2002), *J Biol Chem* 277(15): 13106-14; Potterton, E., et al. (2002), *Acta Crystallogr D Biol Crystallogr* 58(Pt 11): 1955-7; Powell, H. R. (1999), *Acta Crystallogr D Biol Crystallogr* 55 (Pt 10): 1690-5; Price, A. C., et al. (2001), *Biochemistry* 40(43): 12772-81; Qiu, X., et al. (1999), *Protein Sci* 8(11): 2529-32; Quemard, A., et al. (1995), *Biochemistry* 34(26): 8235-41; Rafferty, J. B., et al. (1995), *Structure* 3(9): 927-38; Roujeinikova, A., et al. (1999), *J Mol Biol* 294(2): 527-35; Roujeinikova, A., et al. (1999), *Biol Chem* 274(43): 30811-7; Rozwarski, D. A., et al. (1998), *Science* 279(5347): 98-102; Rozwarski, D. A., et al. (1999), *J Biol Chem* 274(22): 15582-9; Saito, K., A., et al. (1981), *Eur J Biochem* 116(3): 581-6; Seefeld, M. A., et al. (2003), *J Med Chem* 46(9): 1627-35; Seefeld, M. A., et al. (2001), *Bioorg Med Chem Lett* 11(17): 2241-4; Turnowsky, F., K. Fuchs, et al. (1989), *J Bacteriol* 171(12): 6555-65; and Ward, W. H., et al. (1999), *Biochemistry* 38(38): 12514-25.

The following U.S. patent applications are hereby incorporated by reference in their entireties: U.S. Ser. No. 08/790,043, filed Jan. 28, 1997, entitled "Polynucleotide Encoding the Enoyl-Acyl Carrier Protein Reductase of *Staphylococcus Aureus*, Fab I"; U.S. Ser. No. 10/009,219, filed May 4, 2000, entitled "Methods of Using FabI and Compounds Modulating FabI Activity"; U.S. Ser. No. 60/486,540 filed Jul. 11, 2003 entitled "Novel Purified Polypeptides from *Staphylococcus Aureus*"; U.S. Ser. No. 60/490,383 filed Jul. 25, 2003 entitled "Novel Purified Polypeptides from *Staphylococcus Aureus*"

We claim:

1. A composition comprising an isolated, recombinant polypeptide, wherein the polypeptide comprises: (a) the amino acid sequence set forth in SEQ ID NO: 2; or (b) the amino acid sequence having at least about 95% identity with the amino acid sequence set forth in SEQ ID NO: 2; wherein the polypeptide of (a), or (b) is at least about 90% pure in a sample of the composition; and wherein the polypeptide is in non-crystalline form.

2. The composition of claim 1, wherein the polypeptide is at least about 95% pure as determined by gel electrophoresis.

3. The composition of claim 1, wherein the polypeptide is purified to essential homogeneity.

4. The composition of claim 1, wherein at least about two-thirds of the polypeptide in the sample is soluble.

5. The composition of claim 1, wherein the polypeptide is fused to at least one heterologous polypeptide that increases the solubility or stability of the polypeptide.

6. The composition of claim 1, which further comprises a matrix suitable for mass spectrometry.

7. The composition of claim 6, wherein the matrix is a nicotinic acid derivative or a cinnamic acid derivative.

8. A sample comprising an isolated, recombinant polypeptide, wherein the polypeptide comprises the amino acid sequence set forth in SEQ ID NO: 2; wherein the polypeptide is labeled with a heavy atom; and wherein the polypeptide is in non-crystalline form.

9. The sample of claim 8, wherein the heavy atom is one of the following: cobalt, selenium, krypton, bromine, strontium, molybdenum, ruthenium, rhodium, palladium, silver, cadmium, tin, iodine, xenon, barium, lanthanum, cerium, praseodymium, neodymium, samarium, europium, gadolinium, terbium, dysprosium, holmium, erbium, thulium, ytterbium, lutetium, tantalum, tungsten, rhenium, osmium, iridium, platinum, gold, mercury, thallium, lead, thorium and uranium.

10. The sample of claim 8, wherein the polypeptide is labeled with seleno-methionine.

11. The sample of claim 8, further comprising a cryo-protectant.

12. The sample of claim 11, wherein the cryo-protectant is one of the following: methyl pentanediol, isopropanol, ethylene glycol, glycerol, formate, citrate, mineral oil and a low-molecular-weight polyethylene glycol.

13. A sample comprising an isolated, recombinant polypeptide, wherein the polypeptide comprises: (a) the amino acid sequence set forth in SEQ ID NO: 2; or (b) the amino acid sequence having at least about 95% identity with the amino acid sequence set forth in SEQ ID NO: 2; wherein the polypeptide is enriched in at least one NMR isotope; and wherein the polypeptide is in non-crystalline form.

14. The sample of claim 13, wherein the NMR isotope is one of the following:

hydrogen-1 ($^{1}$H), hydrogen-2 ($^{2}$H), hydrogen-3 ($^{3}$H), phosphorous-31 ($^{31}$P), sodium-23 ($^{23}$Na), nitrogen-14 ($^{14}$N), nitrogen-15 ($^{15}$N), carbon-13 ($^{13}$C) and fluorine-19 ($^{19}$F).

15. The sample of claim 13, further comprising a deuterium lock solvent.

16. The sample of claim 15, wherein the deuterium lock solvent is one of the following: acetone ($CD_3COCD_3$), chloroform ($CDCl_3$), dichloromethane ($CD_2Cl_2$), methylnitrile ($CD_3CN$), benzene ($C_6D_6$), water ($D_2O$), diethylether (($CD_3CD_2)_2O$), dimethylether (($CD_3)_2O$), N,N-dimethylformamide (($CD_3)_2NCDO$), dimethyl sulfoxide ($CD_3SOCD_3$), ethanol ($CD_3CD_2OD$), methanol ($CD_3OD$), tetrahydrofuran ($C_4D_8O$), toluene ($C_6D_5CD_3$), pyridine ($C_5D_5N$) and cyclohexane ($C_6H_{12}$).

17. The sample of claim 13, which is contained within an NMR tube.

* * * * *

SEQUENCE LISTING

<160> NUMBER OF SEQ ID NOS: 33

<210> SEQ ID NO 1
<211> LENGTH: 783
<212> TYPE: DNA
<213> ORGANISM: Francisella tularensis

<400> SEQUENCE: 1

```
atgggttttc tagcaggaaa aaaaatatta atcactggac ttttaagtaa taagtcaatt      60
gcatatggta ttgctaaagc tatgcataga gagggagccg agcttgcttt tacttatgtt     120
ggacagttca aagatagagt ggaaaaatta tgtgcagaat ttaatccagc tgcagttttg     180
ccttgcgatg tgatttctga tcaagagatt aaggatttat ttgtagagct aggtaaagtt     240
tgggatggtc tagatgccat agttcattct atagcttttg caccgcgtga tcagttagaa     300
ggtaacttta ttgactgtgt aactcgcgag ggtttagta tcgctcatga tattagtgcc      360
tattcttttg cagcattagc taaagaaggt cgtagtatga tgaaaaatcg taatgcttct     420
atggtagcac ttacttatat tggagcagaa aaagctatgc caagttacaa tactatggga     480
gttgctaaag catctctaga agctacagtt agatatacag cgttagcttt aggtgaggat     540
ggtatcaagg taaatgctgt atcagctggt cctatcaaaa ctctggcagc ttctggtata     600
tcaaacttca agaagatgct tgattataat gctatggttt ctccacttaa gaaaaatgtt     660
```

```
gatattatgg aagttggtaa tactgtagcg tttttatgtt cagatatggc aactggtatc    720
actggagaag ttgtccatgt tgatgctgga tatcattgtg tgtctatggg taatgttctt    780
taa                                                                  783
```

<210> SEQ ID NO 2
<211> LENGTH: 260
<212> TYPE: PRT
<213> ORGANISM: Francisella tularensis

<400> SEQUENCE: 2

```
Met Gly Phe Leu Ala Gly Lys Lys Ile Leu Ile Thr Gly Leu Leu Ser
1               5                   10                  15

Asn Lys Ser Ile Ala Tyr Gly Ile Ala Lys Ala Met His Arg Glu Gly
            20                  25                  30

Ala Glu Leu Ala Phe Thr Tyr Val Gly Gln Phe Lys Asp Arg Val Glu
        35                  40                  45

Lys Leu Cys Ala Glu Phe Asn Pro Ala Ala Val Leu Pro Cys Asp Val
    50                  55                  60

Ile Ser Asp Gln Glu Ile Lys Asp Leu Phe Val Glu Leu Gly Lys Val
65                  70                  75                  80

Trp Asp Gly Leu Asp Ala Ile Val His Ser Ile Ala Phe Ala Pro Arg
                85                  90                  95

Asp Gln Leu Glu Gly Asn Phe Ile Asp Cys Val Thr Arg Glu Gly Phe
            100                 105                 110

Ser Ile Ala His Asp Ile Ser Ala Tyr Ser Phe Ala Ala Leu Ala Lys
        115                 120                 125

Glu Gly Arg Ser Met Met Lys Asn Arg Asn Ala Ser Met Val Ala Leu
    130                 135                 140

Thr Tyr Ile Gly Ala Glu Lys Ala Met Pro Ser Tyr Asn Thr Met Gly
145                 150                 155                 160

Val Ala Lys Ala Ser Leu Glu Ala Thr Val Arg Tyr Thr Ala Leu Ala
                165                 170                 175

Leu Gly Glu Asp Gly Ile Lys Val Asn Ala Val Ser Ala Gly Pro Ile
            180                 185                 190

Lys Thr Leu Ala Ala Ser Gly Ile Ser Asn Phe Lys Lys Met Leu Asp
        195                 200                 205

Tyr Asn Ala Met Val Ser Pro Leu Lys Lys Asn Val Asp Ile Met Glu
    210                 215                 220

Val Gly Asn Thr Val Ala Phe Leu Cys Ser Asp Met Ala Thr Gly Ile
225                 230                 235                 240

Thr Gly Glu Val Val His Val Asp Ala Gly Tyr His Cys Val Ser Met
                245                 250                 255

Gly Asn Val Leu
260
```

<210> SEQ ID NO 3
<211> LENGTH: 792
<212> TYPE: DNA
<213> ORGANISM: Francisella tularensis

<400> SEQUENCE: 3

```
atgggtacca tgggttttct agcaggaaaa aaaatattaa tcactggact tttaagtaat    60
aagtcaattg catatggtat tgctaaagct atgcatagag agggagccga gcttgctttt    120
acttatgttg gacagttcaa agatagagtg gaaaaattat gtgcagaatt taatccagct    180
```

-continued

```
gcagttttgc cttgcgatgt gatttctgat caagagatta aggatttatt tgtagagcta    240
ggtaaagttt gggatggtct agatgccata gttcattcta tagcttttgc accgcgtgat    300
cagttagaag gtaactttat tgactgtgta actcgcgagg gttttagtat cgctcatgat    360
attagtgcct attcttttgc agcattagct aaagaaggtc gtagtatgat gaaaaatcgt    420
aatgcttcta tggtagcact tacttatatt ggagcagaaa aagctatgcc aagttacaat    480
actatgggag ttgctaaagc atctctagaa gctacagtta gatatacagc gttagcttta    540
ggtgaggatg gtatcaaggt aaatgctgta tcagctggtc ctatcaaaac tctggcagct    600
tctggtatat caaacttcaa gaagatgctt gattataatg ctatggtttc tccacttaag    660
aaaaatgttg atattatgga agttggtaat actgtagcgt ttttatgttc agatatggca    720
actggtatca ctggagaagt tgtccatgtt gatgctggat atcattgtgt gtctatgggt    780
aatgttcttt aa                                                        792
```

```
<210> SEQ ID NO 4
<211> LENGTH: 263
<212> TYPE: PRT
<213> ORGANISM: Francisella tularensis

<400> SEQUENCE: 4

Met Gly Thr Met Gly Phe Leu Ala Gly Lys Lys Ile Leu Ile Thr Gly
1               5                   10                  15

Leu Leu Ser Asn Lys Ser Ile Ala Tyr Gly Ile Ala Lys Ala Met His
            20                  25                  30

Arg Glu Gly Ala Glu Leu Ala Phe Thr Tyr Val Gly Gln Phe Lys Asp
        35                  40                  45

Arg Val Glu Lys Leu Cys Ala Glu Phe Asn Pro Ala Ala Val Leu Pro
    50                  55                  60

Cys Asp Val Ile Ser Asp Gln Glu Ile Lys Asp Leu Phe Val Glu Leu
65                  70                  75                  80

Gly Lys Val Trp Asp Gly Leu Asp Ala Ile Val His Ser Ile Ala Phe
                85                  90                  95

Ala Pro Arg Asp Gln Leu Glu Gly Asn Phe Ile Asp Cys Val Thr Arg
            100                 105                 110

Glu Gly Phe Ser Ile Ala His Asp Ile Ser Ala Tyr Ser Phe Ala Ala
        115                 120                 125

Leu Ala Lys Glu Gly Arg Ser Met Met Lys Asn Arg Asn Ala Ser Met
    130                 135                 140

Val Ala Leu Thr Tyr Ile Gly Ala Glu Lys Ala Met Pro Ser Tyr Asn
145                 150                 155                 160

Thr Met Gly Val Ala Lys Ala Ser Leu Glu Ala Thr Val Arg Tyr Thr
                165                 170                 175

Ala Leu Ala Leu Gly Glu Asp Gly Ile Lys Val Asn Ala Val Ser Ala
            180                 185                 190

Gly Pro Ile Lys Thr Leu Ala Ala Ser Gly Ile Ser Asn Phe Lys Lys
        195                 200                 205

Met Leu Asp Tyr Asn Ala Met Val Ser Pro Leu Lys Lys Asn Val Asp
    210                 215                 220

Ile Met Glu Val Gly Asn Thr Val Ala Phe Leu Cys Ser Asp Met Ala
225                 230                 235                 240

Thr Gly Ile Thr Gly Glu Val Val His Val Asp Ala Gly Tyr His Cys
                245                 250                 255
```

Val Ser Met Gly Asn Val Leu
260

<210> SEQ ID NO 5
<211> LENGTH: 792
<212> TYPE: DNA
<213> ORGANISM: Francisella tularensis

<400> SEQUENCE: 5

| | | | | | |
|---|---|---|---|---|---|
| atgggtacca tgggttttct agcaggaaaa aaaatattaa tcactggact tttaagtaat | | | | | 60 |
| aagtcaattg catatggtat tgctaaagct atgcatagag agggagccga gcttgctttt | | | | | 120 |
| acttatgttg gacagttcaa agatagagtg gaaaaattat gtgcagaatt taatccagct | | | | | 180 |
| gcagttttgc cttgcgatgt gatttctgat caagagatta aggatttatt tgtagagcta | | | | | 240 |
| ggtaaagttt gggatggtct agatgccata gttcattcta tagcttttgc accgcgtgat | | | | | 300 |
| cagttagaag gtaactttat tgactgtgta actcgcgagg gttttagtat cgctcatgat | | | | | 360 |
| attagtgcct attcttttgc agcattagct aaagaaggtc gtagtatgat gaaaaatcgt | | | | | 420 |
| aatgcttcta tggtagcact tacttatatt ggagcagaaa aagctatgcc aagttacaat | | | | | 480 |
| actatgggag ttgctaaagc atctctagaa gctacagtta gatatacagc gttagcttta | | | | | 540 |
| ggtgaggatg gtatcaaggt aaatgctgta tcagctggtc ctatcaaaac tctggcagct | | | | | 600 |
| tctggtatat caaacttcaa gaagatgctt gattataatg ctatggtttc tccacttaag | | | | | 660 |
| aaaaatgttg atattatgga agttggtaat actgtagcgt ttttatgttc agatatggca | | | | | 720 |
| actggtatca ctggagaagt tgtccatgtt gatgctggat tcattgtgt gtctatgggt | | | | | 780 |
| aatgttcttt aa | | | | | 792 |

<210> SEQ ID NO 6
<211> LENGTH: 282
<212> TYPE: PRT
<213> ORGANISM: Francisella tularensis

<400> SEQUENCE: 6

Met Gly Ser His His His His His His Ser Gly Leu Val Pro Arg
1               5                   10                  15

Gly Ser His Met Gly Thr Met Gly Phe Leu Ala Gly Lys Lys Ile Leu
            20              25                  30

Ile Thr Gly Leu Leu Ser Asn Lys Ser Ile Ala Tyr Gly Ile Ala Lys
35                  40                  45

Ala Met His Arg Glu Gly Ala Glu Leu Ala Phe Thr Tyr Val Gly Gln
50                  55                  60

Phe Lys Asp Arg Val Glu Lys Leu Cys Ala Glu Phe Asn Pro Ala Ala
65                  70                  75                  80

Val Leu Pro Cys Asp Val Ile Ser Asp Gln Glu Ile Lys Asp Leu Phe
            85                  90                  95

Val Glu Leu Gly Lys Val Trp Asp Gly Leu Asp Ala Ile Val His Ser
            100                 105                 110

Ile Ala Phe Ala Pro Arg Asp Gln Leu Glu Gly Asn Phe Ile Asp Cys
115                 120                 125

Val Thr Arg Glu Gly Phe Ser Ile Ala His Asp Ile Ser Ala Tyr Ser
130                 135                 140

Phe Ala Ala Leu Ala Lys Glu Gly Arg Ser Met Met Lys Asn Arg Asn
145                 150                 155                 160

Ala Ser Met Val Ala Leu Thr Tyr Ile Gly Ala Glu Lys Ala Met Pro
            165                 170                 175

```
Ser Tyr Asn Thr Met Gly Val Ala Lys Ala Ser Leu Glu Ala Thr Val
180                 185                 190

Arg Tyr Thr Ala Leu Ala Leu Gly Glu Asp Gly Ile Lys Val Asn Ala
195                 200                 205

Val Ser Ala Gly Pro Ile Lys Thr Leu Ala Ala Ser Gly Ile Ser Asn
210                 215                 220

Phe Lys Lys Met Leu Asp Tyr Asn Ala Met Val Ser Pro Leu Lys Lys
225                 230                 235                 240

Asn Val Asp Ile Met Glu Val Gly Asn Thr Val Ala Phe Leu Cys Ser
245                 250                 255

Asp Met Ala Thr Gly Ile Thr Gly Glu Val Val His Val Asp Ala Gly
260                 265                 270

Tyr His Cys Val Ser Met Gly Asn Val Leu
275                 280
```

```
<210> SEQ ID NO 7
<211> LENGTH: 795
<212> TYPE: DNA
<213> ORGANISM: Francisella tularensis

<400> SEQUENCE: 7
atgggtacca tgggttttct agcaggaaaa aaaatattaa tcactggact tttaagtaat     60
aagtcaattg catatggtat tgctaaagct atgcatagag agggagccga gcttgctttt    120
acttatgttg gacagttcaa agatagagtg gaaaaattat gtgcagaatt taatccagct    180
gcagttttgc cttgcgatgt gatttctgat caagagatta aggatttatt tgtagagcta    240
ggtaaagttt gggatggtct agatgccata gttcattcta tagcttttgc accgcgtgat    300
cagttagaag gtaactttat tgactgtgta actcgcgagg gttttagtat cgctcatgat    360
attagtgcct attcttttgc agcattagct aaagaaggtc gtagtatgat gaaaaatcgt    420
aatgcttcta tggtagcact tacttatatt ggagcagaaa aagctatgcc aagttacaat    480
actatgggag ttgctaaagc atctctagaa gctacagtta gatatacagc gttagcttta    540
ggtgaggatg gtatcaaggt aaatgctgta tcagctggtc ctatcaaaac tctggcagct    600
tctggtatat caaacttcaa gaagatgctt gattataatg ctatggtttc tccacttaag    660
aaaaatgttg atattatgga agttggtaat actgtagcgt ttttatgttc agatatggca    720
actggtatca ctggagaagt tgtccatgtt gatgctggat atcattgtgt gtctatgggt    780
aatgttcttg gatcc                                                    795
```

```
<210> SEQ ID NO 8
<211> LENGTH: 277
<212> TYPE: PRT
<213> ORGANISM: Francisella tularensis

<400> SEQUENCE: 8

Met Gly Thr Met Gly Phe Leu Ala Gly Lys Lys Ile Leu Ile Thr Gly
1               5                   10                  15

Leu Leu Ser Asn Lys Ser Ile Ala Tyr Gly Ile Ala Lys Ala Met His
20                  25                  30

Arg Glu Gly Ala Glu Leu Ala Phe Thr Tyr Val Gly Gln Phe Lys Asp
35                  40                  45

Arg Val Glu Lys Leu Cys Ala Glu Phe Asn Pro Ala Ala Val Leu Pro
50                  55                  60

Cys Asp Val Ile Ser Asp Gln Glu Ile Lys Asp Leu Phe Val Glu Leu
```

```
                65                  70                  75                  80
Gly Lys Val Trp Asp Gly Leu Asp Ala Ile Val His Ser Ile Ala Phe
 85                  90                  95

Ala Pro Arg Asp Gln Leu Glu Gly Asn Phe Ile Asp Cys Val Thr Arg
100                 105                 110

Glu Gly Phe Ser Ile Ala His Asp Ile Ser Ala Tyr Ser Phe Ala Ala
115                 120                 125

Leu Ala Lys Glu Gly Arg Ser Met Met Lys Asn Arg Asn Ala Ser Met
130                 135                 140

Val Ala Leu Thr Tyr Ile Gly Ala Glu Lys Ala Met Pro Ser Tyr Asn
145                 150                 155                 160

Thr Met Gly Val Ala Lys Ala Ser Leu Glu Ala Thr Val Arg Tyr Thr
165                 170                 175

Ala Leu Ala Leu Gly Glu Asp Gly Ile Lys Val Asn Ala Val Ser Ala
180                 185                 190

Gly Pro Ile Lys Thr Leu Ala Ala Ser Gly Ile Ser Asn Phe Lys Lys
195                 200                 205

Met Leu Asp Tyr Asn Ala Met Val Ser Pro Leu Lys Lys Asn Val Asp
210                 215                 220

Ile Met Glu Val Gly Asn Thr Val Ala Phe Leu Cys Ser Asp Met Ala
225                 230                 235                 240

Thr Gly Ile Thr Gly Glu Val Val His Val Asp Ala Gly Tyr His Cys
245                 250                 255

Val Ser Met Gly Asn Val Leu Gly Ser Glu Asn Leu Tyr Phe Gln His
260                 265                 270

His His His His His
275

<210> SEQ ID NO 9
<211> LENGTH: 256
<212> TYPE: PRT
<213> ORGANISM: Staphylococcus aureus

<400> SEQUENCE: 9

Met Leu Asn Leu Glu Asn Lys Thr Tyr Val Ile Met Gly Ile Ala Asn
  1                   5                  10                  15

Lys Arg Ser Ile Ala Phe Gly Val Ala Lys Val Leu Asp Gln Leu Gly
 20                  25                  30

Ala Lys Leu Val Phe Thr Tyr Arg Lys Glu Arg Ser Arg Lys Glu Leu
 35                  40                  45

Glu Lys Leu Leu Glu Gln Leu Asn Gln Pro Glu Ala His Leu Tyr Gln
 50                  55                  60

Ile Asp Val Gln Ser Asp Glu Glu Val Ile Asn Gly Phe Glu Gln Ile
 65                  70                  75                  80

Gly Lys Asp Val Gly Asn Ile Asp Gly Val Tyr His Ser Ile Ala Phe
 85                  90                  95

Ala Asn Met Glu Asp Leu Arg Gly Arg Phe Ser Glu Thr Ser Arg Glu
100                 105                 110

Gly Phe Leu Leu Ala Gln Asp Ile Ser Ser Tyr Ser Leu Thr Ile Val
115                 120                 125

Ala His Glu Ala Lys Lys Leu Met Pro Glu Gly Gly Ser Ile Val Ala
130                 135                 140

Thr Thr Tyr Leu Gly Gly Glu Phe Ala Val Gln Asn Tyr Asn Val Met
145                 150                 155                 160
```

```
Gly Val Ala Lys Ala Ser Leu Glu Ala Asn Val Lys Tyr Leu Ala Leu
165                 170                 175

Asp Leu Gly Pro Asp Asn Ile Arg Val Asn Ala Ile Ser Ala Gly Pro
180                 185                 190

Ile Arg Thr Leu Ser Ala Lys Gly Val Gly Phe Asn Thr Ile Leu
195                 200                 205

Lys Glu Ile Lys Glu Arg Ala Pro Leu Lys Arg Asn Val Asp Gln Val
210                 215                 220

Glu Val Gly Lys Thr Ala Ala Tyr Leu Leu Ser Asp Leu Ser Ser Gly
225                 230                 235                 240

Val Thr Gly Glu Asn Ile His Val Asp Ser Gly Phe His Ala Ile Lys
245                 250                 255

<210> SEQ ID NO 10
<211> LENGTH: 262
<212> TYPE: PRT
<213> ORGANISM: Escherichia coli

<400> SEQUENCE: 10

Met Gly Phe Leu Ser Gly Lys Arg Ile Leu Val Thr Gly Val Ala Ser
1               5                   10                  15

Lys Leu Ser Ile Ala Tyr Gly Ile Ala Gln Ala Met His Arg Glu Gly
20                  25                  30

Ala Glu Leu Ala Phe Thr Tyr Gln Asn Asp Lys Leu Lys Gly Arg Val
35                  40                  45

Glu Glu Phe Ala Ala Gln Leu Gly Ser Asp Ile Val Leu Gln Cys Asp
50                  55                  60

Val Ala Glu Asp Ala Ser Ile Asp Thr Met Phe Ala Glu Leu Gly Lys
65                  70                  75                  80

Val Trp Pro Lys Phe Asp Gly Phe Val His Ser Ile Gly Phe Ala Pro
85                  90                  95

Gly Asp Gln Leu Asp Gly Asp Tyr Val Asn Ala Val Thr Arg Glu Gly
100                 105                 110

Phe Lys Ile Ala His Asp Ile Ser Ser Tyr Ser Phe Val Ala Met Ala
115                 120                 125

Lys Ala Cys Arg Ser Met Leu Asn Pro Gly Ser Ala Leu Leu Thr Leu
130                 135                 140

Ser Tyr Leu Gly Ala Glu Arg Ala Ile Pro Asn Tyr Asn Val Met Gly
145                 150                 155                 160

Leu Ala Lys Ala Ser Leu Glu Ala Asn Val Arg Tyr Met Ala Asn Ala
165                 170                 175

Met Gly Pro Glu Gly Val Arg Val Asn Ala Ile Ser Ala Gly Pro Ile
180                 185                 190

Arg Thr Leu Ala Ala Ser Gly Ile Lys Asp Phe Arg Lys Met Leu Ala
195                 200                 205

His Cys Glu Ala Val Thr Pro Ile Arg Arg Thr Val Thr Ile Glu Asp
210                 215                 220

Val Gly Asn Ser Ala Ala Phe Leu Cys Ser Asp Leu Ser Ala Gly Ile
225                 230                 235                 240

Ser Gly Glu Val Val His Val Asp Gly Gly Phe Ser Ile Ala Ala Met
245                 250                 255

Asn Glu Leu Glu Leu Lys
260

<210> SEQ ID NO 11
```

```
<211> LENGTH: 275
<212> TYPE: PRT
<213> ORGANISM: Helicobacter pylori

<400> SEQUENCE: 11

Met Gly Phe Leu Lys Gly Lys Gly Leu Ile Val Gly Val Ala Asn
1               5                   10                  15

Asn Lys Ser Ile Ala Tyr Gly Ile Ala Gln Ser Cys Phe Asn Gln Gly
20                  25                  30

Ala Thr Leu Ala Phe Thr Tyr Leu Asn Glu Ser Leu Glu Lys Arg Val
35                  40                  45

Arg Pro Ile Ala Gln Glu Leu Asn Ser Pro Tyr Val Tyr Glu Leu Asp
50                  55                  60

Val Ser Lys Glu Glu His Phe Lys Ser Leu Tyr Asn Ser Val Lys Lys
65                  70                  75                  80

Asp Leu Gly Ser Leu Asp Phe Ile Val His Ser Val Ala Phe Ala Pro
85                  90                  95

Lys Glu Ala Leu Glu Gly Ser Leu Leu Glu Thr Ser Lys Ser Ala Phe
100                 105                 110

Asn Thr Ala Met Glu Ile Ser Val Tyr Ser Leu Ile Glu Leu Thr Asn
115                 120                 125

Thr Leu Lys Pro Leu Leu Asn Asn Gly Ala Ser Val Leu Thr Leu Ser
130                 135                 140

Tyr Leu Gly Ser Thr Lys Tyr Met Ala His Tyr Asn Val Met Gly Leu
145                 150                 155                 160

Ala Lys Ala Ala Leu Glu Ser Ala Val Arg Tyr Leu Ala Val Asp Leu
165                 170                 175

Gly Lys His His Ile Arg Val Asn Ala Leu Ser Ala Gly Pro Ile Arg
180                 185                 190

Thr Leu Ala Ser Ser Gly Ile Ala Asp Phe Arg Met Ile Leu Lys Trp
195                 200                 205

Asn Glu Ile Asn Ala Pro Leu Arg Lys Asn Val Ser Leu Glu Glu Val
210                 215                 220

Gly Asn Ala Gly Met Tyr Leu Leu Ser Ser Leu Ser Ser Gly Val Ser
225                 230                 235                 240

Gly Glu Val His Phe Val Asp Ala Gly Tyr His Val Met Gly Met Gly
245                 250                 255

Ala Val Glu Glu Lys Asp Asn Lys Ala Thr Leu Leu Trp Asp Leu His
260                 265                 270

Lys Glu Gln
275

<210> SEQ ID NO 12
<211> LENGTH: 279
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)..(12)
```

```
<223> OTHER INFORMATION: Variable amino acid
<220> FEATURE:
<221> NAME/KEY: MOD_RES
<222> LOCATION: (14)..(18)
<223> OTHER INFORMATION: Variable amino acid
<220> FEATURE:
<221> NAME/KEY: MOD_RES
<222> LOCATION: (22)
<223> OTHER INFORMATION: Variable amino acid
<220> FEATURE:
<221> NAME/KEY: MOD_RES
<222> LOCATION: (24)
<223> OTHER INFORMATION: Variable amino acid
<220> FEATURE:
<221> NAME/KEY: MOD_RES
<222> LOCATION: (26)..(31)
<223> OTHER INFORMATION: Variable amino acid
<220> FEATURE:
<221> NAME/KEY: MOD_RES
<222> LOCATION: (34)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (40)..(65)
<223> OTHER INFORMATION: Variable amino acid
<220> FEATURE:
<221> NAME/KEY: MOD_RES
<222> LOCATION: (68)..(81)
<223> OTHER INFORMATION: Variable amino acid
<220> FEATURE:
<221> NAME/KEY: MOD_RES
<222> LOCATION: (83)..(87)
<223> OTHER INFORMATION: Variable amino acid
<220> FEATURE:
<221> NAME/KEY: MOD_RES
<222> LOCATION: (89)..(91)
<223> OTHER INFORMATION: Variable amino acid
<220> FEATURE:
<221> NAME/KEY: MOD_RES
<222> LOCATION: (94)..(95)
<223> OTHER INFORMATION: Variable amino acid
<220> FEATURE:
<221> NAME/KEY: MOD_RES
<222> LOCATION: (98)..(101)
<223> OTHER INFORMATION: Variable amino acid
<220> FEATURE:
<221> NAME/KEY: MOD_RES
<222> LOCATION: (103)
<223> OTHER INFORMATION: Variable amino acid
<220> FEATURE:
<221> NAME/KEY: MOD_RES
<222> LOCATION: (105)..(114)
<223> OTHER INFORMATION: Variable amino acid
<220> FEATURE:
<221> NAME/KEY: MOD_RES
<222> LOCATION: (116)..(117)
<223> OTHER INFORMATION: Variable amino acid
<220> FEATURE:
<221> NAME/KEY: MOD_RES
<222> LOCATION: (119)..(120)
<223> OTHER INFORMATION: Variable amino acid
<220> FEATURE:
<221> NAME/KEY: MOD_RES
<222> LOCATION: (123)
<223> OTHER INFORMATION: Variable amino acid
<220> FEATURE:
<221> NAME/KEY: MOD_RES
<222> LOCATION: (126)..(148)
<223> OTHER INFORMATION: Variable amino acid
<220> FEATURE:
<221> NAME/KEY: MOD_RES
<222> LOCATION: (150)
<223> OTHER INFORMATION: Variable amino acid
<220> FEATURE:
<221> NAME/KEY: MOD_RES
```

```
<222> LOCATION: (152)..(158)
<223> OTHER INFORMATION: Variable amino acid
<220> FEATURE:
<221> NAME/KEY: MOD_RES
<222> LOCATION: (161)
<223> OTHER INFORMATION: Variable amino acid
<220> FEATURE:
<221> NAME/KEY: MOD_RES
<222> LOCATION: (164)
<223> OTHER INFORMATION: Variable amino acid
<220> FEATURE:
<221> NAME/KEY: MOD_RES
<222> LOCATION: (168)
<223> OTHER INFORMATION: Variable amino acid
<220> FEATURE:
<221> NAME/KEY: MOD_RES
<222> LOCATION: (171)..(172)
<223> OTHER INFORMATION: Variable amino acid
<220> FEATURE:
<221> NAME/KEY: MOD_RES
<222> LOCATION: (176)
<223> OTHER INFORMATION: Variable amino acid
<220> FEATURE:
<221> NAME/KEY: MOD_RES
<222> LOCATION: (178)..(180)
<223> OTHER INFORMATION: Variable amino acid
<220> FEATURE:
<221> NAME/KEY: MOD_RES
<222> LOCATION: (182)..(186)
<223> OTHER INFORMATION: Variable amino acid
<220> FEATURE:
<221> NAME/KEY: MOD_RES
<222> LOCATION: (190)
<223> OTHER INFORMATION: Variable amino acid
<220> FEATURE:
<221> NAME/KEY: MOD_RES
<222> LOCATION: (196)
<223> OTHER INFORMATION: Variable amino acid
<220> FEATURE:
<221> NAME/KEY: MOD_RES
<222> LOCATION: (199)..(201)
<223> OTHER INFORMATION: Variable amino acid
<220> FEATURE:
<221> NAME/KEY: MOD_RES
<222> LOCATION: (203)..(205)
<223> OTHER INFORMATION: Variable amino acid
<220> FEATURE:
<221> NAME/KEY: MOD_RES
<222> LOCATION: (207)..(209)
<223> OTHER INFORMATION: Variable amino acid
<220> FEATURE:
<221> NAME/KEY: MOD_RES
<222> LOCATION: (211)..(217)
<223> OTHER INFORMATION: Variable amino acid
<220> FEATURE:
<221> NAME/KEY: MOD_RES
<222> LOCATION: (219)..(222)
<223> OTHER INFORMATION: Variable amino acid
<220> FEATURE:
<221> NAME/KEY: MOD_RES
<222> LOCATION: (224)..(227)
<223> OTHER INFORMATION: Variable amino acid
<220> FEATURE:
<221> NAME/KEY: MOD_RES
<222> LOCATION: (230)..(234)
<223> OTHER INFORMATION: Variable amino acid
<220> FEATURE:
<221> NAME/KEY: MOD_RES
<222> LOCATION: (236)
<223> OTHER INFORMATION: Variable amino acid
<220> FEATURE:
<221> NAME/KEY: MOD_RES
<222> LOCATION: (238)..(241)
<223> OTHER INFORMATION: Variable amino acid
<220> FEATURE:
<221> NAME/KEY: MOD_RES
<222> LOCATION: (243)..(244)
<223> OTHER INFORMATION: Variable amino acid
<220> FEATURE:
```

```
<221> NAME/KEY: MOD_RES
<222> LOCATION: (247)..(249)
<223> OTHER INFORMATION: Variable amino acid
<220> FEATURE:
<221> NAME/KEY: MOD_RES
<222> LOCATION: (252)
<223> OTHER INFORMATION: Variable amino acid
<220> FEATURE:
<221> NAME/KEY: MOD_RES
<222> LOCATION: (254)..(279)
<223> OTHER INFORMATION: Variable amino acid

<400> SEQUENCE: 12

Met Xaa Xaa Leu Xaa Xaa Lys Xaa Xaa Xaa Xaa Gly Xaa Xaa Xaa
1               5                   10                  15

Xaa Xaa Ser Ile Ala Xaa Gly Xaa Ala Xaa Xaa Xaa Xaa Xaa Gly
        20                  25                  30

Ala Xaa Leu Xaa Phe Thr Tyr Xaa Xaa Xaa Xaa Xaa Xaa Xaa Xaa
35                  40                  45

Xaa Xaa Xaa Xaa Xaa Xaa Xaa Xaa Xaa Xaa Xaa Xaa Xaa Xaa Xaa
50                  55                  60

Xaa Asp Val Xaa Xaa Xaa Xaa Xaa Xaa Xaa Xaa Xaa Xaa Xaa Xaa
65                  70                  75                  80

Xaa Lys Xaa Xaa Xaa Xaa Xaa Asp Xaa Xaa Xaa His Ser Xaa Xaa Phe
85                  90                  95

Ala Xaa Xaa Xaa Xaa Leu Xaa Gly Xaa Xaa Xaa Xaa Xaa Xaa Xaa
100                 105                 110

Xaa Xaa Phe Xaa Xaa Ala Xaa Xaa Ile Ser Xaa Tyr Ser Xaa Xaa
115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Tyr Xaa Gly Xaa Xaa Xaa Xaa Xaa Xaa Tyr Asn
145                 150                 155                 160

Xaa Met Gly Xaa Ala Lys Ala Xaa Leu Glu Xaa Xaa Val Arg Tyr Xaa
165                 170                 175

Ala Xaa Xaa Xaa Gly Xaa Xaa Xaa Xaa Xaa Val Asn Ala Xaa Ser Ala
180                 185                 190

Gly Pro Ile Xaa Thr Leu Xaa Xaa Xaa Gly Xaa Xaa Xaa Phe Xaa Xaa
195                 200                 205

Xaa Leu Xaa Xaa Xaa Xaa Xaa Xaa Xaa Pro Xaa Xaa Xaa Xaa Val Xaa
210                 215                 220

Xaa Xaa Xaa Val Gly Xaa Xaa Xaa Xaa Xaa Leu Xaa Ser Xaa Xaa Xaa
225                 230                 235                 240

Xaa Gly Xaa Xaa Gly Glu Xaa Xaa Xaa Val Asp Xaa Gly Xaa Xaa
245                 250                 255

Xaa Xaa Xaa Xaa Xaa Xaa Xaa Xaa Xaa Xaa Xaa Xaa Xaa Xaa Xaa
260                 265                 270

Xaa Xaa Xaa Xaa Xaa Xaa Xaa
275

<210> SEQ ID NO 13
<211> LENGTH: 260
<212> TYPE: PRT
<213> ORGANISM: Francisella tularensis
<220> FEATURE:
<221> NAME/KEY: MOD_RES
<222> LOCATION: (1)..(91)
<223> OTHER INFORMATION: Variable amino acid
<220> FEATURE:
<221> NAME/KEY: MOD_RES
```

```
<222> LOCATION: (95)
<223> OTHER INFORMATION: Variable amino acid
<220> FEATURE:
<221> NAME/KEY: MOD_RES
<222> LOCATION: (97)..(98)
<223> OTHER INFORMATION: Variable amino acid
<220> FEATURE:
<221> NAME/KEY: MOD_RES
<222> LOCATION: (100)..(145)
<223> OTHER INFORMATION: Variable amino acid
<220> FEATURE:
<221> NAME/KEY: MOD_RES
<222> LOCATION: (147)..(152)
<223> OTHER INFORMATION: Variable amino acid
<220> FEATURE:
<221> NAME/KEY: MOD_RES
<222> LOCATION: (157)..(158)
<223> OTHER INFORMATION: Variable amino acid
<220> FEATURE:
<221> NAME/KEY: MOD_RES
<222> LOCATION: (160)..(162)
<223> OTHER INFORMATION: Variable amino acid
<220> FEATURE:
<221> NAME/KEY: MOD_RES
<222> LOCATION: (164)..(190)
<223> OTHER INFORMATION: Variable amino acid
<220> FEATURE:
<221> NAME/KEY: MOD_RES
<222> LOCATION: (192)..(194)
<223> OTHER INFORMATION: Variable amino acid
<220> FEATURE:
<221> NAME/KEY: MOD_RES
<222> LOCATION: (197)
<223> OTHER INFORMATION: Variable amino acid
<220> FEATURE:
<221> NAME/KEY: MOD_RES
<222> LOCATION: (199)
<223> OTHER INFORMATION: Variable amino acid
<220> FEATURE:
<221> NAME/KEY: MOD_RES
<222> LOCATION: (202)
<223> OTHER INFORMATION: Variable amino acid
<220> FEATURE:
<221> NAME/KEY: MOD_RES
<222> LOCATION: (204)..(205)
<223> OTHER INFORMATION: Variable amino acid
<220> FEATURE:
<221> NAME/KEY: MOD_RES
<222> LOCATION: (207)..(260)
<223> OTHER INFORMATION: Variable amino acid

<400> SEQUENCE: 13

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Ala Phe Ala Xaa Arg
            85                  90                  95

Xaa Xaa Leu Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140
```

```
Xaa Tyr Xaa Xaa Xaa Xaa Xaa Xaa Met Pro Ser Tyr Xaa Xaa Met Xaa
145                 150                 155                 160

Xaa Xaa Lys Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Pro Xaa
180                 185                 190

Xaa Xaa Leu Ala Xaa Ser Xaa Ile Ser Xaa Phe Xaa Xaa Met Xaa Xaa
195                 200                 205

Xaa Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
245                 250                 255

Xaa Xaa Xaa Xaa
260

<210> SEQ ID NO 14
<211> LENGTH: 256
<212> TYPE: PRT
<213> ORGANISM: Staphylococcus aureus
<220> FEATURE:
<221> NAME/KEY: MOD_RES
<222> LOCATION: (1)..(94)
<223> OTHER INFORMATION: Variable amino acid
<220> FEATURE:
<221> NAME/KEY: MOD_RES
<222> LOCATION: (98)
<223> OTHER INFORMATION: Variable amino acid
<220> FEATURE:
<221> NAME/KEY: MOD_RES
<222> LOCATION: (100)..(101)
<223> OTHER INFORMATION: Variable amino acid
<220> FEATURE:
<221> NAME/KEY: MOD_RES
<222> LOCATION: (103)..(146)
<223> OTHER INFORMATION: Variable amino acid
<220> FEATURE:
<221> NAME/KEY: MOD_RES
<222> LOCATION: (148)..(153)
<223> OTHER INFORMATION: Variable amino acid
<220> FEATURE:
<221> NAME/KEY: MOD_RES
<222> LOCATION: (158)..(159)
<223> OTHER INFORMATION: Variable amino acid
<220> FEATURE:
<221> NAME/KEY: MOD_RES
<222> LOCATION: (161)..(163)
<223> OTHER INFORMATION: Variable amino acid
<220> FEATURE:
<221> NAME/KEY: MOD_RES
<222> LOCATION: (165)..(191)
<223> OTHER INFORMATION: Variable amino acid
<220> FEATURE:
<221> NAME/KEY: MOD_RES
<222> LOCATION: (193)..(195)
<223> OTHER INFORMATION: Variable amino acid
<220> FEATURE:
<221> NAME/KEY: MOD_RES
<222> LOCATION: (198)
<223> OTHER INFORMATION: Variable amino acid
<220> FEATURE:
<221> NAME/KEY: MOD_RES
<222> LOCATION: (200)
<223> OTHER INFORMATION: Variable amino acid
<220> FEATURE:
<221> NAME/KEY: MOD_RES
<222> LOCATION: (203)
<223> OTHER INFORMATION: Variable amino acid
<220> FEATURE:
```

<221> NAME/KEY: MOD_RES
<222> LOCATION: (205)..(206)
<223> OTHER INFORMATION: Variable amino acid
<220> FEATURE:
<221> NAME/KEY: MOD_RES
<222> LOCATION: (208)..(256)
<223> OTHER INFORMATION: Variable amino acid

<400> SEQUENCE: 14

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
 20                  25                  30

Xaa Xaa Xaa Xaa Xaa Xaa Xaa Xaa Xaa Xaa Xaa Xaa Xaa Xaa Xaa
 35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Ala Phe
 85                  90                  95

Ala Xaa Met Xaa Xaa Leu Xaa Xaa Xaa Xaa Xaa Xaa Xaa Xaa Xaa
100                 105                 110

Xaa Xaa Xaa Xaa Xaa Xaa Xaa Xaa Xaa Xaa Xaa Xaa Xaa Xaa Xaa
115                 120                 125

Xaa Xaa Xaa Xaa Xaa Xaa Xaa Xaa Xaa Xaa Xaa Xaa Xaa Xaa Xaa
130                 135                 140

Xaa Xaa Tyr Xaa Xaa Xaa Xaa Xaa Xaa Val Gln Asn Tyr Xaa Xaa Met
145                 150                 155                 160

Xaa Xaa Xaa Lys Xaa Xaa Xaa Xaa Xaa Xaa Xaa Xaa Xaa Xaa Xaa
165                 170                 175

Xaa Xaa Xaa Xaa Xaa Xaa Xaa Xaa Xaa Xaa Xaa Xaa Xaa Xaa Pro
180                 185                 190

Xaa Xaa Xaa Leu Ser Xaa Lys Xaa Val Gly Xaa Phe Xaa Xaa Ile Xaa
195                 200                 205

Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
245                 250                 255
```

<210> SEQ ID NO 15
<211> LENGTH: 262
<212> TYPE: PRT
<213> ORGANISM: Escherichia coli
<220> FEATURE:
<221> NAME/KEY: MOD_RES
<222> LOCATION: (1)..(92)
<223> OTHER INFORMATION: Variable amino acid
<220> FEATURE:
<221> NAME/KEY: MOD_RES
<222> LOCATION: (96)
<223> OTHER INFORMATION: Variable amino acid
<220> FEATURE:
<221> NAME/KEY: MOD_RES
<222> LOCATION: (98)..(99)
<223> OTHER INFORMATION: Variable amino acid
<220> FEATURE:
<221> NAME/KEY: MOD_RES
<222> LOCATION: (101)..(145)
<223> OTHER INFORMATION: Variable amino acid -continued

```
<220> FEATURE:
<221> NAME/KEY: MOD_RES
<222> LOCATION: (147)..(152)
<223> OTHER INFORMATION: Variable amino acid
<220> FEATURE:
<221> NAME/KEY: MOD_RES
<222> LOCATION: (157)..(158)
<223> OTHER INFORMATION: Variable amino acid
<220> FEATURE:
<221> NAME/KEY: MOD_RES
<222> LOCATION: (160)..(162)
<223> OTHER INFORMATION: Variable amino acid
<220> FEATURE:
<221> NAME/KEY: MOD_RES
<222> LOCATION: (164)..(190)
<223> OTHER INFORMATION: Variable amino acid
<220> FEATURE:
<221> NAME/KEY: MOD_RES
<222> LOCATION: (192)..(194)
<223> OTHER INFORMATION: Variable amino acid
<220> FEATURE:
<221> NAME/KEY: MOD_RES
<222> LOCATION: (197)
<223> OTHER INFORMATION: Variable amino acid
<220> FEATURE:
<221> NAME/KEY: MOD_RES
<222> LOCATION: (199)
<223> OTHER INFORMATION: Variable amino acid
<220> FEATURE:
<221> NAME/KEY: MOD_RES
<222> LOCATION: (202)
<223> OTHER INFORMATION: Variable amino acid
<220> FEATURE:
<221> NAME/KEY: MOD_RES
<222> LOCATION: (204)..(205)
<223> OTHER INFORMATION: Variable amino acid
<220> FEATURE:
<221> NAME/KEY: MOD_RES
<222> LOCATION: (207)..(262)
<223> OTHER INFORMATION: Variable amino acid

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Gly Phe Ala Xaa
                85                  90                  95

Gly Xaa Xaa Leu Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Tyr Xaa Xaa Xaa Xaa Xaa Xaa Ile Pro Asn Tyr Xaa Xaa Met Xaa
145                 150                 155                 160

Xaa Xaa Lys Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Pro Xaa
            180                 185                 190
```

```
Xaa Xaa Leu Ala Xaa Ser Xaa Ile Lys Xaa Phe Xaa Xaa Met Xaa Xaa
195                 200                 205

Xaa Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
245                 250                 255

Xaa Xaa Xaa Xaa Xaa Xaa
260

<210> SEQ ID NO 16
<211> LENGTH: 275
<212> TYPE: PRT
<213> ORGANISM: Helicobacter pylori
<220> FEATURE:
<221> NAME/KEY: MOD_RES
<222> LOCATION: (1)..(92)
<223> OTHER INFORMATION: Variable amino acid
<220> FEATURE:
<221> NAME/KEY: MOD_RES
<222> LOCATION: (96)
<223> OTHER INFORMATION: Variable amino acid
<220> FEATURE:
<221> NAME/KEY: MOD_RES
<222> LOCATION: (98)..(99)
<223> OTHER INFORMATION: Variable amino acid
<220> FEATURE:
<221> NAME/KEY: MOD_RES
<222> LOCATION: (101)..(144)
<223> OTHER INFORMATION: Variable amino acid
<220> FEATURE:
<221> NAME/KEY: MOD_RES
<222> LOCATION: (146)..(151)
<223> OTHER INFORMATION: Variable amino acid
<220> FEATURE:
<221> NAME/KEY: MOD_RES
<222> LOCATION: (156)..(157)
<223> OTHER INFORMATION: Variable amino acid
<220> FEATURE:
<221> NAME/KEY: MOD_RES
<222> LOCATION: (159)..(161)
<223> OTHER INFORMATION: Variable amino acid
<220> FEATURE:
<221> NAME/KEY: MOD_RES
<222> LOCATION: (163)..(189)
<223> OTHER INFORMATION: Variable amino acid
<220> FEATURE:
<221> NAME/KEY: MOD_RES
<222> LOCATION: (191)..(193)
<223> OTHER INFORMATION: Variable amino acid
<220> FEATURE:
<221> NAME/KEY: MOD_RES
<222> LOCATION: (196)
<223> OTHER INFORMATION: Variable amino acid
<220> FEATURE:
<221> NAME/KEY: MOD_RES
<222> LOCATION: (198)
<223> OTHER INFORMATION: Variable amino acid
<220> FEATURE:
<221> NAME/KEY: MOD_RES
<222> LOCATION: (201)
<223> OTHER INFORMATION: Variable amino acid
<220> FEATURE:
<221> NAME/KEY: MOD_RES
<222> LOCATION: (203)..(204)
<223> OTHER INFORMATION: Variable amino acid
<220> FEATURE:
<221> NAME/KEY: MOD_RES
<222> LOCATION: (206)..(275)
<223> OTHER INFORMATION: Variable amino acid

<400> SEQUENCE: 16
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Ala Phe Ala Xaa
            85                  90                  95

Lys Xaa Xaa Leu Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140

Tyr Xaa Xaa Xaa Xaa Xaa Xaa Met Ala His Tyr Xaa Xaa Met Xaa Xaa
145                 150                 155                 160

Xaa Lys Xaa Xaa Xaa Xaa Xaa Xaa Xaa Xaa Xaa Xaa Xaa Xaa Xaa
        165                 170                 175

Xaa Xaa Xaa Xaa Xaa Xaa Xaa Xaa Xaa Xaa Xaa Xaa Pro Xaa Xaa
    180                 185                 190

Xaa Leu Ala Xaa Ser Xaa Ile Ala Xaa Phe Xaa Xaa Ile Xaa Xaa Xaa
195                 200                 205

Xaa Xaa Xaa Xaa Xaa Xaa Xaa Xaa Xaa Xaa Xaa X

```
        encompass 44 to 46 residues
<220> FEATURE:
<221> NAME/KEY: MOD_RES
<222> LOCATION: (150)..(158)
<223> OTHER INFORMATION: Variable amino acid
<220> FEATURE:
<221> NAME/KEY: MOD_RES
<222> LOCATION: (160)..(161)
<223> OTHER INFORMATION: Variable amino acid
<220> FEATURE:
<221> NAME/KEY: MOD_RES
<222> LOCATION: (163)..(165)
<223> OTHER INFORMATION: Variable amino acid
<220> FEATURE:
<221> NAME/KEY: MOD_RES
<222> LOCATION: (167)..(193)
<223> OTHER INFORMATION: Variable amino acid
<220> FEATURE:
<221> NAME/KEY: MOD_RES
<222> LOCATION: (195)..(197)
<223> OTHER INFORMATION: Variable amino acid
<220> FEATURE:
<221> NAME/KEY: MOD_RES
<222> LOCATION: (199)
<223> OTHER INFORMATION: Ala or Ser
<220> FEATURE:
<221> NAME/KEY: MOD_RES
<222> LOCATION: (200)
<223> OTHER INFORMATION: Variable amino acid
<220> FEATURE:
<221> NAME/KEY: MOD_RES
<222> LOCATION: (201)
<223> OTHER INFORMATION: Ser or Lys
<220> FEATURE:
<221> NAME/KEY: MOD_RES
<222> LOCATION: (202)
<223> OTHER INFORMATION: Variable amino acid
<220> FEATURE:
<221> NAME/KEY: MOD_RES
<222> LOCATION: (203)
<223> OTHER INFORMATION: Ile or Val
<220> FEATURE:
<221> NAME/KEY: MOD_RES
<222> LOCATION: (204)..(205)
<223> OTHER INFORMATION: Variable amino acid
<220> FEATURE:
<221> NAME/KEY: MOD_RES
<222> LOCATION: (207)..(208)
<223> OTHER INFORMATION: Variable amino acid
<220> FEATURE:
<221> NAME/KEY: MOD_RES
<222> LOCATION: (209)
<223> OTHER INFORMATION: Met or Ile
<220> FEATURE:
<221> NAME/KEY: MOD_RES
<222> LOCATION: (210)..(279)
<223> OTHER INFORMATION: Variable amino acid and this region may
        encompass 54 to 70 residues

<400> SEQUENCE: 17

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Phe
                85                  90                  95
```

```
Ala Xaa Xaa Xaa Xaa Leu Xaa Xaa Xaa Xaa Xaa Xaa Xaa Xaa
100                 105                 110

Xaa Xaa Xaa Xaa Xaa Xaa Xaa Xaa Xaa Xaa Xaa Xaa Xaa Xaa
115                 120                 125

Xaa Xaa Xaa Xaa Xaa Xaa Xaa Xaa Xaa Xaa Xaa Xaa Xaa Xaa
130                 135                 140

Xaa Xaa Xaa Xaa Tyr Xaa Xaa Xaa Xaa Xaa Xaa Xaa Tyr Xaa
145                 150                 155                 160

Xaa Met Xaa Xaa Xaa Lys Xaa Xaa Xaa Xaa Xaa Xaa Xaa Xaa
165                 170                 175

Xaa Xaa Xaa Xaa Xaa Xaa Xaa Xaa Xaa Xaa Xaa Xaa Xaa Xaa
180                 185                 190

Xaa Pro Xaa Xaa Xaa Leu Xaa Xaa Xaa Xaa Xaa Xaa Phe Xaa Xaa
195                 200                 205

Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa
245                 250                 255

Xaa Xaa Xaa Xaa Xaa Xaa Xaa Xaa Xaa Xaa Xaa Xaa Xaa Xaa
260                 265                 270

Xaa Xaa Xaa Xaa Xaa Xaa Xaa
275

<210> SEQ ID NO 18
<211> LENGTH: 8
<212> TYPE: PRT
<213> ORGANISM: Francisella tularensis
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid

<400> SEQUENCE: 18

Ala Phe Ala Xaa Arg Xaa Xaa Leu
1               5

<210> SEQ ID NO 19
<211> LENGTH: 18
<212> TYPE: PRT
<213> ORGANISM: Francisella tularensis
<220> FEATURE:
<221> NAME/KEY: MOD_RES
<222> LOCATION: (2)..(7)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid

<400> SEQUENCE: 19

Tyr Xaa Xaa Xaa Xaa Xaa Xaa Met Pro Ser Tyr Xaa Xaa Met Xaa Xaa
1               5                   10                  15

Xaa Lys
```

```
<210> SEQ ID NO 20
<211> LENGTH: 16
<212> TYPE: PRT
<213> ORGANISM: Francisella tularensis
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (7)
<223> OTHER INFORMATION: Variable amino acid
<220> FEATURE:
<221> NAME/KEY: MOD_RES
<222> LOCATION: (9)
<223> OTHER INFORMATION: Variable amino acid
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (14)..(15)
<223> OTHER INFORMATION: Variable amino acid

<400> SEQUENCE: 20

Pro Xaa Xaa Xaa Leu Ala Xaa Ser Xaa Ile Ser Xaa Phe Xaa Xaa Met
1               5                   10                  15

<210> SEQ ID NO 21
<211> LENGTH: 61
<212> TYPE: PRT
<213> ORGANISM: Francisella tularensis
<220> FEATURE:
<221> NAME/KEY: MOD_RES
<222> LOCATION: (2)..(7)
<223> OTHER INFORMATION: Variable amino acid
<220> FEATURE:
<221> NAME/KEY: MOD_RES
<222> LOCATION: (12)..(13)
<223> OTHER INFORMATION: Variable amino acid
<220> FEATURE:
<221> NAME/KEY: MOD_RES
<222> LOCATION: (15)..(17)
<223> OTHER INFORMATION: Variable amino acid
<220> FEATURE:
<221> NAME/KEY: MOD_RES
<222> LOCATION: (19)..(45)
<223> OTHER INFORMATION: Variable amino acid
<220> FEATURE:
<221> NAME/KEY: MOD_RES
<222> LOCATION: (47)..(49)
<223> OTHER INFORMATION: Variable amino acid
<220> FEATURE:
<221> NAME/KEY: MOD_RES
<222> LOCATION: (52)
<223> OTHER INFORMATION: Variable amino acid
<220> FEATURE:
<221> NAME/KEY: MOD_RES
<222> LOCATION: (54)
<223> OTHER INFORMATION: Variable amino acid
<220> FEATURE:
<221> NAME/KEY: MOD_RES
<222> LOCATION: (57)
<223> OTHER INFORMATION: Variable amino acid
<220> FEATURE:
<221> NAME/KEY: MOD_RES
<222> LOCATION: (59)..(60)
<223> OTHER INFORMATION: Variable amino acid

<400> SEQUENCE: 21

Tyr Xaa Xaa Xaa Xaa Xaa Xaa Met Pro Ser Tyr Xaa Xaa Met Xaa Xaa
1               5                   10                  15
```

-continued

```
Xaa Lys Xaa Xaa Xaa Xaa Xaa Xaa Xaa Xaa Xaa Xaa Xaa Xaa
 20                  25                  30

Xaa Xaa Xaa Xaa Xaa Xaa Xaa Xaa Xaa Xaa Xaa Xaa Pro Xaa Xaa
 35                  40                  45

Xaa Leu Ala Xaa Ser Xaa Ile Ser Xaa Phe Xaa Xaa Met
 50                  55                  60

<210> SEQ ID NO 22
<211> LENGTH: 115
<212> TYPE: PRT
<213> ORGANISM: Francisella tularensis
<220> FEATURE:
<221> NAME/KEY: MOD_RES
<222> LOCATION: (4)
<223> OTHER INFORMATION: Variable amino acid
<220> FEATURE:
<221> NAME/KEY: MOD_RES
<222> LOCATION: (6)..(7)
<223> OTHER INFORMATION: Variable amino acid
<220> FEATURE:
<221> NAME/KEY: MOD_RES
<222> LOCATION: (9)..(54)
<223> OTHER INFORMATION: Variable amino acid and this region may
      encompass 44 to 46 residues
<220> FEATURE:
<221> NAME/KEY: MOD_RES
<222> LOCATION: (56)..(61)
<223> OTHER INFORMATION: Variable amino acid
<220> FEATURE:
<221> NAME/KEY: MOD_RES
<222> LOCATION: (66)..(67)
<223> OTHER INFORMATION: Variable amino acid
<220> FEATURE:
<221> NAME/KEY: MOD_RES
<222> LOCATION: (69)..(71)
<223> OTHER INFORMATION: Variable amino acid
<220> FEATURE:
<221> NAME/KEY: MOD_RES
<222> LOCATION: (73)..(99)
<223> OTHER INFORMATION: Variable amino acid
<220> FEATURE:
<221> NAME/KEY: MOD_RES
<222> LOCATION: (101)..(103)
<223> OTHER INFORMATION: Variable amino acid
<220> FEATURE:
<221> NAME/KEY: MOD_RES
<222> LOCATION: (106)
<223> OTHER INFORMATION: Variable amino acid
<220> FEATURE:
<221> NAME/KEY: MOD_RES
<222> LOCATION: (108)
<223> OTHER INFORMATION: Variable amino acid
<220> FEATURE:
<221> NAME/KEY: MOD_RES
<222> LOCATION: (111)
<223> OTHER INFORMATION: Variable amino acid
<220> FEATURE:
<221> NAME/KEY: MOD_RES
<222> LOCATION: (113)..(114)
<223> OTHER INFORMATION: Variable amino acid

<400> SEQUENCE: 22

Ala Phe Ala Xaa Arg Xaa Xaa Leu Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa
 20                  25                  30

Xaa Xaa Xaa Xaa Xaa Xaa Xaa Xaa Xaa Xaa Xaa Xaa Xaa Xaa
 35                  40                  45

Xaa Xaa Xaa Xaa Xaa Xaa Tyr Xaa Xaa Xaa Xaa Xaa Met Pro Ser
 50                  55                  60

Tyr Xaa Xaa Met Xaa Xaa Xaa Lys Xaa Xaa Xaa Xaa Xaa Xaa Xaa
```

```
                65                  70                  75                  80
Xaa Xaa Xaa Xaa Xaa Xaa Xaa Xaa Xaa Xaa Xaa Xaa Xaa Xaa Xaa Xaa
                85                  90                  95

Xaa Xaa Xaa Pro Xaa Xaa Xaa Leu Ala Xaa Ser Xaa Ile Ser Xaa Phe
100                 105                 110

Xaa Xaa Met
115

<210> SEQ ID NO 23
<211> LENGTH: 115
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)
<223> OTHER INFORMATION: Gly or Arg
<220> FEATURE:
<221> NAME/KEY: MOD_RES
<222> LOCATION: (4)..(7)
<223> OTHER INFORMATION: Variable amino acid
<220> FEATURE:
<221> NAME/KEY: MOD_RES
<222> LOCATION: (9)..(54)
<223> OTHER INFORMATION: Variable amino acid and this region may
      encompass 44 to 46 residues
<220> FEATURE:
<221> NAME/KEY: MOD_RES
<222> LOCATION: (56)..(64)
<223> OTHER INFORMATION: Variable amino acid
<220> FEATURE:
<221> NAME/KEY: MOD_RES
<222> LOCATION: (66)..(67)
<223> OTHER INFORMATION: Variable amino acid
<220> FEATURE:
<221> NAME/KEY: MOD_RES
<222> LOCATION: (69)..(71)
<223> OTHER INFORMATION: Variable amino acid
<220> FEATURE:
<221> NAME/KEY: MOD_RES
<222> LOCATION: (73)..(99)
<223> OTHER INFORMATION: Variable amino acid
<220> FEATURE:
<221> NAME/KEY: MOD_RES
<222> LOCATION: (101)..(103)
<223> OTHER INFORMATION: Variable amino acid
<220> FEATURE:
<221> NAME/KEY: MOD_RES
<222> LOCATION: (105)
<223> OTHER INFORMATION: Ala or Ser
<220> FEATURE:
<221> NAME/KEY: MOD_RES
<222> LOCATION: (106)
<223> OTHER INFORMATION: Variable amino acid
<220> FEATURE:
<221> NAME/KEY: MOD_RES
<222> LOCATION: (107)
<223> OTHER INFORMATION: Ser or Lys
<220> FEATURE:
<221> NAME/KEY: MOD_RES
<222> LOCATION: (108)
<223> OTHER INFORMATION: Variable amino acid
<220> FEATURE:
<221> NAME/KEY: MOD_RES
<222> LOCATION: (109)
<223> OTHER INFORMATION: Ile or Val
<220> FEATURE:
<221> NAME/KEY: MOD_RES
<222> LOCATION: (110)..(111)
<223> OTHER INFORMATION: Variable amino acid
<220> FEATURE:
<221> NAME/KEY: MOD_RES
<222> LOCATION: (113)..(114)
```

```
<223> OTHER INFORMATION: Variable amino acid
<220> FEATURE:
<221> NAME/KEY: MOD_RES
<222> LOCATION: (115)
<223> OTHER INFORMATION: Met or Ile

<400> SEQUENCE: 23

Xaa Phe Ala Xaa Xaa Xaa Leu Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Tyr Xaa Xaa Xaa Xaa Xaa Xaa Xaa Xaa
    50                  55                  60

Tyr Xaa Xaa Met Xaa Xaa Xaa Lys Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Pro Xaa Xaa Xaa Leu Xaa Xaa Xaa Xaa Xaa Xaa Phe
        100                 105                 110

Xaa Xaa Xaa
115

<210> SEQ ID NO 24
<211> LENGTH: 11
<212> TYPE: PRT
<213> ORGANISM: Francisella tularensis

<400> SEQUENCE: 24

Ile Lys Thr Leu Ala Ala Ser Gly Ile Ser Asn
1               5                   10

<210> SEQ ID NO 25
<211> LENGTH: 11
<212> TYPE: PRT
<213> ORGANISM: Staphylococcus aureus

<400> SEQUENCE: 25

Ile Arg Thr Leu Ser Ala Lys Gly Val Gly Gly
1               5                   10

<210> SEQ ID NO 26
<211> LENGTH: 11
<212> TYPE: PRT
<213> ORGANISM: Escherichia coli

<400> SEQUENCE: 26

Ile Arg Thr Leu Ala Ala Ser Gly Ile Lys Asp
1               5                   10

<210> SEQ ID NO 27
<211> LENGTH: 11
<212> TYPE: PRT
<213> ORGANISM: Helicobacter pylori

<400> SEQUENCE: 27

Ile Arg Thr Leu Ala Ser Ser Gly Ile Ala Asp
1               5                   10

<210> SEQ ID NO 28
<211> LENGTH: 279
```

```
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)
<223> OTHER INFORMATION: Gly or Leu
<220> FEATURE:
<221> NAME/KEY: MOD_RES
<222> LOCATION: (3)
<223> OTHER INFORMATION: Phe or Asn
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (6)
<223> OTHER INFORMATION: Gly or Asn
<220> FEATURE:
<221> NAME/KEY: MOD_RES
<222> LOCATION: (8)..(9)
<223> OTHER INFORMATION: Variable amino acid
<220> FEATURE:
<221> NAME/KEY: MOD_RES
<222> LOCATION: (10)
<223> OTHER INFORMATION: Leu or Val
<220> FEATURE:
<221> NAME/KEY: MOD_RES
<222> LOCATION: (11)
<223> OTHER INFORMATION: Ile or Val
<220> FEATURE:
<221> NAME/KEY: MOD_RES
<222> LOCATION: (12)
<223> OTHER INFORMATION: Variable amino acid
<220> FEATURE:
<221> NAME/KEY: MOD_RES
<222> LOCATION: (14)
<223> OTHER INFORMATION: Variable amino acid
<220> FEATURE:
<221> NAME/KEY: MOD_RES
<222> LOCATION: (15)
<223> OTHER INFORMATION: Ala or Leu
<220> FEATURE:
<221> NAME/KEY: MOD_RES
<222> LOCATION: (16)..(18)
<223> OTHER INFORMATION: Variable amino acid
<220> FEATURE:
<221> NAME/KEY: MOD_RES
<222> LOCATION: (22)
<223> OTHER INFORMATION: Tyr or Phe
<220> FEATURE:
<221> NAME/KEY: MOD_RES
<222> LOCATION: (24)
<223> OTHER INFORMATION: Ile or Val
<220> FEATURE:
<221> NAME/KEY: MOD_RES
<222> LOCATION: (26)..(31)
<223> OTHER INFORMATION: Variable amino acid
<220> FEATURE:
<221> NAME/KEY: MOD_RES
<222> LOCATION: (34)
<223> OTHER INFORMATION: Variable amino acid
<220> FEATURE:
<221> NAME/KEY: MOD_RES
<222> LOCATION: (36)
<223> OTHER INFORMATION: Ala or Val
<220> FEATURE:
<221> NAME/KEY: MOD_RES
<222> LOCATION: (40)..(46)
<223> OTHER INFORMATION: Variable amino acid and this region may
      encompass 6 or 7 residues
<220> FEATURE:
<221> NAME/KEY: MOD_RES
<222> LOCATION: (47)
<223> OTHER INFORMATION: Arg or Glu
<220> FEATURE:
```

```
<221> NAME/KEY: MOD_RES
<222> LOCATION: (48)
<223> OTHER INFORMATION: Val or Leu
<220> FEATURE:
<221> NAME/KEY: MOD_RES
<222> LOCATION: (49)
<223> OTHER INFORMATION: Glu or Arg
<220> FEATURE:
<221> NAME/KEY: MOD_RES
<222> LOCATION: (50)..(54)
<223> OTHER INFORMATION: Variable amino acid
<220> FEATURE:
<221> NAME/KEY: MOD_RES
<222> LOCATION: (55)
<223> OTHER INFORMATION: Phe or Leu
<220> FEATURE:
<221> NAME/KEY: MOD_RES
<222> LOCATION: (56)
<223> OTHER INFORMATION: Asn or Gly
<220> FEATURE:
<221> NAME/KEY: MOD_RES
<222> LOCATION: (57)..(61)
<223> OTHER INFORMATION: Variable amino acid and this region may
      encompass 3 to 5 residues
<220> FEATURE:
<221> NAME/KEY: MOD_RES
<222> LOCATION: (62)
<223> OTHER INFORMATION: Val or Leu
<220> FEATURE:
<221> NAME/KEY: MOD_RES
<222> LOCATION: (63)..(65)
<223> OTHER INFORMATION: Variable amino acid
<220> FEATURE:
<221> NAME/KEY: MOD_RES
<222> LOCATION: (68)..(69)
<223> OTHER INFORMATION: Variable amino acid
<220> FEATURE:
<221> NAME/KEY: MOD_RES
<222> LOCATION: (70)
<223> OTHER INFORMATION: Asp or Glu
<220> FEATURE:
<221> NAME/KEY: MOD_RES
<222> LOCATION: (71)..(76)
<223> OTHER INFORMATION: Variable amino acid
<220> FEATURE:
<221> NAME/KEY: MOD_RES
<222> LOCATION: (77)
<223> OTHER INFORMATION: Phe or Tyr
<220> FEATURE:
<221> NAME/KEY: MOD_RES
<222> LOCATION: (78)..(80)
<223> OTHER INFORMATION: Variable amino acid
<220> FEATURE:
<221> NAME/KEY: MOD_RES
<222> LOCATION: (81)
<223> OTHER INFORMATION: Gly or Lys
<220> FEATURE:
<221> NAME/KEY: MOD_RES
<222> LOCATION: (83)..(87)
<223> OTHER INFORMATION: Variable amino acid
<220> FEATURE:
<221> NAME/KEY: MOD_RES
<222> LOCATION: (89)..(90)
<223> OTHER INFORMATION: Variable amino acid
<220> FEATURE:
<221> NAME/KEY: MOD_RES
<222> LOCATION: (91)
<223> OTHER INFORMATION: Val or Tyr
<220> FEATURE:
<221> NAME/KEY: MOD_RES
<222> LOCATION: (94)
<223> OTHER INFORMATION: Ile or Val
<220> FEATURE:
<221> NAME/KEY: MOD_RES
<222> LOCATION: (95)
<223> OTHER INFORMATION: Ala or Gly
<220> FEATURE:
<221> NAME/KEY: MOD_RES
<222> LOCATION: (98)
```

```
<223> OTHER INFORMATION: Pro or Asn
<220> FEATURE:
<221> NAME/KEY: MOD_RES
<222> LOCATION: (99)..(101)
<223> OTHER INFORMATION: Variable amino acid
<220> FEATURE:
<221> NAME/KEY: MOD_RES
<222> LOCATION: (103)
<223> OTHER INFORMATION: Variable amino acid
<220> FEATURE:
<221> NAME/KEY: MOD_RES
<222> LOCATION: (105)..(111)
<223> OTHER INFORMATION: Variable amino acid and this region may
      encompass 6 or 7 residues
<220> FEATURE:
<221> NAME/KEY: MOD_RES
<222> LOCATION: (112)
<223> OTHER INFORMATION: Arg or Lys
<220> FEATURE:
<221> NAME/KEY: MOD_RES
<222> LOCATION: (113)
<223> OTHER INFORMATION: Glu or Ser
<220> FEATURE:
<221> NAME/KEY: MOD_RES
<222> LOCATION: (114)
<223> OTHER INFORMATION: Gly or Ala
<220> FEATURE:
<221> NAME/KEY: MOD_RES
<222> LOCATION: (116)..(117)
<223> OTHER INFORMATION: Variable amino acid
<220> FEATURE:
<221> NAME/KEY: MOD_RES
<222> LOCATION: (119)
<223> OTHER INFORMATION: Variable amino acid
<220> FEATURE:
<221> NAME/KEY: MOD_RES
<222> LOCATION: (120)
<223> OTHER INFORMATION: Asp or Gly
<220> FEATURE:
<221> NAME/KEY: MOD_RES
<222> LOCATION: (123)
<223> OTHER INFORMATION: Variable amino acid
<220> FEATURE:
<221> NAME/KEY: MOD_RES
<222> LOCATION: (126)..(129)
<223> OTHER INFORMATION: Variable amino acid
<220> FEATURE:
<221> NAME/KEY: MOD_RES
<222> LOCATION: (130)
<223> OTHER INFORMATION: Ala or Thr
<220> FEATURE:
<221> NAME/KEY: MOD_RES
<222> LOCATION: (131)..(138)
<223> OTHER INFORMATION: Variable amino acid and this region may
      encompass 7 to 8 residues
<220> FEATURE:
<221> NAME/KEY: MOD_RES
<222> LOCATION: (139)
<223> OTHER INFORMATION: Asn or Pro
<220> FEATURE:
<221> NAME/KEY: MOD_RES
<222> LOCATION: (140)
<223> OTHER INFORMATION: Variable amino acid
<220> FEATURE:
<221> NAME/KEY: MOD_RES
<222> LOCATION: (141)
<223> OTHER INFORMATION: Gly or Asn
<220> FEATURE:
<221> NAME/KEY: MOD_RES
<222> LOCATION: (142)
<223> OTHER INFORMATION: Variable amino acid
<220> FEATURE:
<221> NAME/KEY: MOD_RES
<222> LOCATION: (143)
<223> OTHER INFORMATION: Ser or Ala
<220> FEATURE:
<221> NAME/KEY: MOD_RES
<222> LOCATION: (144)..(146)
<223> OTHER INFORMATION: Variable amino acid
```

```
<220> FEATURE:
<221> NAME/KEY: MOD_RES
<222> LOCATION: (147)
<223> OTHER INFORMATION: Leu or Thr
<220> FEATURE:
<221> NAME/KEY: MOD_RES
<222> LOCATION: (148)
<223> OTHER INFORMATION: Variable amino acid
<220> FEATURE:
<221> NAME/KEY: MOD_RES
<222> LOCATION: (150)
<223> OTHER INFORMATION: Ile or Leu
<220> FEATURE:
<221> NAME/KEY: MOD_RES
<222> LOCATION: (152)
<223> OTHER INFORMATION: Variable amino acid
<220> FEATURE:
<221> NAME/KEY: MOD_RES
<222> LOCATION: (153)
<223> OTHER INFORMATION: Glu or Thr
<220> FEATURE:
<221> NAME/KEY: MOD_RES
<222> LOCATION: (154)
<223> OTHER INFORMATION: Variable amino acid
<220> FEATURE:
<221> NAME/KEY: MOD_RES
<222> LOCATION: (155)
<223> OTHER INFORMATION: Ala or Tyr
<220> FEATURE:
<221> NAME/KEY: MOD_RES
<222> LOCATION: (156)..(158)
<223> OTHER INFORMATION: Variable amino acid
<220> FEATURE:
<221> NAME/KEY: MOD_RES
<222> LOCATION: (161)
<223> OTHER INFORMATION: Thr or Val
<220> FEATURE:
<221> NAME/KEY: MOD_RES
<222> LOCATION: (164)
<223> OTHER INFORMATION: Variable amino acid
<220> FEATURE:
<221> NAME/KEY: MOD_RES
<222> LOCATION: (168)
<223> OTHER INFORMATION: Ser or Ala
<220> FEATURE:
<221> NAME/KEY: MOD_RES
<222> LOCATION: (171)
<223> OTHER INFORMATION: Ala or Ser
<220> FEATURE:
<221> NAME/KEY: MOD_RES
<222> LOCATION: (172)
<223> OTHER INFORMATION: Variable amino acid
<220> FEATURE:
<221> NAME/KEY: MOD_RES
<222> LOCATION: (176)
<223> OTHER INFORMATION: Variable amino acid
<220> FEATURE:
<221> NAME/KEY: MOD_RES
<222> LOCATION: (178)..(179)
<223> OTHER INFORMATION: Variable amino acid
<220> FEATURE:
<221> NAME/KEY: MOD_RES
<222> LOCATION: (180)
<223> OTHER INFORMATION: Arg or Lys
<220> FEATURE:
<221> NAME/KEY: MOD_RES
<222> LOCATION: (182)..(184)
<223> OTHER INFORMATION: Variable amino acid
<220> FEATURE:
<221> NAME/KEY: MOD_RES
<222> LOCATION: (185)
<223> OTHER INFORMATION: Leu or Met
<220> FEATURE:
<221> NAME/KEY: MOD_RES
<222> LOCATION: (186)
<223> OTHER INFORMATION: Ile or Val
<220> FEATURE:
<221> NAME/KEY: MOD_RES
<222> LOCATION: (190)
```

-continued

```
<223> OTHER INFORMATION: Variable amino acid
<220> FEATURE:
<221> NAME/KEY: MOD_RES
<222> LOCATION: (196)
<223> OTHER INFORMATION: Arg or Lys
<220> FEATURE:
<221> NAME/KEY: MOD_RES
<222> LOCATION: (199)
<223> OTHER INFORMATION: Lys or Arg
<220> FEATURE:
<221> NAME/KEY: MOD_RES
<222> LOCATION: (200)
<223> OTHER INFORMATION: Ala or Ser
<220> FEATURE:
<221> NAME/KEY: MOD_RES
<222> LOCATION: (201)
<223> OTHER INFORMATION: Ser or Lys
<220> FEATURE:
<221> NAME/KEY: MOD_RES
<222> LOCATION: (203)
<223> OTHER INFORMATION: Ile or Val
<220> FEATURE:
<221> NAME/KEY: MOD_RES
<222> LOCATION: (204)..(205)
<223> OTHER INFORMATION: Variable amino acid
<220> FEATURE:
<221> NAME/KEY: MOD_RES
<222> LOCATION: (207)..(209)
<223> OTHER INFORMATION: Variable amino acid
<220> FEATURE:
<221> NAME/KEY: MOD_RES
<222> LOCATION: (211)..(217)
<223> OTHER INFORMATION: Variable amino acid
<220> FEATURE:
<221> NAME/KEY: MOD_RES
<222> LOCATION: (219)
<223> OTHER INFORMATION: Leu or Ile
<220> FEATURE:
<221> NAME/KEY: MOD_RES
<222> LOCATION: (220)..(221)
<223> OTHER INFORMATION: Variable amino acid
<220> FEATURE:
<221> NAME/KEY: MOD_RES
<222> LOCATION: (222)
<223> OTHER INFORMATION: Asn or Thr
<220> FEATURE:
<221> NAME/KEY: MOD_RES
<222> LOCATION: (224)..(226)
<223> OTHER INFORMATION: Variable amino acid
<220> FEATURE:
<221> NAME/KEY: MOD_RES
<222> LOCATION: (227)
<223> OTHER INFORMATION: Glu or Asp
<220> FEATURE:
<221> NAME/KEY: MOD_RES
<222> LOCATION: (230)
<223> OTHER INFORMATION: Asn or Lys
<220> FEATURE:
<221> NAME/KEY: MOD_RES
<222> LOCATION: (231)..(232)
<223> OTHER INFORMATION: Variable amino acid
<220> FEATURE:
<221> NAME/KEY: MOD_RES
<222> LOCATION: (233)
<223> OTHER INFORMATION: Ala or Met
<220> FEATURE:
<221> NAME/KEY: MOD_RES
<222> LOCATION: (234)
<223> OTHER INFORMATION: Variable amino acid
<220> FEATURE:
<221> NAME/KEY: MOD_RES
<222> LOCATION: (236)
<223> OTHER INFORMATION: Variable amino acid
<220> FEATURE:
<221> NAME/KEY: MOD_RES
<222> LOCATION: (238)
<223> OTHER INFORMATION: Asp or Ser
<220> FEATURE:
<221> NAME/KEY: MOD_RES
```

-continued

```
<222> LOCATION: (239)
<223> OTHER INFORMATION: Leu or Met
<220> FEATURE:
<221> NAME/KEY: MOD_RES
<222> LOCATION: (240)
<223> OTHER INFORMATION: Ser or Ala
<220> FEATURE:
<221> NAME/KEY: MOD_RES
<222> LOCATION: (241)
<223> OTHER INFORMATION: Variable amino acid
<220> FEATURE:
<221> NAME/KEY: MOD_RES
<222> LOCATION: (243)..(244)
<223> OTHER INFORMATION: Variable amino acid
<220> FEATURE:
<221> NAME/KEY: MOD_RES
<222> LOCATION: (247)
<223> OTHER INFORMATION: Val or Asn
<220> FEATURE:
<221> NAME/KEY: MOD_RES
<222> LOCATION: (248)
<223> OTHER INFORMATION: Variable amino acid
<220> FEATURE:
<221> NAME/KEY: MOD_RES
<222> LOCATION: (249)
<223> OTHER INFORMATION: His or Phe
<220> FEATURE:
<221> NAME/KEY: MOD_RES
<222> LOCATION: (252)
<223> OTHER INFORMATION: Variable amino acid
<220> FEATURE:
<221> NAME/KEY: MOD_RES
<222> LOCATION: (254)
<223> OTHER INFORMATION: Variable amino acid
<220> FEATURE:
<221> NAME/KEY: MOD_RES
<222> LOCATION: (255)
<223> OTHER INFORMATION: His or Ser
<220> FEATURE:
<221> NAME/KEY: MOD_RES
<222> LOCATION: (256)..(258)
<223> OTHER INFORMATION: Variable amino acid
<220> FEATURE:
<221> NAME/KEY: MOD_RES
<222> LOCATION: (259)
<223> OTHER INFORMATION: May or may not be present
<220> FEATURE:
<221> NAME/KEY: MOD_RES
<222> LOCATION: (260)..(279)
<223> OTHER INFORMATION: Variable amino acid and this region may
      encompass 0 to 20 residues

<400> SEQUENCE: 28

Met Xaa Xaa Leu Xaa Xaa Lys Xaa Xaa Xaa Xaa Gly Xaa Xaa Xaa
1               5                   10                  15

Xaa Xaa Ser Ile Ala Xaa Gly Xaa Ala Xaa Xaa Xaa Xaa Xaa Gly
            20                  25                  30

Ala Xaa Leu Xaa Phe Thr Tyr Xaa Xaa Xaa Xaa Xaa Xaa Xaa Xaa
35                  40                  45

Xaa Xaa Xaa Xaa Xaa Xaa Xaa Xaa Xaa Xaa Xaa Xaa Xaa Xaa Xaa
50                  55                  60

Xaa Asp Val Xaa Xaa Xaa Xaa Xaa Xaa Xaa Xaa Xaa Xaa Xaa Xaa
65                  70                  75                  80

Xaa Lys Xaa Xaa Xaa Xaa Xaa Asp Xaa Xaa Xaa His Ser Xaa Xaa Phe
85                  90                  95

Ala Xaa Xaa Xaa Xaa Leu Xaa Gly Xaa Xaa Xaa Xaa Xaa Xaa Xaa
                100                 105                 110

Xaa Xaa Phe Xaa Xaa Ala Xaa Xaa Ile Ser Xaa Tyr Ser Xaa Xaa
115                 120                 125

Xaa Xaa Xaa Xaa Xaa Xaa Xaa Xaa Xaa Xaa Xaa Xaa Xaa Xaa Xaa
```

```
                130                 135                 140

Xaa Xaa Xaa Xaa Tyr Xaa Gly Xaa Xaa Xaa Xaa Xaa Xaa Tyr Asn
145                 150                 155                 160

Xaa Met Gly Xaa Ala Lys Ala Xaa Leu Glu Xaa Xaa Val Arg Tyr Xaa
165                 170                 175

Ala Xaa Xaa Xaa Gly Xaa Xaa Xaa Xaa Val Asn Ala Xaa Ser Ala
180                 185                 190

Gly Pro Ile Xaa Thr Leu Xaa Xaa Xaa Gly Xaa Xaa Phe Xaa Xaa
195                 200                 205

Xaa Leu Xaa Xaa Xaa Xaa Xaa Xaa Pro Xaa Xaa Xaa Xaa Val Xaa
210                 215                 220

Xaa Xaa Xaa Val Gly Xaa Xaa Xaa Xaa Xaa Leu Xaa Ser Xaa Xaa Xaa
225                 230                 235                 240

Xaa Gly Xaa Xaa Gly Glu Xaa Xaa Xaa Val Asp Xaa Gly Xaa Xaa Xaa
245                 250                 255

Xaa Xaa Met Xaa Xaa Xaa Xaa Xaa Xaa Xaa Xaa Xaa Xaa Xaa Xaa
260                 265                 270

Xaa Xaa Xaa Xaa Xaa Xaa Xaa
275

<210> SEQ ID NO 29
<211> LENGTH: 279
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)..(12)
<223> OTHER INFORMATION: Variable amino acid
<220> FEATURE:
<221> NAME/KEY: MOD_RES
<222> LOCATION: (14)..(18)
<223> OTHER INFORMATION: Variable amino acid
<220> FEATURE:
<221> NAME/KEY: MOD_RES
<222> LOCATION: (22)
<223> OTHER INFORMATION: Variable amino acid
<220> FEATURE:
<221> NAME/KEY: MOD_RES
<222> LOCATION: (24)
<223> OTHER INFORMATION: Variable amino acid
<220> FEATURE:
<221> NAME/KEY: MOD_RES
<222> LOCATION: (26)..(31)
<223> OTHER INFORMATION: Variable amino acid
<220> FEATURE:
<221> NAME/KEY: MOD_RES
<222> LOCATION: (34)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (40)..(65)
<223> OTHER INFORMATION: Variable amino acid and this region may
      encompass 23 to 26 residues
<220> FEATURE:
```

```
<221> NAME/KEY: MOD_RES
<222> LOCATION: (68)..(81)
<223> OTHER INFORMATION: Variable amino acid
<220> FEATURE:
<221> NAME/KEY: MOD_RES
<222> LOCATION: (83)..(87)
<223> OTHER INFORMATION: Variable amino acid
<220> FEATURE:
<221> NAME/KEY: MOD_RES
<222> LOCATION: (89)..(91)
<223> OTHER INFORMATION: Variable amino acid
<220> FEATURE:
<221> NAME/KEY: MOD_RES
<222> LOCATION: (94)
<223> OTHER INFORMATION: Variable amino acid
<220> FEATURE:
<221> NAME/KEY: MOD_RES
<222> LOCATION: (98)
<223> OTHER INFORMATION: Variable amino acid
<220> FEATURE:
<221> NAME/KEY: MOD_RES
<222> LOCATION: (100)..(101)
<223> OTHER INFORMATION: Variable amino acid
<220> FEATURE:
<221> NAME/KEY: MOD_RES
<222> LOCATION: (103)
<223> OTHER INFORMATION: Variable amino acid
<220> FEATURE:
<221> NAME/KEY: MOD_RES
<222> LOCATION: (105)..(114)
<223> OTHER INFORMATION: Variable amino acid and this region may
      encompass 9 or 10 residues
<220> FEATURE:
<221> NAME/KEY: MOD_RES
<222> LOCATION: (116)..(117)
<223> OTHER INFORMATION: Variable amino acid
<220> FEATURE:
<221> NAME/KEY: MOD_RES
<222> LOCATION: (119)..(120)
<223> OTHER INFORMATION: Variable amino acid
<220> FEATURE:
<221> NAME/KEY: MOD_RES
<222> LOCATION: (123)
<223> OTHER INFORMATION: Variable amino acid
<220> FEATURE:
<221> NAME/KEY: MOD_RES
<222> LOCATION: (126)..(148)
<223> OTHER INFORMATION: Variable amino acid and this region may
      encompass 22 or 23 residues
<220> FEATURE:
<221> NAME/KEY: MOD_RES
<222> LOCATION: (150)
<223> OTHER INFORMATION: Variable amino acid
<220> FEATURE:
<221> NAME/KEY: MOD_RES
<222> LOCATION: (152)..(155)
<223> OTHER INFORMATION: Variable amino acid
<220> FEATURE:
<221> NAME/KEY: MOD_RES
<222> LOCATION: (161)
<223> OTHER INFORMATION: Variable amino acid
<220> FEATURE:
<221> NAME/KEY: MOD_RES
<222> LOCATION: (164)
<223> OTHER INFORMATION: Variable amino acid
<220> FEATURE:
<221> NAME/KEY: MOD_RES
<222> LOCATION: (168)
<223> OTHER INFORMATION: Variable amino acid
<220> FEATURE:
<221> NAME/KEY: MOD_RES
<222> LOCATION: (171)..(172)
<223> OTHER INFORMATION: Variable amino acid
<220> FEATURE:
<221> NAME/KEY: MOD_RES
<222> LOCATION: (176)
<223> OTHER INFORMATION: Variable amino acid
<220> FEATURE:
<221> NAME/KEY: MOD_RES
```

```
<222> LOCATION: (178)..(180)
<223> OTHER INFORMATION: Variable amino acid
<220> FEATURE:
<221> NAME/KEY: MOD_RES
<222> LOCATION: (182)..(186)
<223> OTHER INFORMATION: Variable amino acid
<220> FEATURE:
<221> NAME/KEY: MOD_RES
<222> LOCATION: (190)
<223> OTHER INFORMATION: Variable amino acid
<220> FEATURE:
<221> NAME/KEY: MOD_RES
<222> LOCATION: (196)
<223> OTHER INFORMATION: Variable amino acid
<220> FEATURE:
<221> NAME/KEY: MOD_RES
<222> LOCATION: (200)
<223> OTHER INFORMATION: Variable amino acid
<220> FEATURE:
<221> NAME/KEY: MOD_RES
<222> LOCATION: (205)
<223> OTHER INFORMATION: Variable amino acid
<220> FEATURE:
<221> NAME/KEY: MOD_RES
<222> LOCATION: (207)..(208)
<223> OTHER INFORMATION: Variable amino acid
<220> FEATURE:
<221> NAME/KEY: MOD_RES
<222> LOCATION: (211)..(217)
<223> OTHER INFORMATION: Variable amino acid
<220> FEATURE:
<221> NAME/KEY: MOD_RES
<222> LOCATION: (219)..(222)
<223> OTHER INFORMATION: Variable amino acid
<220> FEATURE:
<221> NAME/KEY: MOD_RES
<222> LOCATION: (224)..(227)
<223> OTHER INFORMATION: Variable amino acid
<220> FEATURE:
<221> NAME/KEY: MOD_RES
<222> LOCATION: (230)..(234)
<223> OTHER INFORMATION: Variable amino acid
<220> FEATURE:
<221> NAME/KEY: MOD_RES
<222> LOCATION: (236)
<223> OTHER INFORMATION: Variable amino acid
<220> FEATURE:
<221> NAME/KEY: MOD_RES
<222> LOCATION: (238)..(241)
<223> OTHER INFORMATION: Variable amino acid
<220> FEATURE:
<221> NAME/KEY: MOD_RES
<222> LOCATION: (243)..(244)
<223> OTHER INFORMATION: Variable amino acid
<220> FEATURE:
<221> NAME/KEY: MOD_RES
<222> LOCATION: (247)..(249)
<223> OTHER INFORMATION: Variable amino acid
<220> FEATURE:
<221> NAME/KEY: MOD_RES
<222> LOCATION: (252)
<223> OTHER INFORMATION: Variable amino acid
<220> FEATURE:
<221> NAME/KEY: MOD_RES
<222> LOCATION: (254)..(279)
<223> OTHER INFORMATION: Variable amino acid and this region may
      encompass 5 to 26 residues

<400> SEQUENCE: 29

Met Xaa Xaa Leu Xaa Xaa Lys Xaa Xaa Xaa Xaa Gly Xaa Xaa Xaa
1               5                   10                  15

Xaa Xaa Ser Ile Ala Xaa Gly Xaa Ala Xaa Xaa Xaa Xaa Xaa Gly
            20                  25                  30

Ala Xaa Leu Xaa Phe Thr Tyr Xaa Xaa Xaa Xaa Xaa Xaa Xaa Xaa
        35                  40                  45
```

```
Xaa Xaa Xaa Xaa Xaa Xaa Xaa Xaa Xaa Xaa Xaa Xaa Xaa Xaa Xaa
 50                  55                  60

Xaa Asp Val Xaa Xaa Xaa Xaa Xaa Xaa Xaa Xaa Xaa Xaa Xaa Xaa Xaa
 65                  70                  75                  80

Xaa Lys Xaa Xaa Xaa Xaa Xaa Asp Xaa Xaa Xaa Xaa His Ser Xaa Ala Phe
 85                  90                  95

Ala Xaa Arg Xaa Xaa Leu Xaa Gly Xaa Xaa Xaa Xaa Xaa Xaa Xaa
100                 105                 110

Xaa Xaa Phe Xaa Xaa Ala Xaa Xaa Ile Ser Xaa Tyr Ser Xaa Xaa
115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Tyr Xaa Gly Xaa Xaa Xaa Xaa Met Pro Ser Tyr Asn
145                 150                 155                 160

Xaa Met Gly Xaa Ala Lys Ala Xaa Leu Glu Xaa Xaa Val Arg Tyr Xaa
165                 170                 175

Ala Xaa Xaa Xaa Gly Xaa Xaa Xaa Xaa Xaa Val Asn Ala Xaa Ser Ala
180                 185                 190

Gly Pro Ile Xaa Thr Leu Ala Xaa Ser Gly Ile Ser Xaa Phe Xaa Xaa
195                 200                 205

Met Leu Xaa Xaa Xaa Xaa Xaa Xaa Xaa Pro Xaa Xaa Xaa Xaa Val Xaa
210                 215                 220

Xaa Xaa Xaa Val Gly Xaa Xaa Xaa Xaa Xaa Leu Xaa Ser Xaa Xaa Xaa
225                 230                 235                 240

Xaa Gly Xaa Xaa Gly Glu Xaa Xaa Xaa Val Asp Xaa Gly Xaa Xaa Xaa
245                 250                 255

Xaa Xaa Xaa Xaa Xaa Xaa Xaa Xaa Xaa Xaa Xaa Xaa Xaa Xaa Xaa
260                 265                 270

Xaa Xaa Xaa Xaa Xaa Xaa Xaa
275

<210> SEQ ID NO 30
<211> LENGTH: 279
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (2)..(3)
<223> OTHER INFORMATION: Variable amino acid
<220> FEATURE:
<221> NAME/KEY: MOD_RES
<222> LOCATION: (5)..(6)
<223> OTHER INFORMATION: Variable amino acid
<220> FEATURE:
<221> NAME/KEY: MOD_RES
<222> LOCATION: (8)..(12)
<223> OTHER INFORMATION: Variable amino acid
<220> FEATURE:
<221> NAME/KEY: MOD_RES
<222> LOCATION: (14)..(18)
<223> OTHER INFORMATION: Variable amino acid
<220> FEATURE:
<221> NAME/KEY: MOD_RES
<222> LOCATION: (22)
<223> OTHER INFORMATION: Variable amino acid
<220> FEATURE:
<221> NAME/KEY: MOD_RES
<222> LOCATION: (24)
<223> OTHER INFORMATION: Variable amino acid
<220> FEATURE:
<221> NAME/KEY: MOD_RES
```

```
<222> LOCATION: (26)..(31)
<223> OTHER INFORMATION: Variable amino acid
<220> FEATURE:
<221> NAME/KEY: MOD_RES
<222> LOCATION: (34)
<223> OTHER INFORMATION: Variable amino acid
<220> FEATURE:
<221> NAME/KEY: MOD_RES
<222> LOCATION: (36)
<223> OTHER INFORMATION: Variable amino acid
<220> FEATURE:
<221> NAME/KEY: MOD_RES
<222> LOCATION: (40)..(65)
<223> OTHER INFORMATION: Variable amino acid and this region may
      encompass 23 to 26 residues
<220> FEATURE:
<221> NAME/KEY: MOD_RES
<222> LOCATION: (68)..(81)
<223> OTHER INFORMATION: Variable amino acid
<220> FEATURE:
<221> NAME/KEY: MOD_RES
<222> LOCATION: (83)..(87)
<223> OTHER INFORMATION: Variable amino acid
<220> FEATURE:
<221> NAME/KEY: MOD_RES
<222> LOCATION: (89)..(91)
<223> OTHER INFORMATION: Variable amino acid
<220> FEATURE:
<221> NAME/KEY: MOD_RES
<222> LOCATION: (94)
<223> OTHER INFORMATION: Variable amino acid
<220> FEATURE:
<221> NAME/KEY: MOD_RES
<222> LOCATION: (95)
<223> OTHER INFORMATION: Gly or Ala
<220> FEATURE:
<221> NAME/KEY: MOD_RES
<222> LOCATION: (98)..(101)
<223> OTHER INFORMATION: Variable amino acid
<220> FEATURE:
<221> NAME/KEY: MOD_RES
<222> LOCATION: (103)
<223> OTHER INFORMATION: Variable amino acid
<220> FEATURE:
<221> NAME/KEY: MOD_RES
<222> LOCATION: (105)..(114)
<223> OTHER INFORMATION: Variable amino acid and this region may
      encompass 9 or 10 residues
<220> FEATURE:
<221> NAME/KEY: MOD_RES
<222> LOCATION: (116)..(117)
<223> OTHER INFORMATION: Variable amino acid
<220> FEATURE:
<221> NAME/KEY: MOD_RES
<222> LOCATION: (119)..(120)
<223> OTHER INFORMATION: Variable amino acid
<220> FEATURE:
<221> NAME/KEY: MOD_RES
<222> LOCATION: (123)
<223> OTHER INFORMATION: Variable amino acid
<220> FEATURE:
<221> NAME/KEY: MOD_RES
<222> LOCATION: (126)..(148)
<223> OTHER INFORMATION: Variable amino acid and this region may
      encompass 22 or 23 residues
<220> FEATURE:
<221> NAME/KEY: MOD_RES
<222> LOCATION: (150)
<223> OTHER INFORMATION: Variable amino acid
<220> FEATURE:
<221> NAME/KEY: MOD_RES
<222> LOCATION: (152)..(158)
<223> OTHER INFORMATION: Variable amino acid
<220> FEATURE:
<221> NAME/KEY: MOD_RES
<222> LOCATION: (161)
<223> OTHER INFORMATION: Variable amino acid
<220> FEATURE:
<221> NAME/KEY: MOD_RES
```

```
<222> LOCATION: (164)
<223> OTHER INFORMATION: Variable amino acid
<220> FEATURE:
<221> NAME/KEY: MOD_RES
<222> LOCATION: (168)
<223> OTHER INFORMATION: Variable amino acid
<220> FEATURE:
<221> NAME/KEY: MOD_RES
<222> LOCATION: (171)..(172)
<223> OTHER INFORMATION: Variable amino acid
<220> FEATURE:
<221> NAME/KEY: MOD_RES
<222> LOCATION: (176)
<223> OTHER INFORMATION: Variable amino acid
<220> FEATURE:
<221> NAME/KEY: MOD_RES
<222> LOCATION: (178)..(180)
<223> OTHER INFORMATION: Variable amino acid
<220> FEATURE:
<221> NAME/KEY: MOD_RES
<222> LOCATION: (182)..(186)
<223> OTHER INFORMATION: Variable amino acid
<220> FEATURE:
<221> NAME/KEY: MOD_RES
<222> LOCATION: (190)
<223> OTHER INFORMATION: Variable amino acid
<220> FEATURE:
<221> NAME/KEY: MOD_RES
<222> LOCATION: (196)
<223> OTHER INFORMATION: Variable amino acid
<220> FEATURE:
<221> NAME/KEY: MOD_RES
<222> LOCATION: (199)
<223> OTHER INFORMATION: Ala or Ser
<220> FEATURE:
<221> NAME/KEY: MOD_RES
<222> LOCATION: (200)
<223> OTHER INFORMATION: Variable amino acid
<220> FEATURE:
<221> NAME/KEY: MOD_RES
<222> LOCATION: (201)
<223> OTHER INFORMATION: Ser or Lys
<220> FEATURE:
<221> NAME/KEY: MOD_RES
<222> LOCATION: (203)
<223> OTHER INFORMATION: Ile or Val
<220> FEATURE:
<221> NAME/KEY: MOD_RES
<222> LOCATION: (204)..(205)
<223> OTHER INFORMATION: Variable amino acid
<220> FEATURE:
<221> NAME/KEY: MOD_RES
<222> LOCATION: (207)..(208)
<223> OTHER INFORMATION: Variable amino acid
<220> FEATURE:
<221> NAME/KEY: MOD_RES
<222> LOCATION: (209)
<223> OTHER INFORMATION: Met or Ile
<220> FEATURE:
<221> NAME/KEY: MOD_RES
<222> LOCATION: (211)..(217)
<223> OTHER INFORMATION: Variable amino acid
<220> FEATURE:
<221> NAME/KEY: MOD_RES
<222> LOCATION: (219)..(222)
<223> OTHER INFORMATION: Variable amino acid
<220> FEATURE:
<221> NAME/KEY: MOD_RES
<222> LOCATION: (224)..(227)
<223> OTHER INFORMATION: Variable amino acid
<220> FEATURE:
<221> NAME/KEY: MOD_RES
<222> LOCATION: (230)..(234)
<223> OTHER INFORMATION: Variable amino acid
<220> FEATURE:
<221> NAME/KEY: MOD_RES
<222> LOCATION: (236)
<223> OTHER INFORMATION: Variable amino acid
<220> FEATURE:
```

```
<221> NAME/KEY: MOD_RES
<222> LOCATION: (238)..(241)
<223> OTHER INFORMATION: Variable amino acid
<220> FEATURE:
<221> NAME/KEY: MOD_RES
<222> LOCATION: (243)..(244)
<223> OTHER INFORMATION: Variable amino acid
<220> FEATURE:
<221> NAME/KEY: MOD_RES
<222> LOCATION: (247)..(249)
<223> OTHER INFORMATION: Variable amino acid
<220> FEATURE:
<221> NAME/KEY: MOD_RES
<222> LOCATION: (252)
<223> OTHER INFORMATION: Variable amino acid
<220> FEATURE:
<221> NAME/KEY: MOD_RES
<222> LOCATION: (254)..(279)
<223> OTHER INFORMATION: Variable amino acid and this region may
      encompass 5 to 26 residues

<400> SEQUENCE: 30

Met Xaa Xaa Leu Xaa Xaa Lys Xaa Xaa Xaa Xaa Xaa Gly Xaa Xaa Xaa
1               5                   10                  15

Xaa Xaa Ser Ile Ala Xaa Gly Xaa Ala Xaa Xaa Xaa Xaa Xaa Gly
        20                  25                  30

Ala Xaa Leu Xaa Phe Thr Tyr Xaa Xaa Xaa Xaa Xaa Xaa Xaa Xaa
35                  40                  45

Xaa Xaa Xaa Xaa Xaa Xaa Xaa Xaa Xaa Xaa Xaa Xaa Xaa Xaa Xaa
50                  55                  60

Xaa Asp Val Xaa Xaa Xaa Xaa Xaa Xaa Xaa Xaa Xaa Xaa Xaa Xaa Xaa
65                  70                  75                  80

Xaa Lys Xaa Xaa Xaa Xaa Xaa Asp Xaa Xaa Xaa His Ser Xaa Xaa Phe
            85                  90                  95

Ala Xaa Xaa Xaa Xaa Leu Xaa Gly Xaa Xaa Xaa Xaa Xaa Xaa Xaa
100                 105                 110

Xaa Xaa Phe Xaa Xaa Ala Xaa Xaa Ile Ser Xaa Tyr Ser Xaa Xaa Xaa
115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Tyr Xaa Gly Xaa Xaa Xaa Xaa Xaa Xaa Tyr Asn
145                 150                 155             160

Xaa Met Gly Xaa Ala Lys Ala Xaa Leu Glu Xaa Xaa Val Arg Tyr Xaa
165                 170                 175

Ala Xaa Xaa Xaa Gly Xaa Xaa Xaa Xaa Xaa Val Asn Ala Xaa Ser Ala
180                 185                 190

Gly Pro Ile Xaa Thr Leu Xaa Xaa Xaa Gly Xaa Xaa Xaa Phe Xaa Xaa
195                 200                 205

Xaa Leu Xaa Xaa Xaa Xaa Xaa Xaa Pro Xaa Xaa Xaa Xaa Val Xaa
210                 215                 220

Xaa Xaa Xaa Val Gly Xaa Xaa Xaa Xaa Xaa Leu Xaa Ser Xaa Xaa Xaa
225                 230                 235                 240

Xaa Gly Xaa Xaa Gly Glu Xaa Xaa Xaa Val Asp Xaa Gly Xaa Xaa Xaa
245                 250                 255

Xaa Xaa Xaa Xaa Xaa Xaa Xaa Xaa Xaa Xaa Xaa Xaa Xaa Xaa Xaa
260                 265                 270

Xaa Xaa Xaa Xaa Xaa Xaa Xaa
275

<210> SEQ ID NO 31
```

-continued

```
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
cgcggggtac catgggtttt ctagcaggaa aaaaaatatt aatc                   44

<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcgcggatcc aagaacatta cccatagaca c                                 31

<210> SEQ ID NO 33
<211> LENGTH: 279
<212> TYPE: PRT
<213> ORGANISM: Francisella tularensis
<220> FEATURE:
<221> NAME/KEY: MOD_RES
<222> LOCATION: (1)..(94)
<223> OTHER INFORMATION: Variable amino acid and this region may
      encompass
      91 to 94 residues
<220> FEATURE:
<221> NAME/KEY: MOD_RES
<222> LOCATION: (98)
<223> OTHER INFORMATION: Variable amino acid
<220> FEATURE:
<221> NAME/KEY: MOD_RES
<222> LOCATION: (100)..(101)
<223> OTHER INFORMATION: Variable amino acid
<220> FEATURE:
<221> NAME/KEY: MOD_RES
<222> LOCATION: (103)..(148)
<223> OTHER INFORMATION: Variable amino acid and this region may
      encompass
      44 to 46 residues
<220> FEATURE:
<221> NAME/KEY: MOD_RES
<222> LOCATION: (150)..(155)
<223> OTHER INFORMATION: Variable amino acid
<220> FEATURE:
<221> NAME/KEY: MOD_RES
<222> LOCATION: (160)..(161)
<223> OTHER INFORMATION: Variable amino acid
<220> FEATURE:
<221> NAME/KEY: MOD_RES
<222> LOCATION: (163)..(165)
<223> OTHER INFORMATION: Variable amino acid
<220> FEATURE:
<221> NAME/KEY: MOD_RES
<222> LOCATION: (167)..(193)
<223> OTHER INFORMATION: Variable amino acid
<220> FEATURE:
<221> NAME/KEY: MOD_RES
<222> LOCATION: (195)..(197)
<223> OTHER INFORMATION: Variable amino acid
<220> FEATURE:
<221> NAME/KEY: MOD_RES
<222> LOCATION: (200)
<223> OTHER INFORMATION: Variable amino acid
<220> FEATURE:
<221> NAME/KEY: MOD_RES
<222> LOCATION: (202)
<223> OTHER INFORMATION: Variable amino acid
<220> FEATURE:
<221> NAME/KEY: MOD_RES
```

```
<222> LOCATION: (205)
<223> OTHER INFORMATION: Variable amino acid
<220> FEATURE:
<221> NAME/KEY: MOD_RES
<222> LOCATION: (207)..(208)
<223> OTHER INFORMATION: Variable amino acid
<220> FEATURE:
<221> NAME/KEY: MOD_RES
<222> LOCATION: (210)..(279)
<223> OTHER INFORMATION: Variable amino acid and this region may
      encompass
      49 to 70 residues

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa
    35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Ala Phe
        85                  90                  95

Ala Xaa Arg Xaa Xaa Leu Xaa Xaa Xaa Xaa Xaa Xaa Xaa Xaa Xaa
100                 105                 110

Xaa Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Tyr Xaa Xaa Xaa Xaa Xaa Xaa Met Pro Ser Tyr Xaa
145                 150                 155                 160

Xaa Met Xaa Xaa Xaa Lys Xaa Xaa Xaa Xaa Xaa Xaa Xaa Xaa Xaa
165                 170                 175

Xaa Xaa Xaa Xaa Xaa Xaa Xaa Xaa Xaa Xaa Xaa Xaa Xaa Xaa Xaa
180                 185                 190

Xaa Pro Xaa Xaa Xaa Leu Ala Xaa Ser Xaa Ile Ser Xaa Phe Xaa Xaa
195                 200                 205

Met Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
245                 250                 255

Xaa Xaa Xaa Xaa Xaa Xaa Xaa Xaa Xaa Xaa Xaa Xaa Xaa Xaa Xaa
260                 265                 270

Xaa Xaa Xaa Xaa Xaa Xaa Xaa
275
```